(12) United States Patent
Cummings et al.

(10) Patent No.: US 11,674,962 B2
(45) Date of Patent: Jun. 13, 2023

(54) THERAPEUTIC AND DIAGNOSTIC METHODS FOR CANCER

(71) Applicants: Genentech, Inc., South San Francisco, CA (US); Foundation Medicine, Inc., Cambridge, MA (US)

(72) Inventors: Craig Anthony Cummings, South San Francisco, CA (US); Yan Li, South San Francisco, CA (US); Sarah Margaret Shagan, South San Francisco, CA (US); Erica Beth Schleifman, South San Francisco, CA (US); David Shames, South San Francisco, CA (US); David Fabrizio, Cambridge, MA (US); Daniel Lieber, Cambridge, MA (US); Geoffrey Alan Otto, Cambridge, MA (US); Mark Kennedy, Cambridge, MA (US); Travis Clark, Cambridge, MA (US); Doron Lipson, Cambridge, MA (US); Jie He, Cambridge, MA (US); Shan Zhong, Belmont, MA (US)

(73) Assignees: Genentech, Inc., South San Francisco, CA (US); Foundation Medicine, Inc., Cambridge, MA (US)

( * ) Notice: Subject to any disclaimer, the term of this patent is extended or adjusted under 35 U.S.C. 154(b) by 194 days.

(21) Appl. No.: 16/041,363

(22) Filed: Jul. 20, 2018

(65) Prior Publication Data

US 2019/0025308 A1    Jan. 24, 2019

Related U.S. Application Data

(60) Provisional application No. 62/680,516, filed on Jun. 4, 2018, provisional application No. 62/652,843, filed on Apr. 4, 2018, provisional application No. 62/553,034, filed on Aug. 31, 2017, provisional application No. 62/535,605, filed on Jul. 21, 2017.

(51) Int. Cl.
| | |
|---|---|
| C12Q 1/68 | (2018.01) |
| C12Q 1/6883 | (2018.01) |
| G01N 33/574 | (2006.01) |
| C07K 16/28 | (2006.01) |
| G16H 50/50 | (2018.01) |
| G16H 50/30 | (2018.01) |
| G16H 50/70 | (2018.01) |
| G16H 50/20 | (2018.01) |
| A61P 35/00 | (2006.01) |
| G06F 16/28 | (2019.01) |
| C07K 14/735 | (2006.01) |
| A61K 39/00 | (2006.01) |

(52) U.S. Cl.
CPC ............ *G01N 33/574* (2013.01); *A61P 35/00* (2018.01); *C07K 14/70535* (2013.01); *C07K 16/2827* (2013.01); *C07K 16/2896* (2013.01); *C12Q 1/68* (2013.01); *C12Q 1/6883* (2013.01); *G01N 33/57492* (2013.01); *G06F 16/285* (2019.01); *G16H 50/20* (2018.01); *G16H 50/30* (2018.01); *G16H 50/50* (2018.01); *G16H 50/70* (2018.01); *A61K 2039/505* (2013.01); *A61K 2039/55* (2013.01); *C07K 2317/24* (2013.01); *C12Q 2600/156* (2013.01); *G01N 2333/70532* (2013.01); *G01N 2800/52* (2013.01)

(58) Field of Classification Search
None
See application file for complete search history.

(56) References Cited

U.S. PATENT DOCUMENTS

| | | |
|---|---|---|
| 8,354,509 B2 | 1/2013 | Carven et al. |
| 2012/0208706 A1 | 8/2012 | Downing et al. |
| 2013/0309254 A1 | 11/2013 | Samuels et al. |
| 2014/0287937 A1 | 9/2014 | So et al. |
| 2014/0296081 A1 | 10/2014 | Diehn et al. |
| 2014/0336996 A1 | 11/2014 | Sun et al. |

(Continued)

FOREIGN PATENT DOCUMENTS

| | | |
|---|---|---|
| CN | 105209919 A | 12/2015 |
| JP | 2016-520800 A | 7/2016 |

(Continued)

OTHER PUBLICATIONS

Diaz (Journal of Clinical Oncology vol. 32 No. 6 p. 579-587 Feb. 20, 2014).*

(Continued)

*Primary Examiner* — Amanda Haney
(74) *Attorney, Agent, or Firm* — Clark & Elbing LLP; Thomas J. Takara

(57) ABSTRACT

The present invention provides therapeutic, diagnostic, and prognostic methods for cancer. The invention provides methods of treating a cancer, methods of determining whether an individual having a cancer is likely to respond to a treatment including an immune checkpoint inhibitor (e.g., a PD-L1 axis binding antagonist), methods of predicting responsiveness of an individual having a cancer to a treatment including an immune checkpoint inhibitor (e.g., a PD-L1 axis binding antagonist), methods of selecting a therapy for an individual having a cancer, methods of providing a prognosis for an individual having a cancer, and methods of monitoring a response of an individual having a cancer, based on a blood tumor mutational burden (bTMB) score or a maximum somatic allele frequency (MSAF) from a sample (e.g., a whole blood sample, a plasma sample, a serum sample, or a combination thereof) from the individual.

16 Claims, 59 Drawing Sheets
Specification includes a Sequence Listing.

(56) References Cited

U.S. PATENT DOCUMENTS

| | | |
|---|---|---|
| 2016/0009805 A1 | 1/2016 | Kowanetz et al. |
| 2017/0175197 A1 | 6/2017 | Gatalica et al. |
| 2017/0275689 A1* | 9/2017 | Maguire .............. C12Q 1/6811 |
| 2018/0045727 A1 | 2/2018 | Spetzler et al. |
| 2018/0231554 A1 | 8/2018 | Schatton et al. |
| 2018/0282417 A1* | 10/2018 | Higgs ..................... A61P 35/00 |
| 2018/0291074 A1 | 10/2018 | Chan et al. |
| 2018/0363066 A1 | 12/2018 | Chalmers et al. |
| 2019/0085403 A1 | 3/2019 | Frampton et al. |
| 2019/0219586 A1 | 7/2019 | Fabrizio et al. |

FOREIGN PATENT DOCUMENTS

| | | |
|---|---|---|
| JP | 2017-537087 A | 12/2017 |
| JP | 2018-502828 A | 2/2018 |
| WO | WO-2013/070634 A1 | 5/2013 |
| WO | WO-2014/151006 A2 | 9/2014 |
| WO | WO-2015/095423 A2 | 6/2015 |
| WO | WO-2015/116868 A2 | 8/2015 |
| WO | WO-2015/164862 A1 | 10/2015 |
| WO | WO-2016/018481 A2 | 2/2016 |
| WO | WO-2016/077553 A1 | 5/2016 |
| WO | WO 2016/081947 * | 5/2016 |
| WO | WO-2016/081947 A2 | 5/2016 |
| WO | WO-2016/089873 A1 | 6/2016 |
| WO | WO-2017/151502 A1 | 9/2017 |
| WO | WO-2017/151517 A1 | 9/2017 |
| WO | WO-2017/151524 A1 | 9/2017 |
| WO | WO-2018/068028 A1 | 4/2018 |

OTHER PUBLICATIONS

Frampton (Journal of Clinical Oncology 34, No. 15_suppl (May 20, 2016).*
Dagogo-Jack (Journal of Clinical Oncology 35, No. 15_suppl (May 20, 2017).*
Jing (Onco Targets and Therapy 2016 vol. 9 pp. 489-502).*
Rosenberg (Lancet 2016; 387: 1909-20).*
Campesato (Oncotarget vol. 6, No. 33 Oct. 1, 2015).*
Powles et al., "MPDL3280A (anti-PD-L1) treatment leads to clinical activity in metastatic bladder cancer" Nature. 515(7528): 558-62 (2014) (12 pages).
International Preliminary Report on Patentability for International Patent Application No. PCT/US2017/019763, dated Sep. 4, 2018 (19 pages).
International Preliminary Report on Patentability for International Patent Application No. PCT/US2017/055669, dated Apr. 9, 2019 (13 pages).
Bahary et al., "Genomic profiling of circulating tumor DNA (ctDNA) from patients (pts) with pancreatic ductal adenocarcinoma (PDA)," J Clin Oncol. 35(15):4128 (2017) (Abstract Only) (5 pages).
Campesato et al., "Comprehensive cancer-gene panels can be used to estimate mutational load and predict clinical benefit to PD-1 blockade in clinical practice," Oncotarget. 6(33):34221-7 (2015).
Chalmers et al., "Analysis of 100,000 human cancer genomes reveals the landscape of tumor mutational burden," Genome Med. 9(1):34 (2017) (14 pages).
FoundationOne, "Technical Information and Test Overview," retrieved on Jan. 18, 2018 from <https://assets.contentful.com/vhribv12lmne/6YRrchSINOeSu48YwuesoY/caeec492925a7d569ce4e070866f709b/F1_-_Tech_Specs.pdf> (2 pages).
Gandara et al., "Blood-based tumor mutational burden as a predictor of clinical benefit in non-small-cell lung cancer patients treated with atezolizumab," Nat Med. 24(9):1441-8 (2018) (8 pages).
Govindan et al., "Genomic landscape of non-small cell lung cancer in smokers and never-smokers," Cell. 150(6):1121-34 and supplemental content (2012) (24 pages).
Henick et al., "The PD-1 pathway as a therapeutic target to overcome immune escape mechanisms in cancer," Expert Opin Ther Targets. 18(12):1407-20 (2014).
Kates et al., "Immune checkpoint inhibitors: a new frontier in bladder cancer," World J Urol. 34(1):49-55 (2016).
Marcq et al., "Targeting immune checkpoints: New opportunity for mesothelioma treatment?" Cancer Treat Rev. 41(10):914-24 (2015).
Melero et al., "Evolving synergistic combinations of targeted immunotherapies to combat cancer," Nat Rev Cancer. 15(8):457-72 (2015).
Rizvi et al., "Cancer immunology. Mutational landscape determines sensitivity to PD-1 blockade in non-small cell lung cancer," Science. 348(6230):124-8 and supplementary materials (2015) (37 pages).
Rosenberg et al., "Atezolizumab in patients with locally advanced and metastatic urothelial carcinoma who have progressed following treatment with platinum-based chemotherapy: a single-arm, multicentre, phase 2 trial," Lancet. 387(10031):1909-20 and supplementary appendix (2016) (37 pages).
Stephens et al., "Analytic validation of a clinical circulating tumor DNA assay for patients with solid tumors," Ann Oncol. 27(Suppl. 6):vi401-vi406 (2016) (Abstract Only) (1 page).
Van Allen et al., "Genomic correlates of response to CTLA-4 blockade in metastatic melanoma," Science. 350(6257):207-211 (2015).
Vansteenkiste et al., "Prospects and progress of atezolizumab in non-small cell lung cancer," Expert Opin Biol Ther. 17(6):781-9 (2017) (10 pages).
International Preliminary Report on Patentability for International Patent Application No. PCT/US2017/019682, dated Sep. 4, 2018 (8 pages).
International Search Report and Written Opinion for International Patent Application No. PCT/US2017/019682, dated Apr. 24, 2017 (17 pages).
International Search Report and Written Opinion for International Patent Application No. PCT/US2017/019763, dated Aug. 2, 2017 (25 pages).
International Search Report and Written Opinion for International Patent Application No. PCT/US2017/055669, dated Jan. 8, 2018 (21 pages).
International Search Report and Written Opinion for International Patent Application No. PCT/US2018/043074, dated Oct. 29, 2018 (17 pages).
Rosenberg et al., "Supplement to: Atezolizumab in patients with locally advanced and metastatic urothelial carcinoma who have progressed following treatment with platinum-based chemotherapy: a single arm, phase 2 trial," Lancet. 387(10031):1909-20 (2016), accessed Apr. 8, 2020 (24 pages).
Communication Pursuant to Rules 161(1) and 162 EPC for European Patent Application No. 18750078.0, dated Feb. 28, 2020 (3 pages).
International Preliminary Report on Patentability for International Patent Application No. PCT/US2018/043074, dated Jan. 21, 2020 (9 pages).
Frampton et al. "Development and validation of a clinical cancer genomic profiling test based on massively parallel DNA sequencing," available in PMC Dec. 1, 2017, published in final edited form as: Nat Biotechnol. 31(11): 1023-31 (2013) (25 pages).
Meng et al., "Predictive biomarkers in PD-1/PD-L1 checkpoint blockade immunotherapy," Cancer Treat Rev 41(10):868-76 (2015).
Fabbri et al., "Analysis of the chronic lymphocytic leukemia coding genome: role of NOTCH1 mutational activation," J Exp Med. 208(7):1389-401 (2011).
Johnson et al., "Targeted Next Generation Sequencing Identifies Markers of Response to PD-1 Blockade," available in PMC Nov. 1, 2017, published in final edited form as: Cancer Immunol Res. 4(11):959-67 (2017) (17 pages).
Tamborero et al., "OncodriveCLUST: exploiting the positional clustering of somatic mutations to identify cancer genes," Bioinformatics. 29(18):2238-44 (2013).
Bardoli et al., "The PD-1/PD-L1 axis in the pathogenesis of urothelial bladder cancer and evaluating its potential as a therapeutic target," Future Oncol. 12(5):595-600 (2016).
Bidnur et al., "Inhibiting Immune Checkpoints for the Treatment of Bladder Cancer," Bladder Cancer. 2(1): 15-25 (2016) (11 pages).

(56) References Cited

OTHER PUBLICATIONS

Castro et al., "Mismatch repair deficiency associate with complete remission to combination programmed cell death ligan immune therapy in a patient with sporadic urothelial carcinoma: immunotheranostic considerations," J ImmunoTher Cancer. 3:58 (2015).
Cazier et al., "Whole-genome sequencing of bladder cancers reveals somatic CDKN1A mutations and clinicopathological associations with mutation burden," Nat Commun. 5:4809 (2014).
Champiat et al., "Exomics and immunogenics," OncoImmunology. 3(1):e27817 (2014).
Choudhury et al., "Low T-cell Receptor Diversity, High Somatic Mutation Burden, and High Neoantigen Load as Predictors of Clinical Outcome in Muscle-invasive Bladder Cancer," Eur Urol Focus. 2(4):445-452 (2015).
Fakhrejahani et al., "Immunotherapies for bladder cancer: a new hope," Curr Opin Urol. 25(6):586-596 (2015).
Gabril et al., "Molecular Testing in Urothelial Tumors," Springer. 301-17 (2014).
Gatalica et al., "Programmed Cell Death 1 (PD-1) and Its Ligand (PD-L1) in Common Cancers and Their Correlation with Molecular Cancer Type," Cancer Epidemiol Biomarkers Prev. 23(12): 2965-2970 (2014).
Gubin et al., "Checkpoint Blockade Cancer Immunotherapy Targets Tumour-Specific Mutant Antigens," Nature. 515(7528):577-81 (2014).
Gui et al., "Frequent mutations of chromatin remodeling genes in transitional cell carcinoma of the bladder," Nat Genet. 43(9):875-8 (2011).
Howitt et al., "Association of Polymerase e-Mutated and Microsatellite-Instable Endometrial Cancers With Neoantigen Load, Number of Tumor-Infiltrating Lymphocytes, and Expression of PD-1 and PL-L1," JAMA Oncol. 1(9):1319-23 (2015).
Kim et al., "Emerging immunotherapies for bladder cancer," Curr Opin Oncol. 27(3):191-200 (2015).
Knowles et al., "Molecular biology of bladder cancer: new insights into pathogenesis and clinical diversity," Nature Reviews Cancer. 15(1):25-41 (2015).
Kowanetz et al., "Tumor Mutation Burden (TMB) is Associated with Improved Efficacy of Atezolizumab in 1L and 2L+ NSCLC Patients," J Thorac Oncol. 12(1):S321-2 OA20.01 (Abstract) (2017).
Kurtoglu et al., "Elevating the Horizon: Emerging Molecular and Genomic Targets in the Treatment of Advanced Urothelial Carcinoma," Clin Genitourin Cancer. 13(5):410-20 (2015).
Le et al., "PD-1 Blockade in Tumors with Mismatch-Repair Deficiency," N Engl J Med. 372(26):2509-2520 (2015).
Llosa et al., "The Vigorous Immune Microenvironment of Microsatellite Instable Colon Cancer Is Balanced by Multiple Counter-Inhibitory Checkpoints," Cancer Discov. 5(1):43-51 (2015).
Maby et al., "Correlation between Density of CD8+ T-cell Infiltrate in Microsatellite Unstable Colorectal Cancers and Frameshift Mutations: A Rationale for Personalized Immunotherapy," Cancer Res. 75(17):3446-55 (2015).
Millis et al., "Molecular Profiling of Infiltrating Urothelial Carcinoma of Bladder and Nonbladder Origin," Clin Genitourin Cancer. 13(1):e37-49 (2015).
Rooney et al., "Molecular and Genetic Properties of Tumors Associated with Local Immune Cytolytic Activity," Cell. 160(1-2):48-61 (2015).
Schumacher et al., "Neoantigens in cancer immunotherapy," Science. 348(6230):69-74 (2015).
Strickland et al., "Association and prognostic significance of BRCA1/2-mutation status with neoantigen load, number of tumor-infiltrating lymphocytes and expression of PD-1/PD-L1 in high grade serous ovarian cancer," Oncotarget. 7(12):13587-13598 (2016).
The Cancer Genome Atlas Research Network, "Comprehensive molecular characterization or urothelial bladder carcinoma," Nature. 507:315-22 (2014).
Vaish et al., "Microsatellite instability as prognostic marker in bladder tumors: a clinical significance," BMC Urol. 5:2 (2005).

Van Buuren et al., "High sensitivity of cancer exome-based CD8 T cell neo-antigen identification," OncoImmunology. 3:e28836 (2014).
Yamamoto et al., "Microsatellite instability: an update," Arch Toxicol. 89(6):899-921 (2015).
Yap et al., "Whole-Exome Sequencing of Muscle-Invasive Bladder Cancer Identifies Recurrent Mutations of UNC5C and Prognostic Importance of DNA Repair Gene Mutations on Survival," Clin Cancer Res. 20(24):6605-17 (2014).
Examination Report No. 1 for Australian Patent Application No. 2018304458, dated Jan. 11, 2021 (6 pages).
Office Action for Canadian Patent Application No. 3,069,469, dated Feb. 5, 2021 (5 pages).
"Exome," Wikipedia. Retrieved from <https://en.wikipedia.org/w/index.php?title=Exome&oldid=1010823778> on Jun. 17, 2021 (6 pages).
Caris Life Sciences, "Total Mutational Load—Immune Checkpoint Inhibitors Response," <https://www.carismolecularintelligence.com/wp-content/uploads/2016/12/TN0291-v1_Total-Mutational-Load-Immunotherapy-REVERSED-PAGES.pdf>, dated Aug. 10, 2016, retrieved Jul. 13, 2021 (2 pages).
Asmar et al., "Clinical utility of nivolumab in the treatment of advanced melanoma," Ther Clin Risk Manag. 12:313-325 (2016).
Bettegowda et al., "Detection of Circulating Tumor DNA in Early- and Late-Stage Human Malignancies," Sci Transl Med. 6(224):224ra24 (2014) (13 pages).
Legrand et al., "Association of high tissue TMB and atezolizumab efficacy across multiple tumor types," retrieved from <https://ascopubs.org/doi/abs/10.1200/JCO.2018.36.15_suppl.12000> on Jul. 29, 2021, J Clin Oncol. 36(15 suppl): 12000 (2018) (4 pages).
Rothé et al., "Plasma circulating tumor DNA as an alternative to metastatic biopsies for mutational analysis in breast cancer," Ann Oncol. 25(10):1959-1965 (2014).
Communication pursuant to Rule 114(2) EPC for European Patent Application No. 18750078.0, dated Jul. 22, 2021 (11 pages).
Notification of material filed by a third party for Australian Patent Application No. 2018304458, dated Aug. 6, 2021 (26 pages).
Chen et al., "Effect of Combined Immune Checkpoint Inhibition vs Best Supportive Care Alone in Patients with Advanced Colorectal Cancer: The Canadian Cancer Trials Group CO.26 Study," JAMA Oncol. 6(6):831-838 (May 2020).
Gubin et al., "CANCER. The odds of immunotherapy success," Science. 350(6257):158-9 (2015) (3 pages).
Peters et al., "Atezolizumab versus chemotherapy in advanced or metastatic NSCLC with high blood-based tumor mutational burden: primary analysis of BFAST cohort C randomized phase 3 trial," Nat Med. 28(9):1831-1839 (2022) (23 pages).
Schrock et al., "Characterization of 298 Patients with Lung Cancer Harboring MET Exon 14 Skipping Alterations," J Thorac Oncol. 11(9):1493-502 (2016).
Snyder et al., "Genetic Basis for Clinical Response to CTLA-4 Blockade in Melanoma," N Engl J Med. 371(23):2189-2199 (2014).
Ghasemzadeh et al., "New Strategies in Bladder Cancer: A Second Coming for Immunotherapy," epublished as: Clin Cancer Res. 22(4):1-9 (2015) (10 pages).
Morse et al., "Elevated tumor mutational burden and prolonged clinical response to anti-PD-L1 antibody in platinum-resistant recurrent ovarian cancer," Gynecol Oncol Rep. 21:78-80 (2017).
Notice of Reasons for Rejection for Japanese Patent Application No. 2020-502304, dated Aug. 17, 2021 (10 pages).
Protest and Filing of Prior Art References Prior to Grant for Canadian Patent Application No. 3,069,469, dated Aug. 20, 2021 (24 pages).
Chaudhuri et al., "Analysis of circulating tumor DNA in localized lung cancer for detection of molecular residual disease and personalization of adjuvant strategies," J Clin Oncol. 35 (15 suppl): 8519 (May 30, 2017) (Abstract Only) (3 pages).
Dagogo-Jack et al., "Genomic profiling of circulating tumor DNA (ctDNA) from patients (pts) with advanced non-small cell lung cancer (NSCLC)," J Clin Oncol. 35 (15 suppl): 9025 (May 30, 2017) (Abstract Only) (3 pages).
Davis et al., "Comparison of tumor mutational burden (TMB) across tumor tissue and circulating tumor DNA (ctDNA)," J of Clin Oncol. 35(15 suppl): e23028-e23028 (May 30, 2017) (2 pages).

(56) References Cited

OTHER PUBLICATIONS

Fehrenbacher et al., "Atezolizumab versus docetaxel for patients with previously treated non-small-cell lung cancer (POPLAR): a multicentre, open-label, phase 2 randomised controlled trial" Lancet. 387(10030): 1837-46 (2016).

Santini et al., "Atezolizumab for the treatment of non-small cell lung cancer," available in PMC Aug. 13, 2018, published in final edited form as: Expert Rev Clin Pharmacol. 10(9):935-945 (Jul. 17, 2017) (28 pages).

Sato et al., "Individualized Mutation Detection in Circulating Tumor DNA for Monitoring Colorectal Tumor Burden Using a Cancer-Associated Gene Sequencing Panel," PLoS One. 11(1):e0146275 (2016) (15 pages).

* cited by examiner

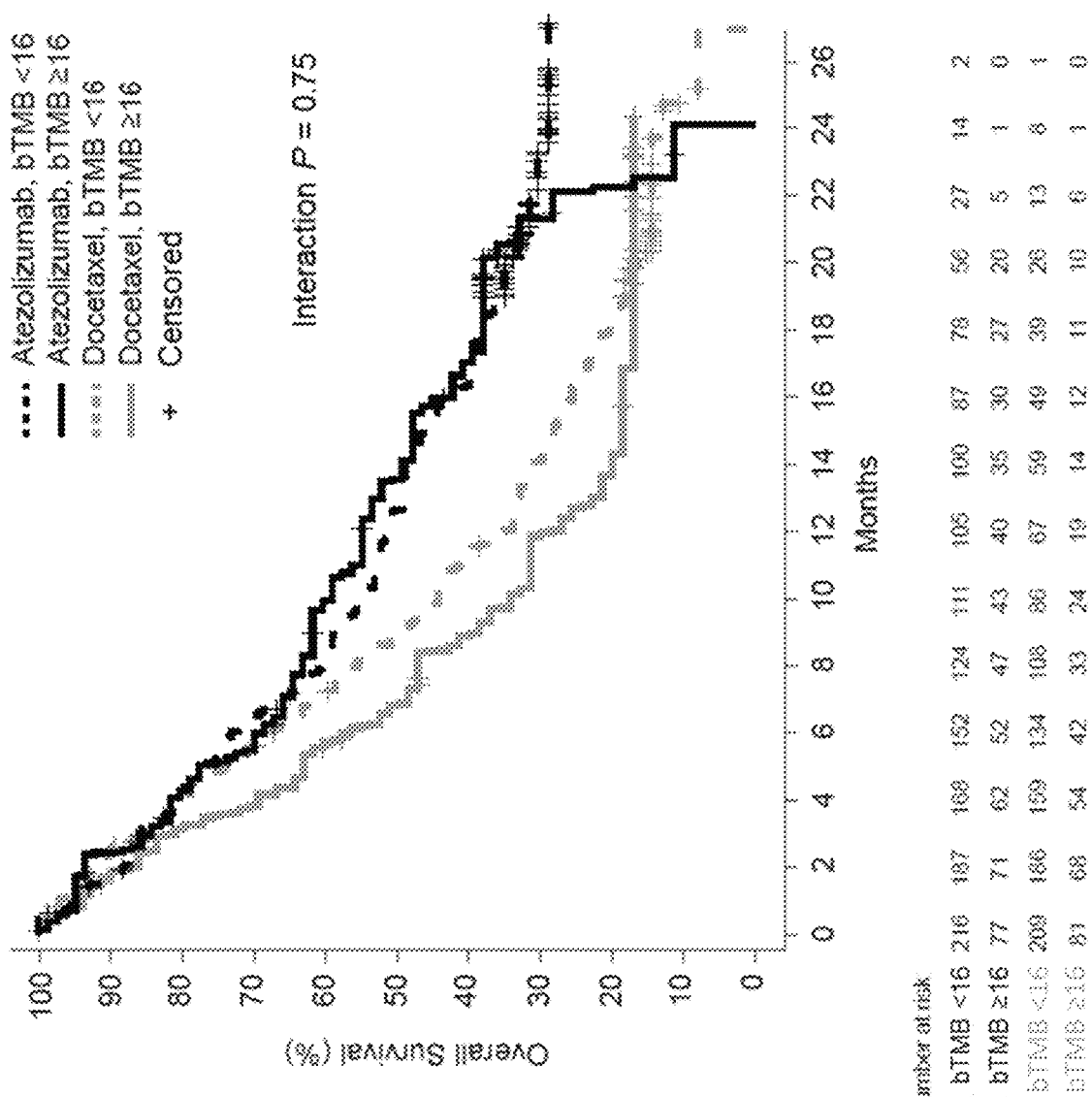

FIG. 9A

| bTMB Quartile | TC0 and IC0 | TC1/2/3 or IC1/2/3[a] | TC2/3 or IC2/3[b] | TC3 or IC3 |
|---|---|---|---|---|
| 0% | 0 | 1 | 0 | 0 |
| 25% | 3 | 4 | 4 | 3 |
| 50% | 7 | 8 | 9 | 10 |
| 75% | 14 | 18 | 18 | 18 |
| 100% | 67 | 40 | 66 | 57 |

[a] TC1/2/3 or IC1/2/3 excluding TC2/3 or IC2/3 patients, [b] TC2/3 or IC2/3 excluding TC3 or IC3 patients.

FIG. 11C

| bTMB | PPA | NPA |
|---|---|---|
| ≥ 10 | 100.0% | 100.0% |
| ≥ 11 | 94.6% | 92.3% |
| ≥ 12 | 89.1% | 92.9% |
| ≥ 13 | 94.0% | 84.2% |
| ≥ 14 | 90.0% | 89.5% |
| ≥ 15 | 85.7% | 90.0% |
| ≥ 16 | 89.1% | 100.0% |
| ≥ 17 | 90.2% | 89.3% |
| ≥ 18 | 92.1% | 83.9% |
| ≥ 19 | 94.4% | 81.8% |
| ≥ 20 | 97.1% | 82.4% |

FIG. 11

| Metric | Value | cfDNA samples | Comments |
|---|---|---|---|
| PPA compare FACT to bTMB | Overall (variants) | 93.4% (171/183) | 69 samples with variants, 81 total | False negative VAFs range from 0.5-1.1% (comes from FACT) |
| | % Perfect samples | 84.1% (58/69) | | |
| PPV compare bTMB to FACT | Overall (variants) | 93.5% (43/46) | 33 samples with variants, 81 total | False positive VAFs: 0.76, 0.82, 1.56% (comes from bTMB – homopolymeric tract) |
| | % Perfect samples | 90.9% (30/33) | | |

FIG. 20

| Characteristic | IAP (n = 78) | BEP (n = 58) | bTMB low (<16; n = 47) | bTMB high (≥16; n = 11) |
|---|---|---|---|---|
| Median age (range), y | 68.0 (39-90) | 69.0 (47-90) | 69.0 (47-90) | 69.0 (54-86) |
| Male | Female | 62.8% | 37.2% | 58.6% | 41.4% | 55.3% | 44.7% | 72.7% | 27.3% |
| ECOG PS, % 0 | 1 | 30.8% | 69.2% | 25.9% | 74.1% | 23.4% | 76.6% | 36.4% | 63.6% |
| Tobacco use history, % Never Current \| Previous | 1.3% 19.2% \| 79.5% | 0 22.4% \| 77.6% | 0 17.0% \| 83.0% | 0 45.5% \| 54.5% |
| Histology n (%) Non-squamous Squamous | 57 (73.1%) 21 (26.9%) | 41 (70.7%) 17 (29.3%) | 36 (76.6%) 11 (23.4%) | 5 (45.5%) 6 (54.5%) |
| PD-L1 IHC, n (%) Negative Positive Missing | 14 (17.9%) 33 (42.3%) 31 (39.7%) | 12 (20.7%) 23 (39.7%) 23 (39.7%) | 8 (17.0%) 22 (46.8%) 17 (36.2%) | 4 (36.4%) 1 (9.1%) 6 (54.5%) |
| Median SLD of target lesions (range), mm | 69.5 (15.0-257.0) | 77.0 (15.0-257.0) | 70.0 (15.0-172.7) | 113.0 (29.0-257.0) |

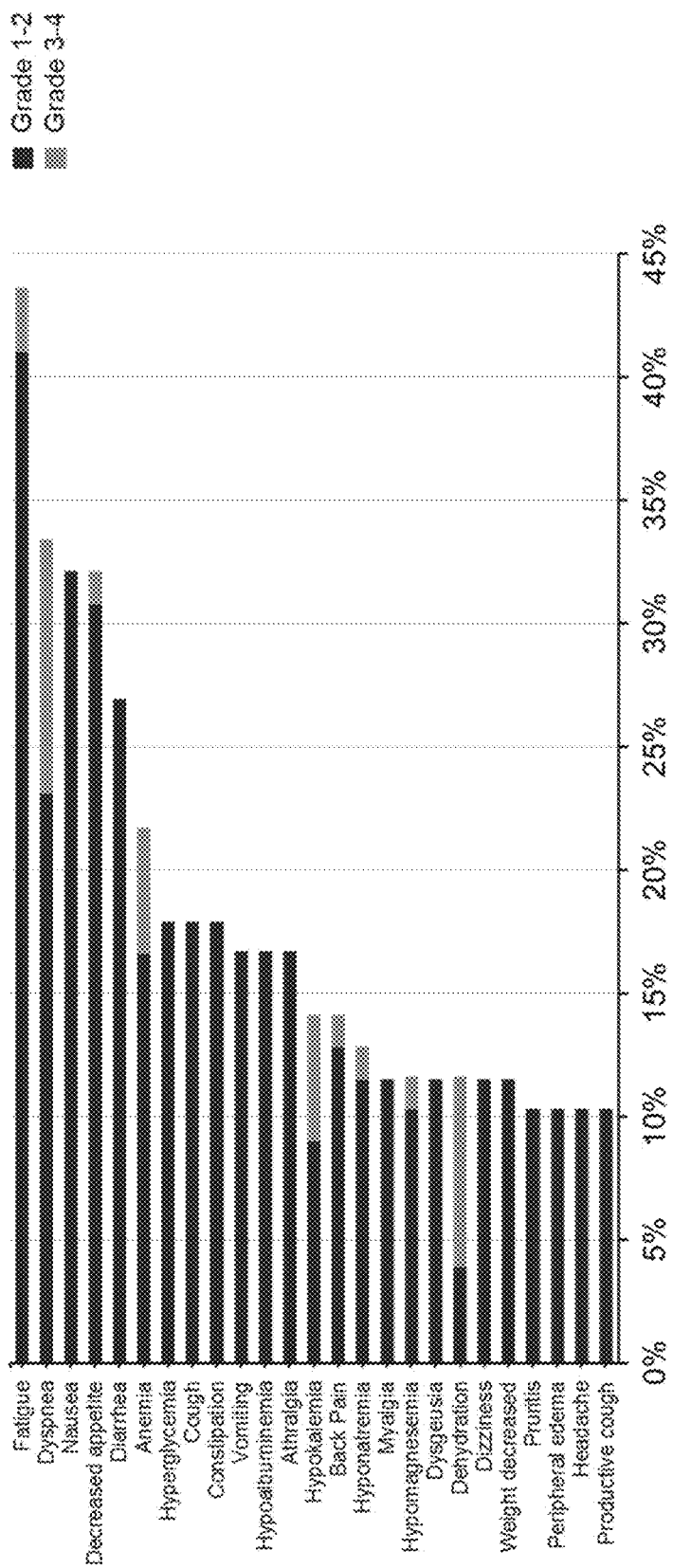

THERAPEUTIC AND DIAGNOSTIC METHODS FOR CANCER

FIELD OF THE INVENTION

Provided herein are diagnostic, therapeutic, and prognostic methods for the treatment of cancer using immune checkpoint inhibitors (e.g., PD-L1 axis binding antagonists). In particular, the invention provides methods for patient selection and diagnosis, methods of treatment, and diagnostic kits.

BACKGROUND

Cancer remains one of the most deadly threats to human health. In the U.S., cancer affects nearly 1.3 million new patients each year and is the second leading cause of death after heart disease, accounting for approximately 1 in 4 deaths. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Malignant solid tumors, in particular, metastasize and grow rapidly in an uncontrolled manner, making their timely detection and treatment extremely difficult. Despite the significant advancement in the treatment of cancer, improved diagnostic methods are still being sought.

Recent studies suggest that analysis of tumor mutational burden (TMB), a measure of tumor neo-antigenicity derived from tissue biopsies, has shown clinical utility in predicting outcomes for patients treated with PD-L1 axis binding antagonists across a range of tumor types. However, some patients are unsuitable or unwilling to undergo biopsy to obtain a tumor sample for somatic mutation analysis, for example, due to their health status.

Thus, there exists an unmet need for orthogonal, non-invasive diagnostic approaches that enable the analysis of TMB in patient samples without requiring a tumor tissue biopsy.

SUMMARY OF THE INVENTION

The present invention provides therapeutic, diagnostic, and prognostic methods and compositions for treating an individual having a cancer.

In one aspect, the invention features a method of identifying an individual having a cancer who may benefit from a treatment comprising an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof), the method comprising determining a blood tumor mutational burden (bTMB) score from a sample from the individual, wherein a bTMB score from the sample that is at or above a reference bTMB score identifies the individual as one who may benefit from a treatment comprising an immune checkpoint inhibitor. In some embodiments, the immune checkpoint inhibitor is a PD-L1 axis binding antagonist.

In another aspect, the invention features a method for selecting a therapy for an individual having a cancer, the method comprising determining a bTMB score from a sample from the individual, wherein a bTMB score from the sample that is at or above a reference bTMB score identifies the individual as one who may benefit from a treatment comprising an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof). In some embodiments, the immune checkpoint inhibitor is a PD-L1 axis binding antagonist.

In some embodiments of any of the preceding aspects, the bTMB score determined from the sample is at or above the reference bTMB score, and the method further comprises administering to the individual an effective amount of a PD-L1 axis binding antagonist. In some embodiments, the bTMB score determined from the sample is below the reference bTMB score.

In another aspect, the invention features a method of treating an individual having a cancer, the method comprising: (a) determining a bTMB score from a sample from the individual, wherein the bTMB score from the sample is at or above a reference bTMB score, and (b) administering an effective amount of a PD-L1 axis binding antagonist to the individual.

In another aspect, the invention features a method of treating an individual having a cancer, the method comprising administering to the individual an effective amount of an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof), wherein prior to the administering a bTMB score that is at or above a reference bTMB score has been determined from a sample from the individual. In some embodiments, the immune checkpoint inhibitor is a PD-L1 axis binding antagonist.

In some embodiments of any of the preceding aspects, the reference bTMB score is a bTMB score in a reference population of individuals having the cancer, the population of individuals consisting of a first subset of individuals who have been treated with a PD-L1 axis binding antagonist therapy and a second subset of individuals who have been treated with a non-PD-L1 axis binding antagonist therapy, wherein the non-PD-L1 axis binding antagonist therapy does not comprise an immune checkpoint inhibitor (e.g., a PD-L1 axis binding antagonist (e.g., an anti-PD-L1 antibody) or an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)). In some embodiments, the reference bTMB score is a bTMB score in a reference population of individuals having the cancer, the population of individuals consisting of a first subset of individuals who have been treated with a PD-L1 axis binding antagonist therapy and a second subset of individuals who have been treated with a non-PD-L1 axis binding antagonist therapy, wherein the non-PD-L1 axis binding antagonist therapy does not comprise a PD-L1 axis binding antagonist. In some embodiments, the reference bTMB score significantly separates each of the first and second subsets of individuals based on a significant difference in responsiveness to treatment with the PD-L1 axis binding antagonist therapy relative to responsiveness to treatment with the non-PD-L1 axis binding antagonist therapy. In some embodiments, responsiveness to treatment is an increase in progression-free survival (PFS). In some embodiments, responsiveness to treatment is an increase in overall survival (OS).

In some embodiments of any of the preceding aspects, the reference bTMB score is a pre-assigned bTMB score. In some embodiments, the reference bTMB score is between 4 and 30 (e.g., between about 3.6 mut/Mb and about 26.7 mut/Mb). In some embodiments, the reference bTMB score is between 8 and 30 (e.g., between about 7.1 mut/Mb and about 26.7 mut/Mb). In some embodiments, the reference bTMB score is between 10 and 20 (e.g., between about 9 mut/Mb and about 17.8 mut/Mb). In some embodiments, the reference bTMB score is 10 (e.g., about 9 mut/Mb). In some embodiments, the reference bTMB score is 16 (e.g., about 14 mut/Mb). In some embodiments, the reference bTMB score is 20 (e.g., about 17.8 mut/Mb).

In some embodiments of any of the preceding aspects, the bTMB score from the sample is greater than, or equal to, 4 (e.g., greater than, or equal to, about 3.6 mut/Mb). In some embodiments, the bTMB score from the sample is between 4 and 100 (e.g., between about 3.6 mut/Mb and about 88.9 mut/Mb).

In some embodiments of any of the preceding aspects, the bTMB score from the sample is greater than, or equal to, 8 (e.g., greater than, or equal to, about 7.1 mut/Mb). In some embodiments, the bTMB score from the sample is between 8 and 100 (e.g., between about 7.1 mut/Mb and about 88.9 mut/Mb).

In some embodiments of any of the preceding aspects, the bTMB score from the sample is less than 4 (e.g., less than about 3.6 mut/Mb). In some embodiments, the bTMB score from the sample is less than 8 (e.g., less than about 7.1 mut/Mb).

In some embodiments of any of the preceding aspects, the bTMB score (e.g., reference bTMB score) is represented as the number of somatic mutations counted over a defined number of sequenced bases (e.g., about 100 kb to about 10 Mb, about 200 kb to about 10 Mb, about 300 kb to about 10 Mb, about 400 kb to about 10 Mb, about 500 kb to about 10 Mb, about 600 kb to about 10 Mb, about 700 kb to about 10 Mb, about 800 kb to about 10 Mb, about 900 kb to about 10 Mb, about 1 Mb to about 10 Mb, about 100 kb to about 5 Mb, about 200 kb to about 5 Mb, about 300 kb to about 5 Mb, about 400 kb to about 5 Mb, about 500 kb to about 5 Mb, about 600 kb to about 5 Mb, about 700 kb to about 5 Mb, about 800 kb to about 5 Mb, about 900 kb to about 5 Mb, or about 1 Mb to about 5 Mb, about 100 kb to about 2 Mb, about 200 kb to about 2 Mb, about 300 kb to about 2 Mb, about 400 kb to about 2 Mb, about 500 kb to about 2 Mb, about 600 kb to about 2 Mb, about 700 kb to about 2 Mb, about 800 kb to about 2 Mb (e.g., about 800 kb (e.g., about 795 kb), e.g., as assessed by the FOUNDATIONONE CDX™ panel), about 900 kb to about 2 Mb, or about 1 Mb to about 2 Mb, for example, about 1.1 Mb (e.g., about 1.125 Mb), e.g., as assessed by the FOUNDATIONONE® panel). In some embodiments, the defined number of sequenced bases is about 100 kb, about 200 kb, about 300 kb, about 400 kb, about 500 kb, about 600 kb, about 700 kb, about 800 kb, about 900 kb, about 1 Mb, about 2 Mb, about 3 Mb, about 4 Mb, about 5 Mb, about 6 Mb, about 7 Mb, about 8 Mb, about 9 Mb, or about 10 Mb. In some embodiments, the number of somatic mutations is the number of single nucleotide variants (SNVs) counted or a sum of the number of SNVs and the number of indel mutations counted. In some embodiments, the number of somatic mutations is the number of SNVs counted. In some embodiments, the number of somatic mutations is the number of synonymous and non-synonymous SNVs and/or indels. In some embodiments, the bTMB score (e.g., reference bTMB score) is an equivalent bTMB value, for example, as determined by whole-exome sequencing.

In another aspect, the invention features a method of identifying an individual having a cancer who may benefit from a treatment comprising an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof), the method comprising determining an equivalent bTMB value from a sample from the individual, wherein an equivalent bTMB value from the sample that is at or above a reference equivalent bTMB value identifies the individual as one who may benefit from a treatment comprising an immune checkpoint inhibitor. In some embodiments, the immune checkpoint inhibitor is a PD-L1 axis binding antagonist.

In another aspect, the invention features a method for selecting a therapy for an individual having a cancer, the method comprising determining an equivalent bTMB value from a sample from the individual, wherein an equivalent bTMB value from the sample that is at or above a reference equivalent bTMB value identifies the individual as one who may benefit from a treatment comprising an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof). In some embodiments, the immune checkpoint inhibitor is a PD-L1 axis binding antagonist.

In some embodiments of any of the preceding aspects, the equivalent bTMB value determined from the sample is at or above the reference equivalent bTMB value, and the method further comprises administering to the individual an effective amount of a PD-L1 axis binding antagonist. In some embodiments, the equivalent bTMB value determined from the sample is below the reference equivalent bTMB value.

In another aspect, the invention features a method of treating an individual having a cancer, the method comprising: (a) determining an equivalent bTMB value from a sample from the individual, wherein the equivalent bTMB value from the sample is at or above a reference equivalent bTMB value, and (b) administering an effective amount of an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof) to the individual. In some embodiments, the immune checkpoint inhibitor is a PD-L1 axis binding antagonist. In some embodiments, the method further comprises monitoring the response of the individual to treatment with the immune checkpoint inhibitor (e.g., PD-L1 axis binding antagonist). In some embodiments, the monitoring comprises: (a) determining a bTMB score in a further sample obtained from the individual at a time point following administration of the immune checkpoint inhibitor (e.g., PD-L1 axis binding antagonist); and (b) comparing the bTMB score in the further sample to a reference bTMB score, thereby monitoring the response in the individual to the treatment with the immune checkpoint inhibitor (e.g., PD-L1 axis binding antagonist).

In another aspect, the invention features a method of treating an individual having a cancer, the method comprising administering to the individual an effective amount of an immune checkpoint inhibitor (e.g., a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof), wherein prior to the administering an equivalent bTMB value that is at or above a reference equivalent bTMB value has been determined from a sample from the individual. In some embodiments, the immune checkpoint inhibitor is a PD-L1 axis binding antagonist. In some embodiments, the method further comprises monitoring the response of the individual to treatment with the immune checkpoint inhibitor (e.g., PD-L1 axis binding antagonist). In some embodiments, the monitoring comprises: (a) determining a bTMB score in a further sample obtained from the individual at a time point following administration of the immune checkpoint inhibitor (e.g., PD-L1 axis binding antagonist); and (b) comparing the bTMB score in the further sample to a reference bTMB score, thereby monitoring the response in the individual to the treatment with the immune checkpoint inhibitor (e.g., PD-L1 axis binding antagonist).

In another aspect, the invention features a method of providing a prognosis for an individual having a cancer, the method comprising determining a MSAF from a sample from the individual, wherein a MSAF from the sample that is at or above a reference MSAF identifies the individual as one who may have a poor prognosis.

In another aspect, the invention features a method of monitoring a response of an individual having a cancer to treatment with an anti-cancer therapy comprising a PD-L1 axis binding antagonist, the method comprising: (a) determining a bTMB score in a sample obtained from an individual at a time point following administration of the anti-cancer therapy to the individual; and (b) comparing the bTMB score in the sample to a reference bTMB score, thereby monitoring the response in the individual to the treatment with the anti-cancer therapy.

In another aspect, the invention features a method of predicting disease progression in an individual having a cancer, the method comprising determining a bTMB score in a sample obtained from the individual, wherein a bTMB score in the sample that is at or above a reference bTMB score identifies the individual as one who is more likely to exhibit disease progression. In some embodiments, disease progression is an increase in tumor burden. In some embodiments, the increase in tumor burden is characterized by an increase in the sum of longest diameters (SLD). In some embodiments, disease progression is characterized by an increase in squamous morphology, e.g., as assessed by tumor histology. In other embodiments, disease progression is characterized by an increase in non-squamous morphology, e.g., as assessed by tumor histology.

In a still further aspect, the invention features a method of predicting disease progression in an individual having a cancer, the method comprising determining an MSAF in a sample obtained from the individual, wherein an MSAF in the sample that is at or above a reference MSAF identifies the individual as one who is more likely to exhibit disease progression. In some embodiments, disease progression is an increase in tumor burden. In some embodiments, the increase in tumor burden is characterized by an increase in the sum of longest diameters (SLD). In some embodiments, disease progression is characterized by an increase in squamous morphology, e.g., as assessed by tumor histology. In other embodiments, disease progression is characterized by an increase in non-squamous morphology, e.g., as assessed by tumor histology. In some embodiments of any of the preceding aspects, the reference equivalent bTMB value is a pre-assigned equivalent bTMB value. In some embodiments, the reference equivalent bTMB value corresponds to a reference bTMB score between 4 and 30 (e.g., between about 3.6 mut/Mb and about 26.7 mut/Mb). In some embodiments, the reference equivalent bTMB value corresponds to a reference bTMB score between 8 and 30 (e.g., between about 7.1 mut/Mb and about 26.7 mut/Mb). In some embodiments, the reference equivalent bTMB value corresponds to a reference bTMB score between 10 and 20 (e.g., between about 9 mut/Mb and about 17.8 mut/Mb). In some embodiments, the reference equivalent bTMB value corresponds to a reference bTMB score of 10 (e.g., about 9 mut/Mb). In some embodiments, the reference equivalent bTMB value corresponds to a reference bTMB score of 16 (e.g., about 14 mut/Mb). In some embodiments, the reference equivalent bTMB value corresponds to a reference bTMB score of 20 (e.g., about 17.8 mut/Mb).

In some embodiments of any of the preceding aspects, the equivalent bTMB value from the sample corresponds to a bTMB score of greater than, or equal to, 4 (e.g., greater than, or equal to, about 3.6 mut/Mb). In some embodiments, the equivalent bTMB value from the sample is between 4 and 100 (e.g., between about 3.6 mut/Mb and about 88.9 mut/Mb).

In some embodiments of any of the preceding aspects, the equivalent bTMB value from the sample is greater than, or equal to, 8 (e.g., greater than, or equal to, about 7.1 mut/Mb). In some embodiments, the equivalent bTMB value from the sample is between 8 and 100 (e.g., between about 7.1 mut/Mb and about 88.9 mut/Mb).

In some embodiments of any of the preceding aspects, the equivalent bTMB value from the sample is less than 4 (e.g., less than about 3.6 mut/Mb). In some embodiments, the equivalent bTMB value from the sample is less than 8 (e.g., less than about 7.1 mut/Mb).

In some embodiments of any of the preceding aspects, benefit from the treatment comprising a PD-L1 axis binding antagonist is an increase in OS. In other embodiments of any of the preceding aspects, benefit from the treatment comprising a PD-L1 axis binding antagonist is an increase in PFS. In some embodiments, benefit from the treatment comprising a PD-L1 axis binding antagonist is an increase in OS and PFS.

In some embodiments of any of the preceding aspects, the method further comprises determining a maximum somatic allele frequency (MSAF) from a sample from the individual, wherein the MSAF from the sample is greater than, or equal to, 1%. In some embodiments, prior to the administering a sample from the individual has been determined to have an MSAF greater than, or equal to, 1%.

In other embodiments of any of the preceding aspects, the method further comprises determining an MSAF from a sample from the individual, wherein the MSAF from the sample is less than 1%. In some embodiments, prior to the administering a sample from the individual has been determined to have an MSAF less than 1%.

In some embodiments of any of the preceding aspects, the method further comprises determining an MSAF from a sample from the individual, wherein the MSAF from the sample has been determined to be greater than, or equal to, 1%, and the method further comprises administering to the individual an effective amount of an anti-cancer therapy other than, or in addition to, a PD-L1 axis binding antagonist.

In some embodiments of any of the preceding aspects, the method further comprises determining an MSAF from a sample from the individual, wherein the MSAF from the sample has been determined to be less than 1%, and the method further comprises administering an effective amount of a PD-L1 axis binding antagonist to the individual.

In some embodiments of any of the preceding aspects, determining the MSAF is prior to determining the bTMB score. In some embodiments, the MSAF has been determined prior to the bTMB score.

In some embodiments of any of the preceding aspects, the bTMB score from the sample has a prevalence of greater than, or equal to, about 5% in the reference population. In some embodiments, the bTMB score from the sample has a prevalence of between about 5% and about 75% in the reference population. In some embodiments, the bTMB score from the sample has a prevalence of between about 20% and about 30% in the reference population.

In some embodiments of any of the preceding aspects, the method further comprises determining a tissue tumor mutational burden (tTMB) score from a tumor sample from the individual. In other embodiments of any of the preceding aspects, prior to the administration a tTMB score has been determined from a sample from the individual. In some embodiments, a tTMB score from the tumor sample that is at or above a reference tTMB score identifies the individual as one who may benefit from a treatment comprising a PD-L1 axis binding antagonist. In some embodiments, the tTMB score determined from the tumor sample is at or above the reference tTMB score. In some embodiments, the tTMB score determined from the tumor sample is below the reference tTMB. In some embodiments, the reference tTMB score is a tTMB score in a reference population of individuals having the cancer, the population of individuals consisting of a first subset of individuals who have been treated with a PD-L1 axis binding antagonist therapy and a second subset of individuals who have been treated with a non-PD-L1 axis binding antagonist therapy, wherein the non-PD-L1 axis binding antagonist therapy does not comprise a PD-L1 axis binding antagonist. In some embodiments, the reference tTMB score significantly separates each of the first and second subsets of individuals based on a significant difference in responsiveness to treatment with the PD-L1 axis binding antagonist therapy relative to responsiveness to treatment with the non-PD-L1 axis binding antagonist therapy. In some embodiments, responsiveness to treatment is an increase in PFS, an increase in OS, and/or an increase in the overall response rate (ORR). In some embodiments, the tumor sample has been determined to have an increased level of somatic mutation relative to a reference level of somatic mutation. In some embodiments, the tumor sample has been determined to have an increased level of somatic mutation in at least one gene set forth in Table 1 relative to a reference level of somatic mutation in the at least one gene set forth in Table 1. In some embodiments, the somatic mutations are protein-altering somatic mutations or synonymous mutations. In some embodiments, the somatic mutations are protein-altering somatic mutations. In some embodiments, the somatic mutations are substitutions, deletions, and/or insertions. In some embodiments, the substitutions, deletions, and/or insertions are in coding regions. In some embodiments, the deletions and/or insertions are indels. In some embodiments, the reference tTMB score is a pre-assigned tTMB score. In some embodiments, the reference tTMB score is between about 5 and about 50 mutations per megabase (mut/Mb). In some embodiments, the reference tTMB score is between about 8 and about 30 mut/Mb. In some embodiments, the reference tTMB score is between about 10 and about 20 mut/Mb. In some embodiments, the reference tTMB score is about 10 mut/Mb. In some embodiments, the reference tTMB score is about 16 mut/Mb. In some embodiments, the reference tTMB score is about 20 mut/Mb. In some embodiments, the tTMB score from the tumor sample is greater than, or equal to, about 5 mut/Mb. In some embodiments, the tTMB score from the tumor sample is between about 5 and about 100 mut/Mb. In some embodiments, the tTMB score from the tumor sample is greater than, or equal to, about 10 mut/Mb. In some embodiments, the tTMB score from the tumor sample is between about 10 and about 100 mut/Mb. In some embodiments, the tTMB score from the tumor sample is greater than, or equal to, about 16 mut/Mb. In some embodiments, the reference tTMB score is about 16 mut/Mb. In some embodiments, the tTMB score from the tumor sample is greater than, or equal to, about 20 mut/Mb. In some embodiments, the reference tTMB score is about 20 mut/Mb. In some embodiments, the tTMB score or the reference tTMB score is represented as the number of somatic mutations counted per a defined number of sequenced bases. In some embodiments, the defined number of sequenced bases is between about 100 kb to about 10 Mb. In some embodiments, the defined number of sequenced bases is about 0.8 Mb. In some embodiments, the defined number of sequenced bases is about 1.1 Mb. In some embodiments, the tTMB score or the reference tTMB score is an equivalent tTMB value. In some embodiments, the equivalent tTMB value is determined by whole-exome sequencing (WES).

In some embodiments of any of the preceding aspects, a tumor sample obtained from the patient has been determined to have a detectable expression level of PD-L1 in less than 1% of the tumor cells in the tumor sample. In other embodiments of any of the preceding aspects, a tumor sample obtained from the patient has been determined to have a detectable expression level of PD-L1 in 1% or more of the tumor cells in the tumor sample. In some embodiments, the tumor sample obtained from the patient has been determined to have a detectable expression level of PD-L1 in from 1% to less than 5% of the tumor cells in the tumor sample. In some embodiments, the tumor sample obtained from the patient has been determined to have a detectable expression level of PD-L1 in 5% or more of the tumor cells in the tumor sample. In some embodiments, the tumor sample obtained from the patient has been determined to have a detectable expression level of PD-L1 in from 5% to less than 50% of the tumor cells in the tumor sample. In some embodiments, the tumor sample obtained from the patient has been determined to have a detectable expression level of PD-L1 in 50% or more of the tumor cells in the tumor sample.

In some embodiments of any of the preceding aspects, a tumor sample obtained from the patient has been determined to have a detectable expression level of PD-L1 in tumor-infiltrating immune cells that comprise less than 1% of the tumor sample. In other embodiments of any of the preceding aspects, a tumor sample obtained from the patient has been determined to have a detectable expression level of PD-L1 in tumor-infiltrating immune cells that comprise more than 1% of the tumor sample. In some embodiments, the tumor sample obtained from the patient has been determined to have a detectable expression level of PD-L1 in tumor-infiltrating immune cells that comprise from 1% to less than 5% of the tumor sample. In some embodiments, the tumor sample obtained from the patient has been determined to have a detectable expression level of PD-L1 in tumor-infiltrating immune cells that comprise more than 5% of the tumor sample.

In some embodiments, the tumor sample obtained from the patient has been determined to have a detectable expression level of PD-L1 in tumor-infiltrating immune cells that comprise from 5% to less than 10% of the tumor sample. In some embodiments, the tumor sample obtained from the patient has been determined to have a detectable expression level of PD-L1 in tumor-infiltrating immune cells that comprise more than 10% of the tumor sample.

In some embodiments of any of the preceding aspects, the sample is a whole blood sample, a plasma sample, a serum sample, or a combination thereof. In some embodiments, the sample is an archival sample, a fresh sample, or a frozen sample.

In some embodiments of any of the preceding aspects, the cancer is selected from the group consisting of a lung cancer, a kidney cancer, a bladder cancer, a breast cancer, a colorectal cancer, an ovarian cancer, a pancreatic cancer, a gastric carcinoma, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, a mycoses fungoides, a merkel cell cancer, or a hematologic malignancy. In some embodiments, the cancer is a lung cancer, a bladder cancer, a melanoma, a kidney cancer, a colorectal cancer, or a head and neck cancer. In some embodiments, the lung cancer is a non-small cell lung cancer (NSCLC). In some embodiments, the bladder cancer is a bladder urothelial (transitional cell) carcinoma. In some embodiments, the melanoma is a skin melanoma. In some embodiments, the kidney cancer is a kidney urothelial carcinoma. In some embodiments, the colorectal cancer is a colon adenocarcinoma. In some embodiments, the head and neck cancer is a head and neck squamous cell carcinoma (HNSCC).

In some embodiments of any of the preceding aspects, the PD-L1 axis binding antagonist is selected from the group consisting of a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an anti-PD-L1 antibody. In some embodiments, the anti-PD-L1 antibody is selected from the group consisting of atezolizumab (MPDL3280A), YW243.55.S70, MDX-1105, MED14736 (durvalumab), and MSB0010718C (avelumab). In some embodiments, the anti-PD-L1 antibody comprises the following hypervariable regions: (a) an HVR-H1 sequence of GFTFSDSWIH (SEQ ID NO: 19); (b) an HVR-H2 sequence of AWISPYGG-STYYADSVKG (SEQ ID NO: 20); (c) an HVR-H3 sequence of RHWPGGFDY (SEQ ID NO: 21); (d) an HVR-L1 sequence of RASQDVSTAVA (SEQ ID NO: 22); (e) an HVR-L2 sequence of SASFLYS (SEQ ID NO: 23); and (f) an HVR-L3 sequence of QQYLYHPAT (SEQ ID NO: 24). In some embodiments, the anti-PD-L1 antibody comprises: (a) a heavy chain variable (VH) domain comprising an amino acid sequence having at least 90% sequence identity to the amino acid sequence of SEQ ID NO: 3; (b) a light chain variable (VL) domain comprising an amino acid sequence having at least 90% sequence identity to the amino acid sequence of SEQ ID NO: 4; or (c) a VH domain as in (a) and a VL domain as in (b). In some embodiments, the anti-PD-L1 antibody comprises: (a) a heavy chain variable (VH) domain comprising an amino acid sequence having at least 95% sequence identity to the amino acid sequence of SEQ ID NO: 3; (b) a light chain variable (VL) domain comprising an amino acid sequence having at least 95% sequence identity to the amino acid sequence of SEQ ID NO: 4; or (c) a VH domain as in (a) and a VL domain as in (b). In some embodiments, the anti-PD-L1 antibody comprises: (a) a heavy chain variable (VH) domain comprising an amino acid sequence having at least 96% sequence identity to the amino acid sequence of SEQ ID NO: 3; (b) a light chain variable (VL) domain comprising an amino acid sequence having at least 96% sequence identity to the amino acid sequence of SEQ ID NO: 4; or (c) a VH domain as in (a) and a VL domain as in (b). In some embodiments, the anti-PD-L1 antibody comprises: (a) a heavy chain variable (VH) domain comprising an amino acid sequence having at least 97% sequence identity to the amino acid sequence of SEQ ID NO: 3; (b) a light chain variable (VL) domain comprising an amino acid sequence having at least 97% sequence identity to the amino acid sequence of SEQ ID NO: 4; or (c) a VH domain as in (a) and a VL domain as in (b). In some embodiments, the anti-PD-L1 antibody comprises: (a) a heavy chain variable (VH) domain comprising an amino acid sequence having at least 98% sequence identity to the amino acid sequence of SEQ ID NO: 3; (b) a light chain variable (VL) domain comprising an amino acid sequence having at least 98% sequence identity to the amino acid sequence of SEQ ID NO: 4; or (c) a VH domain as in (a) and a VL domain as in (b). In some embodiments, the anti-PD-L1 antibody comprises: (a) a heavy chain variable (VH) domain comprising an amino acid sequence having at least 99% sequence identity to the amino acid sequence of SEQ ID NO: 3; (b) a light chain variable (VL) domain comprising an amino acid sequence having at least 99% sequence identity to the amino acid sequence of SEQ ID NO: 4; or (c) a VH domain as in (a) and a VL domain as in (b). In some embodiments, the anti-PD-L1 antibody comprises: (a) a VH domain comprising the amino acid sequence of SEQ ID NO: 3; (b) a VL domain comprising the amino acid sequence of SEQ ID NO: 4; or (c) a VH domain as in (a) and a VL domain as in (b). In some embodiments, the anti-PD-L1 antibody comprises:
(a) a VH domain comprising the amino acid sequence of SEQ ID NO: 3; and (b) a VL domain comprising the amino acid sequence of SEQ ID NO: 4. In some embodiments, the antibody is atezolizumab (MPDL3280A). In some embodiments, the PD-L1 axis binding antagonist is a PD-1 binding antagonist. In some embodiments, the PD-1 binding antagonist inhibits the binding of PD-1 to one or more of its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an anti-PD-1 antibody. In some embodiments, the anti-PD-1 antibody is selected from the group consisting of: MDX-1106 (nivolumab), MK-3475 (pembrolizumab), CT-011 (pidilizumab), MEDI-0680 (AMP-514), PDR001, REGN2810, and BGB-108. In some embodiments, the PD-1 binding antagonist is an Fc-fusion protein. In some embodiments, the Fc-fusion protein is AMP-224.

In some embodiments of any of the preceding aspects, the non-PD-L1 axis binding antagonist is an anti-neoplastic agent, a chemotherapeutic agent, a growth inhibitory agent, an anti-angiogenic agent, a radiation therapy, or a cytotoxic agent. In some embodiments, the anti-cancer therapy other than, or in addition to, a PD-L1 axis binding antagonist is an anti-neoplastic agent, a chemotherapeutic agent, a growth inhibitory agent, an anti-angiogenic agent, a radiation therapy, or a cytotoxic agent.

In some embodiments of any of the preceding aspects, the individual has not been previously treated for the cancer. In some embodiments, the individual has not been previously administered a PD-L1 axis binding antagonist.

In some embodiments of any of the preceding aspects, the treatment comprising a PD-L1 axis binding antagonist is a monotherapy.

In some embodiments of any of the preceding aspects, the method further comprises administering to the individual an effective amount of an additional therapeutic agent. In some embodiments, the additional therapeutic agent is an anti-neoplastic agent, a chemotherapeutic agent, a growth inhibitory agent, an anti-angiogenic agent, a radiation therapy, or a cytotoxic agent.

In some embodiments of any of the preceding aspects, the individual is a human.

In another aspect, the invention features a kit for identifying an individual having a cancer who may benefit from a treatment comprising a PD-L1 axis binding antagonist, the kit comprising: (a) reagents for determining a bTMB score from a sample from the individual; and, optionally, (b) instructions for using the reagents to identify an individual having a cancer who may benefit from a treatment comprising a PD-L1 axis binding antagonist, wherein a bTMB score from the sample that is at or above a reference bTMB score identifies the individual as one who may benefit from the treatment comprising a PD-L1 axis binding antagonist.

In another aspect, the invention features an assay for identifying an individual having a cancer who is a candidate for a treatment comprising a PD-L1 axis binding antagonist, the assay comprising determining a bTMB score from a sample from the individual, wherein a bTMB score from the sample that is at or above a reference bTMB score identifies the individual as one who may benefit from the treatment comprising a PD-L1 axis binding antagonist.

In another aspect, the invention features a PD-L1 axis binding antagonist for use in treating an individual having a cancer, wherein a bTMB score that is at or above a reference bTMB score has been determined from a sample from the individual.

In another aspect, the invention provides for the use of a PD-L1 axis binding antagonist in the manufacture of a medicament for treating an individual having a cancer, wherein a bTMB score that is at or above a reference bTMB score has been determined from a sample from the individual.

In some embodiments of any of the preceding aspects, the bTMB score (e.g., reference bTMB score) is represented as the number of somatic mutations counted over a defined number of sequenced bases (e.g., about 1.1 Mb (e.g., about 1.125 Mb), e.g., as assessed by the FOUNDATIONONE® panel). In some embodiments, the bTMB score (e.g., reference bTMB score) is an equivalent bTMB value, for example, as determined by whole-exome sequencing.

BRIEF DESCRIPTION OF THE DRAWINGS

FIG. 5C is a graph showing the Kaplan-Meier Curve of OS in the bTMB<16 and bTMB≥16 subgroups in the atezolizumab and docetaxel treatment arms. An interaction p-value from an unstratified proportional cox model including terms of treatment, bTMB subgroup, and treatment by subgroup interaction is shown.

Figure 9B:
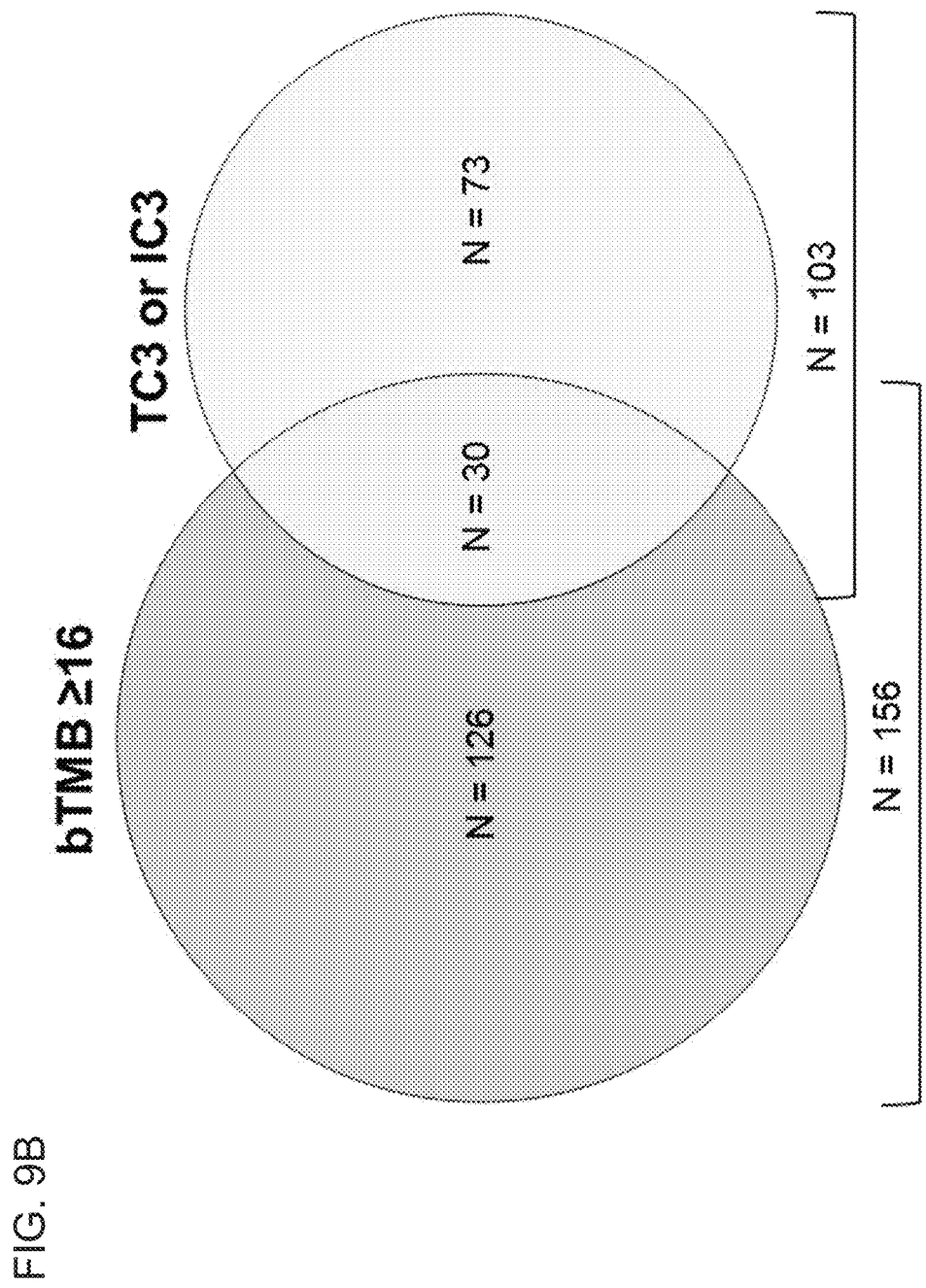
FIG. 9B is a Venn diagram showing that of the 229 patients with bTMB and IHC data, 30 were both bTMB≥16 and TC3 or IC3 PD-L1 expression as measured by the Ventana PD-L1 (SP142) assay; bTMB≥16 (n=156); TC3 or IC3 (n=103).
Figure 9D:
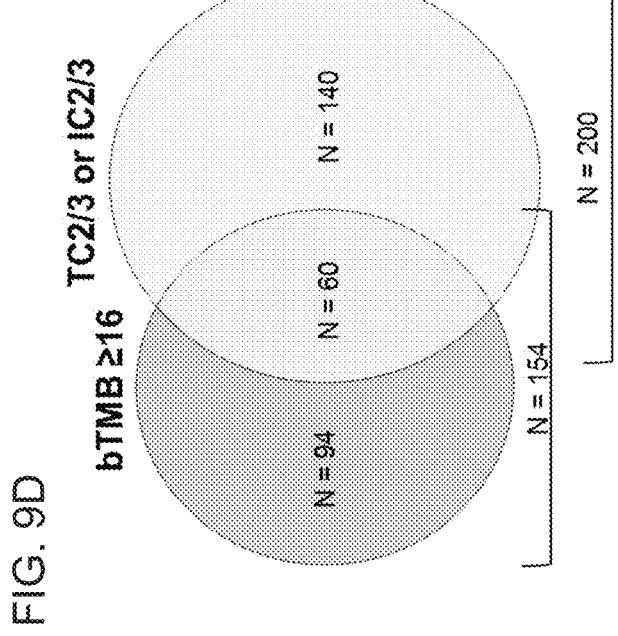
FIG. 9A is a table showing bTMB quantile by mutually exclusive PD-L1 IHC subgroup in OAK.
Figure 9C:
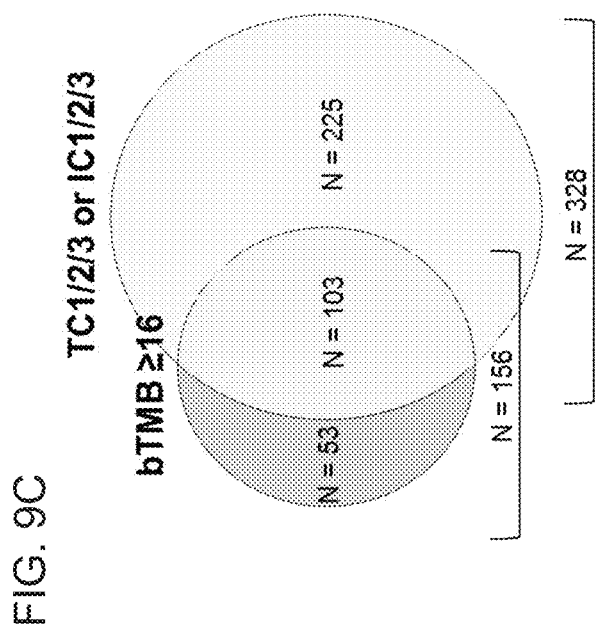

FIGS. 9C and 9D are Venn diagrams showing overlap between bTMB level and various PD-L1 expression subgroups in the OAK study. The Venn diagrams show overlap between high bTMB (≥16) and TC1/2/3 or IC1/2/3 (FIG. 9C) and TC2/3 or IC2/3 (FIG. 9D) PD-L1 expression as measured by the Ventana PD-L1 SP142 assay.

Figure 9E:
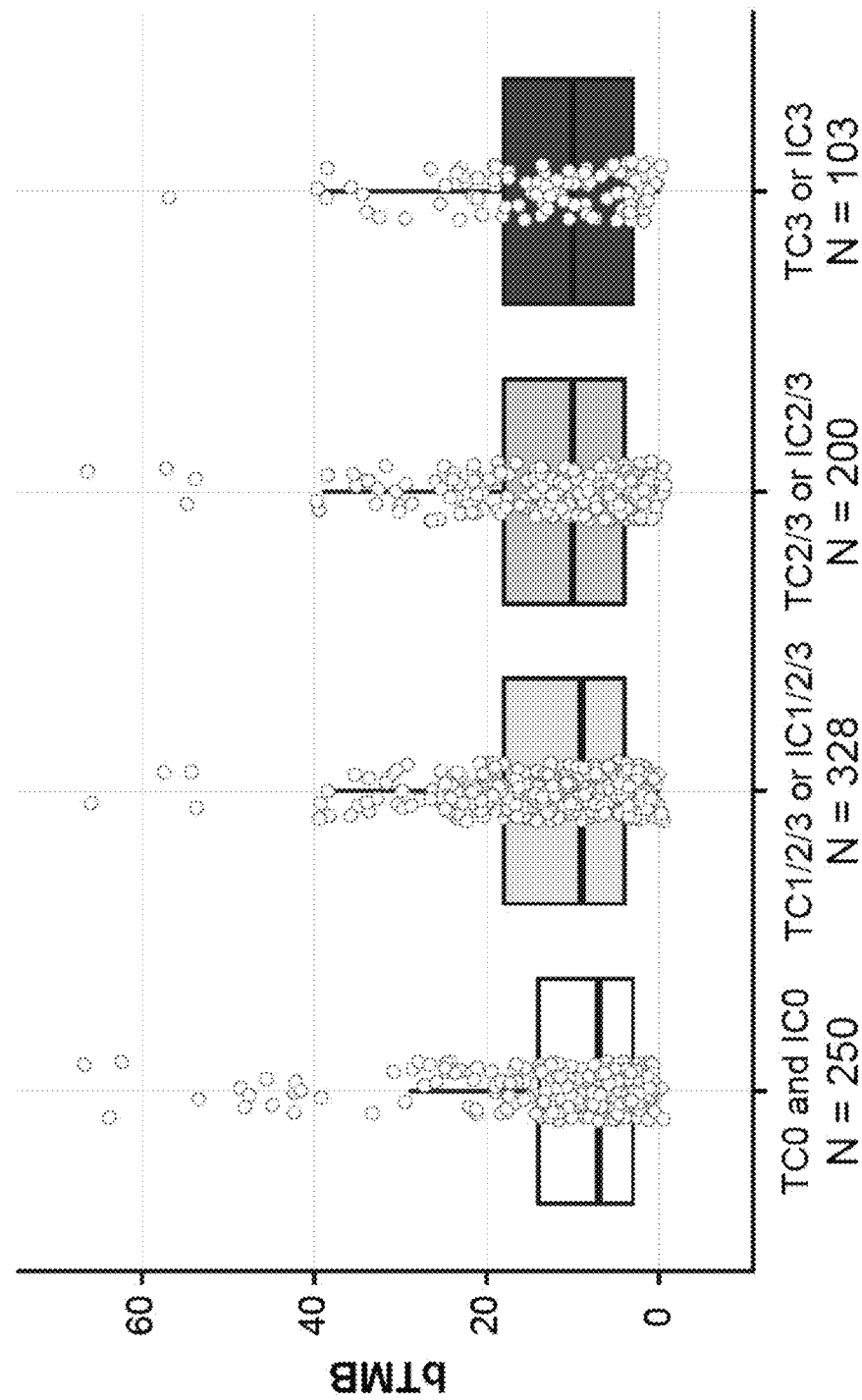

FIG. 9E is a graph showing the raw bTMB score plotted for each sample, grouped according to PD-L1 IHC subgroup. The boxes and line within indicate the 25%, 50% and 75% quartiles for each PD-L1 subgroup. Individual observations are shown as open dots. Within each mutually exclusive IHC subgroup, the lower and upper hinges correspond to the first and third quartiles; the bar in between indicates the median. The upper whisker extends from the hinge to the largest value no further than 1.5*inter-quartile range (IQR) from the hinge (where IQR is the distance between the first and third quartiles). The lower whisker extends from the hinge to the smallest value at most 1.5*IQR of the hinge.

Figure 10:
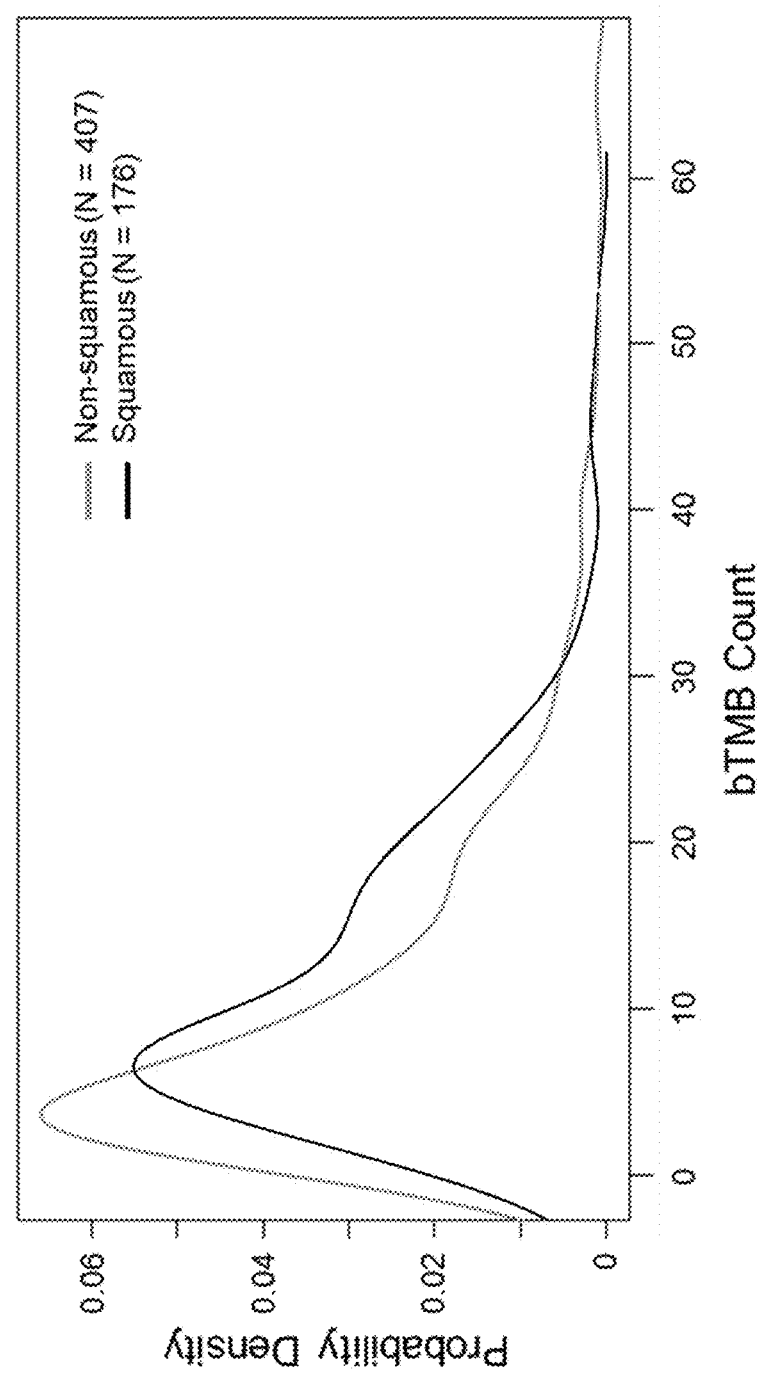

FIG. 10 is a graph showing the probability density of patients from the OAK study with non-squamous and squamous tumors. This analysis excluded EGFR and ALK mutant tumors. The mean bTMB count for tumors with non-squamous histology was 11.2 mutations, and the mean bTMB count for tumors with squamous histology was 12.4 mutations.

Figure 11B:
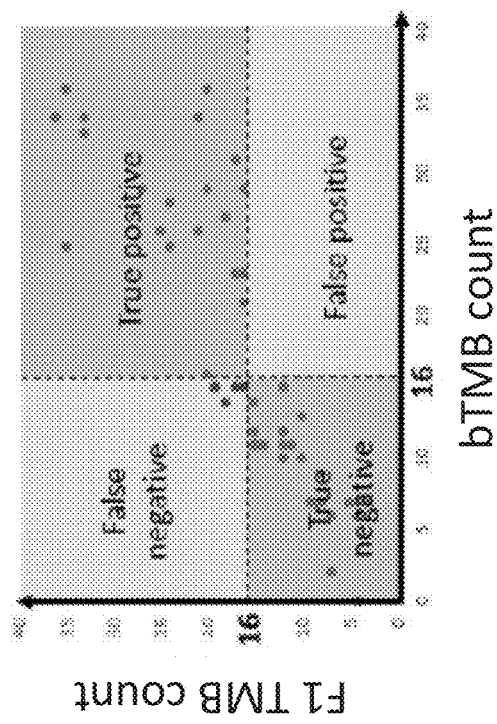
Figure 11A:
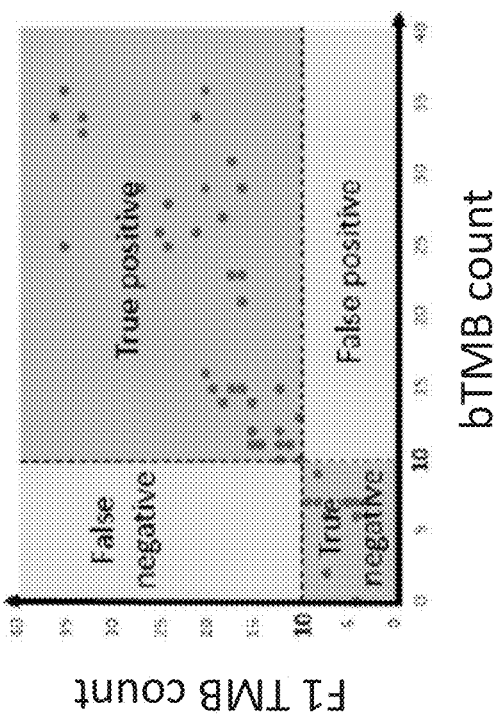

FIGS. 11A and 11B are graphs showing an agreement analysis of bTMB thresholds ≥10 (equivalent to about 9 mut/Mb) (FIG. 11A) and ≥16 (equivalent to about 14 mut/Mb) (FIG. 11B) against the FOUNDATIONONE® (F1) TMB workflow. Agreement was established by splitting samples post-DNA extraction and evaluating in the previously validated F1 workflow, as well as the bTMB workflow. Each workflow utilizes distinct pipelines to calculate the subsequent TMB values. Using the bTMB cut-point (referred to interchangeably with "cutoff" or "cut-off" herein) of ≥16, 41 of 46 samples were true positives and 23 of 23 were true negatives (FIG. 11B). The 4 false negative samples all had insertions or deletions that are counted in F1 TMB and are omitted in the bTMB assay, which subsequently reduces the bTMB count. The graphs in FIGS. 11A and 11B correspond to the same scatter plot with different quadrants overlaid.

FIG. 11C is a table showing PPA and NPA for various cut-points for the comparison of TMB calculated using the F1 computational pipeline versus the bTMB computational pipeline from split ctDNA samples run on each assay as shown in FIG. 11B.

Figure 11D:
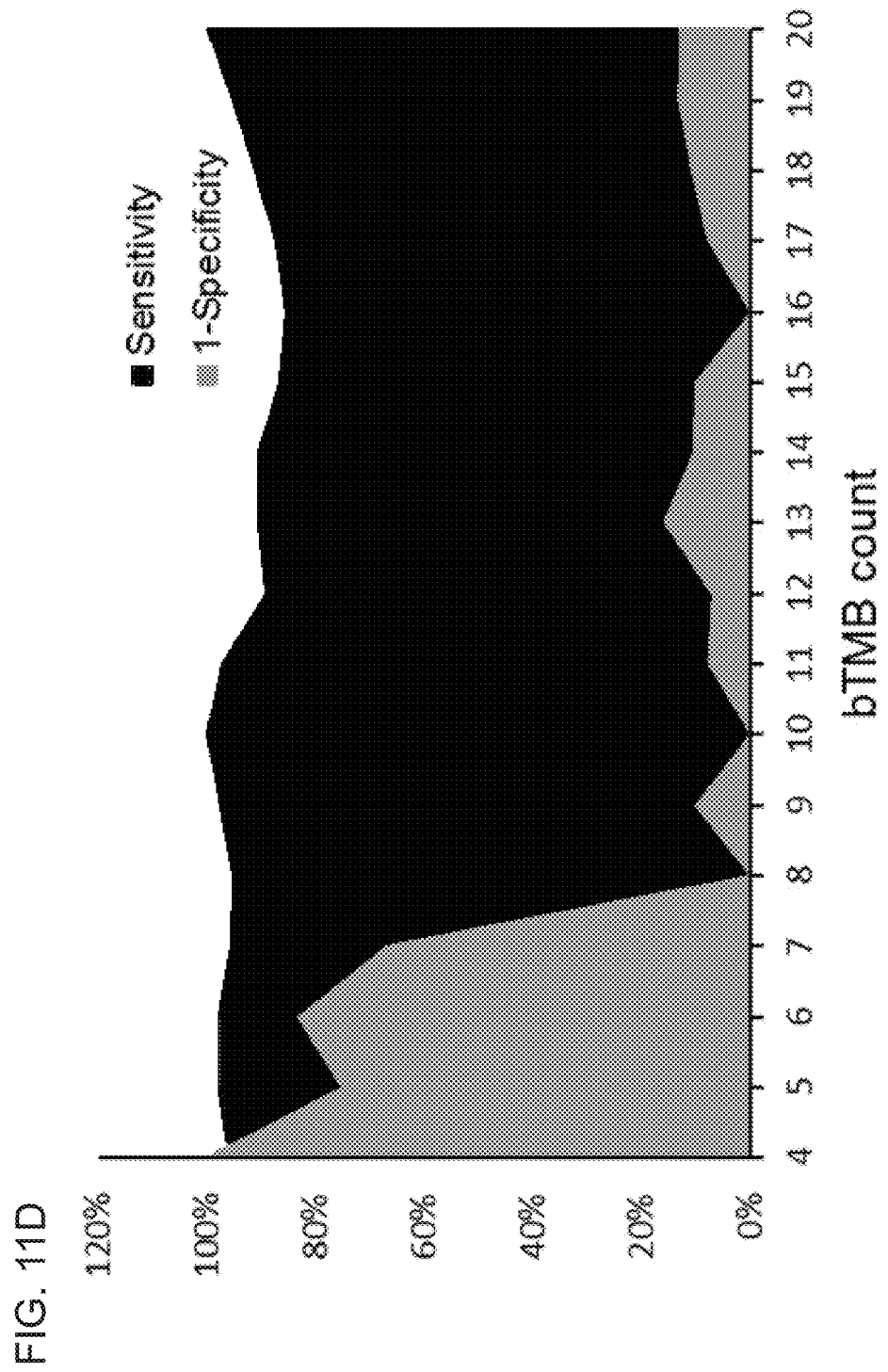

FIG. 11D is a graph showing receiver operator curve (ROC) analysis of the sensitivity and 1-specificity values for bTMB across a range of bTMB cut points, from 4 to 20. Samples were split post-DNA extraction and evaluated in the previously validated F1 workflow, as well as the bTMB workflow. Each workflow utilizes distinct pipelines to calculate the subsequent TMB values. The plot shows sensitivity (PPA) versus 1-specificity (1-NPA). 1-specificity is equivalent to the false positive rate, and specificity is equivalent to the true positive rate. TMB, as assessed by the F1 assay, does not comprehensively examine all the potential neoantigens that the immune system might encounter. Rather, by sequencing the coding regions of a non-random, cancer-specific gene set and identifying single-nucleotide variants (SNVs), TMB may reflect the rate of mutations in the genome and serve as a proxy for neoantigen burden.

Figure 11E:
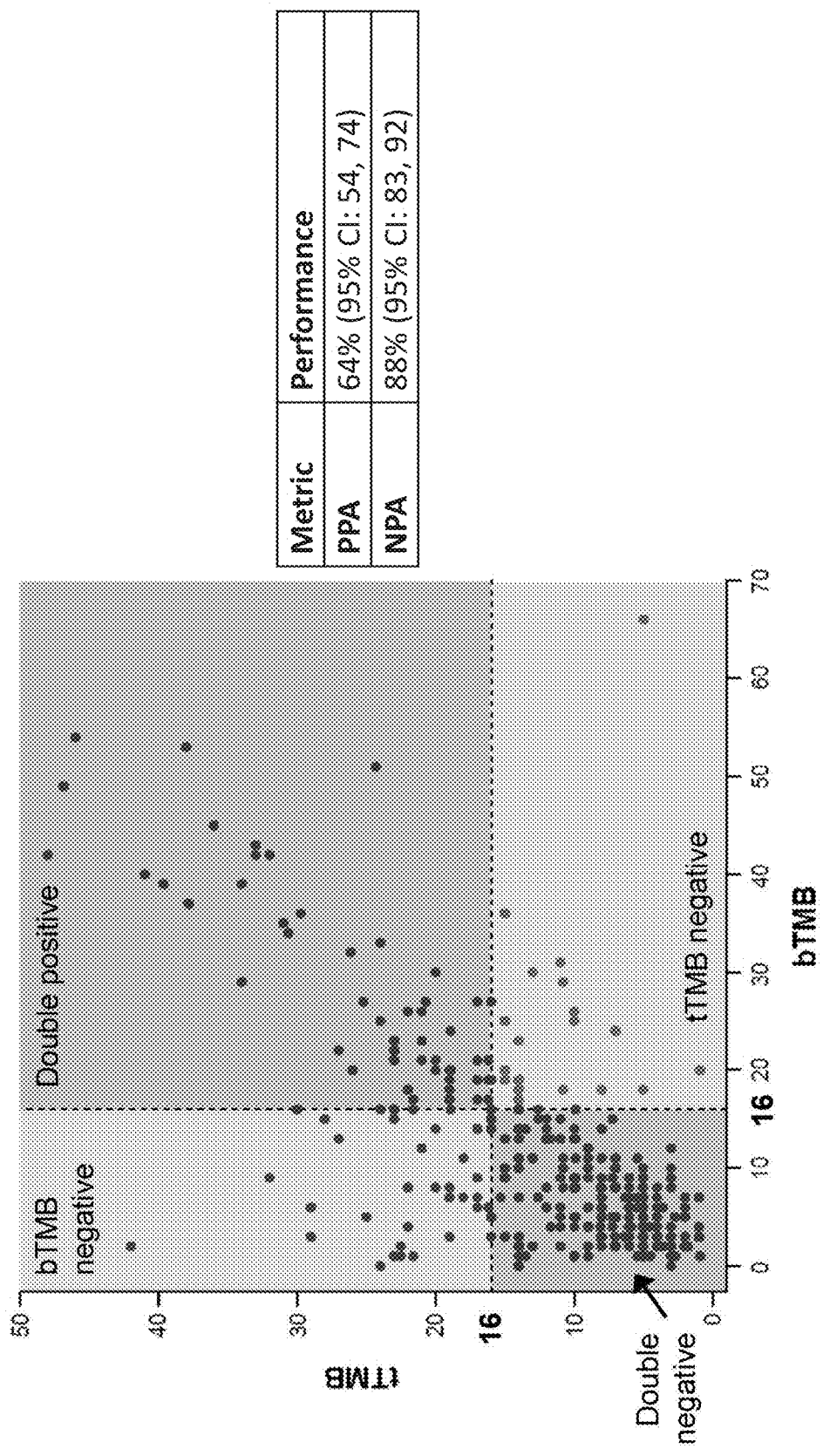

FIG. 11E is a graph showing a pairwise comparison of tissue TMB (tTMB) and bTMB in POPLAR (N=74) and OAK (N=224) for patients with adequate data from both platforms. The number of detected mutations is represented on each axis of the graph in the left panel: for tTMB, mutation counts include SNVs and insertions and deletions (indels) at AF≥5%; for bTMB, mutation counts include only SNVs at AF≥0.5%. Spearman's correlation=0.59, (95% CI: 0.49, 0.67). The dashed lines represent the ≥16 cut-point. The PPA and NPA are shown in the table in the right panel.

Figure 11F:
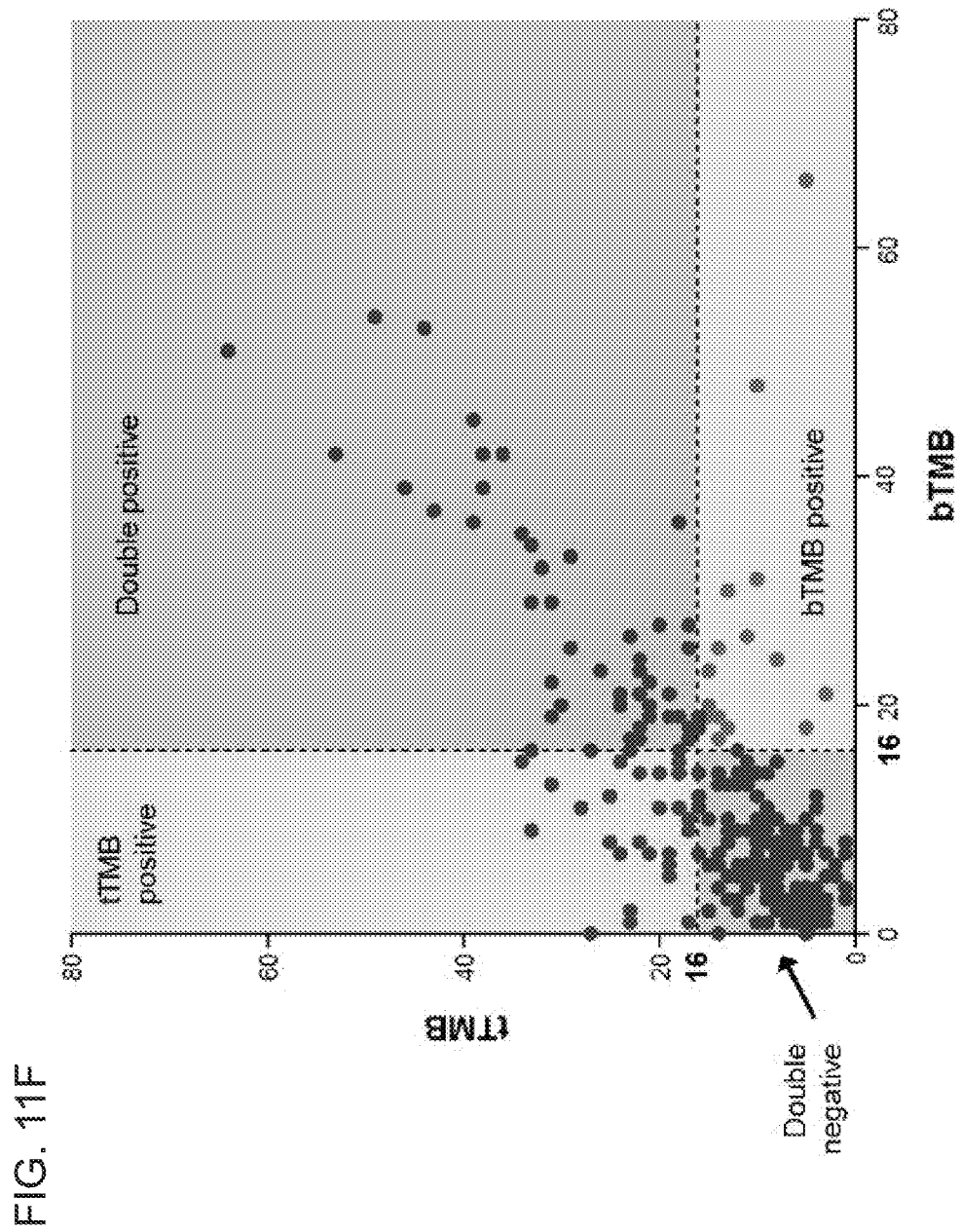

FIG. 11F is a graph showing a pairwise comparison of tTMB and bTMB in patients from POPLAR and OAK with adequate data (SNP-matched, passed QC) from both platforms (N=259). The number of detected mutations is represented on each axis: for tTMB mutations, counts include SNVs and insertions and deletions (indels) at AF≥5%; for bTMB mutations, counts include only SNVs at AF≥0.5%. Spearman rank correlation=0.64 (95% CI: 0.56, 071). The dashed lines represent the ≥16 cut-point. The PPA was 64% (95% CI: 54, 74) and the NPA was 88% (95% CI: 83, 92). One sample was omitted from the graph for presentation purposes because it had very high bTMB (152) and tTMB (133).

Figure 11G:
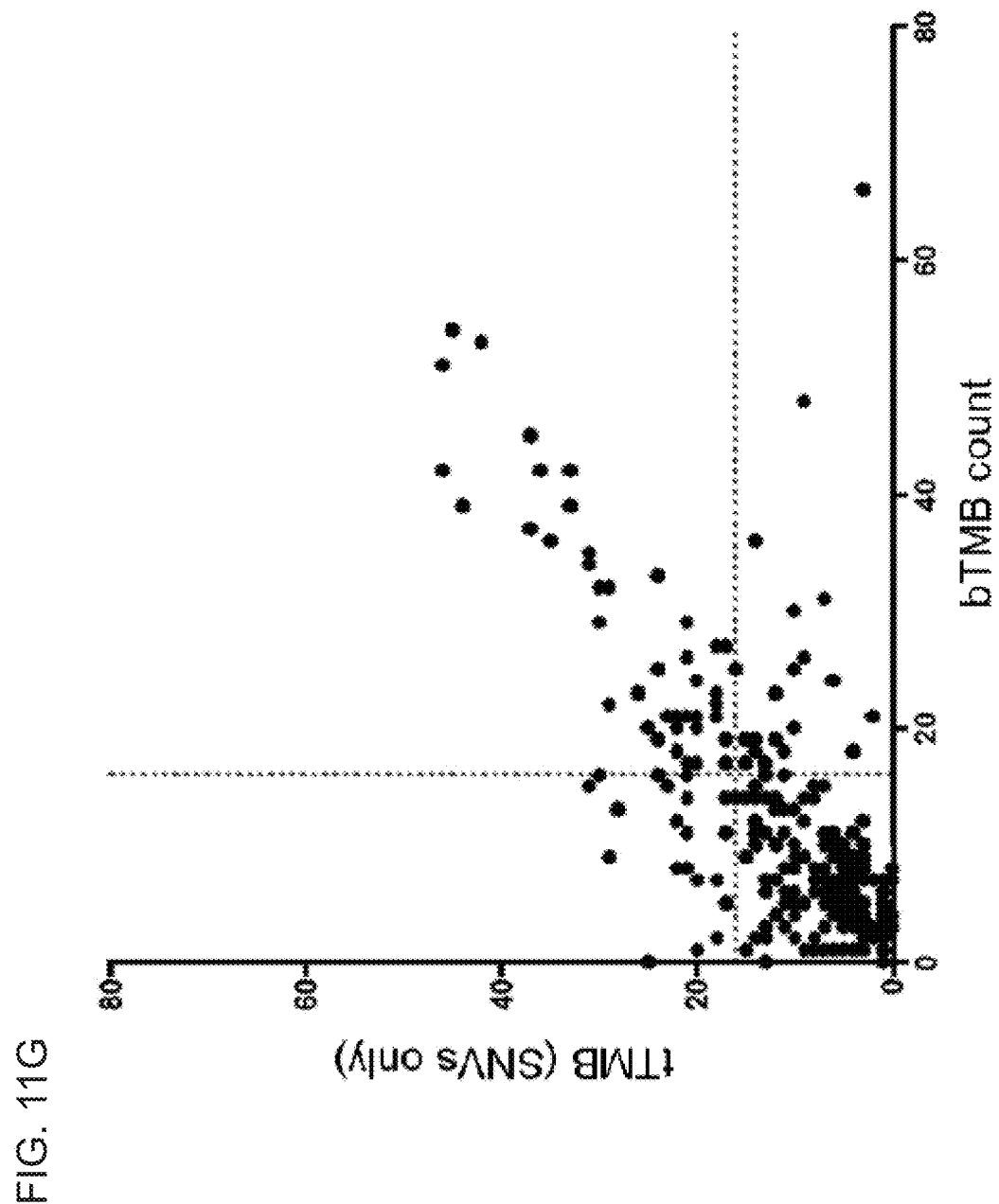

FIG. 11G is a graph showing a pairwise comparison of tTMB (only SNVs) and bTMB. The tTMB computational algorithm counts both indels and SNVs, whereas the bTMB computational algorithm only counts SNVs. Therefore, we compared the correlation between the two measures using only SNVs (N=258; Spearman correlation=0.65; 95% CI: 0.57, 0.71). One sample was omitted from the graph for presentation purposes because it had very high bTMB (152) and tTMB (133).

Figure 11H:
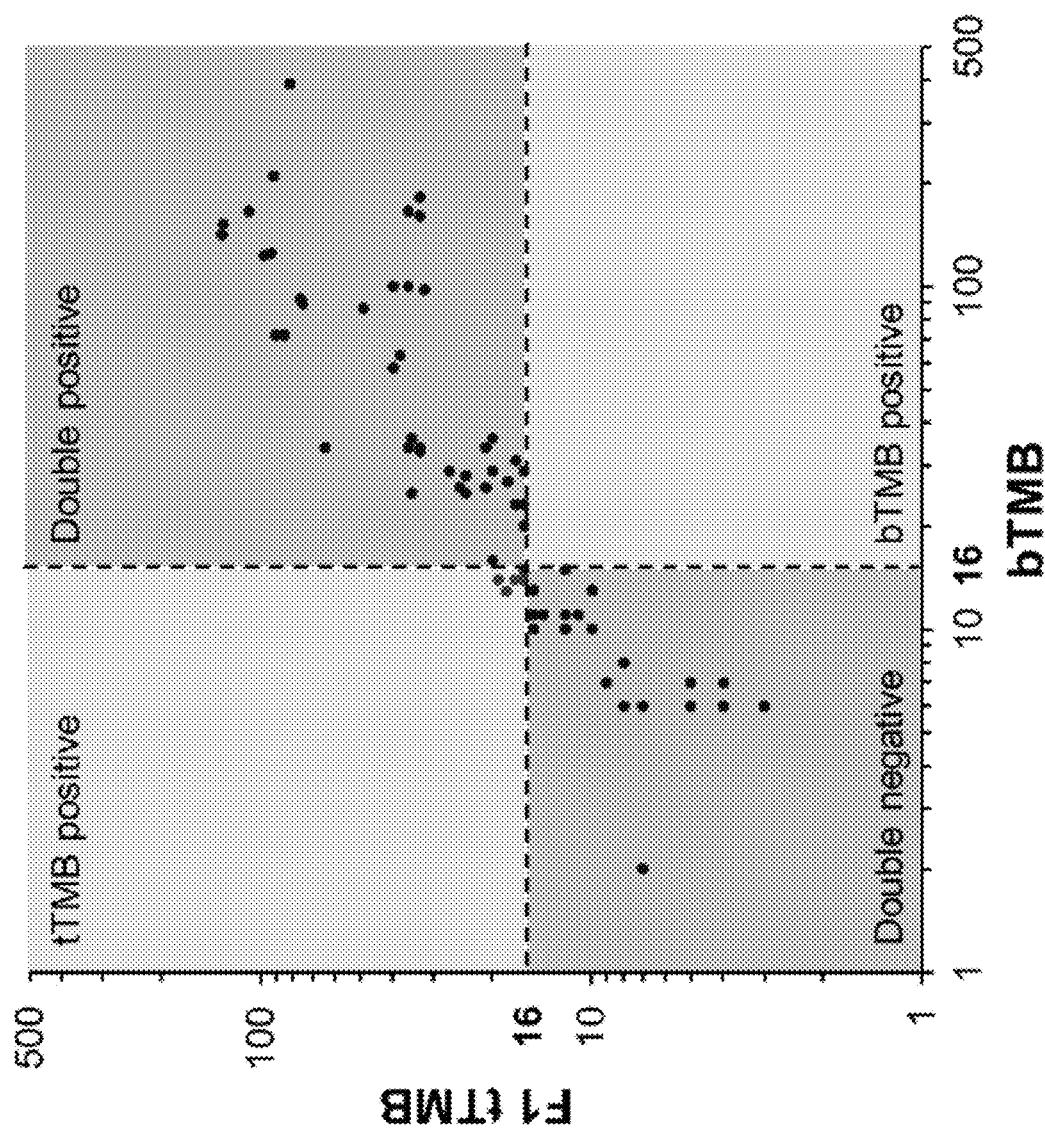

FIG. 11H is a graph showing a comparison of TMB (number of mutations) calculated using the F1 assay versus the bTMB assay from split ctDNA samples (N=69). The four discordant samples that were above the threshold for F1 TMB but not bTMB are largely explained by indels that were included in the F1 TMB calculation, but omitted in the bTMB calculation.

FIG. 11I is a table showing PPA and PPV from a comparison of the FOUNDATIONACT® (FACT) assay and the bTMB assay. Samples were split and analyzed according to both assays, and the agreement of somatic variants from the FACT assay that were also detected by the bTMB assay were used to calculate the PPA. The somatic variants present in the FACT limited region of the bTMB assay that were also detected by the FACT assay were used to calculate the PPV. Data are plotted according to overall agreement by analyzing individual variants, as well as the percent of all evaluated samples with perfect agreement between the two assays. The percentage of shared variants in overlapping baited regions between both assays is 93%. Restricting the allele frequency cutoff to at least 1% increases the agreement to 99%.

Figure 11J:
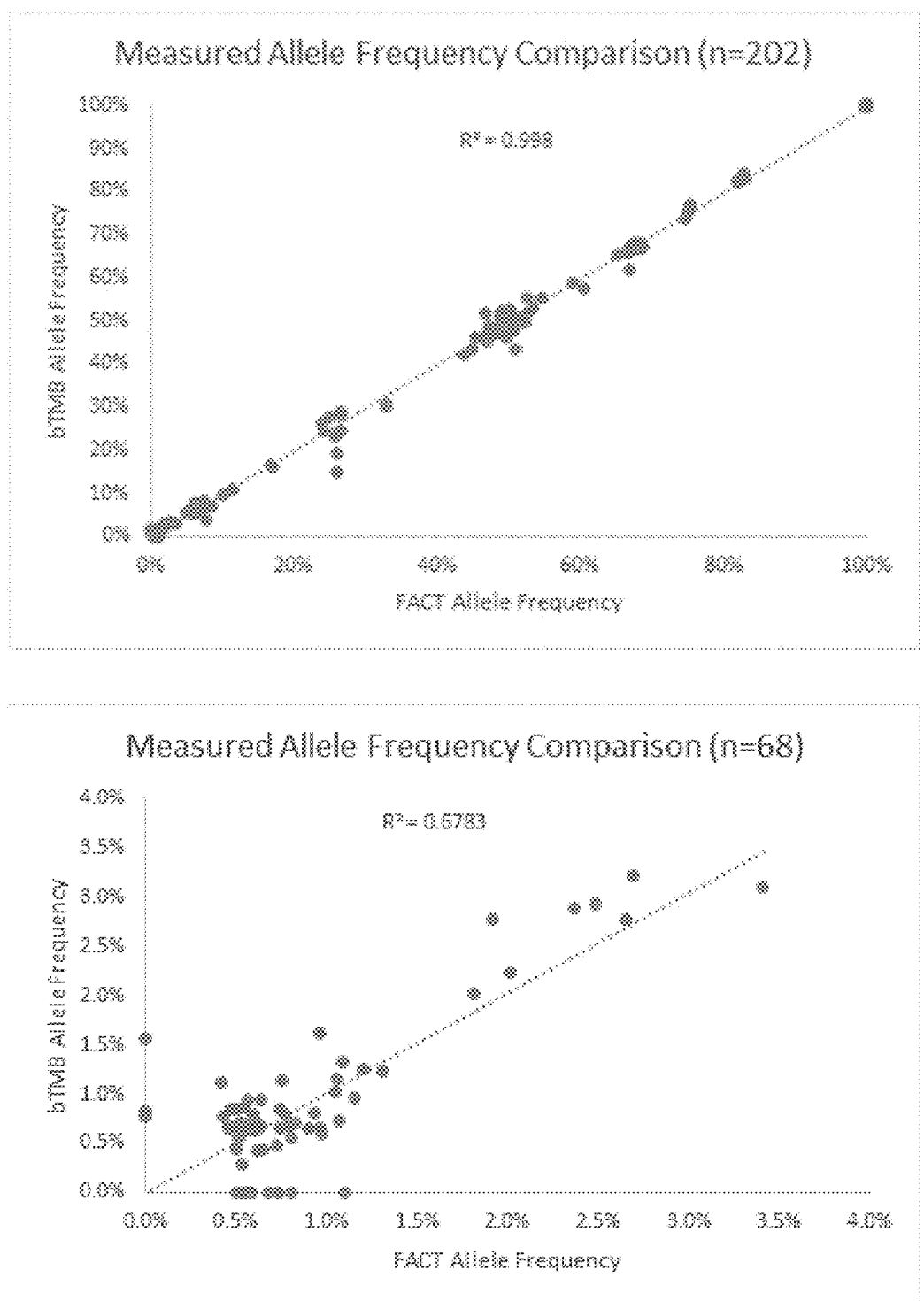

FIG. 11J is a series of graphs showing variant allele frequencies (VAF) for matching variants detected in the overlapping regions for FACT and bTMB. For undetected variants, the VAF is 0.0. Known artifacts are excluded. The top panel (N=202) represents the full distribution of matched variants in bTMB and FACT; the lower panel shows a close-up of low allele frequency variants.

Figure 11K:
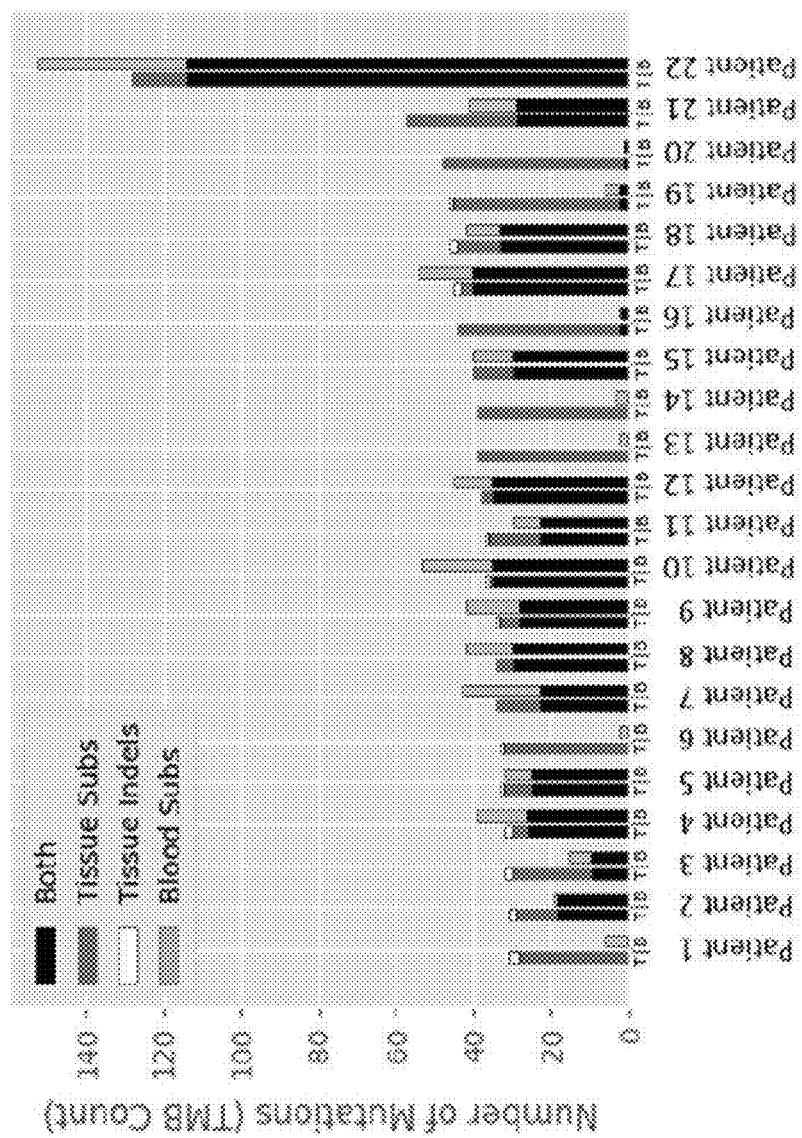

FIG. 11K is a graph showing a comparison of TMB count between tissue and blood samples for patients with high (>30) total mutation count derived from tissue. Samples are arranged in order of increasing tTMB.

Figure 11L:
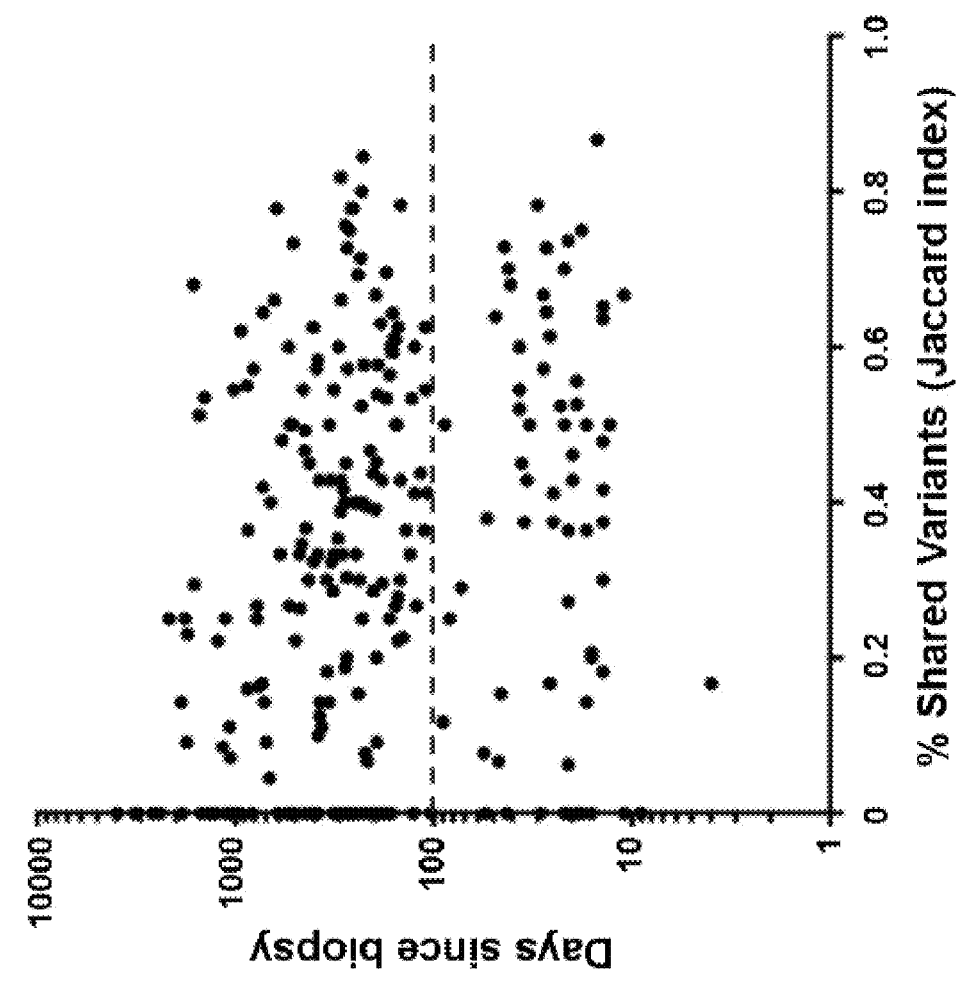
Figure 11M:
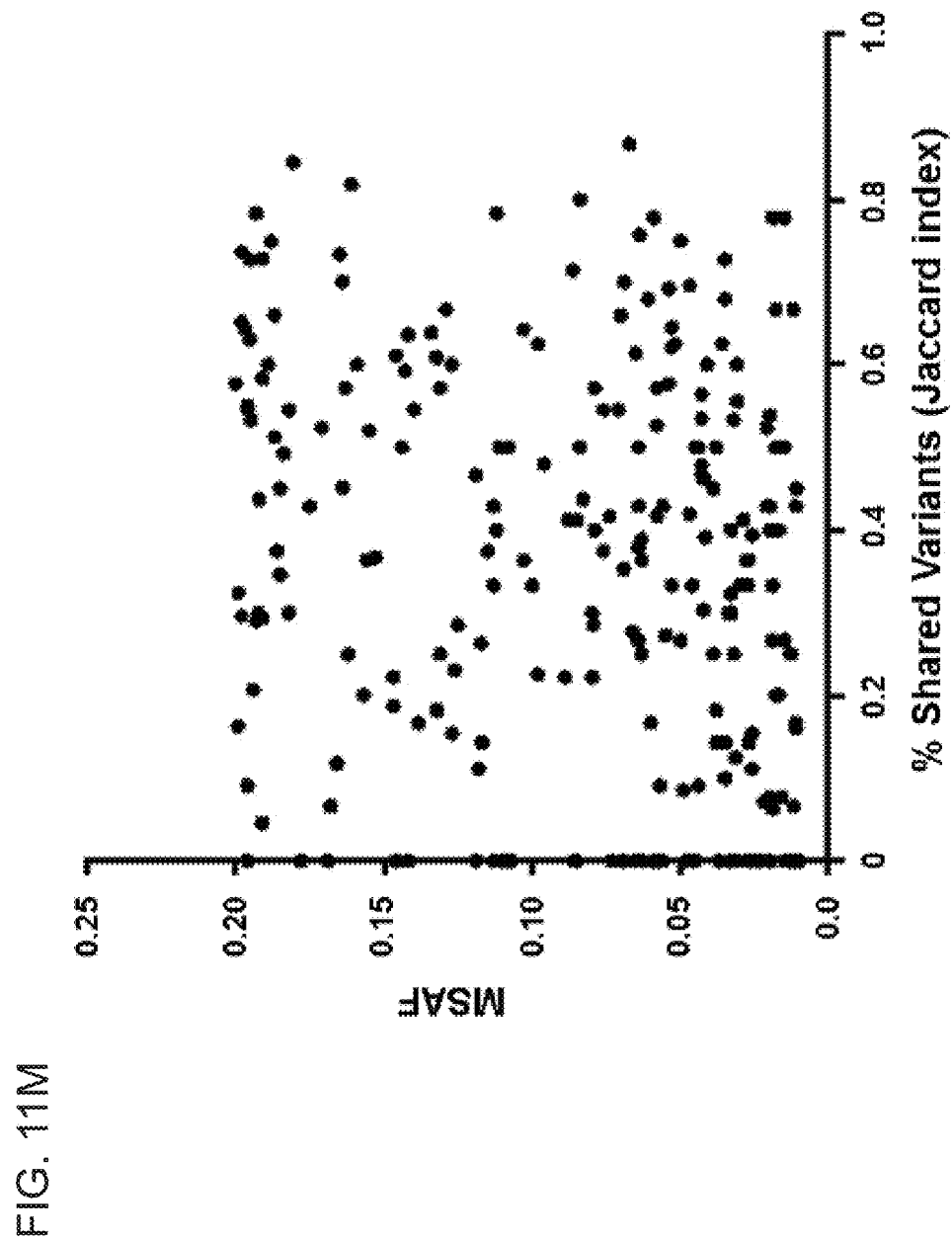

FIGS. 11L and 11M are a series of graphs showing blood/tissue TMB concordance versus time between sample collections and MSAF. Pairwise correlation between bTMBtTMB concordance (as a percentage of shared variants) and the interval (days in log scale) (FIG. 11L) and MSAF (FIG. 11M) between tumor tissue sample collection and blood sample collection are shown. In FIG. 11L, the dashed line indicates 100 days; the Spearman correlation (bootstrap 95% CI) was −0.25 (−0.37, −0.13) overall; 0.06 (−0.18, 0.3) for tissue samples collected <100 days before blood; and −0.3 (−0.42, −0.16) for tissue samples collected ≥100 days before blood. In FIG. 11M, the Spearman correlation (bootstrap) was 0.30 (95% CI: 0.19, 0.41).

Figure 11N:
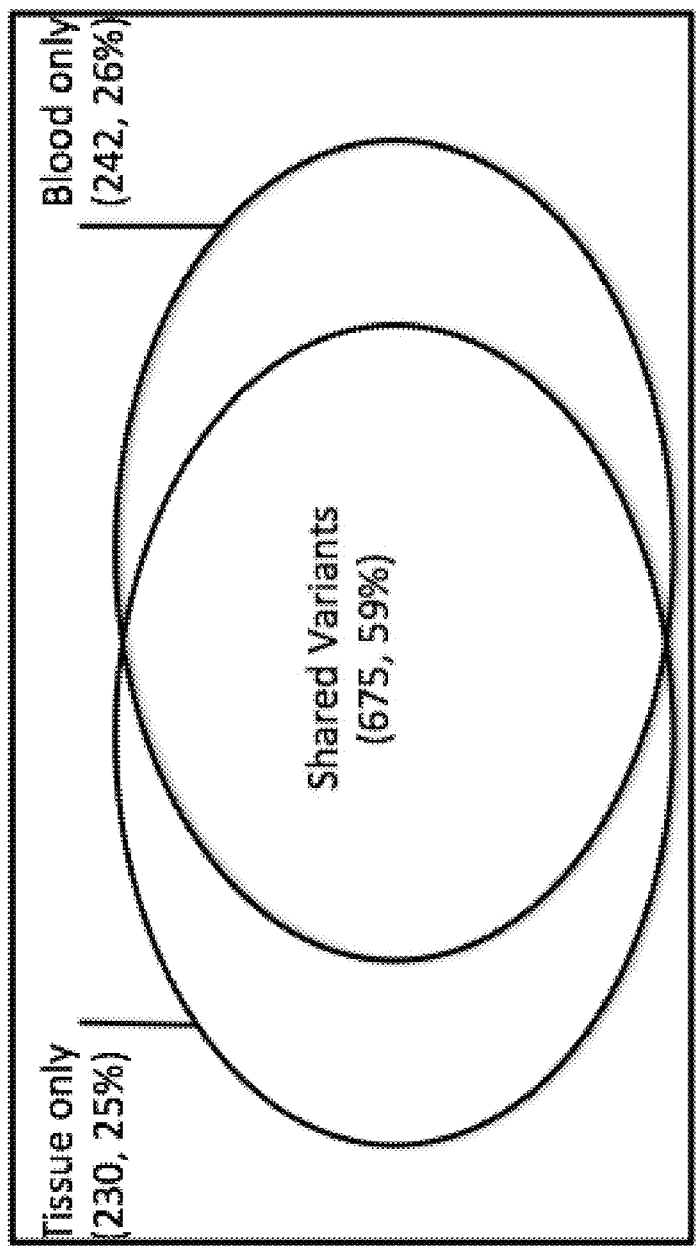

FIG. 11N is a Venn diagram showing SNVs detected by the tTMB and bTMB assays.

Figure 12:
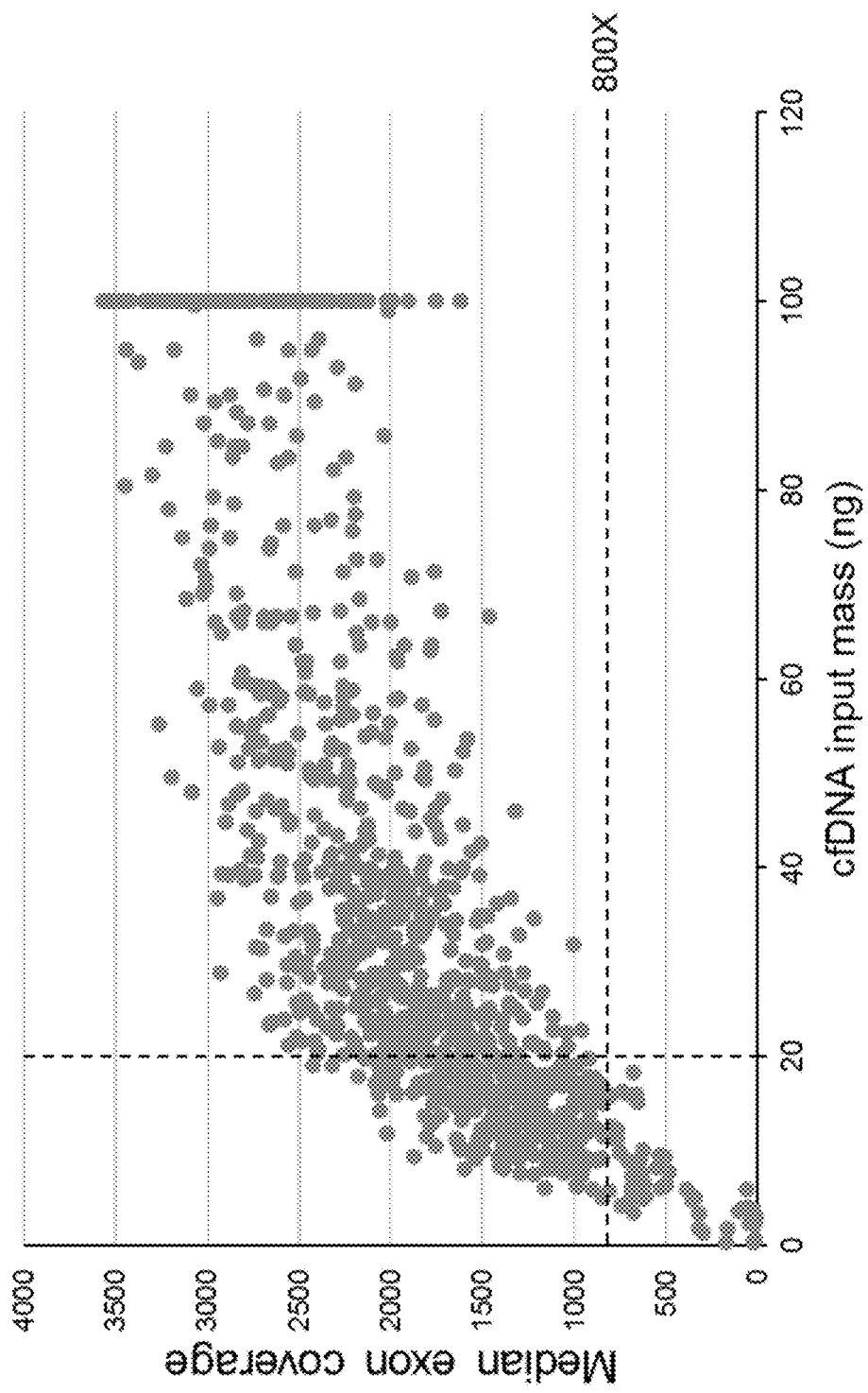

FIG. 12 is a graph showing median exon coverage as a factor of cfDNA input. In an analysis of 1,076 clinical samples, 100% achieved >800× median exon coverage when ≥20 ng of cfDNA was used as input into library construction.

Figure 13A:
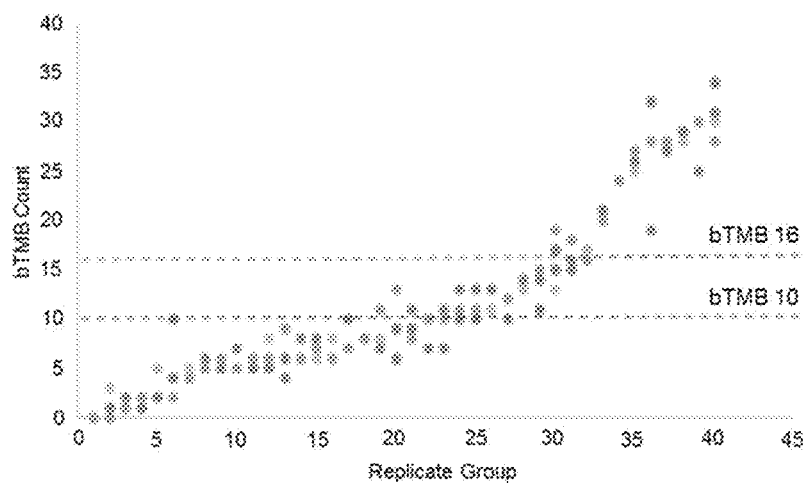
Figure 13B:
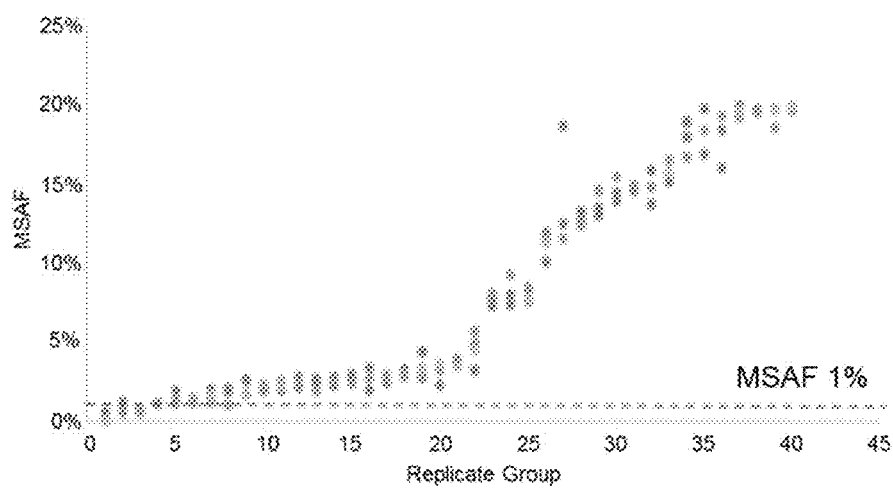

FIGS. 13A and 13B are graphs showing a precision analysis of bTMB and MSAF. Precision was evaluated according to reproducibility of the assay result, according to the two distinct bTMB thresholds of ≥10 (equivalent to about 9 mut/Mb) and ≥16 (equivalent to about 14 mut/Mb), as well as the quality control metric of 1% circulating tumor DNA (ctDNA), estimated by MSAF. For bTMB precision studies, 40 replicate groups with at least triplicate samples that spanned a range of clinically meaningful bTMB values were compared to the majority call. For MSAF precision studies, 37 replicate groups with at least triplicate samples that spanned a range of clinically meaningful values were compared to the majority call. Each data point indicates a different replicate.

Figure 14:
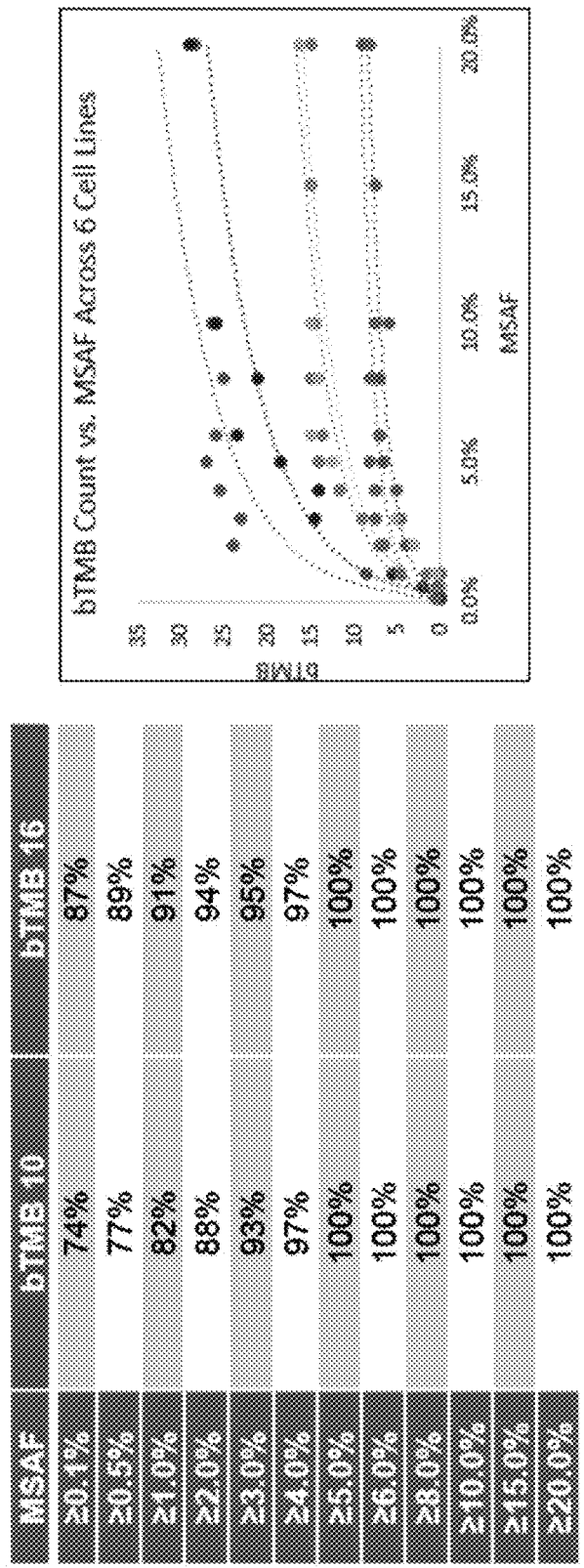

FIG. 14 shows reproducibility of the bTMB assay according to the thresholds of ≥10 and ≥16 as a function of tumor content in a sample, estimated by the MSAF. Reproducibility of at least 80% was achieved with at least 1% MSAF for both bTMB cut-points of ≥10 ("bTMB 10") and ≥16 ("bTMB 16").

Figure 15:
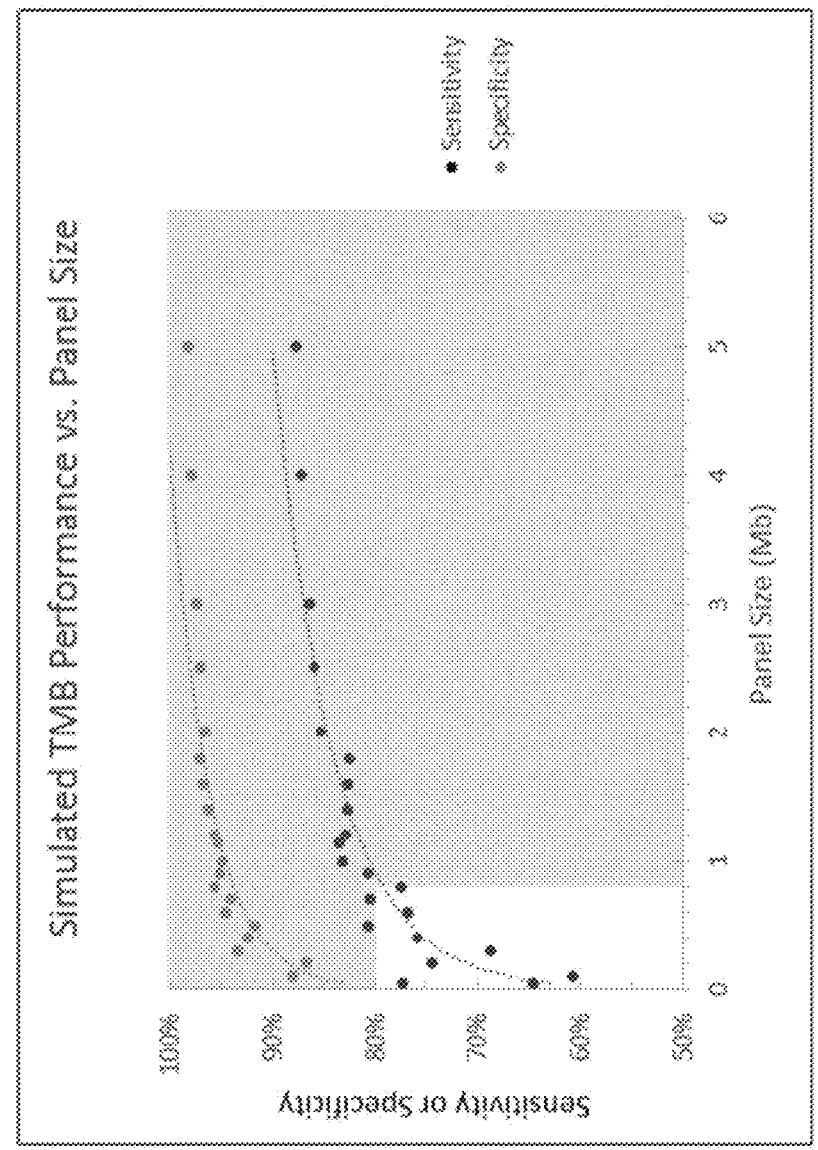

FIG. 15 is a graph showing simulated assay performance versus panel size. The simulated sensitivity and specificity of a TMB assay are shown according to the size of the panel used for its calculation. To generate these values, TMB values were calculated from whole-exome sequencing (WES) data on 25 patient samples from The Cancer Genome Atlas. Each patient was chosen to represent a range of TMB values, from 100 mut/Mb down to 1 mut/Mb. Additionally, TMB values were calculated from random samplings of the WES data by limiting the counting region from 5 Mb down to 50 Kb. Within each limited target region, a total of 250 million random samplings were performed as a Poisson distribution to calculate an equivalent tTMB value. The fraction of these target-limited TMB values that maintained a result consistent with the WES-derived TMB value, using a cut-point of 14 mut/Mb (16 total mutations in the bTMB assay), was computed for each respective simulated panel size. The results were compared with the real-world distribution of TMB values derived from patients with non-small cell lung cancer using the Foundation Medicine database (n=19,320). The sensitivity was calculated as the fraction of true positives divided by the sum of all true positives and false negatives, and the specificity was calculated as the number of true negatives divided by the sum of all true negatives and false positives. The plotted values represent the results derived from this analysis, and the shaded regions represent size of the panel required to maintain at least 80% sensitivity and specificity.

Figure 16:
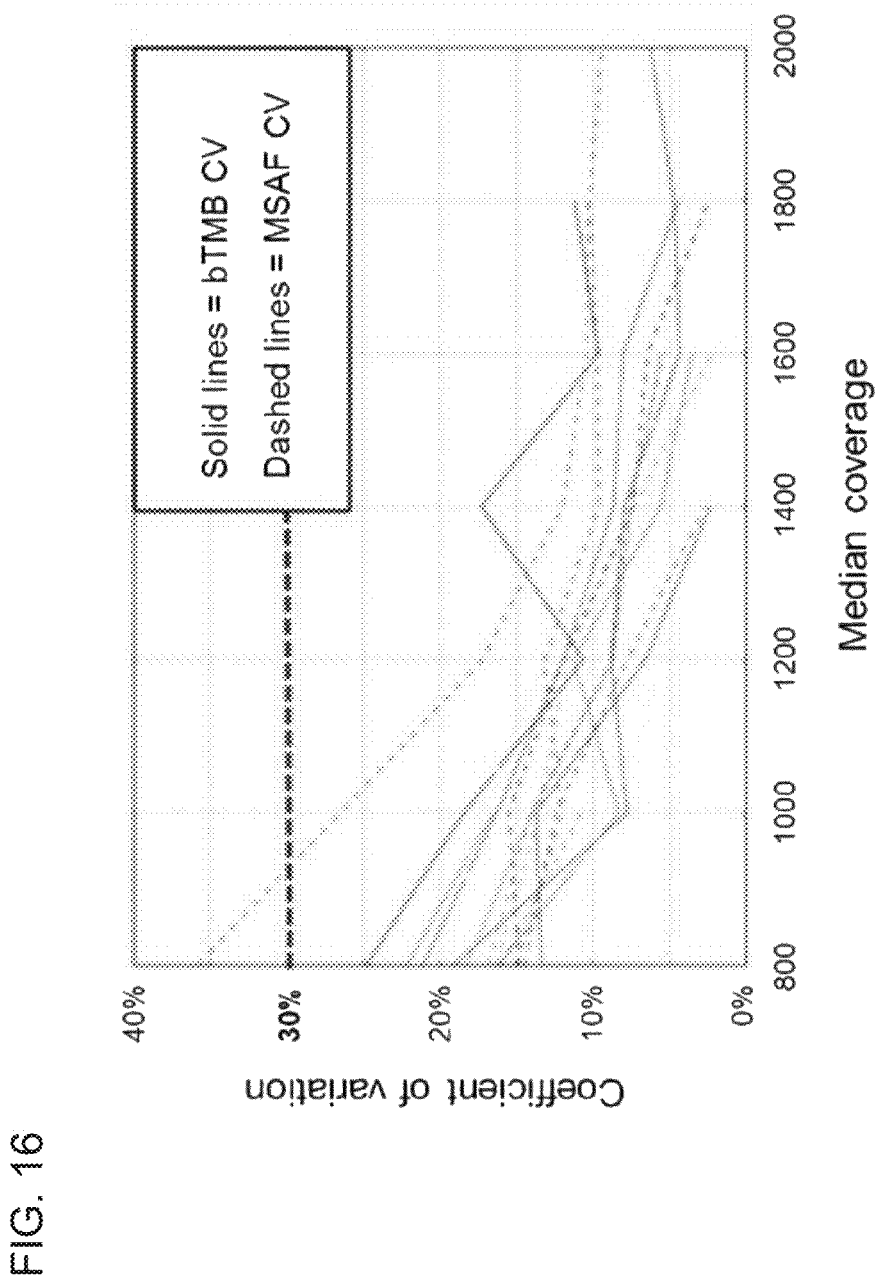

FIG. 16 is a graph showing the distributions of bTMB and MSAF coefficient of variation (CV) at various coverage levels. To assess the minimum coverage required to maintain precision, in silico downsampling of 80 replicates from eight different samples with bTMB scores ≥10 and MSAF≥1% was performed to achieve median sequence coverage spanning a range of 800× to 2000×. The % CV for bTMB and MSAF values was calculated from downsampled specimens at various sequence coverages. The minimum coverage was defined as the lower bound from the downsampling exercise that still achieved the precision as defined by ≤30% CV of the bTMB and MSAF values. The minimum sequence coverage to maintain the precision of bTMB and MSAF values was confirmed down to 800×.

Figure 17:
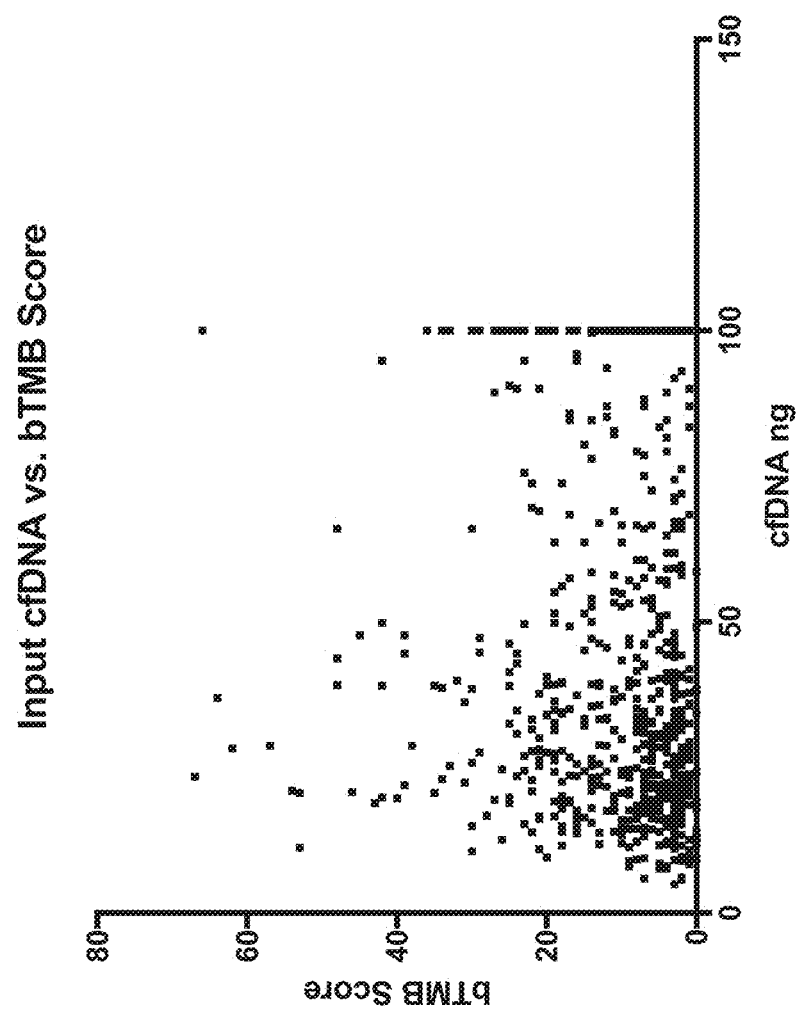

FIG. 17 is a graph showing a pairwise comparison of mass of cfDNA extracted from plasma samples versus bTMB score in the OAK study. The bTMB score is plotted against the total cfDNA extracted from plasma. There was a small but statistically significant positive Spearman correlation between total extracted cfDNA and bTMB score (Spearman r=0.15, [95% CI: 0.07, 0.23]).

Figure 18A:
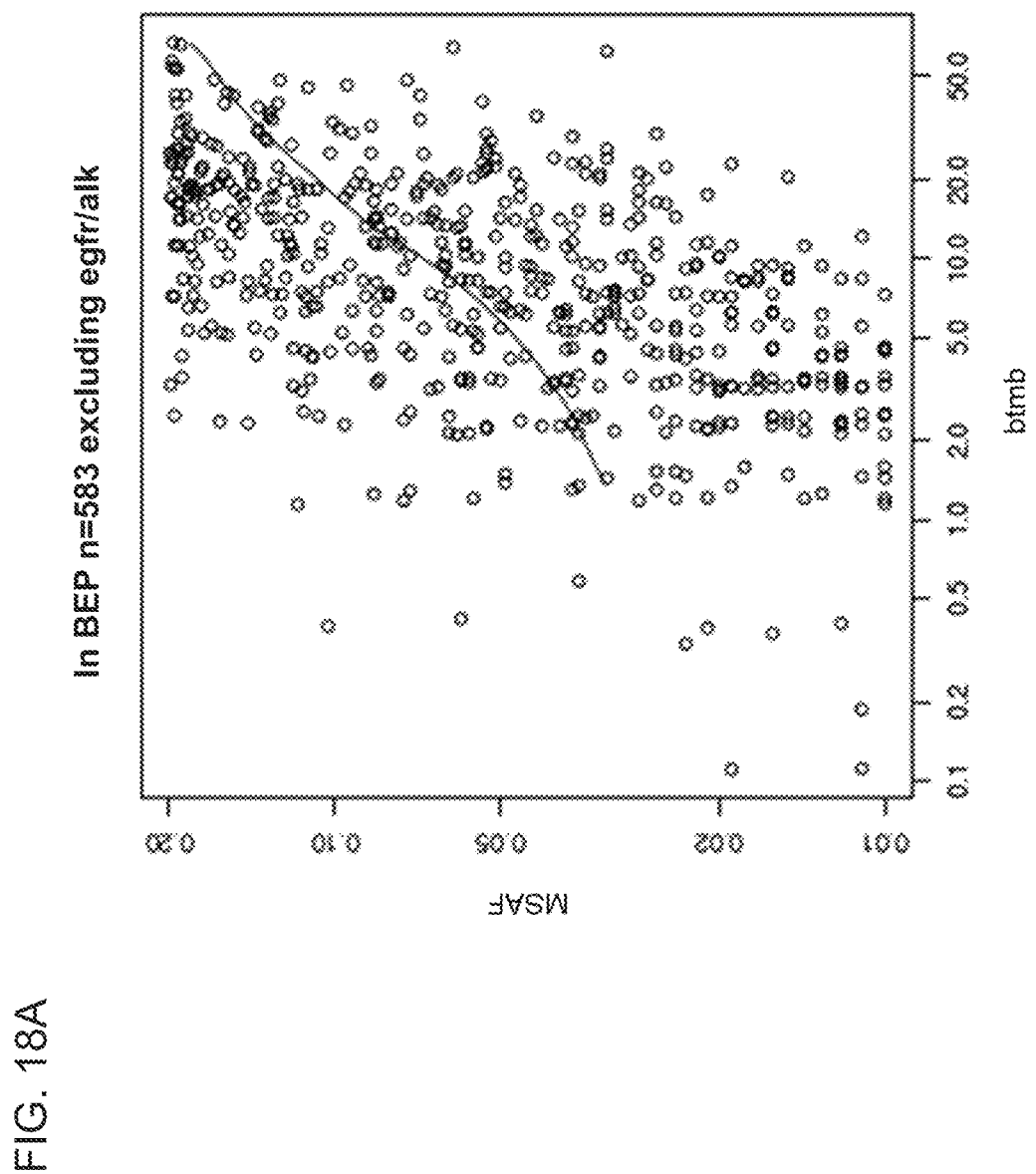
Figure 18B:
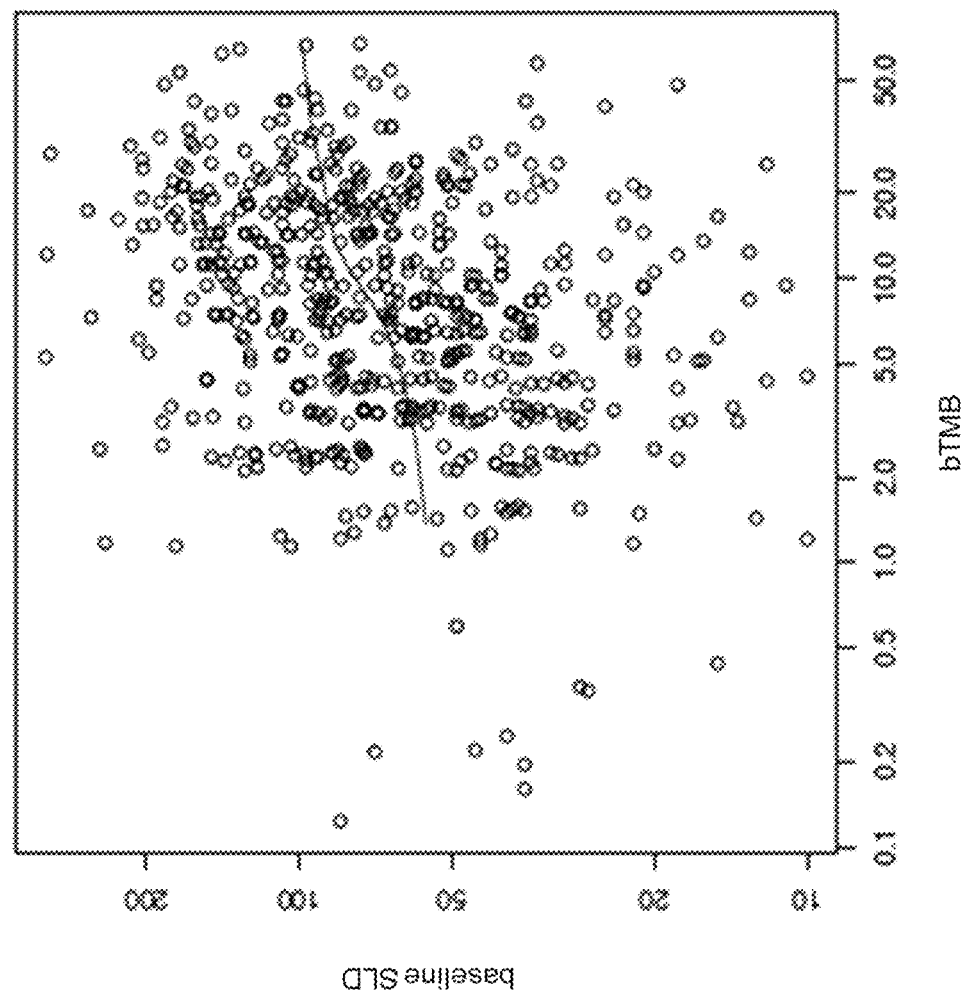

FIGS. 18A and 18B are a series of graphs showing the correlation between bTMB and MSAF (FIG. 18A) and between bTMB and the sum of the longest diameters (SLD) (FIG. 18B).

Figure 19:
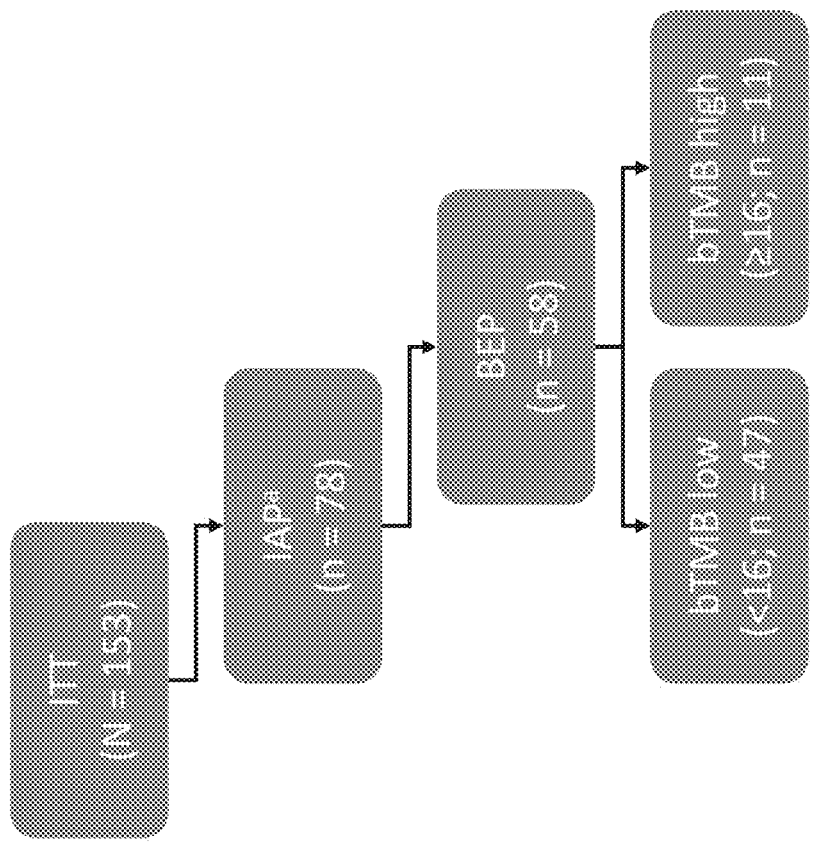

FIG. 19 is a schematic diagram showing the patient population of the interim analysis from the BF1 RST trial.

FIG. 20 is a table showing baseline demographics and clinical characteristics from the interim analysis population of the B-F1 RST trial.

Figure 21:
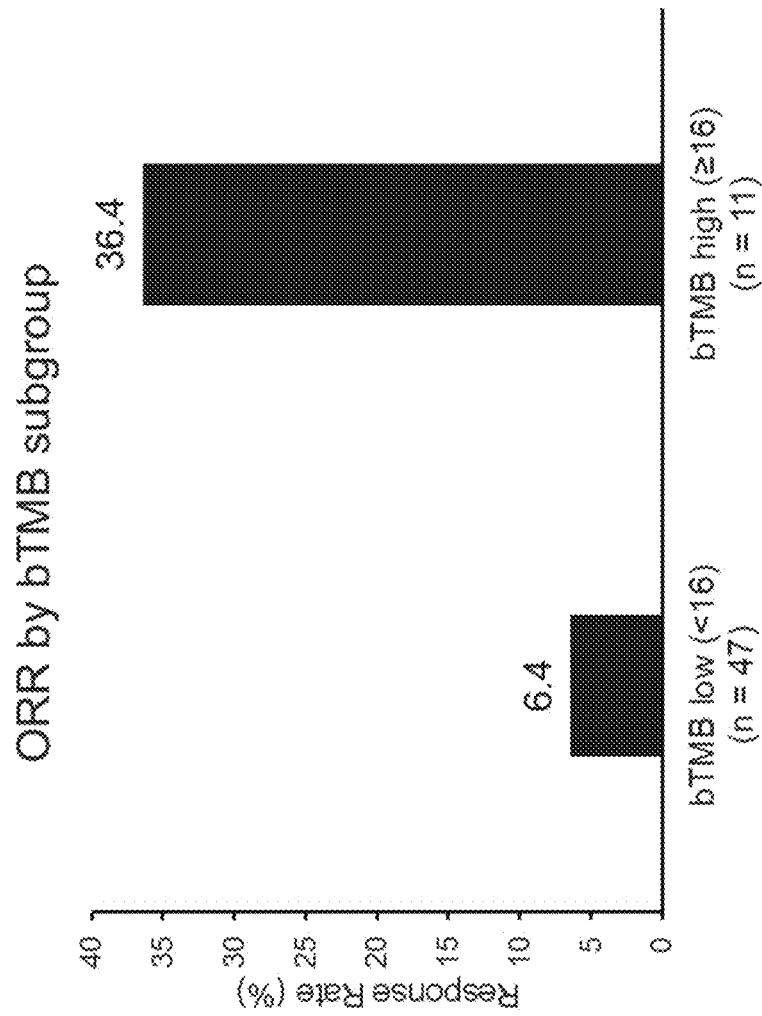

FIG. 21 is a graph showing ORR by bTMB subgroup in the interim analysis population of the BF1 RST trial.

Figure 22:
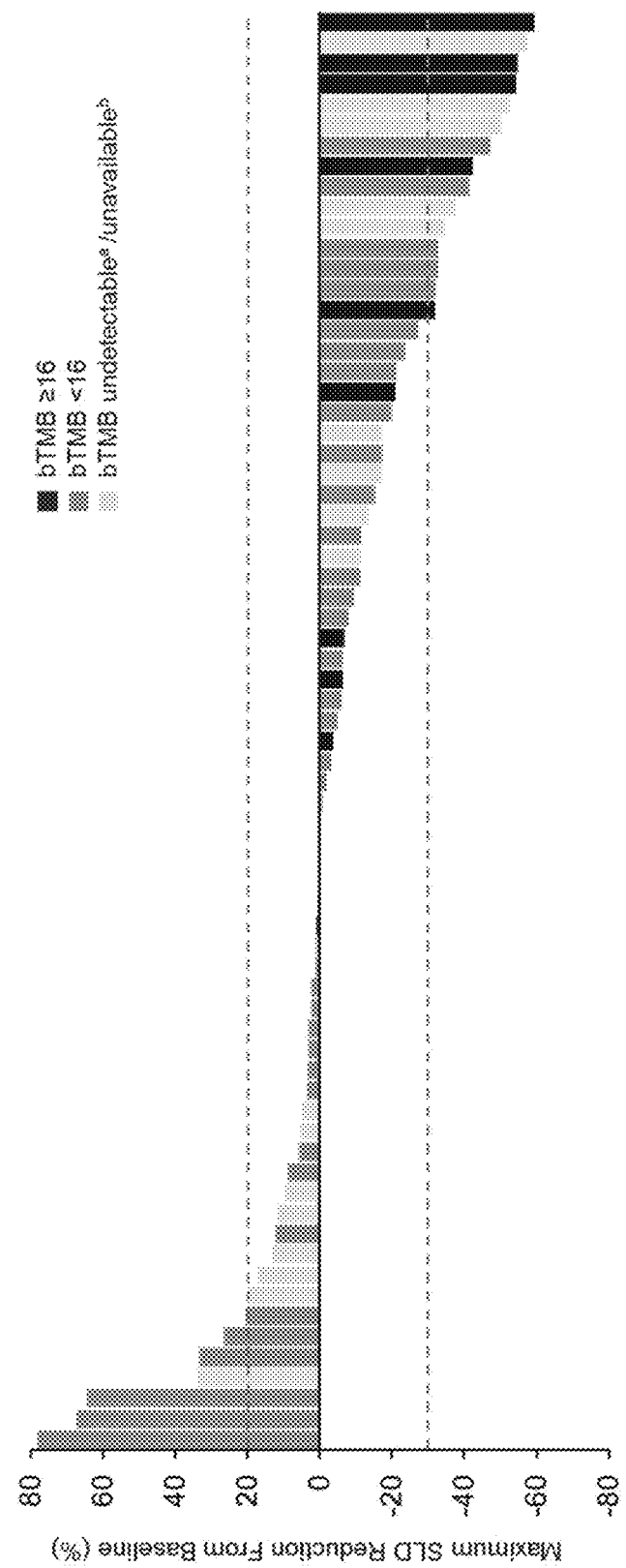

FIG. 22 is a graph showing the maximum sum of longest diameters (SLD) reduction from baseline by bTMB subgroup in the interim analysis population. [a]15 patients had MSAF<1%; [b]4 patients without a valid sample. Only patients with post-baseline target lesion measurements are shown in the graph (n=70).

Figure 23A:
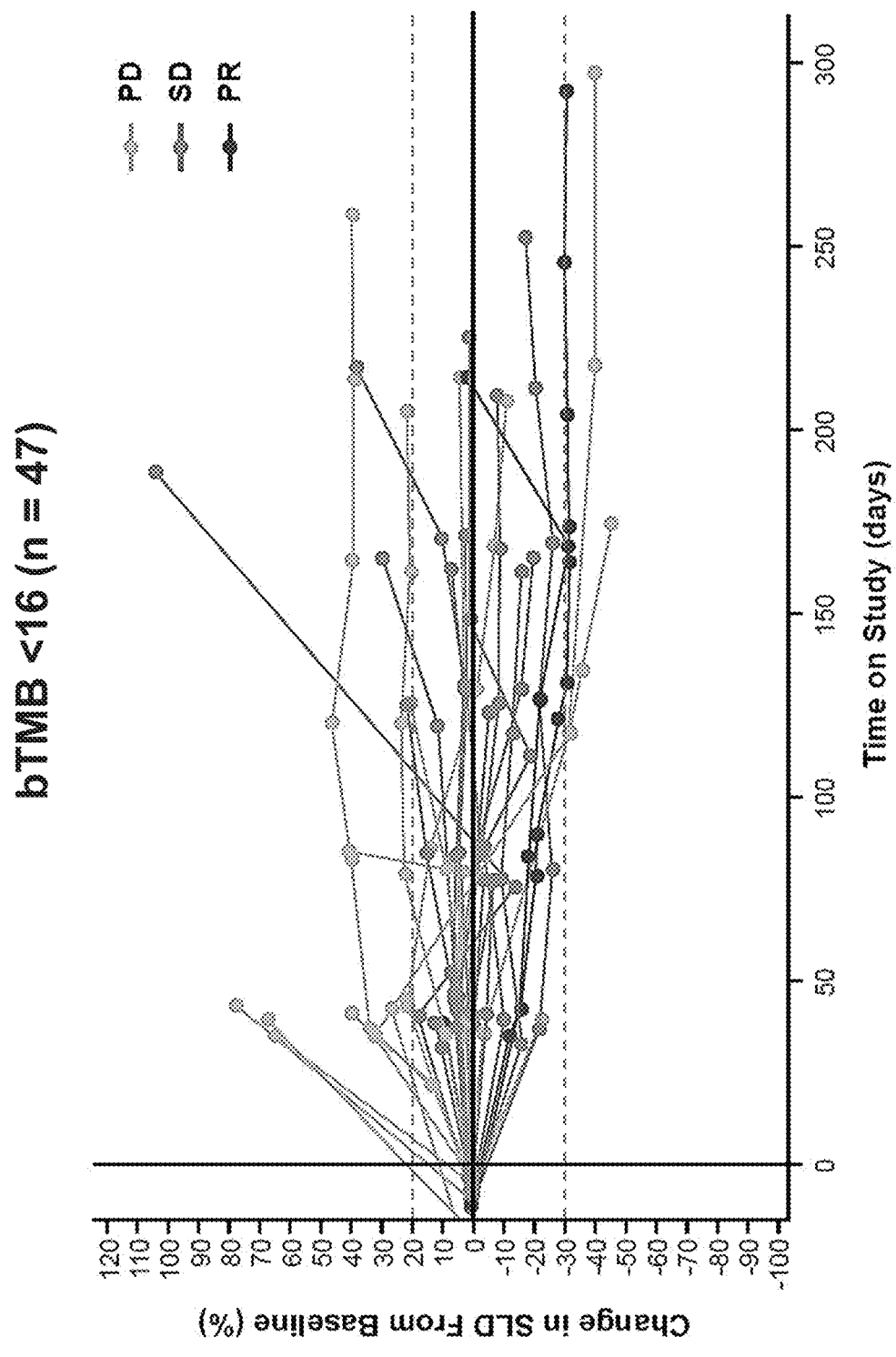
Figure 23B:
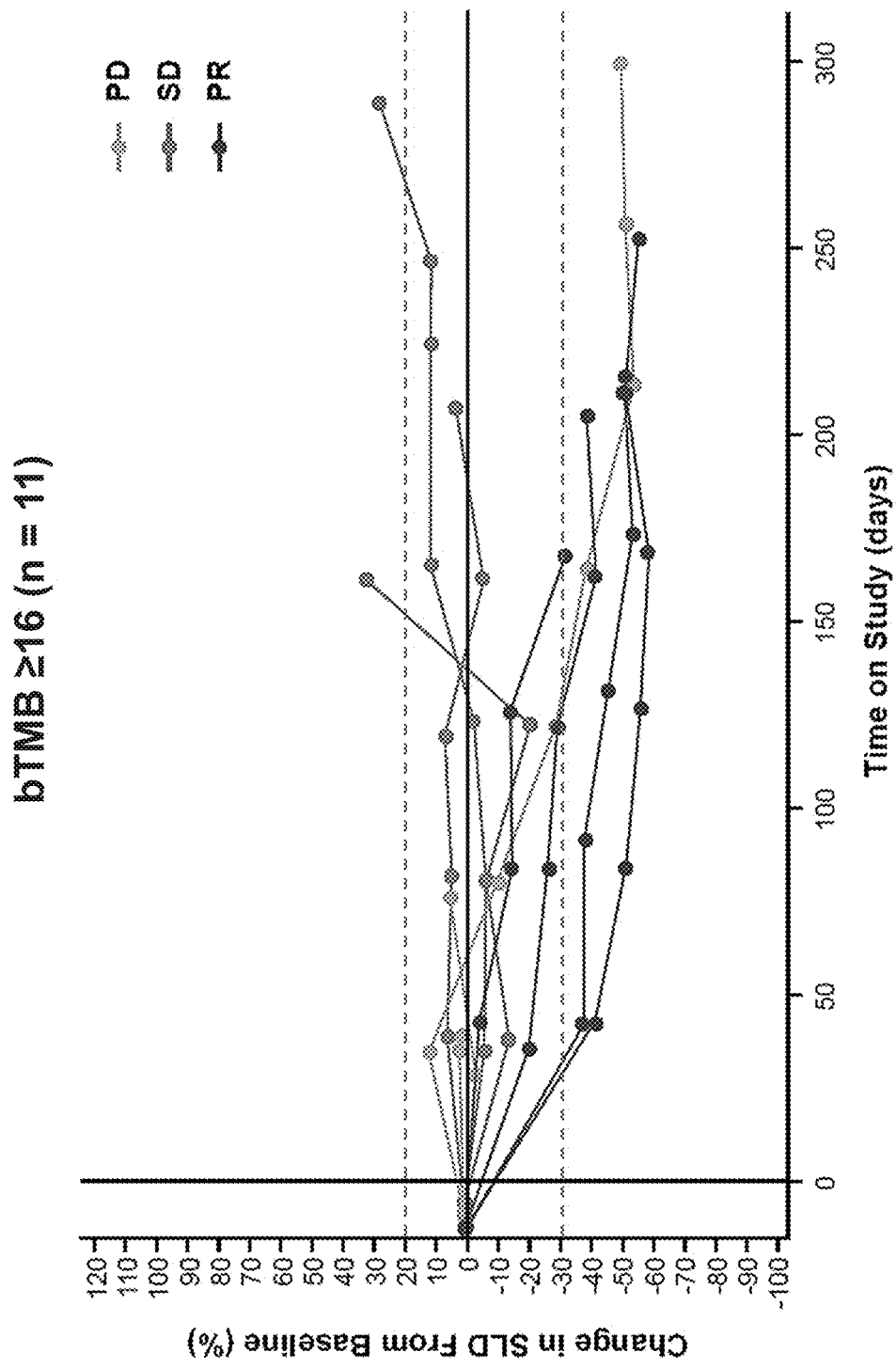

FIGS. 23A and 23B are a series of graphs showing changes in tumor burden over time by bTMB subgroup for the bTMB<16 (FIG. 23A) and bTMB≥16 (FIG. 23B) subgroups of the interim analysis population of the B-F1 RST trial.

Figure 24:
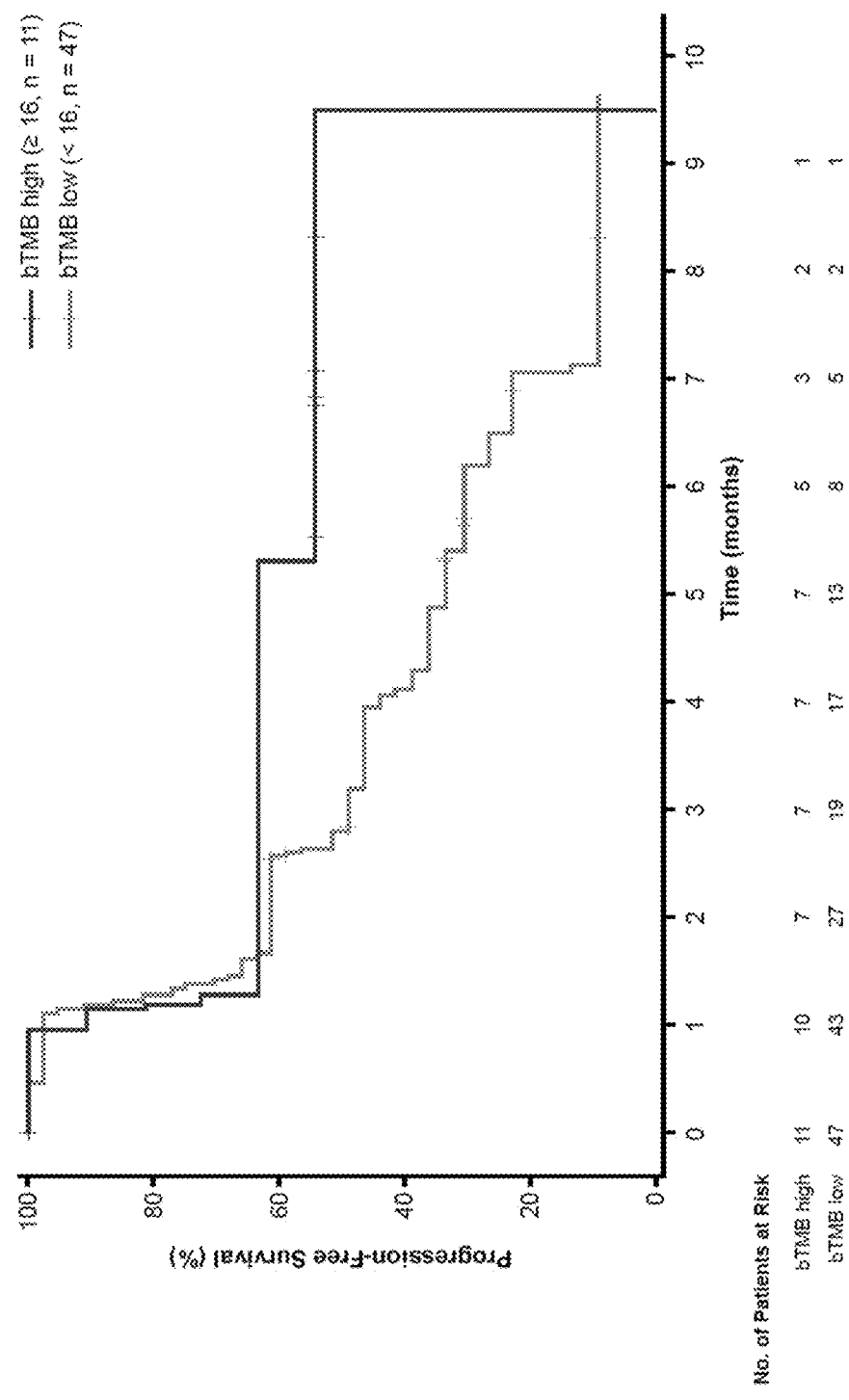

FIG. 24 is a graph showing the Kaplan-Meier Curve of PFS of the bTMB<16 and bTMB≥16 subgroups of the interim analysis population of the B-F1 RST trial.

Figure 25:
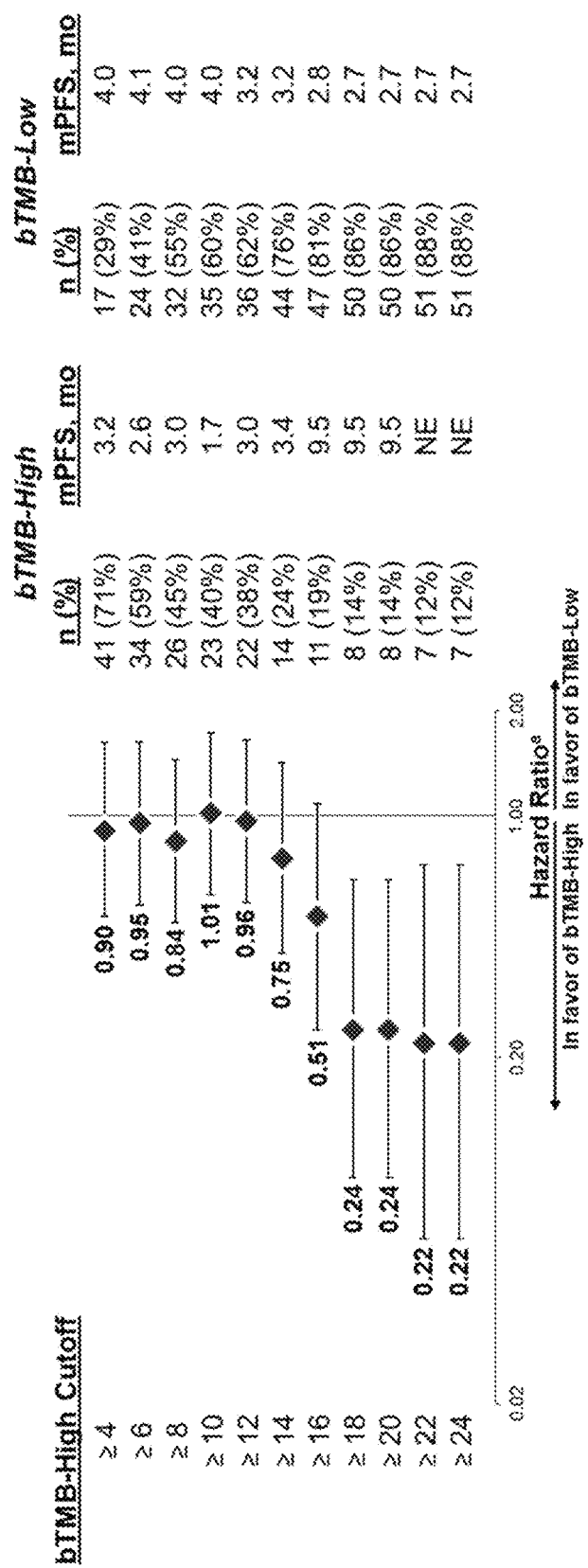

FIG. 25 is a graph showing a Forest plot of PFS by bTMB cutoff scores of the interim analysis population of the B-F1 RST trial. [a]Unstratified hazard ratio (90% CI).

Figure 26A:
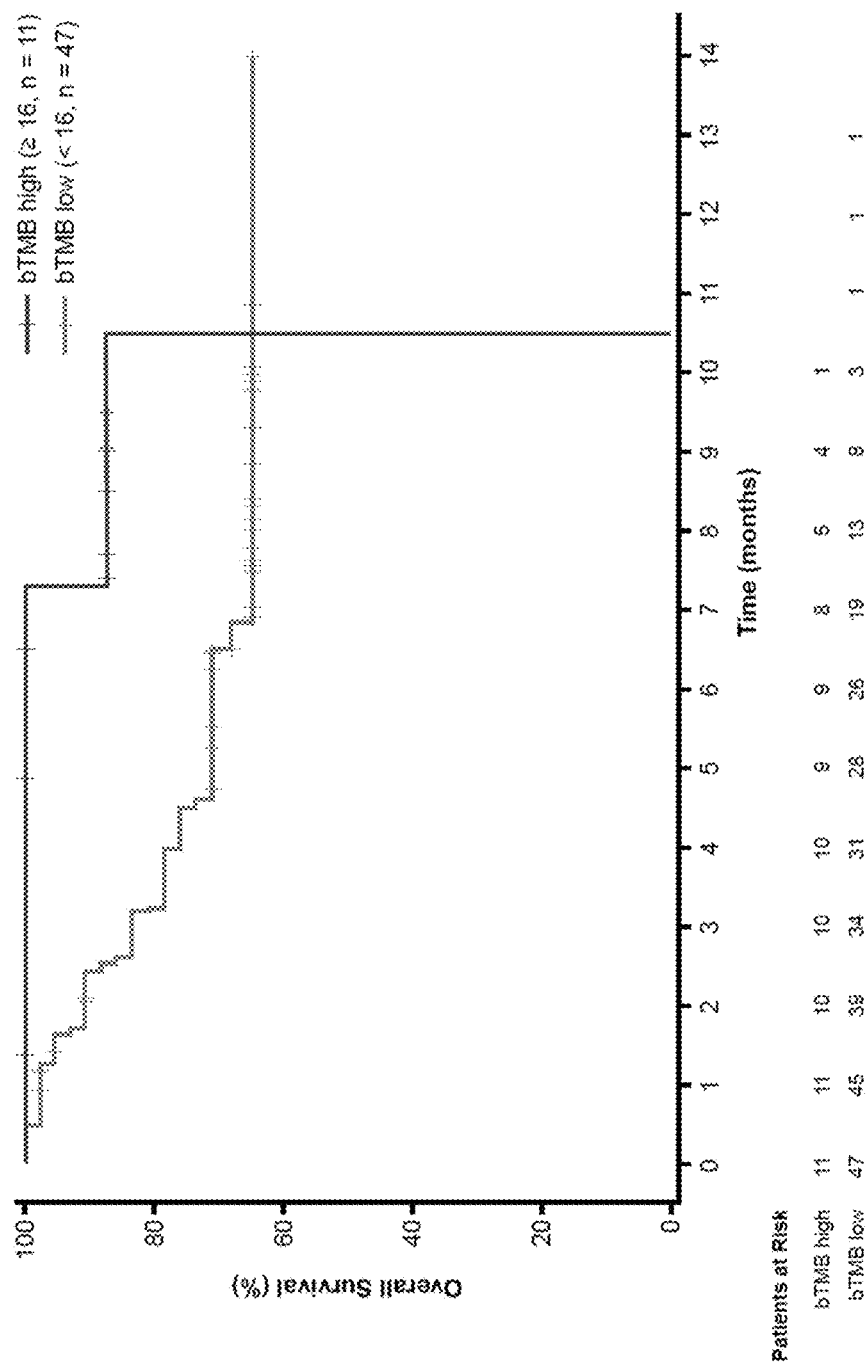

FIG. 26A is a graph showing the Kaplan-Meier Curve of OS of the bTMB<16 and bTMB≥16 subgroups of the interim analysis population of the B-F1 RST trial.

Figure 26B:
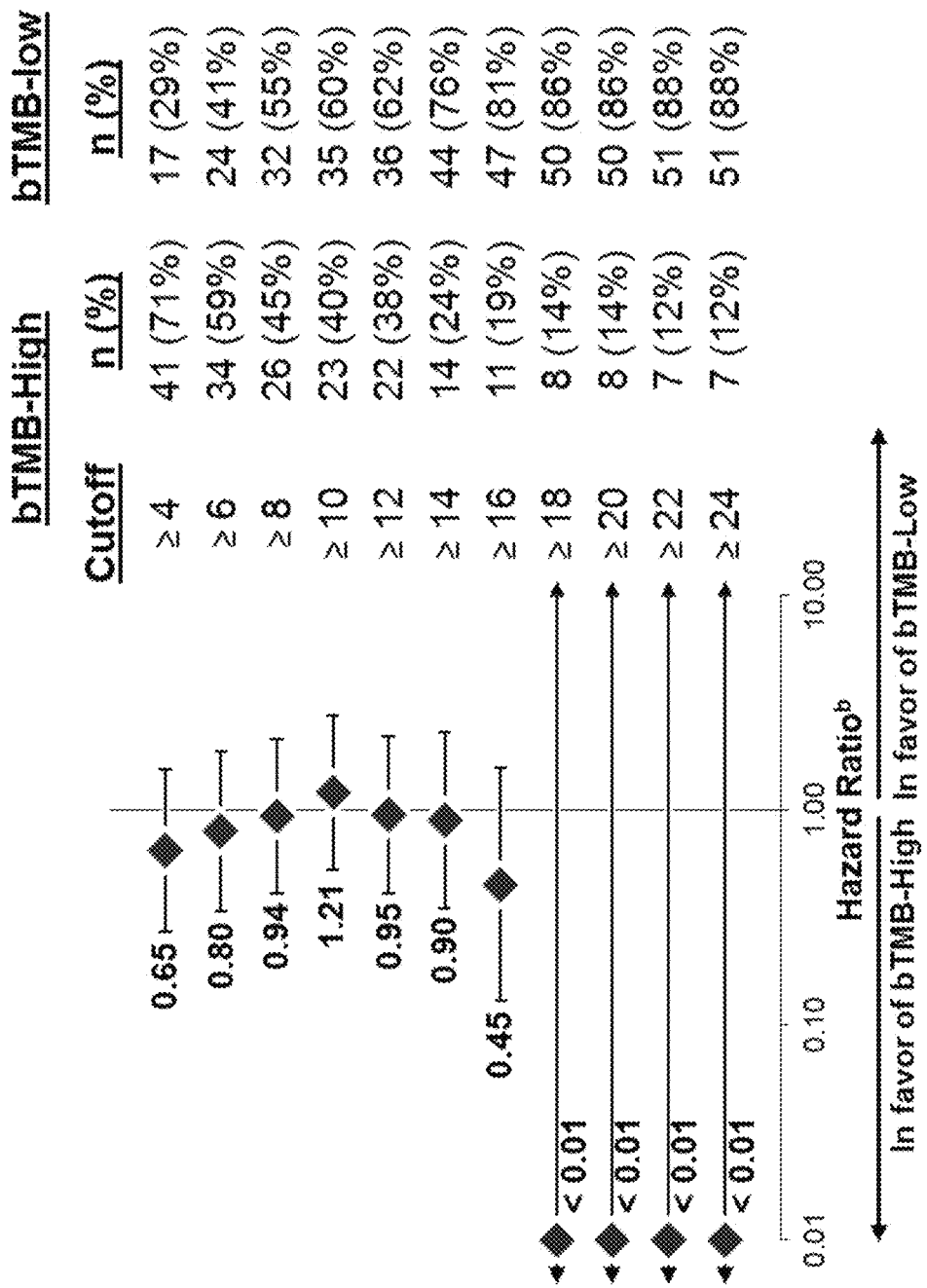

FIG. 26B is a graph showing a Forest plot of OS by bTMB cutoff scores of the interim analysis population of the B-F1 RST trial. [b]Unstratified hazard ratio (90% CI).

FIG. 27 is a graph showing AEs observed in ≥10% of the safety-evaluable interim analysis population of the B-F1 RST trial.

DETAILED DESCRIPTION OF THE INVENTION

I. Introduction

The present invention provides therapeutic, diagnostic, and prognostic methods and compositions for cancer. The invention is based, at least in part, on the discovery that determining a total number of somatic mutations in a sample obtained from an individual and deriving a blood tumor mutational burden (bTMB) score can be used as a biomarker (e.g., a predictive biomarker) in the treatment of an individual having a cancer; for diagnosing an individual having a cancer; determining whether an individual having a cancer is likely to respond to treatment with an anti-cancer therapy that includes an immune checkpoint inhibitor, for example, a PD-L1 axis binding antagonist (e.g., an anti-PD-L1 antibody, e.g., atezolizumab (MPDL3280A)), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof; optimizing therapeutic efficacy of an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof; and selecting a therapy for an individual having a cancer. The invention also provides methods for providing a prognosis for an individual having a cancer, as well as methods of monitoring a response of an individual to a treatment that includes an immune checkpoint inhibitor, for example, a PD-L1 axis binding antagonist (e.g., an anti-PD-L1 antibody, e.g., atezolizumab (MPDL3280A)), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

II. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

As used herein, the terms "blood tumor mutational burden score," "blood tumor mutation burden score," and "bTMB score," each of which may be used interchangeably, refer to a numerical value that reflects the number of somatic mutations detected in a blood sample (e.g., a whole blood sample, a plasma sample, a serum sample, or a combination thereof) obtained from an individual (e.g., an individual at risk of or having a cancer). The bTMB score can be measured, for example, on a whole genome or exome basis, or on the basis of a subset of the genome or exome (e.g., a predetermined set of genes). In certain embodiments, a bTMB score can be measured based on intergenic sequences. In some embodiments, the bTMB score measured on the basis of a subset of genome or exome can be extrapolated to determine a whole genome or exome bTMB score. In certain embodiments, the predetermined set of genes does not comprise the entire genome or the entire exome. In other embodiments, the set of subgenomic intervals does not comprise the entire genome or the entire exome. In some embodiments, the predetermined set of genes comprise a plurality of genes, which in mutant form, are associated with an effect on cell division, growth or survival, or are associated with cancer. In some embodiments, the predetermined set of genes comprise at least about 50 or more, about 100 or more, about 150 or more, about 200 or more, about 250 or more, about 300 or more, about 350 or more, about 400 or more, about 450 or more, or about 500 or more genes. In some embodiments, the pre-determined set of genes covers about 1 Mb (e.g., about 1.1 Mb, e.g., about 1.125 Mb).

In some embodiments, the bTMB score is determined from measuring the number of somatic mutations in cell-free DNA (cfDNA) in a sample. In some embodiments, the bTMB score is determined from measuring the number of somatic mutations in circulating tumor DNA (ctDNA) in a sample. In some embodiments, the number of somatic mutations is the number of single nucleotide variants (SNVs) counted or a sum of the number of SNVs and the number of indel mutations counted. In some embodiments, the bTMB score refers to the number of accumulated somatic mutations in a tumor. A bTMB score can therefore be used as a surrogate for the number of neoantigens on oncogenic (e.g., tumor) cells. A bTMB score can also be used as a surrogate for the rate of mutation within a tumor, which is a proxy for the number of neoantigens on oncogenic (e.g., tumor) cells. In some embodiments, a bTMB score at or above a reference bTMB score identifies an individual as one who may benefit from a treatment comprising an immune checkpoint inhibitor, for example, a PD-L1 axis binding antagonist (e.g., atezolizumab). In some embodiments, a bTMB score below a reference bTMB score identifies an individual as one who may benefit from a treatment comprising an anti-cancer therapy other than, or in addition to, a PD-L1 axis binding antagonist. In some embodiments, a bTMB score can be used to monitor response of an individual having a cancer to a treatment comprising an immune checkpoint inhibitor, for example, a PD-L1 axis binding antagonist (e.g., atezolizumab).

As used herein, the term "reference bTMB score" refers to a bTMB score against which another bTMB score is compared, e.g., to make a diagnostic, predictive, prognostic, and/or therapeutic determination.

For example, the reference bTMB score may be a bTMB score in a reference sample, a reference population, and/or a pre-determined value. In some instances, the reference bTMB score is a cut-off value that significantly separates a first subset of individuals who have been treated with an immune checkpoint inhibitor, for example, a PD-L1 axis binding antagonist therapy, in a reference population and a second subset of individuals who have been treated with a non-PD-L1 axis binding antagonist therapy that does not comprise an immune checkpoint inhibitor, for example, a PD-L1 axis binding antagonist, in the same reference population based on a significant difference between an individual's responsiveness to treatment with the immune checkpoint inhibitor, for example, a PD-L1 axis binding antagonist therapy, and an individual's responsiveness to treatment with the non-PD-L1 axis binding antagonist therapy at or above the cut-off value and/or below the cut-off value. In some instances, the individual's responsiveness to treatment with the immune checkpoint inhibitor, for example, a PD-L1 axis binding antagonist therapy, is significantly improved relative to the individual's responsiveness to treatment with the non-PD-L1 axis binding antagonist therapy at or above the cut-off value. In some instances, the individual's responsiveness to treatment with the non-PD-L1 axis binding antagonist therapy is significantly improved relative to the individual's responsiveness to treatment with the immune checkpoint inhibitor, for example, a PD-L1 axis binding antagonist therapy, below the cut-off value.

It will be appreciated by one skilled in the art that the numerical value for the reference bTMB score may vary depending on the type of cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor), the methodology used to measure a bTMB score, and/or the statistical methods used to generate a bTMB score.

The term "equivalent bTMB value" refers to a numerical value that corresponds to a bTMB score that is represented as the number of somatic mutations counted over a defined number of sequenced bases (e.g., about 1.1 Mb (e.g., about 1.125 Mb), e.g., as assessed by the FOUNDATIONONE® panel). It is to be understood that, in general, the bTMB score is linearly related to the size of the genomic region sequenced. Such equivalent bTMB values indicate an equivalent degree of tumor mutational burden as compared to a bTMB score and can be used interchangeably in the methods described herein, for example, to predict response of a cancer patient to an immune checkpoint inhibitor (e.g., an anti-PD-L1 antibody, e.g., atezolizumab). As an example, in some embodiments, an equivalent bTMB value is a normalized bTMB value that can be calculated by dividing the count of somatic variants (e.g., somatic mutations) by the number of bases sequenced. For example, an equivalent bTMB value can be represented, e.g., as the number of mutations per megabase. For example, a bTMB score of about 25 (as determined as the number of somatic mutations counted over about 1.1 Mb) corresponds to an equivalent bTMB value of about 23 mutations/Mb. It is to be understood that bTMB scores as described herein (e.g., bTMB scores represented as the number of somatic mutations counted over a defined number of sequenced bases (e.g., about 1.1 Mb (e.g., about 1.125 Mb), e.g., as assessed by the FOUNDATIONONE® panel)) encompass equivalent bTMB values obtained using different methodologies (e.g., whole-exome sequencing or whole-genome sequencing). As an example, for a whole exome panel, the target region may be approximately 50 Mb, and a sample with about 500 somatic mutations detected has an equivalent bTMB value of about 10 mutations/Mb. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates by less than about 30% (e.g., less than about 30%, about 25%, about 20%, about 15%, about 10%, about 5%, about 4%, about 3%, about 2%, about 1%, or less) from a bTMB score determined by whole-exome sequencing. See, e.g., Chalmers et al. *Genome Medicine* 9:34, 2017.

As used herein, the terms "maximum somatic allele frequency" and "MSAF," each of which may be used interchangeably, refer to the highest frequency of an allele (i.e., a variant of a gene having a somatic mutation (e.g., a base substitution in a coding region and/or an indel mutation in a coding region)) less than about 40% (e.g., less than 40%, 30%, 20%, 10%, 5%, or 1%), expressed as a fraction or percentage, that is detected from a sample (e.g., a whole blood sample, a plasma sample, a serum sample, or a combination thereof) from an individual. The allele frequency for somatic mutations may be calculated by dividing the number of sequence reads indicating a somatic mutation against the total reads aligned to a particular region of the human genome. In some instances, the MSAF is derived from the largest somatic allele frequency less than about 20% in a sample. In some embodiments, the value is the fraction of all cfDNA in the sample from the subject that carries that allele. In some embodiments, the value is the fraction of ctDNA in the sample from the subject that carries that allele. In some embodiments, the value is used to estimate the total amount of tumor content in the sample. In some embodiments, the method comprises determining an allele frequency for each somatic alteration detected from the sample. For example, a sample with multiple somatic alterations may present those alterations as a distribution of somatic allele frequencies, likely dependent upon their original clonal frequency in a cancer (e.g., a tumor). In some embodiments, the value is expressed as a function of the predetermined set of genes, e.g., the coding regions of the predetermined set of genes. In other embodiments, the value is expressed as a function of the subgenomic intervals sequenced, e.g., the coding subgenomic intervals sequenced. In some embodiments, the MSAF can be used to provide a prognosis for an individual having a cancer.

As used herein, the terms "tissue tumor mutational burden score" and "tTMB score," which may be used interchangeably, refer to the level (e.g., number) of an alteration (e.g., one or more alterations, e.g., one or more somatic alterations) per a pre-selected unit (e.g., per megabase) in a pre-determined set of genes (e.g., in the coding regions of the pre-determined set of genes) detected in a tumor tissue sample (e.g., a formalin-fixed and paraffin-embedded (FFPE) tumor sample, an archival tumor sample, a fresh tumor sample, or a frozen tumor sample). The tTMB score can be measured, for example, on a whole genome or exome basis, or on the basis of a subset of the genome or exome. In certain embodiments, the tTMB score measured on the basis of a subset of the genome or exome can be extrapolated to determine a whole genome or exome mutation load. In some embodiments, a tTMB score refers to the level of accumulated somatic mutations within an individual (e.g., an animal (e.g., a human)). The tTMB score may refer to accumulated somatic mutations in a patient with cancer (e.g., lung cancer, e.g., NSCLC). In some embodiments, a tTMB score refers to the accumulated mutations in the whole genome of an individual. In some embodiments, a tTMB score refers to the accumulated mutations within a particular tissue sample (e.g., tumor tissue sample biopsy, e.g., a lung cancer tumor sample, e.g., an NSCLC tumor sample) collected from an individual.

As used herein, the term "reference tTMB score" refers to a tTMB score against which another tTMB score is compared, e.g., to make a diagnostic, predictive, prognostic, and/or therapeutic determination. For example, the reference tTMB score may be a tTMB score in a reference sample, a reference population, and/or a pre-determined value. In some instances, the reference tTMB score is a cut-off value that significantly separates a first subset of individuals (e.g., patients) who have been treated with an immune checkpoint inhibitor, for example, a PD-L1 axis binding antagonist therapy, in a reference population and a second subset of individuals (e.g., patients) who have been treated with a non-PD-L1 axis binding antagonist therapy that does not comprise an immune checkpoint inhibitor, for example, a PD-L1 axis binding antagonist, in the same reference population based on a significant difference between an individual's responsiveness to treatment with the immune checkpoint inhibitor, for example, a PD-L1 axis binding antagonist therapy, and an individual's responsiveness to treatment with the non-PD-L1 axis binding antagonist therapy at or above the cut-off value and/or below the cut-off value. In some instances, the individual's responsiveness to treatment with the immune checkpoint inhibitor, for example, a PD-L1 axis binding antagonist therapy, is significantly improved relative to the individual's responsiveness to treatment with the non-PD-L1 axis binding antagonist therapy at or above the cut-off value. In some instances, the individual's responsiveness to treatment with the non-PD-L1 axis binding antagonist therapy is significantly improved relative to the individual's responsiveness to treatment with the immune checkpoint inhibitor, for example, a PD-L1 axis binding antagonist therapy, below the cut-off value.

It will be appreciated by one skilled in the art that the numerical value for the reference tTMB score may vary depending on the type of cancer (e.g., a lung cancer (e.g., a non-small cell lung cancer (NSCLC) or a small cell lung cancer), a kidney cancer (e.g., a kidney urothelial carcinoma or a renal cell carcinoma (RCC)), a bladder cancer (e.g., a bladder urothelial (transitional cell) carcinoma (e.g., locally advanced or metastatic urothelial carcinoma, including first-line (1L) or second-line or higher (2L+) locally advanced or metastatic urothelial carcinoma)), a breast cancer (e.g., human epidermal growth factor receptor-2 (HER2)+ breast cancer or hormone receptor-positive (HR+) breast cancer), a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a skin cancer (e.g., squamous cell carcinoma of the skin), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycosis fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor), the methodology used to measure a tTMB score, and/or the statistical methods used to generate a tTMB score.

The term "equivalent tTMB value" refers to a numerical value that corresponds to a tTMB score that can be calculated by dividing the count of somatic variants (e.g., somatic mutations) by the number of bases sequenced (e.g., about 1.1 Mb (e.g., about 1.125 Mb), e.g., as assessed by the FOUNDATIONONE® panel). It is to be understood that, in general, the tTMB score is linearly related to the size of the genomic region sequenced. Such equivalent tTMB values indicate an equivalent degree of tumor mutational burden as compared to a tTMB score and can be used interchangeably in the methods described herein, for example, to predict response of a cancer patient to an immune checkpoint inhibitor (e.g., an anti-PD-L1 antibody, e.g., atezolizumab). As an example, in some embodiments, an equivalent tTMB value is a normalized tTMB value that can be calculated by dividing the count of somatic variants (e.g., somatic mutations) by the number of bases sequenced. For example, an equivalent tTMB value can be represented as the number of somatic mutations counted over a defined number of sequenced bases (e.g., about 1.1 Mb (e.g., about 1.125 Mb), e.g., as assessed by the FOUNDATIONONE® panel). For example, a tTMB score of about 25 (as determined as the number of somatic mutations counted over about 1.1 Mb) corresponds to an equivalent tTMB value of about 23 mutations/Mb. It is to be understood that tTMB scores as described herein (e.g., TMB scores represented as the number of somatic mutations counted over a defined number of sequenced bases (e.g., about 1.1 Mb (e.g., about 1.125 Mb), e.g., as assessed by the FOUNDATIONONE® panel)) encompass equivalent tTMB values obtained using different methodologies (e.g., whole-exome sequencing or whole-genome sequencing). As an example, for a whole-exome panel, the target region may be approximately 50 Mb, and a sample with about 500 somatic mutations detected is an equivalent tTMB value to a tTMB score of about 10 mutations/Mb. In some embodiments, a tTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates by less than about 30% (e.g., less than about 30%, about 25%, about 20%, about 15%, about 10%, about 5%, about 4%, about 3%, about 2%, about 1%, or less) from a tTMB score determined by whole-exome sequencing. See, e.g., Chalmers et al. *Genome Medicine* 9:34, 2017.

The term "somatic mutation" or "somatic alteration" refers to a genetic alteration occurring in the somatic tissues (e.g., cells outside the germline). Examples of genetic alterations include, but are not limited to, point mutations (e.g., the exchange of a single nucleotide for another (e.g., silent mutations, missense mutations, and nonsense mutations)), insertions and deletions (e.g., the addition and/or removal of one or more nucleotides (e.g., indels)), amplifications, gene duplications, copy number alterations (CNAs), rearrangements, and splice variants. In some embodiments, an indel may be a frameshift mutation or in-frame mutations of one or more nucleotides (e.g., about 1-40 nucleotides). The presence of particular mutations can be associated with disease states (e.g., cancer, e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor).

In certain embodiments, the somatic alteration is a silent mutation (e.g., a synonymous alteration). In other embodiments, the somatic alteration is a non-synonymous single nucleotide variant (SNV). In other embodiments, the somatic alteration is a passenger mutation (e.g., an alteration that has no detectable effect on the fitness of a clone). In certain embodiments, the somatic alteration is a variant of unknown significance (VUS), for example, an alteration, the pathogenicity of which can neither be confirmed nor ruled out. In certain embodiments, the somatic alteration has not been identified as being associated with a cancer phenotype.

In certain embodiments, the somatic alteration is not associated with, or is not known to be associated with, an effect on cell division, growth, or survival. In other embodiments, the somatic alteration is associated with an effect on cell division, growth, or survival.

In certain embodiments, the number of somatic alterations excludes one or more functional alterations in a sub-genomic interval.

As used herein, the terms "sub-genomic interval" and "subgenomic interval," each of which may be used interchangeably, refers to a portion of a genomic sequence. In some embodiments, a subgenomic interval can be a single nucleotide position, e.g., a nucleotide position variant of which is associated (positively or negatively) with a tumor phenotype. In some embodiments, a subgenomic interval comprises more than one nucleotide position. Such embodiments include sequences of at least 2, 5, 10, 50, 100, 150, or 250 nucleotide positions in length. Subgenomic intervals can comprise an entire gene, or a preselected portion thereof, e.g., the coding region (or portions thereof), a preselected intron (or portion thereof) or exon (or portion thereof). A subgenomic interval can comprise all or a part of a fragment of a naturally occurring, e.g., genomic DNA, nucleic acid. For example, a subgenomic interval can correspond to a fragment of genomic DNA, which is subjected to a sequencing reaction. In certain embodiments, a subgenomic interval is continuous sequence from a genomic source. In other embodiments, a subgenomic interval includes sequences that are not contiguous in the genome, e.g., it can include junctions formed at exon-exon junctions in cDNA.

In an embodiment, a subgenomic interval comprises or consists of: a single nucleotide position; an intragenic region or an intergenic region; an exon or an intron, or a fragment thereof, typically an exon sequence or a fragment thereof; a coding region or a non-coding region, e.g., a promoter, an enhancer, a 5' untranslated region (5' UTR), or a 3' untranslated region (3' UTR), or a fragment thereof; a cDNA or a fragment thereof; an SNV; an SNP; a somatic mutation, a germline mutation or both; an alteration, e.g., a point or a single mutation; a deletion mutation (e.g., an in-frame deletion, an intragenic deletion, a full gene deletion); an insertion mutation (e.g., intragenic insertion); an inversion mutation (e.g., an intra-chromosomal inversion); a linking mutation; a linked insertion mutation; an inverted duplication mutation; a tandem duplication (e.g., an intrachromosomal tandem duplication); a translocation (e.g., a chromosomal translocation, a non-reciprocal translocation); a rearrangement (e.g., a genomic rearrangement (e.g., a rearrangement of one or more introns, or a fragment thereof; a rearranged intron can include a 5'- and/or 3'-UTR)); a change in gene copy number; a change in gene expression; a change in RNA levels; or a combination thereof.

The "copy number of a gene" refers to the number of DNA sequences in a cell encoding a particular gene product. Generally, for a given gene, a mammal has two copies of each gene. The copy number can be increased, e.g., by gene amplification or duplication, or reduced by deletion.

In some embodiments, the functional alteration is an alteration that, compared with a reference sequence (e.g., a wild-type or unmutated sequence) has an effect on cell division, growth, or survival (e.g., promotes cell division, growth, or survival). In certain embodiments, the functional alteration is identified as such by inclusion in a database of functional alterations, e.g., the COSMIC database (see Forbes et al. *Nucl. Acids Res.* 43 (D1): D805-D811, 2015, which is herein incorporated by reference in its entirety). In other embodiments, the functional alteration is an alteration with known functional status (e.g., occurring as a known somatic alteration in the COSMIC database). In certain embodiments, the functional alteration is an alteration with a likely functional status (e.g., a truncation in a tumor suppressor gene). In certain embodiments, the functional alteration is a driver mutation (e.g., an alteration that gives a selective advantage to a clone in its microenvironment, e.g., by increasing cell survival or reproduction). In other embodiments, the functional alteration is an alteration capable of causing clonal expansions. In certain embodiments, the functional alteration is an alteration capable of causing one, two, three, four, five, or all six of the following: (a) self-sufficiency in a growth signal; (b) decreased, e.g., insensitivity, to an antigrowth signal; (c) decreased apoptosis; (d) increased replicative potential; (e) sustained angiogenesis; or (f) tissue invasion or metastasis.

In certain embodiments, the functional alteration is not a passenger mutation (e.g., is not an alteration that has no detectable effect on the fitness of a clone of cells). In certain embodiments, the functional alteration is not a variant of unknown significance (VUS) (e.g., is not an alteration, the pathogenicity of which can neither be confirmed nor ruled out).

In certain embodiments, a plurality (e.g., about 10%, 20%, 30%, 40%, 50%, 60%, 70%, 80%, 90%, or more) of functional alterations in a pre-selected tumor gene in the pre-determined set of genes are excluded. In certain embodiments, all functional alterations in a pre-selected gene (e.g., tumor gene) in the pre-determined set of genes are excluded. In certain embodiments, a plurality of functional alterations in a plurality of pre-selected genes (e.g., tumor genes) in the pre-determined set of genes are excluded. In certain embodiments, all functional alterations in all genes (e.g., tumor genes) in the pre-determined set of genes are excluded.

In certain embodiments, the number of somatic alterations excludes a germline mutation in a sub-genomic interval.

In certain embodiments, the germline alteration is an SNP, a base substitution, an insertion, a deletion, an indel, or a silent mutation (e.g., synonymous mutation).

In certain embodiments, the germline alteration is excluded by use of a method that does not use a comparison with a matched normal sequence. In other embodiments, the germline alteration is excluded by a method comprising the use of an algorithm, for example, the somatic-germline-zygosity (SGZ) algorithm (see Sun et al. Cancer Research 2014; 74(19S):1893-1893). In certain embodiments, the germline alteration is identified as such by inclusion in a database of germline alterations, for example, the dbSNP database (see Sherry et al. *Nucleic Acids Res.* 29(1): 308-311, 2001, which is herein incorporated by reference in its entirety). In other embodiments, the germline alteration is identified as such by inclusion in two or more counts of the ExAC database (see Exome Aggregation Consortium et al. bioRxiv preprint, Oct. 30, 2015, which is herein incorporated by reference in its entirety). In some embodiments, the germline alteration is identified as such by inclusion in the 1000 Genome Project database (McVean et al. *Nature* 491, 56-65, 2012, which is herein incorporated by reference in its entirety). In some embodiments, the germline alteration is identified as such by inclusion in the ESP database (Exome Variant Server, NHLBI GO Exome Sequencing Project (ESP), Seattle, Wash.).

The term "PD-L1 axis binding antagonist" refers to a molecule that inhibits the interaction of a PD-L1 axis binding partner with one or more of its binding partners, so as to remove T-cell dysfunction resulting from signaling on the PD-1 signaling axis, with a result being restored or enhanced T-cell function. As used herein, a PD-L1 axis binding antagonist includes a PD-L1 binding antagonist and a PD-1 binding antagonist as well as molecules that interfere with the interaction between PD-L1 and PD-1 (e.g., a PD-L2-Fc fusion).

The term "dysfunction," in the context of immune dysfunction, refers to a state of reduced immune responsiveness to antigenic stimulation. The term includes the common elements of both "exhaustion" and/or "anergy" in which antigen recognition may occur, but the ensuing immune response is ineffective to control infection or tumor growth.

The term "dysfunctional," as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g., increase in intracellular $Ca^{2+}$ in the absence of Ras activation). T-cell anergy can also result upon stimulation with antigen in the absence of co-stimulation, resulting in the cell becoming refractory to subsequent activation by the antigen even in the context of co-stimulation. The unresponsive state can often be overridden by the presence of interleukin-2. Anergic T-cells do not undergo clonal expansion and/or acquire effector functions.

The term "exhaustion" refers to T-cell exhaustion as a state of T-cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T-cells. Exhaustion prevents optimal control of infection and tumors. Exhaustion can result from both extrinsic negative regulatory pathways (e.g., immunoregulatory cytokines) as well as cell-intrinsic negative regulatory (co-stimulatory) pathways (PD-1, B7-H3, B7-H4, etc.).

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include treatment with a PD-L1 axis binding antagonist.

As used herein, the term "immune checkpoint inhibitor" refers to a therapeutic agent that targets at least one immune checkpoint protein to alter the regulation of an immune response, e.g., down-modulating or inhibiting an immune response. Immune checkpoint proteins are known in the art and include, without limitation, cytotoxic T-lymphocyte antigen 4 (CTLA-4), programmed cell death 1 (PD-1), programmed cell death ligand 1 (PD-L1), programmed cell death ligand 2 (PD-L2), V-domain Ig suppressor of T cell activation (VISTA), B7-H2, B7-H3, B7-H4, B7-H6, 2B4, ICOS, HVEM, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, IDO, OX40, and A2aR. In some instances, an immune checkpoint protein may be expressed on the surface of an activated T cell. Therapeutic agents that can act as immune checkpoint inhibitors useful in the methods of the present invention, include, but are not limited to, therapeutic agents that target one or more of CTLA-4, PD-1, PD-L1, PD-L2, VISTA, B7-H2, B7-H3, B7-H4, B7-H6, 2B4, ICOS, HVEM, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, IDO, OX40, and A2aR. In some instances, an immune checkpoint inhibitor enhances or suppresses the function of one or more targeted immune checkpoint proteins. In some instances, the immune checkpoint inhibitor is a PD-L1 axis binding antagonists as described herein.

As used herein, a "PD-L1 binding antagonist" is a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, PD-L1 binding antagonists include anti-PD-L1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative signal mediated by or through cell surface proteins expressed on T lymphocytes and other cells through PD-L1 or PD-1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is atezolizumab (CAS Registry Number: 1422185-06-5), also known as MPDL3280A, described herein. In still another specific aspect, an anti-PD-L1 antibody is MED14736 (druvalumab) described herein. In still another specific aspect, an anti-PD-L1 antibody is MSB0010718C (avelumab) described herein.

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes and other cells through PD-1 or PD-L1 so as to render a dysfunctional T-cell less dysfunctional. In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (pembrolizumab) described herein. In another specific aspect, a PD-1 binding antagonist is CT-011 (pidilizumab) described herein. In another specific aspect, a PD-1 binding antagonist is MEDI-0680 (AMP-514). In another specific aspect, a PD-1 binding antagonist is PDR001. In another specific aspect, a PD-1 binding antagonist is REGN2810. In another specific aspect, a PD-1 binding antagonist is BGB-108. In another specific aspect, a PD-1 binding antagonist is AMP-224 described herein.

The terms "Programmed Death Ligand 1" and "PD-L1" refer herein to a native sequence PD-L1 polypeptide, polypeptide variants (i.e., PD-L1 polypeptide variants), and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature.

A "PD-L1 polypeptide variant," or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 polypeptide variants are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, or 289 amino acids in length, or more. Optionally, PD-L1 polypeptide variants will have no more than one conservative amino acid substitution as compared to a native PD-L1 polypeptide sequence, alternatively no more than 2, 3, 4, 5, 6, 7, 8, 9, or 10 conservative amino acid substitutions as compared to a native PD-L1 polypeptide sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by $P(O)S$ ("thioate"), $P(S)S$ ("dithioate"), "$(O)NR_2$ ("amidate"), $P(O)R$, $P(O)OR'$, CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. A polynucleotide can contain one or more different types of modifications as described herein and/or multiple modifications of the same type. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single-stranded polynucleotide that is capable of hybridizing to a nucleic acid and allowing polymerization of a complementary nucleic acid, generally by providing a free 3'-OH group.

The term "small molecule" refers to any molecule with a molecular weight of about 2000 daltons or less, preferably of about 500 daltons or less.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "light chains" of antibodies (immunoglobulins) from any mammalian species can be assigned to one of two clearly distinct types, called kappa ("K") and lambda ("A"), based on the amino acid sequences of their constant domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2, and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The term "hypervariable region," "HVR," or "HV," as used herein, refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, for example, Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, for example, Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35b | H26-H35b | H26-H32 | H30-H35b (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. In some embodiments, the antibody fragment described herein is an antigen-binding fragment. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of antibodies are called α, δ, ε, γ, and μ, respectively.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target-binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target-binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target-binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature* 256:495-97 (1975); Hongo et al., *Hybridoma* 14 (3): 253-260 (1995), Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg et al., *Intern. Rev. Immunol.* 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, for example, by a radioimmunoassay (RIA). In certain embodiments, an anti-PD-L1 antibody binds to an epitope of PD-L1 that is conserved among PD-L1 from different species.

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, for example, by a radioimmunoassay (RIA). In certain embodiments, an anti-PD-1 antibody binds to an epitope of PD-1 that is conserved among PD-1 from different species.

A "blocking" antibody or an "antagonist" antibody is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

An "immunoconjugate" is an antibody conjugated to one or more heterologous molecule(s), including but not limited to a cytotoxic agent.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2 (including IgG2A and IgG2B), IgG3, or IgG4 subtypes, IgA (including IgA1 and IgA2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. For example, useful immunoadhesins as medicaments useful for therapy herein include polypeptides that comprise the extracellular domain (ECD) or PD-1-binding portions of PD-L1 or PD-L2, or the extracellular or PD-L1- or PD-L2-binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, and the like. The two portions may be linked directly by a single peptide bond or through a peptide linker but are in reading frame with each other.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "detection" includes any means of detecting, including direct and indirect detection.

The term "biomarker" as used herein refers to an indicator, e.g., predictive, diagnostic, and/or prognostic, which can be detected in a sample, e.g., a bTMB score, a tTMB score, or PD-L1. The biomarker may serve as an indicator of a particular subtype of a disease or disorder (e.g., cancer) characterized by certain, molecular, pathological, histological, and/or clinical features (e.g., responsiveness to therapy including a PD-L1 axis binding antagonist). In some embodiments, a biomarker is a collection of genes or a collective number of mutations/alterations (e.g., somatic mutations) in a collection of genes. Biomarkers include, but are not limited to, polynucleotides (e.g., DNA and/or RNA), polynucleotide alterations (e.g., polynucleotide copy number alterations, e.g., DNA copy number alterations), polypeptides, polypeptide and polynucleotide modifications (e.g., post-translational modifications), carbohydrates, and/or glycolipid-based molecular markers.

The "amount" or "number" of somatic mutations associated with an increased clinical benefit to an individual is a detectable level in a biological sample. These can be measured by methods known to one skilled in the art and also disclosed herein. The amount of a somatic mutation assessed can be used to determine the response to the treatment.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., *PCR Technology*, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain somatic mutations in a biological sample from an individual.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, plasma, serum, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof. In some instances, the sample is a whole blood sample, a plasma sample, a serum sample, or a combination thereof.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

A "reference sample," "reference cell," "reference tissue," "control sample," "control cell," or "control tissue," as used herein, refers to a sample, cell, tissue, standard, or level that is used for comparison purposes.

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and/or progression-free survival); resulting in an objective response (including a complete response or a partial response); or improving signs or symptoms of cancer.

In some embodiments, a bTMB score determined using methods disclosed herein to be at or above a reference bTMB score (e.g., a reference bTMB score between about 4 and about 30, e.g., a reference bTMB score of about 4, 5, 6, 7, 8, 9, 10, 11, 12, 13, 14, 15, 16, 17, 18, 19, 20, 21, 22, 23, 24, 25, 26, 27, 28, 29, or 30) is used to identify a patient who is predicted to have an increased likelihood of being responsive to treatment with a medicament (e.g., treatment comprising a PD-L1 axis binding antagonist, e.g., an anti-PD-L1 antibody). In some embodiments, a bTMB score determined using methods disclosed herein to be less than a reference bTMB score (e.g., a reference bTMB score between about 4 and about 30, e.g., a reference bTMB score of about 4, 5, 6, 7, 8, 9, 10, 11, 12, 13, 14, 15, 16, 17, 18, 19, 20, 21, 22, 23, 24, 25, 26, 27, 28, 29, or 30) is used to identify a patient who is predicted to have an increased likelihood of being responsive to treatment with an anti-cancer therapy other than, or in addition to, a PD-L1 axis binding antagonist. In some instances, the bTMB score determined from a sample from an individual is between about 8 and about 100 (e.g., 8, 9, 10, 15, 20, 25, 30, 35, 40, 45, 50, 55, 60, 65, 70, 75, 80, 85, 90, 95, or 100).

In general, the bTMB score (e.g., a reference bTMB score) is linearly related to the size of the genomic region sequenced. The example numbers above refer to bTMB scores obtained by sequencing about 1.1 Mb, e.g., using the FOUNDATIONONE® panel. The bTMB score of a sample when sequencing X times more bases is expected to be about X times higher. In some embodiments, a normalized bTMB value can be calculated by dividing the number of somatic variations (e.g., mutations) counted by the number of bases sequenced, e.g., the number of somatic variations (e.g., mutations) counted per megabase. Accordingly, any of the preceding bTMB scores or reference bTMB scores can be an equivalent bTMB value, for example, an equivalent bTMB value determined by whole-exome sequencing. In some instances, a bTMB score (e.g., a reference bTMB score) may be between about 400 and about 1500 (e.g., a bTMB score of about 400, 500, 600, 700, 800, 900, 1000, 1100, 1200, 1300, 1400, or 1500), for example, in a whole-exome-based assay.

In some embodiments, a combination of a bTMB score and MSAF, determined using methods disclosed herein, is used to identify a patient who is predicted to have an increased likelihood of being responsive to treatment with a medicament (e.g., treatment comprising a PD-L1 axis binding antagonist, e.g., an anti-PD-L1 antibody). In some embodiments, a combination of a bTMB score and MSAF, determined using methods disclosed herein, is used to identify a patient who is predicted to have an increased likelihood of being responsive to treatment with an anti-cancer therapy other than, or in addition to, a PD-L1 axis binding antagonist.

An "objective response" refers to a measurable response, including complete response (CR) or partial response (PR). In some embodiments, the "objective response rate (ORR)" refers to the sum of complete response (CR) rate and partial response (PR) rate.

By "complete response" or "CR" is intended the disappearance of all signs of cancer (e.g., disappearance of all target lesions) in response to treatment. This does not always mean the cancer has been cured.

"Sustained response" refers to the sustained effect on reducing tumor growth after cessation of a treatment. For example, the tumor size may be the same size or smaller as compared to the size at the beginning of the medicament administration phase. In some embodiments, the sustained response has a duration at least the same as the treatment duration, at least 1.5×, 2.0×, 2.5×, or 3.0× length of the treatment duration, or longer.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival As used herein, "progression-free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" or "OS" refers to the percentage of individuals in a group who are likely to be alive after a particular duration of time.

By "extending survival" is meant increasing overall or progression-free survival in a treated patient relative to an untreated patient (i.e. relative to a patient not treated with the medicament), or relative to a patient who does not have somatic mutations at the designated level, and/or relative to a patient treated with an anti-tumor agent.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or mutation levels). The difference between said two values is, for example, less than about 50%, less than about 40%, less than about 30%, less than about 20%, and/or less than about 10%, as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values or mutation levels). The difference between said two values is, for example, greater than about 10%, greater than about 20%, greater than about 30%, greater than about 40%, and/or greater than about 50%, as a function of the value for the reference/comparator molecule.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

An "effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., CR and PR), duration of response, and/or quality of life.

A "disorder" is any condition that would benefit from treatment including, but not limited to, chronic and acute disorders or diseases including those pathological conditions which predispose the mammal to the disorder in question.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or 2 cancer. Examples of a cancer include, but are not limited to, a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familial hypereosinophilia, a neuroendocrine cancer, or a carcinoid tumor. More particular examples of such cancers include lung cancer, including NSCLC, squamous cell cancer (e.g., epithelial squamous cell cancer), lung cancer including small-cell lung cancer (SCLC), and adenocarcinoma of the lung and squamous carcinoma of the lung. In particular examples, the lung cancer is NSCLC, for example a locally advanced or metastatic NSCLC (e.g., stage IIIB NSCLC, stage IV NSCLC, or recurrent NSCLC). In some embodiments, the lung cancer (e.g., NSCLC) is unresectable/inoperable lung cancer (e.g., unresectable NSCLC). In some embodiments, the cancer is triple-negative metastatic breast cancer, including any histologically confirmed triple-negative (ER−, PR−, HER2−) adenocarcinoma of the breast with locally recurrent or metastatic disease (where the locally recurrent disease is not amenable to resection with curative intent.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies (e.g., anti-PD-L1 antibodies and/or anti-PD-1 antibodies) are used to delay development of a disease or to slow the progression of a disease.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-13, BlyS, APRIL, BCMA receptor(s), TRAIL/Apo2, other bioactive and organic chemical agents, and the like. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycin, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; gemcitabine (GEMZAR®); 6-thioguanine; mercaptopurine; methotrexate; platinum or platinum-based chemotherapy agents and platinum analogs, such as cisplatin, carboplatin, oxaliplatin (ELOXATIN™), satraplatin, picoplatin, nedaplatin, triplatin, and lipoplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3, and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP 659,439A2, Merck Patent GmbH). EGFR antagonists include small molecules such as compounds described in U.S. Pat. Nos. 5,616,582, 5,457, 105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitors such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell co-stimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; Secreted homotrimeric LTa3 and membrane bound heterotrimer LTa1/β2 blockers such as Antilymphotoxin alpha (LTa); miscellaneous investigational agents such as thioplatin, PS-341, phenylbutyrate, ET-18-OCH3, and farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g., PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth and/or proliferation of a cell (e.g., a cell whose growth is dependent on PD-L1 expression) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetra-hydro-6,8,11-trihydroxy-8-(hydroxyacetyl)-1-methoxy-5, 12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "The Molecular Basis of Cancer," Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, the terms "individual," "patient," or "subject" are used interchangeably and refer to any single animal, more preferably a mammal (including such non-human animals as, for example, dogs, cats, horses, rabbits, zoo animals, cows, pigs, sheep, and non-human primates) for which treatment is desired. In particular embodiments, the patient herein is a human.

As used herein, "administering" is meant a method of giving a dosage of a compound (e.g., an antagonist) or a pharmaceutical composition (e.g., a pharmaceutical composition including an antagonist) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications, and/or warnings concerning the use of such therapeutic products.

A "sterile" formulation is aseptic or free from all living microorganisms and their spores.

An "article of manufacture" is any manufacture (e.g., a package or container) or kit comprising at least one reagent, e.g., a medicament for treatment of a disease or disorder (e.g., cancer), or a probe for specifically detecting a biomarker (e.g., PD-L1) described herein. In certain embodiments, the manufacture or kit is promoted, distributed, or sold as a unit for performing the methods described herein.

The phrase "based on" when used herein means that the information about one or more biomarkers is used to inform a treatment decision, information provided on a package insert, or marketing/promotional guidance, etc.

III. Methods

Provided herein are methods and assays for treating an individual having a cancer; identifying an individual having a cancer who may benefit from a treatment including an immune checkpoint inhibitor, for example, a PD-L1 axis binding antagonist (e.g., an anti-PD-L1 antibody, e.g., atezolizumab (MPDL3280A)), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof; diagnosing a patient having a cancer; determining whether an individual having a cancer is likely to respond to treatment with an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof; optimizing therapeutic efficacy of an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof; selecting a therapy for an individual having a cancer; providing a prognosis for an individual having a cancer; and monitoring a response of an individual to treatment with an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

The methods and assays described herein are based on the finding that the blood tumor mutational burden (bTMB) score determined from a sample (e.g., a whole blood sample, a plasma sample, a serum sample, or a combination thereof) from an individual may be used to predict the therapeutic efficacy of an immune checkpoint inhibitor, for example, a PD-L1 axis binding antagonist therapy, for example, a PD-L1 axis binding antagonist monotherapy or combination therapy including a PD-L1 axis binding antagonist (e.g., a PD-L1 axis binding antagonist in combination with an antagonist directed against a co-inhibitory molecule (e.g., a CTLA-4 antagonist (e.g., an anti-CTLA-4 antibody), a TIM-3 antagonist (e.g., an anti-TIM-3 antibody), and/or a LAG-3 antagonist (e.g., an anti-LAG-3 antibody)). Any of the methods may further include determining a maximum somatic allele frequency (MSAF). Any of the methods may further include determining a tTMB score. Any of the methods provided herein may further include administering a PD-L1 axis binding antagonist (e.g., as described in Section IV, below) to the individual. Accordingly, provided herein are also methods and assays of evaluating bTMB in a sample from an individual. Any of the methods provided herein may include administering an anti-cancer therapy other than, or in additional to, an immune checkpoint inhibitor, for example, a PD-L1 axis binding antagonist (e.g., as described in Section IV, below), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, to the individual. Any of the methods may further include administering an effective amount of an additional therapeutic agent, as described herein, to the individual.

A. Diagnostic Methods and Assays (i) Predictive Diagnostic Methods

In particular instances, the methods and assays provided herein may be used to identify an individual having a cancer who may benefit from a treatment including an immune checkpoint inhibitor, for example, a PD-L1 axis binding antagonist (e.g., an anti-PD-L1 antibody, e.g., atezolizumab (MPDL3280A)), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, the method including determining a bTMB score from a sample from the individual, wherein a bTMB score from the sample that is at or above a reference bTMB score identifies the individual as one who may benefit from a treatment comprising an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

In particular instances, the methods and assays provided herein may be used to select a therapy for an individual having a cancer, the method including determining a bTMB score from a sample from the individual, wherein a bTMB score from the sample that is at or above a reference bTMB score identifies the individual as one who may benefit from a treatment comprising an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

In particular instances, the methods and assays provided herein may be used to diagnose a patient having a cancer, the method including determining a bTMB score from a sample from the individual, wherein a bTMB score from the sample that is at or above a reference bTMB score identifies the individual as one who is likely to have a cancer. In some instances, a bTMB score below a reference bTMB score identifies the individual as one who is less likely to have a cancer.

The methods provided herein may include determining a bTMB score from a sample (e.g., a whole blood sample, a plasma sample, a serum sample, or a combination thereof) from an individual. The sample from the individual may be an archival sample, a fresh sample, or a frozen sample. The determination step may include determining the total number of somatic mutations (e.g., a base substitution in a coding region and/or an indel mutation in a coding region) occurring in a pre-determined set of genes to derive a bTMB score from the sample from the individual. In some embodiments, the number of somatic mutations is the number of single nucleotide variants (SNVs) counted or a sum of the number of SNVs and the number of indel mutations counted.

The number of somatic mutations can be determined qualitatively and/or quantitatively based on any suitable criterion known in the art, including, but not limited to, the measurement of DNA, mRNA, cDNA, proteins, protein fragments, and/or gene copy number levels in an individual. In some instances, a comprehensive genomic profile of an individual is determined. In some instances, a comprehensive genomic profile of a sample (e.g., a whole blood sample, a plasma sample, a serum sample, or a combination thereof) collected from an individual is determined. In some instances, the determination of the genomic profile comprises applying next-generation sequencing methods, known in the art or described herein, to identify genomic alterations (e.g., somatic mutations (e.g., a base substitution in a coding region and/or an indel mutation in a coding region)). In some instances, the test simultaneously sequences the coding region of about 300 genes (e.g., a diverse set of at least about 300 to about 400 genes, e.g., about 300, 310, 320, 330, 340, 350, 360, 370, 380, 390, or 400 genes) covering at least about 0.05 Mb to about 10 Mb (e.g., 0.05, 0.06. 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 Mb) to a typical median depth of exon coverage of at least about 500× (e.g., 500×, 550×, 600×, 650×, 700×, 750×, 800×, 850×, 900×, 950×, or 1,000×). In other instances, the test simultaneously sequences the coding regions of about 400 genes, about 425 genes, about 450 genes, about 475 genes, about 500 genes, about 525 genes, about 550 genes, about 575 genes, about 600 genes, about 625 genes, about 650 genes, about 675 genes, about 700 genes, about 725 genes, about 750 genes, about 775 genes, about 800 genes, about 825 genes, about 850 genes, about 875 genes, about 900 genes, about 925 genes, about 950 genes, about 975 genes, about 1000 genes, or greater than 1000 genes. In some instances, the set of genes includes one or more genes (e.g., cancer-related genes) set forth in Table 1. In some instances, the set of genes is the set of genes of the FOUNDATIONONE® panel (see, e.g., Frampton et al. *Nat. Biotechnol.* 31:1023-31, 2013, which is incorporated herein by reference in its entirety). In some instances, the set of genes is the set of genes of the FOUNDATIONONE® CDx panel. In some embodiments, the test sequences greater than about 10 Mb of the genome of the individual, e.g., greater than about 10 Mb, greater than about 15 Mb, greater than about 20 Mb, greater than about 25 Mb, greater than about 30 Mb, greater than about 35 Mb, greater than about 40 Mb, greater than about 45 Mb, greater than about 50 Mb, greater than about 55 Mb, greater than about 60 Mb, greater than about 65 Mb, greater than about 70 Mb, greater than about 75 Mb, greater than about 80 Mb, greater than about 85 Mb, greater than about 90 Mb, greater than about 95 Mb, greater than about 100 Mb, greater than about 200 Mb, greater than about 300 Mb, greater than about 400 Mb, greater than about 500 Mb, greater than about 600 Mb, greater than about 700 Mb, greater than about 800 Mb, greater than about 900 Mb, greater than about 1 Gb, greater than about 2 Gb, greater than about 3 Gb, or about 3.3 Gb. In some instances, the bTMB score is determined by whole-exome sequencing. In some instances, the bTMB score is determined by whole-genome sequencing. It is presently understood that a bTMB score may be calculated independent of gene identity. In some instances, each covered sequencing read represents a unique DNA fragment to enable the highly sensitive and specific detection of genomic alterations that occur at low frequencies due to tumor heterogeneity, low tumor purity, and small sample volumes. The determination step may include determining the number of somatic mutations in cell free DNA (cfDNA) and/or circulating tumor DNA (ctDNA) isolated from the sample (e.g., a whole blood sample, a plasma sample, a serum sample, or a combination thereof) from the individual to derive a bTMB score. In some embodiments, the amount of cfDNA isolated from the sample is at least about 5 ng (e.g., at least about 5 ng, at least about 10 ng, at least about 15 ng, at least about 20 ng, at least about 25 ng, at least about 30 ng, at least about 35 ng, at least about 40 ng, at least about 45 ng, at least about 50 ng, at least about 75 ng, at least about 100 ng, at least about 200 ng, at least about 300 ng, at least about 400 ng, or more). For example, in some embodiments, the amount of cfDNA isolated from the sample is at least about 20 ng of cfDNA. In some embodiments, the amount of cfDNA isolated from the sample is, for example, from about 5 ng to about 100 ng (e.g., from about 5 ng to about 100 ng, from about 5 ng to about 90 ng, from about 5 ng to about 80 ng, from about 5 ng to about 70 ng, from about 5 ng to about 60 ng, from about 5 ng to about 50 ng, from about 5 ng to about 40 ng, from about 5 ng to about 30 ng, from about 5 ng to about 20 ng, from about 5 ng to about 15 ng, from about 5 ng to about 10 ng, from about 10 ng to about 100 ng, from about 10 ng to about 90 ng, from about 10 ng to about 80 ng, from about 10 ng to about 70 ng, from about 10 ng to about 60 ng, from about 10 ng to about 50 ng, from about 10 ng to about 40 ng, from about 10 ng to about 30 ng, from about 10 ng to about 20 ng, from about 15 ng to about 100 ng, from about 15 ng to about 90 ng, from about 15 ng to about 80 ng, from about 15 ng to about 70 ng, from about 15 ng to about 60 ng, from about 15 ng to about 50 ng, from about 20 ng to about 100 ng, from about 20 ng to about 90 ng, from about 20 ng to about 80 ng, from about 20 ng to about 70 ng, from about 20 ng to about 60 ng, from about 20 ng to about 50 ng, from about 20 ng to about 40 ng, from about 20 ng to about 30 ng, from about 25 ng to about 100 ng, from about 25 ng to about 90 ng, from about 25 ng to about 80 ng, from about 25 ng to about 70 ng, from about 25 ng to about 60 ng, from about 25 ng to about 50 ng, from about 25 ng to about 40 ng, from about 25 ng to about 30 ng, from about 30 ng to about 100 ng, from about 30 ng to about 90 ng, from about 30 ng to about 80 ng, from about 30 ng to about 70 ng, from about 30 ng to about 60 ng, from about 30 ng to about 50 ng, from about 30 ng to about 40 ng, from about 30 ng to about 35 ng, from about 35 ng to about 100 ng, from about 35 ng to about 90 ng, from about 35 ng to about 80 ng, from about 35 ng to about 70 ng, from about 35 ng to about 60 ng, from about 35 ng to about 50 ng, from about 35 ng to about 40 ng, from about 40 ng to about 100 ng, from about 40 ng to about 90 ng, from about 40 ng to about 80 ng, from about 40 ng to about 70 ng, from about 40 ng to about 60 ng, from about 40 ng to about 50 ng, from about 40 ng to about 45 ng, from about 50 ng to about 100 ng, from about 50 ng to about 90 ng, from about 50 ng to about 80 ng, from about 50 ng to about 70 ng, from about 50 ng to about 60 ng, from about 60 ng to about 100 ng, from about 60 ng to about 90 ng, from about 60 ng to about 80 ng, from about 60 ng to about 70 ng, from about 70 ng to about 100 ng, from about 70 ng to about 90 ng, from about 70 ng to about 80 ng, from about 80 ng to about 100 ng, from about 80 ng to about 90 ng, or from 90 ng to about 100 ng). In some embodiments, the amount of cfDNA isolated from the sample is about 100 ng or more (e.g., about 100 ng or more, about 200 ng or more, about 300 ng or more, about 400 ng or more, about 500 ng or more, about 600 ng or more, about 700 ng or more, about 800 ng or more, about 900 ng or more, or higher).

Any suitable sample volume may be used in any of the preceding methods. For example, in some instances, the sample (e.g., a whole blood sample, a plasma sample, a serum sample, or a combination thereof) may have a volume of about 1 mL to about 50 mL, e.g., about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 22 mL, about 24 mL, about 26 mL, about 28 mL, about 30 mL, about 32 mL, about 34 mL, about 36 mL, about 38 mL, about 40 mL, about 42 mL, about 44 mL, about 46 mL, about 48 mL, or about 50 mL. In some instances, the sample (e.g., a whole blood sample, a plasma sample, a serum sample, or a combination thereof) may have a volume of from about 1 mL to about 50 mL, from about 1 mL to about 40 mL, from about 1 mL to about 30 mL, from about 1 mL to about 20 mL, from about 1 mL to about 10 mL, from about 5 mL to about 50 mL, from about 5 mL to about 40 mL, from about 5 mL to about 30 mL, from about 5 mL to about 20 mL, from about 5 mL to about 10 mL, from about 6 mL to about 50 mL, from about 6 mL to about 40 mL, from about 6 mL to about 30 mL, from about 6 mL to about 20 mL, from about 6 mL to about 10 mL, from about 7 mL to about 50 mL, from about 7 mL to about 40 mL, from about 7 mL to about 30 mL, from about 7 mL to about 20 mL, from about 7 mL to about 10 mL, from about 8 mL to about 50 mL, from about 8 mL to about 40 mL, from about 8 mL to about 30 mL, from about 8 mL to about 20 mL, from about 8 mL to about 10 mL, from about 9 mL to about 50 mL, from about 9 mL to about 40 mL, from about 9 mL to about 30 mL, from about 9 mL to about 20 mL, from about 9 mL to about 10 mL, from about 5 mL to about 15 mL, from about 5 mL to about 14 mL, from about 5 mL to about 13 mL, from about 5 mL to about 12 mL, from about 5 mL to about 11 mL, from about 6 mL to about 15 mL, from about 6 mL to about 14 mL, from about 6 mL to about 13 mL, from about 6 mL to about 12 mL, from about 6 mL to about 11 mL, from about 7 mL to about 15 mL, from about 7 mL to about 14 mL, from about 7 mL to about 13 mL, from about 7 mL to about 12 mL, from about 7 mL to about 11 mL, from about 8 mL to about 15 mL, from about 8 mL to about 14 mL, from about 8 mL to about 13 mL, from about 8 mL to about 12 mL, from about 8 mL to about 11 mL, from about 9 mL to about 15 mL, from about 9 mL to about 14 mL, from about 9 mL to about 13 mL, from about 9 mL to about 12 mL, or from about 9 mL to about 11 mL. In some instances, the sample (e.g., a whole blood sample, a plasma sample, a serum sample, or a combination thereof) has a volume of about 10 mL. For example, in some instances, a plasma sample has a volume of 10 mL.

In some embodiments of any of the preceding methods, the somatic mutations evaluated in the assay each have an allele frequency of about 0.1% or more, e.g., about 0.1% or more, about 0.2% or more, about 0.3% or more, about 0.4% or more, about 0.5% or more, about 0.6% or more, about 0.7% or more, about 0.8% or more, about 0.9% or more, about 1.0% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, about 5.0% or more, about 6.0% or more, about 7.0% or more, about 8.0% or more, about 9.0% or more, about 10.0% or more, about 11.0% or more, about 12.0% or more, about 13.0% or more, about 14.0% or more, about 15.0% or more about 16.0% or more, about 17.0% or more, about 18.0% or more, about 19.0% or more, about 20.0% or more, or higher. For example, in some embodiments, the somatic mutations evaluated in the assay each have an allele frequency of 0.5% or more.

TABLE 1

| Cancer-related Genes | | | | | | | | | |
|---|---|---|---|---|---|---|---|---|---|
| ABL1 | BTK | CTNNB1 | FAS (TNFRSF6) | HIST1H1C | KDR | MYCN | PDK1 | RPL13 | SUFU |
| ABI1 | BTLA | CUL4A | FAT3 | CALR | KEAP1 | MYD88 | PHF6 | 5-Sep | SUZ12 |
| ABL2 | c11orf30 (EMSY) | CUL4B | FBXO11 | HIST1H1D | KIT | MYO18A | PIK3C2G | 6-Sep | SYK |
| ACSL6 | CAD | CUX1 | FBXO31 | HIST1H1E | KLHL6 | NBN | PIK3C3 | 9-Sep | TAF1 |
| ACTB | CAMTA1 | CXCR4 | FBXW7 | HIST1H2AC | KMT2A (MLL) | NCOR1 | PIK3CA | RPL15 | TBL1XR1 |
| AFF1 | CARD11 | CYP17A1 | FGF10 | HIST1H2AG | KMT2B (MLL2) | NCOR2 | PIK3CG | RPL35A | TBX3 |
| AFF4 | CARS | DAXX | FGF12 | HIST1H2AL | KMT2C (MLL3) | NCSTN | PIK3R1 | RPS14 | TCF3 |
| AKT1 | CASP8 | DDIT3 | FGF14 | HIST1H2AM | KRAS | NF1 | PIK3R2 | RPS15 | TCL1A |
| AKT2 | CBFA2T3 | DDR1 | FGF19 | HIST1H2BC | LEF1 | NF2 | PIM1 | RPS19 | TET1 |
| AKT3 | CBFB | DDR2 | FGF23 | HIST1H2BJ | LMO1 | NFE2L2 | PLAG1 | RPS26 | TET2 |
| ALK | CBL | DDX10 | FGF3 | HIST1H2BK | LRP1B | NFKBIA | PLCG2 | RPTOR | TFE3 |
| ALOX12B | CCND1 | DDX3X | FGF4 | HIST1H2BO | LRRK2 | NKX2-1 | PML | RUNX1 | TFG |
| AMER1 (FAM123B or WTX) | CCND2 | DDX6 | FGF6 | HIST1H3B | MAF | NOD1 | PMS2 | RUNX1T1 | TFPT |
| APC | CCND3 | DEK | FGF7 | HLA-A | MAFB | NOTCH1 | PNRC1 | RUNX1T1 (ETO) | TFRC |
| APCDD1 | CCNE1 | DIS3 | FGFR1 | HNF1A | MAGED1 | NOTCH2 | POT1 | RUNX2 | TGFBR2 |
| APH1A | CCT6B | DKC1 | FGFR2 | HRAS | MALT1 | NOTCH3 | POU2AF1 | S1PR2 | TIPARP |
| AR | CD22 | DLEU2 | FGFR3 | HSP90AA1 | MAP2K1 | NOTCH4 | PPP1CB | SBDS | TLL2 |
| ARAF | CD247 | DNM2 | FGFR4 | ICK | MAP2K2 | NPM1 | PPP2R1A | SDHA | TLX1 |
| ARFRP1 | CD274 (PDL1) | DNMT3A | FHIT | ID3 | MAP2K4 | NR4A3 | PRDM1 | SDHB | TLX3 |
| ARHGAP26 | CD36 | DOT1L | FLCN | IDH1 | MAP3K1 | NRAS | PRDM16 | SDHC | TMEM30A |
| ARHGAP26 (GRAF) | CD58 | DTX1 | FLI1 | IDH2 | MAP3K13 | NSD1 | PRKAR1A | SDHD | TMPRSS2 |
| ARHGEF12 | CD70 | DUSP2 | FLT1 | IGF1 | MAP3K14 | NT5C2 | PRKDC | SEC31A | TMSB4XP8 (TMSL3) |
| ARID1A | CD79A | DUSP22 | FLT3 | IGF1R | MAP3K6 | NTRK1 | PRRX1 | SERP2 | TNFAIP3 |
| ARID1B | CD79B | DUSP9 | FLT4 | IGF2 | MAP3K7 | NTRK2 | PRSS8 | SET | TNFRSF11A |
| ARID2 | CDC73 | EBF1 | FLYWCH1 | IGH | MAPK1 | NTRK3 | PSIP1 | SETBP1 | TNFRSF14 |
| ARNT | CDH1 | ECT2L | FNBP1 | IGK | MCL1 | NUMA1 | PTCH1 | SETD2 | TNFRSF17 |
| ASMTL | CDK12 | EED | FOXL2 | IGL | MDM2 | NUP214 | PTEN | SF3B1 | TNFSF9 |
| ASXL1 | CDK4 | EGFR | FOXO1 | IKBKE | MDM4 | NUP93 | PTK7 | SGK1 | TOP1 |
| ATF1 | CDK6 | EIF4A2 | FOXO3 | IKZF1 | MDS2 | NUP98 | PTPN11 | SH2B3 | TP53 |
| ATG5 | CDK8 | ELF4 | FOXO4 | IKZF2 | MECOM | NUTM2A | PTPN2 | SH3GL1 | TP63 |
| ATIC | CDKN1B | ELL | FOXP1 | IKZF3 | MED12 | OLIG2 | PTPN6 (SHP-1) | SLC1A2 | TPM3 |
| ATM | CDKN2A | ELN | FRS2 | IL21R | MEF2B | OMD | PTPRO | SMAD2 | TPM4 |
| ATR | CDKN2B | ELP2 | FSTL3 | IL3 | MEF2C | P2RY8 | RABEP1 | SMAD4 | TRAF2 |
| ATRX | CDKN2C | EML4 | FUS | IL7R | MEN1 | PAFAH1B2 | RAD21 | SMARCA1 | TRAF3 |
| ATXN1 | CDX2 | EP300 | GADD45B | INHBA | MET | PAG1 | RAD50 | SMARCA4 | TRAF5 |
| AURKA | CEBPA | EPHA3 | GAS7 | INPP4B | MIB1 | PAK3 | RAD51 | SMARCB1 | TRG |
| AURKB | CHD2 | EPHA5 | GATA1 | INPP5D (SHIP) | MITF | PAK7 | RAD51B | SMARCD1 | TRIM24 |
| AXIN1 | CHEK1 | EPHA7 | GATA2 | INSR | MKI67 | PALB2 | RAD51C | SMC1A | TRIP11 |
| AXL | CHEK2 | EPHB1 | GATA3 | IRF1 | MKL1 | PARP1 | RAD51D | SMC3 | TRRAP |
| B2M | CHIC2 | EPOR | GID4 (c17orf39) | IRF4 | MKL2 | PARP2 | RAD52 | SMO | TSC1 |
| BAP1 | CHN1 | EPS15 | GLI1 | IRF8 | MLF1 | PARP3 | RAD54L | SNX29 (RUNDC2A) | TSC2 |
| BARD1 | CHTOP (C1orf77) | ERBB2 | GLIS2 | IRS2 | MLH1 | PARP4 | RAF1 | SOCS1 | TSHR |
| BCL10 | CHUK | ERBB3 | GMPS | ITK | MLLT1 (ENL) | PASK | RALGDS | SOCS2 | TTL |
| BCL11A | CIC | ERBB4 | GNA11 | JAK1 | MLLT10 (AF10) | PAX3 | RANBP17 | SOCS3 | TUSC3 |
| BCL11B | CIITA | ERG | GNA12 | JAK2 | MLLT3 | PAX5 | RAP1GDS1 | SOX10 | TYK2 |
| BCL2 | CKS1B | ESR1 | GNA13 | JAK3 | MLLT4 (AF6) | PAX7 | RARA | SOX2 | U2AF1 |
| BCL2L2 | CLP1 | ETS1 | GNAQ | JARID2 | MLLT6 | PBRM1 | RASGEF1A | SPEN | U2AF2 |
| BCL3 | CLTC | ETV1 | GNAS | JAZF1 | MN1 | PBX1 | RB1 | SPOP | USP6 |
| BCL6 | CLTCL1 | ETV4 | GPHN | JUN | MNX1 | PC | RBM15 | SRC | VHL |
| BCL7A | CNTRL (CEP110) | ETV5 | GPR124 | KAT6A (MYST3) | MPL | PCBP1 | RCOR1 | SRSF2 | WDR90 |
| BCL9 | COL1A1 | ETV6 | GRIN2A | KDM2B | MRE11A | PCLO | REL | SRSF3 | WHSC1 |
| BCOR | CPS1 | EWSR1 | GSK3B | KDM4C | MSH2 | PCM1 | RELN | SS18 | WHSC1 (MMSET or NSD2) |
| BCORL1 | CRBN | EXOSC6 | GTSE1 | KDM5A | MSH3 | PCSK7 | RET | SSX1 | WHSC1L1 |
| BCR | CREB3L1 | EZH2 | HDAC1 | KDM5C | MSH6 | PDCD1 | RHOA | SSX2 | WISP3 |
| BIRC3 | CREB3L2 | FAF1 | HDAC4 | KDM6A | MSI2 | PDCD11 | RHOH | SSX4 | WT1 |

TABLE 1-continued

Cancer-related Genes

| | | | | | | | | | |
|---|---|---|---|---|---|---|---|---|---|
| BLM | CREBBP | FAM46C | HDAC7 | KDSR | MSN | PDCD1LG2 (PDL2) | RICTOR | STAG2 | XBP1 |
| BRAF | CRKL | FANCA | HERPUD1 | KIF5B | MTAP | PDCD1LG2 (PDL2) | RMRP | STAT3 | XPO1 |
| BRCA1 | CRLF2 | FANCC | HEY1 | LASP1 | MTCP1 | PDE4DIP | RNF213 | STAT4 | XRCC3 |
| BRCA2 | CSF1 | FANCD2 | HGF | LCK | MTOR | PDGFB | RNF43 | STAT5A | YPEL5 |
| BRD4 | CSF1R | FANCE | HIP1 | LCP1 | MUC1 | PDGFRA | ROS1 | STAT5B | YY1AP1 |
| BRIP1 (BACH1) | CSF3R | FANCF | HIST1H1A | LMO2 | MUTYH | PDGFRB | RPA1 | STAT6 | ZBTB16 |
| BRSK1 | CTCF | FANCG | HIST1H4I | LPP | MYB | PER1 | RPL11 | STK11 | ZMYM2 |
| BTG1 | CTNNA1 | FANCI | HLF | LTK | MYC | PGAM5 | RPL22 | STL | ZMYM3 |
| BTG2 | FANCM | FANCL | HMGA1 | LYL1 | MYCL (MYCL1) | PHF1 | RPN1 | TAF15 | ZNF217 |
| HSP90AB1 | FCGR2B | HOXA9 | HMGA2 | MAGEA5 | MYH11 | PICALM | TCL6 | TAL1 | ZNF24 (ZSCAN3) |
| HOXD13 | FCRL4 | HOXC11 | HOXA11 | MYH9 | NCOA2 | TEC | TAL2 | TCF3 (E2A) | ZNF384 |
| NFKBIE | FEV | HOXC13 | HOXA13 | NACA | NDRG1 | TCL1A (TCL1) | ZRSR2 | ZNF703 | ZNF521 |
| NIN | FGFR1OP | HOXD11 | HOXA3 | NBEAP1 (BCL8) | NFKB2 | | | | |

The determination step may include determining the highest relative frequency of an allele (i.e., a variant of a gene having a somatic mutation (e.g., a base substitution in a coding region and/or an indel mutation in a coding region)) from a sample (e.g., a whole blood sample, a plasma sample, a serum sample, or a combination thereof) from an individual to derive an MSAF. A somatic allele frequency for the next most commonly occurring mutation may also be determined from the sample from the individual. In some instances, a somatic allele frequency is determined for each mutation detected from the sample from the individual. In some instances, samples with multiple somatic mutations will present those mutations as a distribution of somatic allele frequencies, likely dependent upon their original clonal frequency in a cancer (e.g., a tumor). In some instances, somatic allele frequencies greater than 40% (e.g., >40%, ≥50%, ≥60%, ≥70%, ≥80%, ≥90%, or 100%) are discarded, and the variant with the next highest somatic allele frequency below 40% (e.g., ≤40%) is determined to be the MSAF for the sample. In some instances, MSAF is calculated from the largest somatic allele frequency less than 20% in the sample. Germline mutations may be found to have a somatic allele frequency distribution between about 50% and about 100%.

The determination of an MSAF may occur prior to, concurrently with, or after the determination of a bTMB score from a sample from the individual.

In any of the preceding instances, the individual may have a cancer selected from, for example, a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor.

In some instances, the individual has progressed following treatment with a platinum-containing regimen (e.g., a regimen including a platinum-based chemotherapeutic agent, e.g., a regimen including a cisplatin-based chemotherapy) for a cancer. In other instances, the individual may be ineligible for treatment with a platinum-containing regimen (e.g., a regimen including a platinum-based chemotherapeutic agent, e.g., a regimen including a cisplatin-based chemotherapy) and/or has not received prior treatment for a cancer. In some instances, the individual has not received prior treatment with an immune checkpoint inhibitor, for example, a PD-L1 axis binding antagonist, an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

In any of the preceding methods, the sample (e.g., blood sample) obtained from the patient is selected from the group consisting of a whole blood, plasma, serum, or a combination thereof. In some instances, the sample is an archival blood sample, a fresh blood sample, or a frozen blood sample.

In any of the preceding instances, the reference bTMB score may be a bTMB score in a reference population of individuals having a cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor), the population of individuals consisting of a first subset of individuals who have been treated with an immune checkpoint inhibitor, for example, a PD-L1 axis binding antagonist therapy, and a second subset of individuals who have been treated with a non-PD-L1 axis binding antagonist therapy, wherein the non-PD-L1 axis binding antagonist therapy does not comprise an immune checkpoint inhibitor, for example, a PD-L1 axis binding antagonist. In some instances, the reference bTMB score significantly separates each of the first and second subsets of individuals based on a significant difference in responsiveness to treatment with the PD-L1 axis binding antagonist therapy relative to responsiveness to treatment with the non-PD-L1 axis binding antagonist therapy. In some instances, responsiveness to treatment is an increase in progression-free survival (PFS) and/or an increase in overall survival (OS). In some instances, the reference bTMB score may be a pre-assigned bTMB score. The reference bTMB score may be between 4 and 30 (e.g., 4, 5, 6, 7, 8, 9, 10, 11, 12, 13, 14, 15, 16, 17, 18, 19, 20, 21, 22, 23, 24, 25, 26, 27, 28, 29, and 30, e.g., between 8 and 30, e.g., between 10 and 16, or, e.g., between 10 and 20). In some instances, the reference bTMB score may be between 10 and 20 (e.g., 10, 11, 12, 13, 14, 15, 16, 17, 18, 19, or 20). In other instances, the reference bTMB score may be between 16 and 20 (e.g., 16, 17, 18, 19, or 20). For example, in some instances, the reference population of individuals has a lung cancer (e.g., a non-small cell lung cancer (NSCLC)), a kidney cancer (e.g., a kidney urothelial carcinoma) and a reference bTMB score greater than, or equal to, 9. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 10. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 11. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 12. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 13. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 14. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 16. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 18. In some instances, the reference population of individuals has a bladder cancer (e.g., a bladder urothelial (transitional cell) carcinoma) and a reference bTMB score of score greater than, or equal to, 16. In some instances, the reference population of individuals has melanoma and a reference bTMB score of greater than, or equal to, 20. In some instances, the reference population of individuals has melanoma and a reference bTMB score of greater than, or equal to, 21. In some instances, the reference population of individuals has melanoma and a reference bTMB score of greater than, or equal to, 22. In some instances, the reference population of individuals has melanoma and a reference bTMB score of greater than, or equal to, 23. In some instances, the reference population of individuals has melanoma and a reference bTMB score of greater than, or equal to, 24. In some instances, the reference population of individuals has melanoma and a reference bTMB score of greater than, or equal to, 25.

In any of the preceding instances, the bTMB score from the sample may be greater than, or equal to, 4 (e.g., 4, 5, 6, 7, 8, 9, 10, 11, 12, 13, 14, 15, 16, 17, 18, 19, 20, 21, 22, 23, 24, 25, 26, 27, 28, 29, 30, or more). For example, the bTMB score from the sample may be between about 8 and about 100 (e.g., 8, 9, 10, 20, 30, 40, 50, 60, 70, 80, 90, and 100). In some instances, the bTMB score from the sample may be between about 400 and about 1500 (e.g., a bTMB score of about 400, 500, 600, 700, 800, 900, 1000, 1100, 1200, 1300, 1400, or 1500). In some instances, the bTMB score from the sample may be less than 4 (e.g., 0, 1, 2, or 3) or be undetectable.

In some embodiments of any of the preceding instances, the bTMB score (e.g., reference bTMB score) is represented as the number of somatic mutations counted over a defined number of sequenced bases (e.g., about 1.1 Mb (e.g., about 1.125 Mb), e.g., as assessed by the FOUNDATIONONE® panel). In some embodiments, the bTMB score (e.g., reference bTMB score) is an equivalent bTMB value, for example, as determined by whole-exome sequencing.

In some instances, the bTMB score from the sample from the individual may have a prevalence of greater than, or equal to, about 5%, for example, a prevalence of between about 5% and about 75% (e.g., a prevalence between about 5% and about 15%, about 15% and about 30%, about 30% and about 45%, about 45% and about 60%, or about 60% and 75%; e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) in a reference population.

In some instances, the prevalence of a bTMB score that is greater than, or equal to, a reference cut-off bTMB score is about 5%, for example, a prevalence of between about 5% and about 75% (e.g., a prevalence between about 5% and about 15%, about 15% and about 30%, about 30% and about 45%, about 45% and about 60%, or about 60% and 75%; e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) in a reference population.

In some instances, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates by less than about 30% (e.g., less than about 30%, about 25%, about 20%, about 15%, about 10%, about 5%, about 4%, about 3%, about 2%, about 1%, or less) from a bTMB score determined by whole-exome sequencing. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates about 1% to about 30% (e.g., about 1% to about 30%, about 1% to about 25%, about 1% to about 20%, about 1% to about 15%, about 1% to about 10%, about 5% to about 30%, about 5% to about 25%, about 5% to about 20%, about 5% to about 15%, about 5% to about 10%, about 10% to about 30%, about 10% to about 25%, about 10% to about 20%, about 10% to about 15%, about 15% to about 30%, about 15% to about 25%, about 15% to about 20%, about 20% to about 30%, or about 20% to about 25%) from a bTMB score determined by whole-exome sequencing. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates about 10% to about 20% (e.g., about 10%, about 11%, about 12%, about 13%, about 14%, about 15%, about 16%, about 17%, about 18%, about 19%, or about 20%) from a bTMB score determined by whole-exome sequencing. In any of the methods provided here, the benefit from the treatment comprising an immune checkpoint inhibitor, for example, a PD-L1 axis binding antagonist, may be an increase in OS, an increase in PFS, or an increase in OS and PFS.

In any of the preceding methods, the PD-L1 axis binding antagonist may be any PD-L1 axis binding antagonist known in the art or described herein, for example, in Section IV, below.

In some embodiments, the method further comprises generating a report, e.g., an electronic, web-based, or paper report, to the patient or to another person or entity, a caregiver, a physician, an oncologist, a hospital, clinic, third-party payor, insurance company, a pharmaceutical or biotechnology company, or government office. In some embodiments, the report comprises output from the method which comprises evaluation of the bTMB score.

(ii) Prognostic and Pharmacodynamic Diagnostic Methods

The invention provides prognostic and pharmacodynamic methods. In some instances, the methods may involve providing a prognosis for an individual having a cancer. In other instances, the methods may involve monitoring a response of a patient to treatment with an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In particular instances, the methods and assays provided herein may be used to determine whether an individual having a cancer is likely to respond to treatment with an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, the method including determining a bTMB score from a sample from the individual, wherein a bTMB score from the sample that is at or above a reference bTMB score identifies the individual as one who is likely to respond to treatment comprising an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In some instances, a bTMB score from the sample that is below a reference bTMB score identifies the individual as one who is less likely to respond to treatment comprising an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

In one aspect, provided herein is a method of providing a prognosis for an individual having a cancer, the method including determining a bTMB score from a sample from the individual, wherein a bTMB score from the sample that is at or above a reference bTMB score identifies the individual as one who may have a poor prognosis.

In one aspect, provided herein is a method of providing a prognosis for an individual having a cancer, the method including determining a level of ctDNA from a sample from the individual, wherein a level of ctDNA from the sample that is at or above a reference level of ctDNA identifies the individual as one who may have a poor prognosis.

In another aspect, provided herein is a method of providing a prognosis for an individual having a cancer, the method including determining an MSAF from a sample from the individual, wherein an MSAF from the sample that is at or above a reference MSAF identifies the individual as one who may have a poor prognosis. MSAF can be determined using any suitable approach, for example, as described below in Section C, or as described in the Examples.

In another aspect, provided herein is a method of assessing a clinicopathological variable of an individual having a cancer, the method comprising determining a bTMB score in a sample obtained from the individual. The clinicopathological variable may be, e.g., tumor burden, SLD, or tumor histology (e.g., squamous or non-squamous morphology).

In another aspect, provided herein is a method of assessing a clinicopathological variable of an individual having a cancer, the method comprising determining an MSAF in a sample obtained from the individual. The clinicopathological variable may be, e.g., tumor burden, SLD, or tumor histology (e.g., squamous or non-squamous morphology).

In yet another aspect, provided herein is a method of predicting disease progression in an individual having a cancer, the method comprising determining a bTMB score in a sample obtained from the individual, wherein a bTMB score in the sample that is at or above a reference bTMB score identifies the individual as one who is more likely to exhibit disease progression. In some embodiments, disease progression is an increase in tumor burden. In some embodiments, the increase in tumor burden is characterized by an increase in the sum of longest diameters (SLD). In some embodiments, disease progression is characterized by an increase in squamous morphology, e.g., as assessed by tumor histology. In other embodiments, disease progression is characterized by an increase in non-squamous morphology, e.g., as assessed by tumor histology.

In a still further aspect, provided herein is a method of predicting disease progression in an individual having a cancer, the method comprising determining an MSAF in a sample obtained from the individual, wherein an MSAF in the sample that is at or above a reference MSAF identifies the individual as one who is more likely to exhibit disease progression. In some embodiments, disease progression is an increase in tumor burden. In some embodiments, the increase in tumor burden is characterized by an increase in the sum of longest diameters (SLD). In some embodiments, disease progression is characterized by an increase in squamous morphology, e.g., as assessed by tumor histology. In other embodiments, disease progression is characterized by an increase in non-squamous morphology, e.g., as assessed by tumor histology. In some embodiments of any of the preceding methods, the MSAF from the sample from the individual is about 0.01% to about 10%, e.g., about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10%.

In some embodiments, the MSAF from the sample from the individual is about 0.01% to about 10%, about 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2%, about 0.01% to about 1%, about 0.05% to about 10%, about 0.05% to about 9%, about 0.05% to about 8%, about 0.05% to about 7%, about 0.05% to about 6%, about 0.05% to about 5%, about 0.05% to about 4%, about 0.05% to about 3%, about 0.05% to about 2%, about 0.05% to about 1%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, or about 0.1% to about 1%, In particular embodiments, the MSAF from the sample from the individual is about 0.1% to about 5%. In other particular embodiments, the MSAF from the sample from the individual is about 0.1% to about 2%.

In some embodiments, the MSAF from the sample from the individual is about 0.1% to about 5%, about 0.1% to about 4.5%, about 0.1% to about 4%, about 0.1% to about 3.5%, about 0.1% to about 3%, about 0.1% to about 2.5%, about 0.1% to about 2%, about 0.1% to about 1.5%, about 0.1% to about 1%, about 0.1% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, about 0.1% to about 0.2%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 0.5% to about 0.9%, about 0.5% to about 0.8%, about 0.5% to about 0.7%, about 0.5% to about 0.6%, about 1% to about 5%, about 1% to about 4.5%, about 1% to about 4%, about 1% to about 3.5%, about 1% to about 3%, about 1% to about 2.5%, about 1% to about 2%, about 1% to about 1.5%, about 1% to about 1.25%, about 1.25% to about 5%, about 1.25% to about 4.5%, about 1.25% to about 4%, about 1.25% to about 3.5%, about 1.25% to about 3%, about 1.25% to about 2.5%, about 1.25% to about 2%, about 1.25% to about 1.5%, about 1.5% to about 5%, about 1.5% to about 4.5%, about 1.5% to about 4%, about 1.5% to about 3.5%, about 1.5% to about 3%, about 1.5% to about 2.5%, about 1.5% to about 2%, about 1.75% to about 5%, about 1.75% to about 4.5%, about 1.75% to about 4%, about 1.75% to about 3.5%, about 1.75% to about 3%, about 1.75% to about 2.5%, about 1.75% to about 2%, about 2% to about 5%, about 2% to about 4.5%, about 2% to about 4%, about 2% to about 3.5%, about 2% to about 3%, about 2% to about 2.5%, about 2.5% to about 5%, about 2.5% to about 4.5%, about 2.5% to about 4%, about 2.5% to about 3.5%, about 2.5% to about 3%, about 3% to about 5%, about 3% to about 4.5%, about 3% to about 4%, about 3% to about 3.5%, about 3.5% to about 5%, about 3.5% to about 4.5%, about 3.5% to about 4%, about 4% to about 5%, or about 4% to about 4.5%.

In some embodiments, the baseline MSAF from the sample from the individual is about 0.1% to about 5%, about 0.1% to about 4.5%, about 0.1% to about 4%, about 0.1% to about 3.5%, about 0.1% to about 3%, about 0.1% to about 2.5%, about 0.1% to about 2%, about 0.1% to about 1.5%, about 0.1% to about 1%, about 0.1% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, about 0.1% to about 0.2%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 0.5% to about 0.9%, about 0.5% to about 0.8%, about 0.5% to about 0.7%, about 0.5% to about 0.6%, about 1% to about 5%, about 1% to about 4.5%, about 1% to about 4%, about 1% to about 3.5%, about 1% to about 3%, about 1% to about 2.5%, about 1% to about 2%, about 1% to about 1.5%, about 1% to about 1.25%, about 1.25% to about 5%, about 1.25% to about 4.5%, about 1.25% to about 4%, about 1.25% to about 3.5%, about 1.25% to about 3%, about 1.25% to about 2.5%, about 1.25% to about 2%, about 1.25% to about 1.5%, about 1.5% to about 5%, about 1.5% to about 4.5%, about 1.5% to about 4%, about 1.5% to about 3.5%, about 1.5% to about 3%, about 1.5% to about 2.5%, about 1.5% to about 2%, about 1.75% to about 5%, about 1.75% to about 4.5%, about 1.75% to about 4%, about 1.75% to about 3.5%, about 1.75% to about 3%, about 1.75% to about 2.5%, about 1.75% to about 2%, about 2% to about 5%, about 2% to about 4.5%, about 2% to about 4%, about 2% to about 3.5%, about 2% to about 3%, about 2% to about 2.5%, about 2.5% to about 5%, about 2.5% to about 4.5%, about 2.5% to about 4%, about 2.5% to about 3.5%, about 2.5% to about 3%, about 3% to about 5%, about 3% to about 4.5%, about 3% to about 4%, about 3% to about 3.5%, about 3.5% to about 5%, about 3.5% to about 4.5%, about 3.5% to about 4%, about 4% to about 5%, or about 4% to about 4.5%.

In some embodiments, the baseline MSAF from the sample from the individual is about 0.1% to about 5%, about 0.1% to about 4.5%, about 0.1% to about 4%, about 0.1% to about 3.5%, about 0.1% to about 3%, about 0.1% to about 2.5%, about 0.1% to about 2%, about 0.1% to about 1.5%, about 0.1% to about 1%, about 0.1% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, about 0.1% to about 0.2%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 0.5% to about 0.9%, about 0.5% to about 0.8%, about 0.5% to about 0.7%, about 0.5% to about 0.6%, about 1% to about 5%, about 1% to about 4.5%, about 1% to about 4%, about 1% to about 3.5%, about 1% to about 3%, about 1% to about 2.5%, about 1% to about 2%, about 1% to about 1.5%, about 1% to about 1.25%, about 1.25% to about 5%, about 1.25% to about 4.5%, about 1.25% to about 4%, about 1.25% to about 3.5%, about 1.25% to about 3%, about 1.25% to about 2.5%, about 1.25% to about 2%, about 1.25% to about 1.5%, about 1.5% to about 5%, about 1.5% to about 4.5%, about 1.5% to about 4%, about 1.5% to about 3.5%, about 1.5% to about 3%, about 1.5% to about 2.5%, about 1.5% to about 2%, about 1.75% to about 5%, about 1.75% to about 4.5%, about 1.75% to about 4%, about 1.75% to about 3.5%, about 1.75% to about 3%, about 1.75% to about 2.5%, about 1.75% to about 2%, about 2% to about 5%, about 2% to about 4.5%, about 2% to about 4%, about 2% to about 3.5%, about 2% to about 3%, about 2% to about 2.5%, about 2.5% to about 5%, about 2.5% to about 4.5%, about 2.5% to about 4%, about 2.5% to about 3.5%, about 2.5% to about 3%, about 3% to about 5%, about 3% to about 4.5%, about 3% to about 4%, about 3% to about 3.5%, about 3.5% to about 5%, about 3.5% to about 4.5%, about 3.5% to about 4%, about 4% to about 5%, or about 4% to about 4.5%.

In some embodiments of any of the preceding methods, the sample from the individual is obtained from the individual prior to administration of an anti-cancer therapy (e.g., an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof). In other words, the sample may be a baseline sample.

Any of the preceding methods may include selecting an anti-cancer therapy for the individual. In some embodiments, the method further comprises administering an anti-cancer therapy to the individual. In some embodiments, the anti-cancer therapy is selected and/or administered to the individual as soon as possible. In some embodiments, the anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In some embodiments, the method may further include selecting and/or administering an anti-cancer therapy that includes an immune checkpoint inhibitor in combination with an additional therapeutic agent (e.g., a chemotherapeutic agent) to the individual. In some embodiments, the method may further include selecting and/or administering an anti-cancer therapy that does not include an immune checkpoint inhibitor to the individual, for example, an anti-cancer therapy that includes a chemotherapeutic agent. In some embodiments, the chemotherapeutic agent is any chemotherapeutic agent described herein or known in the art. In some embodiments, the anti-cancer therapy includes a cytotoxic combination (e.g., a more aggressive cytotoxic combination).

In yet another aspect, provided herein is a method of monitoring a response of an individual having a cancer to treatment with an anti-cancer therapy that includes an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, the method including: (a) determining a bTMB score in a sample obtained from an individual at a time point following administration of the anti-cancer therapy to the individual; and (b) comparing the bTMB score in the sample to a reference bTMB score, thereby monitoring the response in the individual to the treatment with the anti-cancer therapy. In some embodiments, the method further comprises administering one or more additional doses of the anti-cancer therapy if the bTMB score in the sample decreases relative to the reference bTMB score. In other embodiments, the method may further include selecting an anti-cancer therapy that does not include an immune checkpoint inhibitor for the individual if the bTMB score in the sample increases relative to the reference bTMB score. In other embodiments, the method may further include selecting an anti-cancer therapy that includes an immune checkpoint inhibitor in combination with an additional therapeutic agent for the individual if the bTMB score in the sample increases or remains the same relative to the reference bTMB score. In some embodiments, the method may further include administering the anti-cancer therapy that does not include an immune checkpoint inhibitor to the individual, for example, an anti-cancer therapy that includes a chemotherapeutic agent. In some embodiments, the chemotherapeutic agent is any chemotherapeutic agent described herein or known in the art.

The methods provided herein may include determining a bTMB score or a MSAF from a sample (e.g., a whole blood sample, a plasma sample, a serum sample, or a combination thereof) from an individual. The sample from the individual may be an archival sample, a fresh sample, or a frozen sample. The determination step may include determining the total number of somatic mutations (e.g., a base substitution in a coding region and/or an indel mutation in a coding region) occurring in a pre-determined set of genes to derive a bTMB score from the sample from the individual. In some embodiments, the number of somatic mutations is the number of SNVs counted or a sum of the number of SNVs and the number of indel mutations counted.

The number of somatic mutations can be determined qualitatively and/or quantitatively based on any suitable criterion known in the art, including, but not limited to, the measurement of DNA, mRNA, cDNA, proteins, protein fragments, and/or gene copy number levels in an individual. In some instances, a comprehensive genomic profile of an individual is determined from a sample (e.g., a whole blood sample, a plasma sample, a serum sample, or a combination thereof) collected from an individual. In some instances, the determination of the genomic profile comprises applying next-generation sequencing methods, known in the art or described herein, to identify genomic alterations (e.g., somatic mutations (e.g., a base substitution in a coding region and/or an indel mutation in a coding region)). In some instances, the test simultaneously sequences the coding region of about 300 genes (e.g., a set of at least about 300 to about 400 genes, e.g., about 300, 310, 320, 330, 340, 350, 360, 370, 380, 390, or 400 genes) covering at least about 0.05 Mb to about 10 Mb (e.g., 0.05, 0.06. 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 Mb) to a typical median depth of exon coverage of at least about 500× (e.g., 500×, 550×, 600×, 650×, 700×, 750×, 800×, 850×, 900×, 950×, or 1,000×). In other instances, the test simultaneously sequences the coding regions of about 400 genes, about 425 genes, about 450 genes, about 475 genes, about 500 genes, about 525 genes, about 550 genes, about 575 genes, about 600 genes, about 625 genes, about 650 genes, about 675 genes, about 700 genes, about 725 genes, about 750 genes, about 775 genes, about 800 genes, about 825 genes, about 850 genes, about 875 genes, about 900 genes, about 925 genes, about 950 genes, about 975 genes, about 1000 genes, or greater than 1000 genes. In some instances, the set of genes includes at least two genes (e.g., cancer related genes) set forth in Table 1. In some instances, the set of genes is the set of genes of the FOUNDATIONONE® panel. In some instances, the set of genes is the set of genes of the FOUNDATIONONE® CDx panel. In some embodiments, the test sequences greater than about 10 Mb of the genome of the individual, e.g., greater than about 10 Mb, greater than about 15 Mb, greater than about 20 Mb, greater than about 25 Mb, greater than about 30 Mb, greater than about 35 Mb, greater than about 40 Mb, greater than about 45 Mb, greater than about 50 Mb, greater than about 55 Mb, greater than about 60 Mb, greater than about 65 Mb, greater than about 70 Mb, greater than about 75 Mb, greater than about 80 Mb, greater than about 85 Mb, greater than about 90 Mb, greater than about 95 Mb, greater than about 100 Mb, greater than about 200 Mb, greater than about 300 Mb, greater than about 400 Mb, greater than about 500 Mb, greater than about 600 Mb, greater than about 700 Mb, greater than about 800 Mb, greater than about 900 Mb, greater than about 1 Gb, greater than about 2 Gb, greater than about 3 Gb, or about 3.3 Gb. In some instances, the bTMB score is determined by whole-exome sequencing. In some instances, the bTMB score is determined by whole-genome sequencing. A bTMB score may be calculated independent of gene identity. In some instances, each covered sequencing read represents a unique DNA fragment to enable the highly sensitive and specific detection of genomic alterations that occur at low frequencies due to tumor heterogeneity, low tumor purity, and small sample volumes.

The determination step may include determining the number of somatic mutations in cell free DNA (cfDNA) and/or circulating tumor DNA (ctDNA) isolated from the sample (e.g., a whole blood sample, a plasma sample, a serum sample, or a combination thereof) from the individual to derive a bTMB score. In some embodiments, the amount of cfDNA isolated from the sample is at least about 5 ng (e.g., at least about 5 ng, at least about 10 ng, at least about 15 ng, at least about 20 ng, at least about 25 ng, at least about 30 ng, at least about 35 ng, at least about 40 ng, at least about 45 ng, at least about 50 ng, at least about 75 ng, at least about 100 ng, at least about 200 ng, at least about 300 ng, at least about 400 ng, or more). For example, in some embodiments, the amount of cfDNA isolated from the sample is at least about 20 ng of cfDNA. In some embodiments, the amount of cfDNA isolated from the sample is, for example, from about 5 ng to about 100 ng (e.g., from about 5 ng to about 100 ng, from about 5 ng to about 90 ng, from about 5 ng to about 80 ng, from about 5 ng to about 70 ng, from about 5 ng to about 60 ng, from about 5 ng to about 50 ng, from about 5 ng to about 40 ng, from about 5 ng to about 30 ng, from about 5 ng to about 20 ng, from about 5 ng to about 15 ng, from about 5 ng to about 10 ng, from about 10 ng to about 100 ng, from about 10 ng to about 90 ng, from about 10 ng to about 80 ng, from about 10 ng to about 70 ng, from about 10 ng to about 60 ng, from about 10 ng to about 50 ng, from about 10 ng to about 40 ng, from about 10 ng to about 30 ng, from about 10 ng to about 20 ng, from about 15 ng to about 100 ng, from about 15 ng to about 90 ng, from about 15 ng to about 80 ng, from about 15 ng to about 70 ng, from about 15 ng to about 60 ng, from about 15 ng to about 50 ng, from about 20 ng to about 100 ng, from about 20 ng to about 90 ng, from about 20 ng to about 80 ng, from about 20 ng to about 70 ng, from about 20 ng to about 60 ng, from about 20 ng to about 50 ng, from about 20 ng to about 40 ng, from about 20 ng to about 30 ng, from about 25 ng to about 100 ng, from about 25 ng to about 90 ng, from about 25 ng to about 80 ng, from about 25 ng to about 70 ng, from about 25 ng to about 60 ng, from about 25 ng to about 50 ng, from about 25 ng to about 40 ng, from about 25 ng to about 30 ng, from about 30 ng to about 100 ng, from about 30 ng to about 90 ng, from about 30 ng to about 80 ng, from about 30 ng to about 70 ng, from about 30 ng to about 60 ng, from about 30 ng to about 50 ng, from about 30 ng to about 40 ng, from about 30 ng to about 35 ng, from about 35 ng to about 100 ng, from about 35 ng to about 90 ng, from about 35 ng to about 80 ng, from about 35 ng to about 70 ng, from about 35 ng to about 60 ng, from about 35 ng to about 50 ng, from about 35 ng to about 40 ng, from about 40 ng to about 100 ng, from about 40 ng to about 90 ng, from about 40 ng to about 80 ng, from about 40 ng to about 70 ng, from about 40 ng to about 60 ng, from about 40 ng to about 50 ng, from about 40 ng to about 45 ng, from about 50 ng to about 100 ng, from about 50 ng to about 90 ng, from about 50 ng to about 80 ng, from about 50 ng to about 70 ng, from about 50 ng to about 60 ng, from about 60 ng to about 100 ng, from about 60 ng to about 90 ng, from about 60 ng to about 80 ng, from about 60 ng to about 70 ng, from about 70 ng to about 100 ng, from about 70 ng to about 90 ng, from about 70 ng to about 80 ng, from about 80 ng to about 100 ng, from about 80 ng to about 90 ng, or from 90 ng to about 100 ng). In some embodiments, the amount of cfDNA isolated from the sample is about 100 ng or more (e.g., about 100 ng or more, about 200 ng or more, about 300 ng or more, about 400 ng or more, about 500 ng or more, about 600 ng or more, about 700 ng or more, about 800 ng or more, about 900 ng or more, or higher).

In some embodiments of any of the preceding methods, the somatic mutations evaluated in the assay each have an allele frequency of about 0.1% or more, e.g., about 0.1% or more, about 0.2% or more, about 0.3% or more, about 0.4% or more, about 0.5% or more, about 0.6% or more, about 0.7% or more, about 0.8% or more, about 0.9% or more, about 1.0% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, about 5.0% or more, about 6.0% or more, about 7.0% or more, about 8.0% or more, about 9.0% or more, about 10.0% or more, about 11.0% or more, about 12.0% or more, about 13.0% or more, about 14.0% or more, about 15.0% or more about 16.0% or more, about 17.0% or more, about 18.0% or more, about 19.0% or more, about 20.0% or more, or higher. For example, in some embodiments, the somatic mutations evaluated in the assay each have an allele frequency of 0.5% or more. Any suitable sample volume may be used in any of the preceding methods. For example, in some instances, the sample (e.g., a whole blood sample, a plasma sample, a serum sample, or a combination thereof) may have a volume of about 1 mL to about 50 mL, e.g., about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 22 mL, about 24 mL, about 26 mL, about 28 mL, about 30 mL, about 32 mL, about 34 mL, about 36 mL, about 38 mL, about 40 mL, about 42 mL, about 44 mL, about 46 mL, about 48 mL, or about 50 mL. In some instances, the sample (e.g., a whole blood sample, a plasma sample, a serum sample, or a combination thereof) may have a volume of from about 1 mL to about 50 mL, from about 1 mL to about 40 mL, from about 1 mL to about 30 mL, from about 1 mL to about 20 mL, from about 1 mL to about 10 mL, from about 5 mL to about 50 mL, from about 5 mL to about 40 mL, from about 5 mL to about 30 mL, from about 5 mL to about 20 mL, from about 5 mL to about 10 mL, from about 6 mL to about 50 mL, from about 6 mL to about 40 mL, from about 6 mL to about 30 mL, from about 6 mL to about 20 mL, from about 6 mL to about 10 mL, from about 7 mL to about 50 mL, from about 7 mL to about 40 mL, from about 7 mL to about 30 mL, from about 7 mL to about 20 mL, from about 7 mL to about 10 mL, from about 8 mL to about 50 mL, from about 8 mL to about 40 mL, from about 8 mL to about 30 mL, from about 8 mL to about 20 mL, from about 8 mL to about 10 mL, from about 9 mL to about 50 mL, from about 9 mL to about 40 mL, from about 9 mL to about 30 mL, from about 9 mL to about 20 mL, from about 9 mL to about 10 mL, from about 5 mL to about 15 mL, from about 5 mL to about 14 mL, from about 5 mL to about 13 mL, from about 5 mL to about 12 mL, from about 5 mL to about 11 mL, from about 6 mL to about 15 mL, from about 6 mL to about 14 mL, from about 6 mL to about 13 mL, from about 6 mL to about 12 mL, from about 6 mL to about 11 mL, from about 7 mL to about 15 mL, from about 7 mL to about 14 mL, from about 7 mL to about 13 mL, from about 7 mL to about 12 mL, from about 7 mL to about 11 mL, from about 8 mL to about 15 mL, from about 8 mL to about 14 mL, from about 8 mL to about 13 mL, from about 8 mL to about 12 mL, from about 8 mL to about 11 mL, from about 9 mL to about 15 mL, from about 9 mL to about 14 mL, from about 9 mL to about 13 mL, from about 9 mL to about 12 mL, or from about 9 mL to about 11 mL. In some instances, the sample (e.g., a whole blood sample, a plasma sample, a serum sample, or a combination thereof) has a volume of about 10 mL. For example, in some instances, a plasma sample has a volume of 10 mL. The determination step may include determining the highest relative frequency of an allele (i.e., a variant of a gene having a somatic mutation (e.g., a base substitution in a coding region and/or an indel mutation in a coding region)) from a sample (e.g., a whole blood sample, a plasma sample, a serum sample, or a combination thereof) from an individual to derive an MSAF. A somatic allele frequency for the next most commonly occurring mutation may also be determined from the sample from the individual. In some instances, a somatic allele frequency is determined for each mutation detected from the sample from the individual. In some instances, samples with multiple somatic mutations will present those mutations as a distribution of somatic allele frequencies, likely dependent upon their original clonal frequency in a cancer (e.g., a tumor). In some instances, somatic allele frequencies greater than 40% (e.g., >40%, ≥50%, ≥60%, ≥70%, ≥80%, ≥90%, or 100%) are discarded, and the variant with the next highest somatic allele frequency below 40% (e.g., ≤40%) is determined to be the MSAF for the sample. In some instances, MSAF is calculated from the largest somatic allele frequency less than 20% in the sample. Germline mutations may be found to have a somatic allele frequency distribution between about 50% and about 100%.

In any of the preceding instances, the individual may have a cancer selected from, for example, a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor.

In some instances, the individual has progressed following treatment with a platinum-containing regimen (e.g., a regimen including a platinum-based chemotherapeutic agent, e.g., a regimen including a cisplatin-based chemotherapy) for a cancer. In other instances, the individual may be ineligible for treatment with a platinum-containing regimen (e.g., a regimen including a platinum-based chemotherapeutic agent, e.g., a regimen including a cisplatin-based chemotherapy) and/or has not received prior treatment for a cancer. In some instances, the individual has not received prior treatment with an immune checkpoint inhibitor, for example, a PD-L1 axis binding antagonist.

In any of the preceding methods, the sample (e.g., blood sample) obtained from the patient is selected from the group consisting of a whole blood, plasma, serum, or a combination thereof. In some instances, the sample is an archival blood sample, a fresh blood sample, or a frozen blood sample.

In any of the preceding instances, the reference bTMB score may be a bTMB score in a reference population of individuals having a cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor), the population of individuals consisting of a first subset of individuals who have been treated with an immune checkpoint inhibitor, for example, a PD-L1 axis binding antagonist therapy, and a second subset of individuals who have been treated with a non-PD-L1 axis binding antagonist therapy, wherein the non-PD-L1 axis binding antagonist therapy does not comprise an immune checkpoint inhibitor, for example, a PD-L1 axis binding antagonist. In some instances, the reference bTMB score significantly separates each of the first and second subsets of individuals based on a significant difference in responsiveness to treatment with the PD-L1 axis binding antagonist therapy relative to responsiveness to treatment with the non-PD-L1 axis binding antagonist therapy. In some instances, responsiveness to treatment is an increase in progression-free survival (PFS) and/or an increase in overall survival (OS). In some instances, the reference bTMB score may be a pre-assigned bTMB score. The reference bTMB score may be between 4 and 30 (e.g., 4, 5, 6, 7, 8, 9, 10, 11, 12, 13, 14, 15, 16, 17, 18, 19, 20, 21, 22, 23, 24, 25, 26, 27, 28, 29, and 30, e.g., between 8 and 30, e.g., between 10 and 16, or, e.g., between 10 and 20). In some instances, the reference bTMB score may be between 10 and 20 (e.g., 10, 11, 12, 13, 14, 15, 16, 17, 18, 19, or 20). In other instances, the reference bTMB score may be between 16 and 20 (e.g., 16, 17, 18, 19, or 20). In some instances, the reference population of individuals has a lung cancer (e.g., a non-small cell lung cancer (NSCLC)), a kidney cancer (e.g., a kidney urothelial carcinoma) and a reference bTMB score greater than, or equal to, 14. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 16. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 18. In some instances, the reference population of individuals has a bladder cancer (e.g., a bladder urothelial (transitional cell) carcinoma) and a reference bTMB score of score greater than, or equal to, 16. In some instances, the reference population of individuals has melanoma and a reference bTMB score of greater than, or equal to, 20. In some instances, the reference population of individuals has melanoma and a reference bTMB score of greater than, or equal to, 21. In some instances, the reference population of individuals has melanoma and a reference bTMB score of greater than, or equal to, 22. In some instances, the reference population of individuals has melanoma and a reference bTMB score of greater than, or equal to, 23. In some instances, the reference population of individuals has melanoma and a reference bTMB score of greater than, or equal to, 24. In some instances, the reference population of individuals has melanoma and a reference bTMB score of greater than, or equal to, 25.

In any of the preceding instances, the bTMB score from the sample may be greater than, or equal to, 4 (e.g., 4, 5, 6, 7, 8, 9, 10, 11, 12, 13, 14, 15, 16, 17, 18, 19, 20, 21, 22, 23, 24, 25, 26, 27, 28, 29, 30, or more). For example, the bTMB score from the sample may be between about 8 and about 100 (e.g., 8, 9, 10, 20, 30, 40, 50, 60, 70, 80, 90, and 100). In some instances, the bTMB score from the sample may be between about 400 and about 1500 (e.g., a bTMB score of about 400, 500, 600, 700, 800, 900, 1000, 1100, 1200, 1300, 1400, or 1500). In some instances, the bTMB score from the sample may be less than 4 (e.g., 0, 1, 2, or 3) or be undetectable.

In some embodiments of any of the preceding instances, the bTMB score (e.g., reference bTMB score) is represented as the number of somatic mutations counted over a defined number of sequenced bases (e.g., about 1.1 Mb (e.g., about 1.125 Mb), e.g., as assessed by the FOUNDATIONONE® panel). In some embodiments, the bTMB score (e.g., reference bTMB score) is an equivalent bTMB value, for example, as determined by whole-exome sequencing.

In some instances, the bTMB score from the sample from the individual may have a prevalence of greater than, or equal to, about 5%, for example, a prevalence of between about 5% and about 75% (e.g., a prevalence between about 5% and about 15%, about 15% and about 30%, about 30% and about 45%, about 45% and about 60%, or about 60% and 75%; e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) in a reference population.

In some instances, the prevalence of a bTMB score that is greater than, or equal to, a reference cut-off bTMB score is about 5%, for example, a prevalence of between about 5% and about 75% (e.g., a prevalence between about 5% and about 15%, about 15% and about 30%, about 30% and about 45%, about 45% and about 60%, or about 60% and 75%; e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) in a reference population.

In some instances, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates by less than about 30% (e.g., less than about 30%, about 25%, about 20%, about 15%, about 10%, about 5%, about 4%, about 3%, about 2%, about 1%, or less) from a bTMB score determined by whole-exome sequencing. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates about 1% to about 30% (e.g., about 1% to about 30%, about 1% to about 25%, about 1% to about 20%, about 1% to about 15%, about 1% to about 10%, about 5% to about 30%, about 5% to about 25%, about 5% to about 20%, about 5% to about 15%, about 5% to about 10%, about 10% to about 30%, about 10% to about 25%, about 10% to about 20%, about 10% to about 15%, about 15% to about 30%, about 15% to about 25%, about 15% to about 20%, about 20% to about 30%, or about 20% to about 25%) from a bTMB score determined by whole-exome sequencing. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates about 10% to about 20% (e.g., about 10%, about 11%, about 12%, about 13%, about 14%, about 15%, about 16%, about 17%, about 18%, about 19%, or about 20%) from a bTMB score determined by whole-exome sequencing.

In any of the methods provided here, the benefit from the treatment comprising an immune checkpoint inhibitor, for example, a PD-L1 axis binding antagonist, may be an increase in OS, an increase in PFS, or an increase in OS and PFS.

In any of the preceding methods, the PD-L1 axis binding antagonist may be any PD-L1 axis binding antagonist known in the art or described herein, for example, in Section IV, below.

In some embodiments, the method further comprises generating a report, e.g., an electronic, web-based, or paper report, to the patient or to another person or entity, a caregiver, a physician, an oncologist, a hospital, clinic, third-party payor, insurance company, a pharmaceutical or biotechnology company, or government office. In some embodiments, the report comprises output from the method which comprises evaluation of the bTMB score.

B. Therapeutic Methods

The invention further provides methods for treating an individual having a cancer, the methods including determining a bTMB score from a sample from the individual, wherein the bTMB score from the sample is at or above a reference bTMB score (e.g., a bTMB score in a reference population, e.g., a reference bTMB score between about 4 and about 30, e.g., a reference bTMB score of about 4, 5, 6, 7, 8, 9, 10, 11, 12, 13, 14, 15, 16, 17, 18, 19, 20, 21, 22, 23, 24, 25, 26, 27, 28, 29, or 30), and administering an effective amount of an immune checkpoint inhibitor, for example, a PD-L1 axis binding antagonist (e.g., anti-PD-L1 antibody, e.g., atezolizumab (MPDL3280A)), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, to the individual. In some instances, the reference bTMB score may be between 10 and 20 (e.g., 10, 11, 12, 13, 14, 15, 16, 17, 18, 19, or 20). In other instances, the reference bTMB score may be between 16 and 20 (e.g., 16, 17, 18, 19, or 20). In some instances, a bTMB score from a sample from an individual is less than a reference bTMB score (e.g., a reference bTMB score between about 4 and about 30, e.g., a reference bTMB score of about 4, 5, 6, 7, 8, 9, 10, 11, 12, 13, 14, 15, 16, 17, 18, 19, 20, 21, 22, 23, 24, 25, 26, 27, 28, 29, or 30) and the method further includes administering to the individual an anti-cancer therapy other than, or in addition to, an immune checkpoint inhibitor, for example, a PD-L1 axis binding antagonist, an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In some instances, the bTMB score from a sample from the individual is between about 8 and about 100 (e.g., 8, 9, 10, 15, 20, 25, 30, 35, 40, 45, 50, 55, 60, 65, 70, 75, 80, 85, 90, 95, or 100).

In particular instances, the methods and assays provided herein may be used to optimize therapeutic efficacy of an anti-cancer therapy that may include an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, the method including monitoring the bTMB score from a sample form the individual relative to a reference bTMB score during treatment (e.g., over a treatment period) with the anti-cancer therapy. Monitoring may include, for example, obtaining and comparing bTMB scores from samples from the individual collected at time intervals before and/or after administration of the anti-cancer therapy. In some instances, a bTMB score may be obtained from a sample from the individual that was collected at least about 1, 2, 3, 4, 5, 6, 7, 8, 9, 10, 11, 12, 13, 14, 15, 16, 17, 18, 19, 20, 21, 22, 23, or 24 hours; about 1, 2, 3, 4, 5, 6, 7 days; about 1, 2, 3, or 4 weeks; or about 1, 2, 3, 4, 5, 6, 7, 8, 9, 10, 11, or 12 months before administration of an anti-cancer therapy. In some instances, a bTMB score may be obtained from a sample from the individual that was collected at least about 1, 2, 3, 4, 5, 6, 7, 8, 9, 10, 11, 12, 13, 14, 15, 16, 17, 18, 19, 20, 21, 22, 23, or 24 hours; about 1, 2, 3, 4, 5, 6, 7 days; about 1, 2, 3, or 4 weeks; or about 1, 2, 3, 4, 5, 6, 7, 8, 9, 10, 11, or 12 months after administration of an anti-cancer therapy. The bTMB scores from samples from the individual collected before and/or after the administration of the anti-cancer therapy may be compared, wherein an increase in bTMB score from a sample from the individual collected before treatment relative to a bTMB score from a sample collected after treatment may indicate a low level of therapeutic efficacy of the anti-cancer therapy that was administered, and wherein a decrease in bTMB score from a sample from the individual collected before treatment relative to a bTMB score from a sample collected after treatment may indicate therapeutic efficacy of the anti-cancer therapy that was administered. In some instances, the reference bTMB score may be obtained from the individual prior to treatment with an anti-cancer therapy. In some instances, the method includes monitoring the bTMB score from a sample form the individual relative to a pre-treatment bTMB score during treatment (e.g., over a treatment period) with the anti-cancer therapy.

The determination step may include determining the number of somatic mutations in cell free DNA (cfDNA) and/or circulating tumor DNA (ctDNA) isolated from the sample (e.g., a whole blood sample, a plasma sample, a serum sample, or a combination thereof) from the individual to derive a bTMB score. In some embodiments, the amount of cfDNA isolated from the sample is at least about 5 ng (e.g., at least about 5 ng, at least about 10 ng, at least about 15 ng, at least about 20 ng, at least about 25 ng, at least about 30 ng, at least about 35 ng, at least about 40 ng, at least about 45 ng, at least about 50 ng, at least about 75 ng, at least about 100 ng, at least about 200 ng, at least about 300 ng, at least about 400 ng, or more). For example, in some embodiments, the amount of cfDNA isolated from the sample is at least about 20 ng of cfDNA. In some embodiments, the amount of cfDNA isolated from the sample is, for example, from about 5 ng to about 100 ng (e.g., from about 5 ng to about 100 ng, from about 5 ng to about 90 ng, from about 5 ng to about 80 ng, from about 5 ng to about 70 ng, from about 5 ng to about 60 ng, from about 5 ng to about 50 ng, from about 5 ng to about 40 ng, from about 5 ng to about 30 ng, from about 5 ng to about 20 ng, from about 5 ng to about 15 ng, from about 5 ng to about 10 ng, from about 10 ng to about 100 ng, from about 10 ng to about 90 ng, from about 10 ng to about 80 ng, from about 10 ng to about 70 ng, from about 10 ng to about 60 ng, from about 10 ng to about 50 ng, from about 10 ng to about 40 ng, from about 10 ng to about 30 ng, from about 10 ng to about 20 ng, from about 15 ng to about 100 ng, from about 15 ng to about 90 ng, from about 15 ng to about 80 ng, from about 15 ng to about 70 ng, from about 15 ng to about 60 ng, from about 15 ng to about 50 ng, from about 20 ng to about 100 ng, from about 20 ng to about 90 ng, from about 20 ng to about 80 ng, from about 20 ng to about 70 ng, from about 20 ng to about 60 ng, from about 20 ng to about 50 ng, from about 20 ng to about 40 ng, from about 20 ng to about 30 ng, from about 25 ng to about 100 ng, from about 25 ng to about 90 ng, from about 25 ng to about 80 ng, from about 25 ng to about 70 ng, from about 25 ng to about 60 ng, from about 25 ng to about 50 ng, from about 25 ng to about 40 ng, from about 25 ng to about 30 ng, from about 30 ng to about 100 ng, from about 30 ng to about 90 ng, from about 30 ng to about 80 ng, from about 30 ng to about 70 ng, from about 30 ng to about 60 ng, from about 30 ng to about 50 ng, from about 30 ng to about 40 ng, from about 30 ng to about 35 ng, from about 35 ng to about 100 ng, from about 35 ng to about 90 ng, from about 35 ng to about 80 ng, from about 35 ng to about 70 ng, from about 35 ng to about 60 ng, from about 35 ng to about 50 ng, from about 35 ng to about 40 ng, from about 40 ng to about 100 ng, from about 40 ng to about 90 ng, from about 40 ng to about 80 ng, from about 40 ng to about 70 ng, from about 40 ng to about 60 ng, from about 40 ng to about 50 ng, from about 40 ng to about 45 ng, from about 50 ng to about 100 ng, from about 50 ng to about 90 ng, from about 50 ng to about 80 ng, from about 50 ng to about 70 ng, from about 50 ng to about 60 ng, from about 60 ng to about 100 ng, from about 60 ng to about 90 ng, from about 60 ng to about 80 ng, from about 60 ng to about 70 ng, from about 70 ng to about 100 ng, from about 70 ng to about 90 ng, from about 70 ng to about 80 ng, from about 80 ng to about 100 ng, from about 80 ng to about 90 ng, or from 90 ng to about 100 ng). In some embodiments, the amount of cfDNA isolated from the sample is about 100 ng or more (e.g., about 100 ng or more, about 200 ng or more, about 300 ng or more, about 400 ng or more, about 500 ng or more, about 600 ng or more, about 700 ng or more, about 800 ng or more, about 900 ng or more, or higher).

Any suitable sample volume may be used in any of the preceding methods. For example, in some instances, the sample (e.g., a whole blood sample, a plasma sample, a serum sample, or a combination thereof) may have a volume of about 1 mL to about 50 mL, e.g., about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 22 mL, about 24 mL, about 26 mL, about 28 mL, about 30 mL, about 32 mL, about 34 mL, about 36 mL, about 38 mL, about 40 mL, about 42 mL, about 44 mL, about 46 mL, about 48 mL, or 50 mL. In some instances, the sample (e.g., a whole blood sample, a plasma sample, a serum sample, or a combination thereof) may have a volume of from about 1 mL to about 50 mL, from about 1 mL to about 40 mL, from about 1 mL to about 30 mL, from about 1 mL to about 20 mL, from about 1 mL to about 10 mL, from about 5 mL to about 50 mL, from about 5 mL to about 40 mL, from about 5 mL to about 30 mL, from about 5 mL to about 20 mL, from about 5 mL to about 10 mL, from about 6 mL to about 50 mL, from about 6 mL to about 40 mL, from about 6 mL to about 30 mL, from about 6 mL to about 20 mL, from about 6 mL to about 10 mL, from about 7 mL to about 50 mL, from about 7 mL to about 40 mL, from about 7 mL to about 30 mL, from about 7 mL to about 20 mL, from about 7 mL to about 10 mL, from about 8 mL to about 50 mL, from about 8 mL to about 40 mL, from about 8 mL to about 30 mL, from about 8 mL to about 20 mL, from about 8 mL to about 10 mL, from about 9 mL to about 50 mL, from about 9 mL to about 40 mL, from about 9 mL to about 30 mL, from about 9 mL to about 20 mL, from about 9 mL to about 10 mL, from about 5 mL to about 15 mL, from about 5 mL to about 14 mL, from about 5 mL to about 13 mL, from about 5 mL to about 12 mL, from about 5 mL to about 11 mL, from about 6 mL to about 15 mL, from about 6 mL to about 14 mL, from about 6 mL to about 13 mL, from about 6 mL to about 12 mL, from about 6 mL to about 11 mL, from about 7 mL to about 15 mL, from about 7 mL to about 14 mL, from about 7 mL to about 13 mL, from about 7 mL to about 12 mL, from about 7 mL to about 11 mL, from about 8 mL to about 15 mL, from about 8 mL to about 14 mL, from about 8 mL to about 13 mL, from about 8 mL to about 12 mL, from about 8 mL to about 11 mL, from about 9 mL to about 15 mL, from about 9 mL to about 14 mL, from about 9 mL to about 13 mL, from about 9 mL to about 12 mL, or from about 9 mL to about 11 mL. In some instances, the sample (e.g., a whole blood sample, a plasma sample, a serum sample, or a combination thereof) has a volume of about 10 mL. For example, in some instances, a plasma sample has a volume of 10 mL.

In some embodiments of any of the preceding methods, the somatic mutations evaluated in the assay each have an allele frequency of about 0.1% or more, e.g., about 0.1% or more, about 0.2% or more, about 0.3% or more, about 0.4% or more, about 0.5% or more, about 0.6% or more, about 0.7% or more, about 0.8% or more, about 0.9% or more, about 1.0% or more, about 1.1% or more, about 1.2% or more, about 1.3% or more, about 1.4% or more, about 1.5% or more, about 1.6% or more, about 1.7% or more, about 1.8% or more, about 1.9% or more, about 2.0% or more, about 2.1% or more, about 2.2% or more, about 2.3% or more, about 2.4% or more, about 2.5% or more, about 2.6% or more, about 2.7% or more, about 2.8% or more, about 2.9% or more, about 3.0% or more, about 3.1% or more, about 3.2% or more, about 3.3% or more, about 3.4% or more, about 3.5% or more, about 3.6% or more, about 3.7% or more, about 3.8% or more, about 3.9% or more, about 4.0% or more, about 4.1% or more, about 4.2% or more, about 4.3% or more, about 4.4% or more, about 4.5% or more, about 4.6% or more, about 4.7% or more, about 4.8% or more, about 4.9% or more, about 5.0% or more, about 6.0% or more, about 7.0% or more, about 8.0% or more, about 9.0% or more, about 10.0% or more, about 11.0% or more, about 12.0% or more, about 13.0% or more, about 14.0% or more, about 15.0% or more about 16.0% or more, about 17.0% or more, about 18.0% or more, about 19.0% or more, about 20.0% or more, or higher. For example, in some embodiments, the somatic mutations evaluated in the assay each have an allele frequency of 0.5% or more. In some instances, of any of the methods described herein, wherein a bTMB score determined from the sample from the individual is at or above the reference bTMB score, the method may further include administering to the individual an effective amount of an immune checkpoint inhibitor, for example, a PD-L1 axis binding antagonist (e.g., an anti-PD-L1 antibody, e.g., atezolizumab), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In some instances, the bTMB score determined from the sample from the individual is below the reference bTMB score. In some instances, the method further includes determining an MSAF from the sample from the individual. In some instances, the MSAF from the sample is greater than, or equal to, 1% (e.g., ≥1%, ≥2%, ≥3%, ≥4%, ≥5%, ≥6%, ≥7%, ≥8%, ≥9%, or ≥10%). In some instances, the MSAF from the sample is less than 1% (e.g., <1%, ≤0.9%, ≤0.8%, ≤0.7%, ≤0.6%, ≤0.5%, ≤0.4%, ≤0.3%, ≤0.2%, or ≤0.1%). The MSAF may be determined prior to, concurrently with, or after the determination of a bTMB score.

For example, when a bTMB score at, or above a reference bTMB score and an MSAF greater than, or equal to, 1% (e.g., ≥1%, ≥2%, ≥3%, ≥4%, ≥5%, ≥6%, ≥7%, ≥8%, ≥9%, or ≥10%) is determined from a sample from the individual, the method may further include administering an effective amount of an immune checkpoint inhibitor, for example, a PD-L1 axis binding antagonist (e.g., an anti-PD-L1 antibody, e.g., atezolizumab), to the individual. When a bTMB score at, or above a reference bTMB score and an MSAF less than 1% (e.g., <1%, ≤0.9%, ≤0.8%, ≤0.7%, ≤0.6%, ≤0.5%, ≤0.4%, ≤0.3%, ≤0.2%, or ≤0.1%) is determined from a sample from the individual, the method may further include administering an effective amount of an immune checkpoint inhibitor, for example, a PD-L1 axis binding antagonist (e.g., an anti-PD-L1 antibody, e.g., atezolizumab), to the individual. Similarly, when a bTMB score below a reference bTMB score and an MSAF less than 1% (e.g., <1%, ≤0.9%, ≤0.8%, ≤0.7%, ≤0.6%, ≤0.5%, ≤0.4%, ≤0.3%, ≤0.2%, or ≤0.1%) is determined from a sample from the individual, the method may further include administering an effective amount of an immune checkpoint inhibitor, for example, a PD-L1 axis binding antagonist (e.g., an anti-PD-L1 antibody, e.g., atezolizumab), to the individual. However, when a bTMB score below a reference bTMB score and an MSAF greater than, or equal to, 1% (e.g., ≥1%, ≥2%, ≥3%, ≥4%, ≥5%, ≥6%, ≥7%, ≥8%, ≥9%, or ≥10%) is determined from a sample from the individual, the method may further include administering an effective amount of an anti-cancer therapy other than, or in addition to, an immune checkpoint inhibitor, for example, a PD-L1 axis binding antagonist (e.g., an anti-PD-L1 antibody, e.g., atezolizumab). In any of the preceding instances, the cancer may be, for example, a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor. In some instances, the lung cancer may be NSCLC, including but not limited to a locally advanced or metastatic (e.g., stage IIIB, stage IV, or recurrent) NSCLC. In some instances, the lung cancer (e.g., NSCLC) is unresectable/inoperable lung cancer (e.g., NSCLC). In other instances, the lung cancer (e.g., NSCLC) may have progressed during or following treatment with a prior platinum-containing regimen.

In some instances, the individual has progressed following treatment with a platinum-containing regimen (e.g., a regimen including a platinum-based chemotherapeutic agent, e.g., a regimen including a cisplatin-based chemotherapy) for a cancer. In other instances, the individual may be ineligible for treatment with a platinum-containing regimen (e.g., a regimen including a platinum-based chemotherapeutic agent, e.g., a regimen including a cisplatin-based chemotherapy) and/or has not received prior treatment for a cancer. In some instances, the individual has not received prior treatment with an immune checkpoint inhibitor, for example, a PD-L1 axis binding antagonist.

In any of the preceding methods, the sample (e.g., blood sample) obtained from the patient is selected from the group consisting of a whole blood, plasma, serum, or a combination thereof. In some instances, the sample is an archival blood sample, a fresh blood sample, or a frozen blood sample. The determination step may include determining the total number of somatic mutations (e.g., a base substitution in a coding region and/or an indel mutation in a coding region) occurring in a pre-determined set of genes to derive a bTMB score from the sample from the individual. In some embodiments, the number of somatic mutations is the number of SNVs counted or a sum of the number of SNVs and the number of indel mutations counted.

In any of the preceding instances, the reference bTMB score may be a bTMB score in a reference population of individuals having a cancer (e.g., a lung cancer (e.g., non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma, a prostate cancer, a glioblastoma, a cervical cancer, a thymic carcinoma, a leukemia, a lymphoma, a myeloma, a mycoses fungoides, a merkel cell cancer, a hematologic malignancy), the population of individuals consisting of a first subset of individuals who have been treated with an immune checkpoint inhibitor, for example, a PD-L1 axis binding antagonist therapy, and a second subset of individuals who have been treated with a non-PD-L1 axis binding antagonist therapy, wherein the non-PD-L1 axis binding antagonist therapy does not comprise an immune checkpoint inhibitor, for example, a PD-L1 axis binding antagonist. In some instances, the reference bTMB score significantly separates each of the first and second subsets of individuals based on a significant difference in responsiveness to treatment with the PD-L1 axis binding antagonist therapy relative to responsiveness to treatment with the non-PD-L1 axis binding antagonist therapy. In some instances, responsiveness to treatment is an increase in progression-free survival (PFS) and/or an increase in overall survival (OS). In some instances, the reference bTMB score may be a pre-assigned bTMB score. The reference bTMB score may be between 8 and 30 (e.g., 8, 9, 10, 11, 12, 13, 14, 15, 16, 17, 18, 19, 20, 21, 22, 23, 24, 25, 26, 27, 28, 29, and 30). In some instances, the reference bTMB score may be between 10 and 20 (e.g., 10, 11, 12, 13, 14, 15, 16, 17, 18, 19, or 20). In other instances, the reference bTMB score may be between 16 and 20 (e.g., 16, 17, 18, 19, or 20). In some instances, the reference population of individuals has a lung cancer (e.g., a non-small cell lung cancer (NSCLC)), a kidney cancer (e.g., a kidney urothelial carcinoma) and a reference bTMB score greater than, or equal to, 14. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 16. In some instances, the reference population of individuals has a lung cancer (e.g., a non-small cell lung cancer (NSCLC)), a kidney cancer (e.g., a kidney urothelial carcinoma) and a reference bTMB score greater than, or equal to, 18. In some instances, the reference population of individuals has a bladder cancer (e.g., a bladder urothelial (transitional cell) carcinoma) and a reference bTMB score of score greater than, or equal to, 16. In some instances, the reference population of individuals has melanoma and a reference bTMB score of greater than, or equal to, 20. In some instances, the reference population of individuals has melanoma and a reference bTMB score of greater than, or equal to, 21. In some instances, the reference population of individuals has melanoma and a reference bTMB score of greater than, or equal to, 22. In some instances, the reference population of individuals has melanoma and a reference bTMB score of greater than, or equal to, 23. In some instances, the reference population of individuals has melanoma and a reference bTMB score of greater than, or equal to, 24. In some instances, the reference population of individuals has melanoma and a reference bTMB score of greater than, or equal to, 25.

In any of the preceding instances, the bTMB score from the sample may be greater than, or equal to, 8 (e.g., 8, 9, 10, 11, 12, 13, 14, 15, 16, 17, 18, 19, 20, 21, 22, 23, 24, 25, 26, 27, 28, 29, 30, or more). For example, the bTMB score from the sample may be between about 8 and about 100 (e.g., 8, 9, 10, 20, 30, 40, 50, 60, 70, 80, 90, and 100). In some instances, the bTMB score from the sample may be between about 400 and about 1500 (e.g., a bTMB score of about 400, 500, 600, 700, 800, 900, 1000, 1100, 1200, 1300, 1400, or 1500). In some instances, the bTMB score from the sample may be less than 8 (e.g., 0, 1, 2, 3, 4, 5, 6, or 7) or be undetectable.

In some embodiments of any of the preceding instances, the bTMB score (e.g., reference bTMB score) is represented as the number of somatic mutations counted over a defined number of sequenced bases (e.g., about 1.1 Mb (e.g., about 1.125 Mb), e.g., as assessed by the FOUNDATIONONE® panel). In some embodiments, the bTMB score (e.g., reference bTMB score) is an equivalent bTMB value, for example, as determined by whole-exome sequencing.

In some instances, the bTMB score from the sample from the individual may have a prevalence of greater than, or equal to, about 5%, for example, a prevalence of between about 5% and about 75% (e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) in a reference population.

In some instances, the prevalence of a bTMB score that is greater than, or equal to, a reference cut-off bTMB score is about 5%, for example, a prevalence of between about 5% and about 75% (e.g., a prevalence between about 5% and about 15%, about 15% and about 30%, about 30% and about 45%, about 45% and about 60%, or about 60% and 75%; e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) in a reference population.

In some embodiments of any of the preceding instances, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates by less than about 30% (e.g., less than about 30%, about 25%, about 20%, about 15%, about 10%, about 5%, about 4%, about 3%, about 2%, about 1%, or less) from a bTMB score determined by whole-exome sequencing. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates about 1% to about 30% (e.g., about 1% to about 30%, about 1% to about 25%, about 1% to about 20%, about 1% to about 15%, about 1% to about 10%, about 5% to about 30%, about 5% to about 25%, about 5% to about 20%, about 5% to about 15%, about 5% to about 10%, about 10% to about 30%, about 10% to about 25%, about 10% to about 20%, about 10% to about 15%, about 15% to about 30%, about 15% to about 25%, about 15% to about 20%, about 20% to about 30%, or about 20% to about 25%) from a bTMB score determined by whole-exome sequencing. In some embodiments, a bTMB score determined as the number of somatic mutations counted over a defined number of sequenced bases (e.g., about 1.1 Mb (e.g., about 1.125 Mb), e.g., as assessed by the FOUNDATIONONE® panel) in a subset of the genome or exome (e.g., a predetermined set of genes) deviates about 10% to about 20% (e.g., about 10%, about 11%, about 12%, about 13%, about 14%, about 15%, about 16%, about 17%, about 18%, about 19%, or about 20%) from a bTMB score determined by whole-exome sequencing.

In any of the methods provided here, the benefit from the treatment comprising an immune checkpoint inhibitor, for example, a PD-L1 axis binding antagonist, may be an increase in OS, an increase in PFS, or an increase in OS and PFS.

In any of the preceding methods, the PD-L1 axis binding antagonist may be any PD-L1 axis binding antagonist known in the art or described herein, for example, in Section IV, below.

In some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: MPDL3280A (atezolizumab), YW243.55.S70, MDX-1105, MED14736 (durvalumab), and MSB0010718C (avelumab). In some instances, the antibody comprises a heavy chain comprising HVR-H1 sequence of SEQ ID NO: 19, HVR-H2 sequence of SEQ ID NO: 20, and HVR-H3 sequence of SEQ ID NO: 21; and a light chain comprising HVR-L1 sequence of SEQ ID NO: 22, HVR-L2 sequence of SEQ ID NO: 23, and HVR-L3 sequence of SEQ ID NO: 24. In some instances, the antibody comprises a heavy chain variable region comprising the amino acid sequence of SEQ ID NO: 25 and a light chain variable region comprising the amino acid sequence of SEQ ID NO: 4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In a further aspect, the invention provides for the use of an immune checkpoint inhibitor, for example, a PD-L1 axis binding antagonist, in the manufacture or preparation of a medicament. In one instance, the medicament is for treatment of a cancer. In a further instance, the medicament is for use in a method of treating a cancer comprising administering to an individual having a cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor) an effective amount of the medicament. In one such instance, the method further comprises administering to the individual an effective amount of at least one additional therapeutic agent, e.g., as described below.

The compositions utilized in the methods described herein (e.g., PD-L1 axis binding antagonists) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some instances, the PD-L1 axis binding antagonist is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

PD-L1 axis binding antagonists (e.g., an antibody, binding polypeptide, and/or small molecule) described herein (any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The PD-L1 axis binding antagonist need not be, but is optionally formulated with and/or administered concurrently with one or more agents currently used to prevent or treat the disorder in question. The effective amount of such other agents depends on the amount of the PD-L1 axis binding antagonist present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor), the appropriate dosage of an immune checkpoint inhibitor, for example, a PD-L1 axis binding antagonist, an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, described herein (when used alone or in combination with one or more other additional therapeutic agents) will depend on the type of disease to be treated, the severity and course of the disease, whether the PD-L1 axis binding antagonist is administered for preventive or therapeutic purposes, previous therapy, the patient's clinical history and response to the PD-L1 axis binding antagonist, and the discretion of the attending physician. The PD-L1 axis binding antagonist is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the PD-L1 axis binding antagonist). An initial higher loading dose, followed by one or more lower doses may be administered. However, other dosage regimens may be useful. The progress of this therapy is easily monitored by conventional techniques and assays.

For example, as a general proposition, the therapeutically effective amount of an immune checkpoint inhibitor, for example, a PD-L1 axis binding antagonist antibody, an anti-CTLA-4 antibody, an anti-TIM-3 antibody, or an anti-LAG-3 antibody, administered to human will be in the range of about 0.01 to about 50 mg/kg of patient body weight, whether by one or more administrations. In some instances, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some instances, the antibody is administered at 15 mg/kg. However, other dosage regimens may be useful. In one instance, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, or about 1800 mg on day 1 of 21-day cycles (every three weeks, q3w). In some instances, anti-PD-L1 antibody MPDL3280A is administered at 1200 mg intravenously every three weeks (q3w). The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some instances, the methods include administering to the individual an anti-cancer therapy other than, or in addition to, an immune checkpoint inhibitor, for example, a PD-L1 axis binding antagonist (e.g., an anti-neoplastic agent, a chemotherapeutic agent, a growth inhibitory agent, an anti-angiogenic agent, a radiation therapy, or a cytotoxic agent).

In some instances, the methods further involve administering to the patient an effective amount of an additional therapeutic agent. In some instances, the additional therapeutic agent is selected from the group consisting of an anti-neoplastic agent, a chemotherapeutic agent, a growth inhibitory agent, an anti-angiogenic agent, a radiation therapy, a cytotoxic agent, and combinations thereof. In some instances, an immune checkpoint inhibitor, for example, a PD-L1 axis binding antagonist, may be administered in conjunction with a chemotherapy or chemotherapeutic agent. In some instances, an immune checkpoint inhibitor, for example, a PD-L1 axis binding antagonist, may be administered in conjunction with a radiation therapy agent. In some instances, an immune checkpoint inhibitor, for example, a PD-L1 axis binding antagonist, may be administered in conjunction with a targeted therapy or targeted therapeutic agent. In some instances, an immune checkpoint inhibitor, for example, a PD-L1 axis binding antagonist, may be administered in conjunction with an immunotherapy or immunotherapeutic agent, for example a monoclonal antibody. In some instances, the additional therapeutic agent is an agonist directed against a co-stimulatory molecule. In some instances, the additional therapeutic agent is an antagonist directed against a co-inhibitory molecule. In some instances, the PD-L1 axis binding antagonist is administered as a monotherapy.

Such combination therapies noted above encompass combined administration (where two or more therapeutic agents are included in the same or separate formulations), and separate administration, in which case, administration of an immune checkpoint inhibitor, for example, a PD-L1 axis binding antagonist, can occur prior to, simultaneously, and/or following, administration of the additional therapeutic agent or agents. In one instance, administration of PD-L1 axis binding antagonist and administration of an additional therapeutic agent occur within about one month, or within about one, two or three weeks, or within about one, two, three, four, five, or six days, of each other.

Without wishing to be bound to theory, it is thought that enhancing T-cell stimulation, by promoting a co-stimulatory molecule or by inhibiting a co-inhibitory molecule, may promote tumor cell death thereby treating or delaying progression of cancer. In some instances, an immune checkpoint inhibitor, for example, a PD-L1 axis binding antagonist, may be administered in conjunction with an agonist directed against a co-stimulatory molecule. In some instances, a co-stimulatory molecule may include CD40, CD226, CD28, OX40, GITR, CD137, CD27, HVEM, or CD127. In some instances, the agonist directed against a co-stimulatory molecule is an agonist antibody that binds to CD40, CD226, CD28, OX40, GITR, CD137, CD27, HVEM, or CD127. In some instances, an immune checkpoint inhibitor, for example, a PD-L1 axis binding antagonist, may be administered in conjunction with an antagonist directed against a co-inhibitory molecule. In some instances, a co-inhibitory molecule may include CTLA-4 (also known as CD152), TIM-3, BTLA, VISTA, LAG-3, B7-H3, B7-H4, IDO, TIGIT, MICA/B, or arginase. In some instances, the antagonist directed against a co-inhibitory molecule is an antagonist antibody that binds to CTLA-4, TIM-3, BTLA, VISTA, LAG-3, B7-H3, B7-H4, IDO, TIGIT, MICA/B, or arginase.

In some instances, a PD-L1 axis binding antagonist may be administered in conjunction with an antagonist directed against CTLA-4 (also known as CD152), e.g., a blocking antibody. In some instances, a PD-L1 axis binding antagonist may be administered in conjunction with ipilimumab (also known as MDX-010, MDX-101, or YERVOY®). In some instances, a PD-L1 axis binding antagonist may be administered in conjunction with tremelimumab (also known as ticilimumab or CP-675,206). In some instances, a PD-L1 axis binding antagonist may be administered in conjunction with an antagonist directed against B7-H3 (also known as CD276), e.g., a blocking antibody. In some instances, a PD-L1 axis binding antagonist may be administered in conjunction with MGA271. In some instances, a PD-L1 axis binding antagonist may be administered in conjunction with an antagonist directed against a TGF-beta, e.g., metelimumab (also known as CAT-192), fresolimumab (also known as GC1008), or LY2157299.

In some instances, an immune checkpoint inhibitor, for example, a PD-L1 axis binding antagonist, may be administered in conjunction with a treatment comprising adoptive transfer of a T-cell (e.g., a cytotoxic T-cell or CTL) expressing a chimeric antigen receptor (CAR). In some instances, an immune checkpoint inhibitor, for example, a PD-L1 axis binding antagonist, may be administered in conjunction with a treatment comprising adoptive transfer of a T-cell comprising a dominant-negative TGF beta receptor, e.g., a dominant-negative TGF beta type II receptor. In some instances, an immune checkpoint inhibitor, for example, a PD-L1 axis binding antagonist, may be administered in conjunction with a treatment comprising a HERCREEM protocol (see, e.g., ClinicalTrials.gov Identifier NCT00889954).

In some instances, an immune checkpoint inhibitor, for example, a PD-L1 axis binding antagonist, may be administered in conjunction with an agonist directed against CD137 (also known as TNFRSF9, 4-1BB, or ILA), e.g., an activating antibody. In some instances, an immune checkpoint inhibitor, for example, a PD-L1 axis binding antagonist, may be administered in conjunction with urelumab (also known as BMS-663513). In some instances, an immune checkpoint inhibitor, for example, a PD-L1 axis binding antagonist, may be administered in conjunction with an agonist directed against CD40, e.g., an activating antibody. In some instances, an immune checkpoint inhibitor, for example, a PD-L1 axis binding antagonist, may be administered in conjunction with CP-870893. In some instances, an immune checkpoint inhibitor, for example, a PD-L1 axis binding antagonist, may be administered in conjunction with an agonist directed against OX40 (also known as CD134), e.g., an activating antibody. In some instances, an immune checkpoint inhibitor, for example, a PD-L1 axis binding antagonist, may be administered in conjunction with an anti-OX40 antibody (e.g., AgonOX). In some instances, an immune checkpoint inhibitor, for example, a PD-L1 axis binding antagonist, may be administered in conjunction with an agonist directed against CD27, e.g., an activating antibody. In some instances, an immune checkpoint inhibitor, for example, a PD-L1 axis binding antagonist, may be administered in conjunction with CDX-1127. In some instances, an immune checkpoint inhibitor, for example, a PD-L1 axis binding antagonist, may be administered in conjunction with an antagonist directed against indoleamine-2,3-dioxygenase (IDO). In some instances, with the IDO antagonist is 1-methyl-D-tryptophan (also known as 1-D-MT).

In some instances, an immune checkpoint inhibitor, for example, a PD-L1 axis binding antagonist, may be administered in conjunction with an antibody-drug conjugate. In some instances, the antibody-drug conjugate comprises mertansine or monomethyl auristatin E (MMAE). In some instances, an immune checkpoint inhibitor, for example, a PD-L1 axis binding antagonist, may be administered in conjunction with an anti-NaPi2b antibody-MMAE conjugate (also known as DNIB0600A or RG7599). In some instances, an immune checkpoint inhibitor, for example, a PD-L1 axis binding antagonist, may be administered in conjunction with trastuzumab emtansine (also known as T-DM1, ado-trastuzumab emtansine, or KADCYLA®, Genentech). In some instances, an immune checkpoint inhibitor, for example, a PD-L1 axis binding antagonist, may be administered in conjunction with DMUC5754A. In some instances, an immune checkpoint inhibitor, for example, a PD-L1 axis binding antagonist, may be administered in conjunction with an antibody-drug conjugate targeting the endothelin B receptor (EDNBR), e.g., an antibody directed against EDNBR conjugated with MMAE.

In some instances, an immune checkpoint inhibitor, for example, a PD-L1 axis binding antagonist, may be administered in conjunction with an anti-angiogenesis agent. In some instances, an immune checkpoint inhibitor, for example, a PD-L1 axis binding antagonist, may be administered in conjunction with an antibody directed against a VEGF, e.g., VEGF-A. In some instances, an immune checkpoint inhibitor, for example, a PD-L1 axis binding antagonist, may be administered in conjunction with bevacizumab (also known as AVASTIN®, Genentech). In some instances, an immune checkpoint inhibitor, for example, a PD-L1 axis binding antagonist, may be administered in conjunction with an antibody directed against angiopoietin 2 (also known as Ang2). In some instances, an immune checkpoint inhibitor, for example, a PD-L1 axis binding antagonist, may be administered in conjunction with MEDI3617.

In some instances, an immune checkpoint inhibitor, for example, a PD-L1 axis binding antagonist, may be administered in conjunction with an antineoplastic agent. In some instances, an immune checkpoint inhibitor, for example, a PD-L1 axis binding antagonist, may be administered in conjunction with an agent targeting CSF-1R (also known as M-CSFR or CD115). In some instances, an immune checkpoint inhibitor, for example, a PD-L1 axis binding antagonist, may be administered in conjunction with anti-CSF-1R (also known as IMC-CS4). In some instances, an immune checkpoint inhibitor, for example, a PD-L1 axis binding antagonist, may be administered in conjunction with an interferon, for example interferon alpha or interferon gamma. In some instances, an immune checkpoint inhibitor, for example, a PD-L1 axis binding antagonist, may be administered in conjunction with Roferon-A (also known as recombinant Interferon alpha-2a). In some instances, an immune checkpoint inhibitor, for example, a PD-L1 axis binding antagonist, may be administered in conjunction with GM-CSF (also known as recombinant human granulocyte macrophage colony stimulating factor, rhu GM-CSF, sargramostim, or LEUKINE®). In some instances, an immune checkpoint inhibitor, for example, a PD-L1 axis binding antagonist, may be administered in conjunction with IL-2 (also known as aldesleukin or PROLEUKIN®). In some instances, an immune checkpoint inhibitor, for example, a PD-L1 axis binding antagonist, may be administered in conjunction with IL-12. In some instances, an immune checkpoint inhibitor, for example, a PD-L1 axis binding antagonist, may be administered in conjunction with an antibody targeting CD20. In some instances, the antibody targeting CD20 is obinutuzumab (also known as GA101 or GAZYVA®) or rituximab. In some instances, an immune checkpoint inhibitor, for example, a PD-L1 axis binding antagonist, may be administered in conjunction with an antibody targeting GITR. In some instances, the antibody targeting GITR is TRX518.

In some instances, an immune checkpoint inhibitor, for example, a PD-L1 axis binding antagonist, may be administered in conjunction with a cancer vaccine. In some instances, the cancer vaccine is a peptide cancer vaccine, which in some instances is a personalized peptide vaccine. In some instances the peptide cancer vaccine is a multivalent long peptide, a multi-peptide, a peptide cocktail, a hybrid peptide, or a peptide-pulsed dendritic cell vaccine (see, e.g., Yamada et al., *Cancer Sci.* 104:14-21, 2013). In some instances, an immune checkpoint inhibitor, for example, a PD-L1 axis binding antagonist, may be administered in conjunction with an adjuvant. In some instances, an immune checkpoint inhibitor, for example, a PD-L1 axis binding antagonist, may be administered in conjunction with a treatment comprising a TLR agonist, e.g., Poly-ICLC (also known as HILTONOL®), LPS, MPL, or CpG ODN. In some instances, an immune checkpoint inhibitor, for example, a PD-L1 axis binding antagonist, may be administered in conjunction with tumor necrosis factor (TNF) alpha. In some instances, an immune checkpoint inhibitor, for example, a PD-L1 axis binding antagonist, may be administered in conjunction with IL-1. In some instances, an immune checkpoint inhibitor, for example, a PD-L1 axis binding antagonist, may be administered in conjunction with HMGB1. In some instances, an immune checkpoint inhibitor, for example, a PD-L1 axis binding antagonist, may be administered in conjunction with an IL-10 antagonist. In some instances, an immune checkpoint inhibitor, for example, a PD-L1 axis binding antagonist, may be administered in conjunction with an IL-4 antagonist. In some instances, an immune checkpoint inhibitor, for example, a PD-L1 axis binding antagonist, may be administered in conjunction with an IL-13 antagonist. In some instances, an immune checkpoint inhibitor, for example, a PD-L1 axis binding antagonist, may be administered in conjunction with an HVEM antagonist. In some instances, an immune checkpoint inhibitor, for example, a PD-L1 axis binding antagonist, may be administered in conjunction with an ICOS agonist, e.g., by administration of ICOS-L, or an agonistic antibody directed against ICOS. In some instances, an immune checkpoint inhibitor, for example, a PD-L1 axis binding antagonist, may be administered in conjunction with a treatment targeting CX3CL1. In some instances, an immune checkpoint inhibitor, for example, a PD-L1 axis binding antagonist, may be administered in conjunction with a treatment targeting CXCL9. In some instances, an immune checkpoint inhibitor, for example, a PD-L1 axis binding antagonist, may be administered in conjunction with a treatment targeting CXCL10. In some instances, an immune checkpoint inhibitor, for example, a PD-L1 axis binding antagonist, may be administered in conjunction with a treatment targeting CCL5. In some instances, an immune checkpoint inhibitor, for example, a PD-L1 axis binding antagonist, may be administered in conjunction with an LFA-1 or ICAM1 agonist. In some instances, an immune checkpoint inhibitor, for example, a PD-L1 axis binding antagonist, may be administered in conjunction with a Selectin agonist.

In some instances, an immune checkpoint inhibitor, for example, a PD-L1 axis binding antagonist, may be administered in conjunction with a targeted therapy. In some instances, an immune checkpoint inhibitor, for example, a PD-L1 axis binding antagonist, may be administered in conjunction with an inhibitor of B-Raf. In some instances, an immune checkpoint inhibitor, for example, a PD-L1 axis binding antagonist, may be administered in conjunction with vemurafenib (also known as ZELBORAF®). In some instances, an immune checkpoint inhibitor, for example, a PD-L1 axis binding antagonist, may be administered in conjunction with dabrafenib (also known as TAFINLAR®). In some instances, an immune checkpoint inhibitor, for example, a PD-L1 axis binding antagonist, may be administered in conjunction with erlotinib (also known as TARCEVA®). In some instances, an immune checkpoint inhibitor, for example, a PD-L1 axis binding antagonist, may be administered in conjunction with an inhibitor of a MEK, such as MEK1 (also known as MAP2K1) or MEK2 (also known as MAP2K2). In some instances, an immune checkpoint inhibitor, for example, a PD-L1 axis binding antagonist, may be administered in conjunction with cobimetinib (also known as GDC-0973 or XL-518). In some instances, an immune checkpoint inhibitor, for example, a PD-L1 axis binding antagonist, may be administered in conjunction with trametinib (also known as MEKINIST®). In some instances, an immune checkpoint inhibitor, for example, a PD-L1 axis binding antagonist, may be administered in conjunction with an inhibitor of K-Ras. In some instances, an immune checkpoint inhibitor, for example, a PD-L1 axis binding antagonist, may be administered in conjunction with an inhibitor of c-Met. In some instances, an immune checkpoint inhibitor, for example, a PD-L1 axis binding antagonist, may be administered in conjunction with onartuzumab (also known as MetMAb). In some instances, an immune checkpoint inhibitor, for example, a PD-L1 axis binding antagonist, may be administered in conjunction with an inhibitor of Alk. In some instances, an immune checkpoint inhibitor, for example, a PD-L1 axis binding antagonist, may be administered in conjunction with AF802 (also known as CH5424802 or alectinib). In some instances, an immune checkpoint inhibitor, for example, a PD-L1 axis binding antagonist, may be administered in conjunction with an inhibitor of a phosphatidylinositol 3-kinase (PI3K). In some instances, an immune checkpoint inhibitor, for example, a PD-L1 axis binding antagonist, may be administered in conjunction with BKM120. In some instances, an immune checkpoint inhibitor, for example, a PD-L1 axis binding antagonist, may be administered in conjunction with idelalisib (also known as GS-1101 or CAL-101). In some instances, an immune checkpoint inhibitor, for example, a PD-L1 axis binding antagonist, may be administered in conjunction with perifosine (also known as KRX-0401). In some instances, an immune checkpoint inhibitor, for example, a PD-L1 axis binding antagonist, may be administered in conjunction with an inhibitor of an Akt. In some instances, an immune checkpoint inhibitor, for example, a PD-L1 axis binding antagonist, may be administered in conjunction with MK2206. In some instances, an immune checkpoint inhibitor, for example, a PD-L1 axis binding antagonist, may be administered in conjunction with GSK690693. In some instances, an immune checkpoint inhibitor, for example, a PD-L1 axis binding antagonist, may be administered in conjunction with GDC-0941. In some instances, an immune checkpoint inhibitor, for example, a PD-L1 axis binding antagonist, may be administered in conjunction with an inhibitor of mTOR. In some instances, an immune checkpoint inhibitor, for example, a PD-L1 axis binding antagonist, may be administered in conjunction with sirolimus (also known as rapamycin). In some instances, an immune checkpoint inhibitor, for example, a PD-L1 axis binding antagonist, may be administered in conjunction with temsirolimus (also known as CCI-779 or TORISEL®). In some instances, an immune checkpoint inhibitor, for example, a PD-L1 axis binding antagonist, may be administered in conjunction with everolimus (also known as RAD001). In some instances, an immune checkpoint inhibitor, for example, a PD-L1 axis binding antagonist, may be administered in conjunction with ridaforolimus (also known as AP-23573, MK-8669, or deforolimus). In some instances, an immune checkpoint inhibitor, for example, a PD-L1 axis binding antagonist, may be administered in conjunction with OSI-027. In some instances, an immune checkpoint inhibitor, for example, a PD-L1 axis binding antagonist, may be administered in conjunction with AZD8055. In some instances, an immune checkpoint inhibitor, for example, a PD-L1 axis binding antagonist, may be administered in conjunction with INK128. In some instances, an immune checkpoint inhibitor, for example, a PD-L1 axis binding antagonist, may be administered in conjunction with a dual PI3K/mTOR inhibitor. In some instances, an immune checkpoint inhibitor, for example, a PD-L1 axis binding antagonist, may be administered in conjunction with XL765. In some instances, an immune checkpoint inhibitor, for example, a PD-L1 axis binding antagonist, may be administered in conjunction with GDC-0980. In some instances, an immune checkpoint inhibitor, for example, a PD-L1 axis binding antagonist, may be administered in conjunction with BEZ235 (also known as NVP-BEZ235). In some instances, an immune checkpoint inhibitor, for example, a PD-L1 axis binding antagonist, may be administered in conjunction with BGT226. In some instances, an immune checkpoint inhibitor, for example, a PD-L1 axis binding antagonist, may be administered in conjunction with GSK2126458. In some instances, an immune checkpoint inhibitor, for example, a PD-L1 axis binding antagonist, may be administered in conjunction with PF-04691502. In some instances, an immune checkpoint inhibitor, for example, a PD-L1 axis binding antagonist, may be administered in conjunction with PF-05212384 (also known as PKI-587).

C. Detection Methods and Assays for MSAF

In some aspects, provided herein is a method of evaluating an MSAF in a sample from a subject. The method includes, for example, a) providing sequence, e.g., a nucleotide sequence, of a set of subgenomic intervals (e.g., coding subgenomic intervals) from the subject, wherein the subgenomic intervals are from a predetermined set of genes; and b) determining a value for the MSAF, wherein the value is a function of the frequency of an allele, i.e., a variant of a subgenomic interval having a somatic alteration, in the set of subgenomic intervals.

In some embodiments, the value is expressed as the highest frequency of an allele, e.g., a variant of a subgenomic interval (e.g., a gene) having a somatic alteration (e.g., a base substitution in a coding region and/or an indel mutation in a coding region) less than about 40% (e.g., less than 40%, 30%, 20%, 10%, 5%, or 1%), expressed as a fraction or percentage, that is detected from the sample.

In some embodiments, the value is determined by dividing the number of sequence reads indicating a somatic alteration against the total reads aligned to a subgenomic interval, e.g., by dividing the number of sequence reads indicating a somatic mutation against the total reads aligned to a particular region of the human genome. In some embodiments, the value excludes a frequency greater than 40% (e.g., >40%, ≥50%, ≥60%, ≥70%, ≥80%, ≥90%, or 100%). In some embodiments, the value excludes a frequency greater than or equal to 20% in the sample. In some embodiments, the value is derived from the largest somatic allele frequency less than about 20% in a sample.

In some embodiments, the value is the fraction of all cfDNA in the sample from the subject that carries that allele. In some embodiments, the value is the fraction of ctDNA in the sample from the subject that carries that allele. In some embodiments, the value is used to estimate the total amount of tumor content in the sample.

In some embodiments, the method comprises determining an allele frequency for each somatic alteration detected from the sample. For example, a sample with multiple somatic alterations may present those alterations as a distribution of somatic allele frequencies, likely dependent upon their original clonal frequency in a cancer (e.g., a tumor).

In some embodiments, the value is expressed as a function of the predetermined set of genes, e.g., the coding regions of the predetermined set of genes. In other embodiments, the value is expressed as a function of the subgenomic intervals sequenced, e.g., the coding subgenomic intervals sequenced.

In certain embodiments, the predetermined set of genes does not comprise the entire genome or the entire exome. In other embodiments, the set of subgenomic intervals does not comprise the entire genome or the entire exome.

In some embodiments, the predetermined set of genes comprise a plurality of genes, which in mutant form, are associated with an effect on cell division, growth or survival, or are associated with cancer. In some embodiments, the predetermined set of genes comprise at least about 50 or more, about 100 or more, about 150 or more, about 200 or more, about 250 or more, about 300 or more, about 350 or more, about 400 or more, about 450 or more, or about 500 or more genes.

In certain embodiments, the value is expressed as a function of the frequency of a somatic alteration in a preselected number of positions of the predetermined set of genes, e.g., the coding regions of the predetermined set of genes. In other embodiments, the value is expressed as a function of the frequency of a somatic alteration in a preselected number of positions of the subgenomic intervals (e.g., coding subgenomic intervals) sequenced. In some embodiments, the value is extrapolated to a larger portion of the genome, e.g., to the entire exome or the entire genome.

In certain embodiments, the value excludes a frequency of a functional alteration in a subgenomic interval and/or a germline alteration in a subgenomic interval.

In some embodiments, the functional alteration is identified as such by inclusion in a database of functional alterations, e.g., the COSMIC database (cancer.sanger.ac.uk/cosmic; Forbes et al. Nucl. Acids Res. 2015; 43 (D1): D805-D811). In some embodiments, the functional alteration is an alteration with known functional status, e.g., occurring as a known somatic alteration in the COSMIC database. In some embodiments, the functional alteration is an alteration with a likely functional status, e.g., a truncation in a tumor suppressor gene. In some embodiments, the functional alteration is a driver mutation, e.g., an alteration that gives a selective advantage to a clone in its microenvironment, e.g., by increasing cell survival or reproduction. In some embodiments, the functional alteration is an alteration capable of causing clonal expansions. In some embodiments, the functional alteration is an alteration capable of causing one or more of the following: (a) self-sufficiency in a growth signal; (b) decreased, e.g., insensitivity, to an antigrowth signal; (c) decreased apoptosis; (d) increased replicative potential; (e) sustained angiogenesis; or (f) tissue invasion or metastasis. In some embodiments, the functional alteration is not a passenger mutation, e.g., is an alteration that has a detectable effect on the fitness of a clone. In some embodiments, the functional alteration is not a variant of unknown significance (VUS), e.g., is not an alteration, the pathogenicity of which can neither be confirmed nor ruled out.

In some embodiments, a plurality (e.g., 10%, 20%, 30%, 40%, 50%, or 75% or more) of functional alterations in a preselected gene (e.g., tumor gene) in the predetermined set of genes are excluded. In some embodiments, all functional alterations in a preselected gene (e.g., tumor gene) in the predetermined set of genes are excluded. In some embodiments, a plurality of functional alterations in a plurality of preselected genes (e.g., tumor genes) in the predetermined set of genes are excluded. In some embodiments, all functional alterations in all genes (e.g., tumor genes) in the predetermined set of genes are excluded.

In some embodiments, the germline alteration is a single nucleotide polymorphism (SNP), a base substitution, an indel, or a silent mutation (e.g., synonymous mutation).

In some embodiments, the germline alteration is excluded by use of a method that does not use a comparison with a matched normal sequence. In some embodiments, the germline alteration is excluded by a method comprising the use of an SGZ algorithm (e.g., as described in WO 2014/183078). In some embodiments, the germline alteration is identified as such by inclusion in a database of germline alterations, e.g., the dbSNP database (www.ncbi.nlm.nih.gov/SNP/index.html; Sherry et al. Nucleic Acids Res. 2001; 29(1): 308-311). In some embodiments, the germline alteration is identified as such by inclusion in two or more counts of the ExAC database (exac.broadinstitute.org; Exome Aggregation Consortium et al. "Analysis of protein-coding genetic variation in 60,706 humans," bioRxiv preprint. Oct. 30, 2015). In some embodiments, the germline alteration is identified as such by inclusion in the 1000 Genome Project database (www.1000genomes.org; McVean et al. Nature. 2012; 491, 56-65). In some embodiments, the germline alteration is identified as such by inclusion in the ESP database (Exome Variant Server, NHLBI GO Exome Sequencing Project (ESP), Seattle, Wash. (evs.gs.washington.edu/EVS/).

In some embodiments, the somatic alteration is a silent mutation, e.g., a synonymous alteration. In some embodiments, the somatic alteration is a passenger mutation, e.g., an alteration that has no detectable effect on the fitness of a clone. In some embodiments, the somatic alteration is a variant of unknown significance (VUS), e.g., an alteration, the pathogenicity of which can neither be confirmed nor ruled out. In some embodiments, the somatic alteration is a point mutation. In some embodiments, the somatic alteration is a short variant (e.g., a short coding variant), e.g., a base substitution, an indel, an insertion, or a deletion. In some embodiments, the somatic alteration is a non-synonymous single nucleotide variant (SNV). In some embodiments, the somatic alteration is a splice variant. In some embodiments, the somatic alteration has not been identified as being associated with a cancer phenotype. In some embodiments, the somatic alteration is other than a rearrangement, e.g., other than a translocation.

In some embodiments, the sample comprises one or more premalignant or malignant cells; cells from a solid tumor, a soft tissue tumor or a metastatic lesion; tissue or cells from a surgical margin; a histologically normal tissue; one or more circulating tumor cells (CTC); a normal adjacent tissue (NAT), or an FFPE-sample.

In some embodiments, the sample is a blood sample. In some embodiments, the sample (e.g., blood sample) obtained from the subject is selected from the group consisting of a whole blood, plasma, serum, or a combination thereof. In some embodiments, the sample is an archival blood sample, a fresh blood sample, or a frozen blood sample. In some embodiments, the sample comprises cell free DNA (cfDNA) and/or circulating tumor DNA (ctDNA).

In some embodiments, the sample is acquired from a patient harboring a solid tumor, a hematological cancer, or a metastatic form thereof.

In certain embodiments, the sample is from a subject having a cancer, or a subject who is receiving, or has received, a therapy.

In some embodiments, the sample is acquired from a subject having a cancer selected from, for example, a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinomas, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, a epithelial carcinoma, a glioma, an astrocytoma, a medulloblastoma, a craniopharyngioma, a ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor.

In some embodiments, the subject has progressed following treatment with a platinum-containing regimen (e.g., a regimen including a platinum-based chemotherapeutic agent, e.g., a regimen including a cisplatin-based chemotherapy) for a cancer. In other embodiments, the subject may be ineligible for treatment with a platinum-containing regimen (e.g., a regimen including a platinum-based chemotherapeutic agent, e.g., a regimen including a cisplatin-based chemotherapy) and/or has not received prior treatment for a cancer. In some embodiments, the subject has not received prior treatment with an immune checkpoint inhibitor, for example, a PD-L1 axis binding antagonist. In any of the preceding methods, the PD-L1 axis binding antagonist may be any PD-L1 axis binding antagonist known in the art or described herein, for example, in Section IV, below.

In some embodiments, an MSAF value is obtained from the sample independent of a bTMB score. In some embodiments, the determination of an MSAF value occurs prior to, concurrently with, or after the determination of a bTMB score from the sample.

In some embodiments, the method further comprises acquiring a library comprising a plurality of nucleic acids from the sample.

In some embodiments, the method further comprises contacting the library with a bait set to provide selected nucleic acids, wherein said bait set hybridizes with the nucleic acid, thereby providing a library catch.

In some embodiments, the method further comprises acquiring a read for a subgenomic interval comprising a somatic alteration from a nucleic acid from said library or library catch, thereby acquiring a read for the subgenomic interval, e.g., by a next-generation sequencing method.

In some embodiments, the method further comprises aligning said read by an alignment method.

In some embodiments, the method further comprises assigning a nucleotide value from said read for a preselected nucleotide position. In some embodiments, acquiring a read for the subgenomic interval comprises sequencing a subgenomic interval from at least about 50 or more, about 100 or more, about 150 or more, about 200 or more, about 250 or more, about 300 or more, genes or gene products. In some embodiments, acquiring a read for the subgenomic interval comprises sequencing with greater than about 250×, greater than about 500×, or greater than about 1,000×, average unique coverage. In some embodiments, acquiring a read for the subgenomic interval comprises sequencing with greater than about 250×, greater than about 500×, or greater than about 1,000×, average unique coverage, at greater than 95%, greater than about 97%, or greater than about 99%, of the genes (e.g., exons) sequenced.

In some embodiments, the method further comprises classifying the sample or the subject from which the sample was derived responsive to the evaluation of the MSAF.

In some embodiments, the method further comprises generating a report, e.g., an electronic, web-based, or paper report, to the patient or to another person or entity, a caregiver, a physician, an oncologist, a hospital, clinic, third-party payor, insurance company, a pharmaceutical or biotechnology company, or government office. In some embodiments, the report comprises output from the method which comprises evaluation of the MSAF.

D. Methods of Determining tTMB Scores

Any of the preceding methods can further include determining a tTMB score from a tumor sample from the individual. A tTMB score can be determined using any approach described in International Patent Application Publication No. WO 2017/151524 or in International Patent Application No. PCT/US2017/055669, both of which are incorporated herein by reference in their entirety. In some embodiments, a tTMB score from the tumor sample that is at or above a reference tTMB score identifies the individual as one who may benefit from a treatment comprising an immune checkpoint inhibitor, e.g., a PD-L1 axis binding antagonist, an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof. In some embodiments, the tTMB score determined from the tumor sample is at or above the reference tTMB score. In some embodiments, the tTMB score determined from the tumor sample is below the reference tTMB. In some embodiments of any of the preceding aspects, the reference tTMB score is a tTMB score in a reference population of individuals having the cancer, the population of individuals consisting of a first subset of individuals who have been treated with a PD-L1 axis binding antagonist therapy and a second subset of individuals who have been treated with a non-PD-L1 axis binding antagonist therapy, wherein the non-PD-L1 axis binding antagonist therapy does not comprise an immune checkpoint inhibitor (e.g., a PD-L1 axis binding antagonist (e.g., an anti-PD-L1 antibody) or an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)). In some embodiments, the reference tTMB score is a tTMB score in a reference population of individuals having the cancer, the population of individuals consisting of a first subset of individuals who have been treated with a PD-L1 axis binding antagonist therapy and a second subset of individuals who have been treated with a non-PD-L1 axis binding antagonist therapy, wherein the non-PD-L1 axis binding antagonist therapy does not comprise a PD-L1 axis binding antagonist. In some embodiments, the reference tTMB score significantly separates each of the first and second subsets of individuals based on a significant difference in responsiveness to treatment with the PD-L1 axis binding antagonist therapy relative to responsiveness to treatment with the non-PD-L1 axis binding antagonist therapy. In some embodiments, responsiveness to treatment is an increase in PFS, an increase in OS, and/or an increase in the overall response rate (ORR). In some embodiments, the tumor sample has been determined to have an increased level of somatic mutation relative to a reference level of somatic mutation. In some embodiments, the tumor sample has been determined to have an increased level of somatic mutation in at least one gene set forth in Table 1 relative to a reference level of somatic mutation in the at least one gene set forth in Table 1. In some embodiments, the somatic mutations are protein-altering somatic mutations. In some embodiments, the somatic mutations are substitutions, deletions, and/or insertions. In some embodiments, the substitutions, deletions, and/or insertions are in coding regions. In some embodiments, the deletions and/or insertions are indels.

In any of the preceding methods, in some instances, the reference tTMB score is a pre-assigned tTMB score. In some instances, the reference tTMB score is between about 5 and about 100 mutations per Mb (mut/Mb), for example, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 mut/Mb. For example, in some instances, the reference tTMB score is between about 8 and about 30 mut/Mb (e.g., about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 mut/Mb). In some instances, the reference tTMB score is between about 10 and about 20 mut/Mb (e.g., about 10, about 11, about 12, about 13, about 14, about 15, about 16, about 17, about 18, about 19, or about 20 mut/Mb). In particular instances, the reference tTMB score may be 10 mut/Mb, 16 mut/Mb, or 20 mut/Mb.

In some instances of any of the preceding methods, the tumor sample from the patient has a tTMB score of greater than, or equal to, about 5 mut/Mb. For example, in some instances, the tTMB score from the tumor sample is between about 5 and about 100 mut/Mb (e.g., about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 mut/Mb). In some instance, the tumor sample from the patient has a tTMB score of greater than, or equal to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 mut/Mb. For example, in some instances, the tumor sample from the patient has a tTMB score of greater than, or equal to, about 10 mut/Mb. In some embodiments, the reference tTMB score is 10 mut/Mb. In some instances, the tTMB score from the tumor sample is between about 10 and 100 mut/Mb. In some instances, the tTMB score from the tumor sample is between about 10 and 20 mut/Mb. In some instances, the tumor sample from the patient has a tTMB score of greater than, or equal to, about 16 mut/Mb. In some instances, the tumor sample from the patient has a tTMB score of greater than, or equal to, about 16 mut/Mb, and the reference tTMB score is 16 mut/Mb. In other instances, the tumor sample from the patient has a tTMB score of greater than, or equal to, about 20 mut/Mb. In some instances, the tumor sample from the patient has a tTMB score of greater than, or equal to, about 20 mut/Mb, and the reference tTMB score is about 20 mut/Mb.

In some instances of any of the preceding methods, the tTMB score or the reference tTMB score is represented as the number of somatic mutations counted per a defined number of sequenced bases. For example, in some instances, the defined number of sequenced bases is between about 100 kb to about 10 Mb. In some instances, the defined number of sequenced bases is about 1.1 Mb (e.g., about 1.125 Mb), e.g., as assessed by the FOUNDATIONONE® panel. In some instances, the tTMB score or the reference tTMB score is an equivalent tTMB value. In some instances, the equivalent tTMB value is determined by whole-exome sequencing (WES). In any of the preceding methods, a determined tTMB score may be reflective of the level of somatic mutations and/or rearrangements detected in the genes listed in Table 1. In some instances, the tTMB score has been (or is) determined to be at least about 5 mut/Mb or more (e.g., about 5 mut/Mb or more, about 6 mut/Mb or more, about 7 mut/Mb or more, about 8 mut/Mb or more, about 9 mut/Mb or more, about 10 mut/Mb or more, about 11 mut/Mb or more, about 12 mut/Mb or more, about 13 mut/Mb or more, about 14 mut/Mb or more, about 15 mut/Mb or more, about 16 mut/Mb or more, about 17 mut/Mb or more, about 18 mut/Mb or more, about 19 mut/Mb or more, about 20 mut/Mb or more, about 25 mut/Mb or more, about 30 mut/Mb or more, about 35 mut/Mb or more, about 40 mut/Mb or more, and about 50 mut/Mb or more) is predictive of responsiveness to treatment (e.g., treatment including a PD-L1 axis binding antagonist). In some instances, a tTMB score that is predictive of responsiveness to treatment (e.g., treatment including a PD-L1 axis binding antagonist) may be between about 7 mutations/Mb to about 20 mutations/Mb. In some instances, a tTMB score that is predictive of responsiveness to treatment may be between about 10 mutations/Mb to about 15 mutations/Mb. In some instances, a tTMB score that is predictive of responsiveness to treatment may be between about 11 mutations/Mb to about 13 mutations/Mb. In some instances, a tTMB score that is predictive of responsiveness to treatment may be about 12.5 mutations/Mb. In other instances, a tTMB score that is predictive of responsiveness to treatment may be between about 10 mut/Mb or more, e.g., about 10 mut/Mb or more, about 11 mut/Mb or more, about 12 mut/Mb or more, about 13 mut/Mb or more, about 14 mut/Mb or more, about 15 mut/Mb or more, about 16 mut/Mb or more, about 17 mut/Mb or more, about 18 mut/Mb or more, about 19 mut/Mb or more, about 20 mut/Mb or more.

E. Methods of Determining PD-L1 Expression

Any of the preceding methods may include determining an expression level of PD-L1 in a sample (e.g., a tumor sample) obtained from the individual. Any suitable approach to determine an expression level of PD-L1 may be used, for example, immunohistochemistry (IHC). An exemplary PD-L1 IHC assay is described, for example, in Example 1, and others are known in the art.

In some embodiments, a tumor sample obtained from the patient has been determined to have a detectable expression level of PD-L1 in less than about 1% of the tumor cells in the tumor sample. In other instances, a tumor sample obtained from the patient has been determined to have a detectable expression level of PD-L1 in about 1% or more (e.g., about 1% or more, 2% or more, 3% or more, 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more) of the tumor cells in the tumor sample. For example, in some instances, the tumor sample obtained from the patient has been determined to have a detectable expression level of PD-L1 in from about 1% to less than about 5% (e.g., from 1% to 4.9%, from 1% to 4.5%, from 1% to 4%, from 1% to 3.5%, from 1% to 3%, from 1% to 2.5%, or from 1% to 2%) of the tumor cells in the tumor sample.

In other instances, the tumor sample obtained from the patient has been determined to have a detectable expression level of PD-L1 in about 5% or more of the tumor cells in the tumor sample. For example, in some instances, the tumor sample obtained from the patient has been determined to have a detectable expression level of PD-L1 in from about 5% to less than 50% (e.g., from 5% to 49.5%, from 5% to 45%, from 5% to 40%, from 5% to 35%, from 5% to 30%, from 5% to 25%, from 5% to 20%, from 5% to 15%, from 5% to 10%, from 5% to 9%, from 5% to 8%, from 5% to 7%, from 5% to 6%, from 10% to 49.5%, from 10% to 40%, from 10% to 35%, from 10% to 30%, from 10% to 25%, from 10% to 20%, from 10% to 15%, from 15% to 49.5%, from 15% to 45%, from 15% to 40%, from 15% to 35%, from 15% to 30%, from 15% to 30%, from 15% to 25%, from 15% to 20%, from 20% to 49.5%, from 20% to 45%, from 20% to 40%, from 20% to 35%, from 20% to 30%, from 20% to 25%, from 25% to 49.5%, from 25% to 45%, from 25% to 40%, from 25% to 35%, from 25% to 30%, from 30% to 49.5%, from 30% to 45%, from 30% to 40%, from 30% to 35%, from 35% to 49.5%, from 35% to 45%, from 35% to 40%, from 40% to 49.5%, from 40% to 45%, or from 45% to 49.5%) of the tumor cells in the tumor sample.

In yet other instances, the tumor sample obtained from the patient has been determined to have a detectable expression level of PD-L1 in about 50% or more (e.g., about 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more) of the tumor cells in the tumor sample. In some instances, the tumor sample obtained from the patient has been determined to have a detectable expression level of PD-L1 in from about 50% to about 99% (e.g., from 50% to 99%, from 50% to 95%, from 50% to 90%, from 50% to 85%, from 50% to 80%, from 50% to 75%, from 50% to 70%, from 50% to 65%, from 50% to 60%, from 50% to 55%, from 55% to 99%, from 55% to 95%, from 55% to 90%, from 55% to 85%, from 55% to 80%, from 55% to 75%, from 55% to 70%, from 55% to 65%, from 55% to 60%, from 60% to 99%, from 60% to 95%, from 60% to 90%, from 60% to 85%, from 60% to 80%, from 60% to 75%, from 60% to 70%, from 60% to 65%, from 65% to 99%, from 65% to 95%, from 65% to 90%, from 65% to 85%, from 65% to 80%, from 65% to 75%, from 65% to 70%, from 70% to 99%, from 70% to 95%, from 70% to 90%, from 70% to 85%, from 70% to 80%, from 70% to 75%, from 75% to 99%, from 75% to 95%, from 75% to 90%, from 75% to 85%, from 75% to 80%, from 80% to 99%, from 80% to 95%, from 80% to 90%, from 80% to 85%, from 85% to 99%, from 85% to 95%, from 85% to 90%, from 90% to 99%, or from 90% to 95%) of the tumor cells in the tumor sample.

In some instances of any of the preceding methods, a tumor sample obtained from the patient has been determined to have a detectable expression level of PD-L1 in tumor-infiltrating immune cells that comprise less than about 1% of the tumor sample. In other instances, the tumor sample obtained from the patient has been determined to have a detectable expression level of PD-L1 in tumor-infiltrating immune cells that comprise about 1% or more (e.g., about 1% or more, 2% or more, 3% or more, 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, about 50% or more, about 60% or more, about 70% or more, about 80% or more, about 90% or more, about 95% or more, about 96% or more, about 97% or more, about 98% or more, about 99% or more, or 100%) of the tumor sample. For example, in some instances, the tumor sample obtained from the patient has been determined to have a detectable expression level of PD-L1 in tumor-infiltrating immune cells that comprise from about 1% to less than about 5% (e.g., from 1% to 4.9%, from 1% to 4.5%, from 1% to 4%, from 1% to 3.5%, from 1% to 3%, from 1% to 2.5%, or from 1% to 2%) of the tumor sample.

In some instances of any of the preceding methods, a tumor sample obtained from the patient has been determined to have a detectable expression level of PD-L1 less than about 1% of the tumor-infiltrating immune cells in the tumor sample. In other instances, the tumor sample obtained from the patient has been determined to have a detectable expression level of PD-L1 in about 1% or more (e.g., about 1% or more, 2% or more, 3% or more, 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, about 50% or more, about 60% or more, about 70% or more, about 80% or more, about 90% or more, about 95% or more, about 96% or more, about 97% or more, about 98% or more, about 99% or more, or 100%) of the tumor-infiltrating immune cells in the tumor sample. For example, in some instances, the tumor sample obtained from the patient has been determined to have a detectable expression level of PD-L1 in from about 1% to less than about 5% (e.g., from 1% to 4.9%, from 1% to 4.5%, from 1% to 4%, from 1% to 3.5%, from 1% to 3%, from 1% to 2.5%, or from 1% to 2%) of the tumor-infiltrating immune cells in the tumor sample.

In other instances, the tumor sample obtained from the patient has been determined to have a detectable expression level of PD-L1 in tumor-infiltrating immune cells that comprise about 5% or more of the tumor sample. For example, in some instances, the tumor sample obtained from the patient has been determined to have a detectable expression level of PD-L1 in tumor-infiltrating immune cells that comprise from about 5% to less than about 10% (e.g., from 5% to 9.5%, from 5% to 9%, from 5% to 8.5%, from 5% to 8%, from 5% to 7.5%, from 5% to 7%, from 5% to 6.5%, from 5% to 6%, from 5% to 5.5%, from 6% to 9.5%, from 6% to 9%, from 6% to 8.5%, from 6% to 8%, from 6% to 7.5%, from 6% to 7%, from 6% to 6.5%, from 7% to 9.5%, from 7% to 9%, from 7% to 7.5%, from 8% to 9.5%, from 8% to 9%, or from 8% to 8.5%) of the tumor sample.

In yet other instances, the tumor sample obtained from the patient has been determined to have a detectable expression level of PD-L1 in about 5% or more of the tumor-infiltrating immune cells in the tumor sample. For example, in some instances, the tumor sample obtained from the patient has been determined to have a detectable expression level of PD-L1 in from about 5% to less than about 10% (e.g., from 5% to 9.5%, from 5% to 9%, from 5% to 8.5%, from 5% to 8%, from 5% to 7.5%, from 5% to 7%, from 5% to 6.5%, from 5% to 6%, from 5% to 5.5%, from 6% to 9.5%, from 6% to 9%, from 6% to 8.5%, from 6% to 8%, from 6% to 7.5%, from 6% to 7%, from 6% to 6.5%, from 7% to 9.5%, from 7% to 9%, from 7% to 7.5%, from 8% to 9.5%, from 8% to 9%, or from 8% to 8.5%) of the tumor-infiltrating immune cells in the tumor sample.

In still further instances, the tumor sample obtained from the patient has been determined to have a detectable expression level of PD-L1 in tumor-infiltrating immune cells that comprise about 10% or more (e.g., 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, 50% or more, 60% or more, 70% or more, 80% or more, 90% or more, 95% or more, 96% or more, 97% or more, 98% or more, 99% or more, or 100%) of the tumor sample.

In still further instances, the tumor sample obtained from the patient has been determined to have a detectable expression level of PD-L1 in about 10% or more (e.g., 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, 50% or more, 60% or more, 70% or more, 80% or more, 90% or more, 95% or more, 96% or more, 97% or more, 98% or more, 99% or more, or 100%) of the tumor-infiltrating immune cells in the tumor sample.

In yet other instances, the tumor sample obtained from the patient has been determined to have a detectable expression level of PD-L1 in about 50% or more (e.g., about 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more) of the tumor cells in the tumor sample and/or a detectable expression level of PD-L1 in tumor-infiltrating immune cells that comprise about 10% or more (e.g., 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, 50% or more, 60% or more, 70% or more, 80% or more, 90% or more, 95% or more, 96% or more, 97% or more, 98% or more, 99% or more, or 100%) of the tumor sample.

It is to be understood that in any of the preceding methods, the percentage of the tumor sample comprised by tumor-infiltrating immune cells may be in terms of the percentage of tumor area covered by tumor-infiltrating immune cells in a section of the tumor sample obtained from the patient, for example, as assessed by IHC using an anti-PD-L1 antibody (e.g., the SP142 antibody).

IV. PD-L1 Axis Binding Antagonists for Use in the Methods of the Invention

Provided herein are methods for treating an individual having a cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor). Any of the preceding methods may be based on the determination of a bTMB score from a sample from the individual. Any of the preceding methods may further include determining an MSAF value from a sample from the individual. Any of the preceding methods may further include determining a tTMB value from a sample from the individual.

For example, an immune checkpoint inhibitor, for example, a PD-L1 axis binding antagonist, includes a PD-1 binding antagonist, a PD-L1 binding antagonist, and a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1 LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1 LG2," "CD273," "B7-DC," "Btdc," and "PDL2." An exemplary human PD-L2 is shown in UniProtKB/Swiss-Prot Accession No. Q9BQ51. In some instances, PD-1, PD-L1, and PD-L2 are human PD-1, PD-L1 and PD-L2.

In some instances, the PD-1 binding antagonist is a molecule that inhibits the binding of PD-1 to its ligand binding partners. In a specific aspect the PD-1 ligand binding partners are PD-L1 and/or PD-L2. In another instance, a PD-L1 binding antagonist is a molecule that inhibits the binding of PD-L1 to its binding ligands. In a specific aspect, PD-L1 binding partners are PD-1 and/or B7-1. In another instance, the PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some instances, the PD-1 binding antagonist is an anti-PD-1 antibody (e.g., a human antibody, a humanized antibody, or a chimeric antibody), for example, as described below. In some instances, the anti-PD-1 antibody is selected from the group consisting of MDX-1106 (nivolumab), MK-3475 (pembrolizumab), CT-011 (pidilizumab), MEDI-0680 (AMP-514), PDR001, REGN2810, and BGB-108. MDX-1106, also known as MDX-1106-04, ONO-4538, BMS-936558, or nivolumab, is an anti-PD-1 antibody described in WO2006/121168. MK-3475, also known as pembrolizumab or lambrolizumab, is an anti-PD-1 antibody described in WO 2009/114335. CT-011, also known as hBAT, hBAT-1 or pidilizumab, is an anti-PD-1 antibody described in WO 2009/101611. In some instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some instances, the PD-1 binding antagonist is AMP-224. AMP-224, also known as B7-DCIg, is a PD-L2-Fc fusion soluble receptor described in WO 2010/027827 and WO 2011/066342.

In some instances, the anti-PD-1 antibody is MDX-1106. Alternative names for "MDX-1106" include MDX-1106-04, ONO-4538, BMS-936558, and nivolumab. In some instances, the anti-PD-1 antibody is nivolumab (CAS Registry Number: 946414-94-4). In a still further instance, provided is an isolated anti-PD-1 antibody comprising a heavy chain variable region comprising the heavy chain variable region amino acid sequence from SEQ ID NO: 1 and/or a light chain variable region comprising the light chain variable region amino acid sequence from SEQ ID NO: 2. In a still further instance, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                              (SEQ ID NO: 1)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK,
``` and
(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                              (SEQ ID NO: 2)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In some instances, the PD-L1 axis binding antagonist is a PD-L2 binding antagonist. In some instances, the PD-L2 binding antagonist is an anti-PD-L2 antibody (e.g., a human antibody, a humanized antibody, or a chimeric antibody). In some instances, the PD-L2 binding antagonist is an immunoadhesin.

In some instances, the PD-L1 binding antagonist is an anti-PD-L1 antibody, for example, as described below. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')$_2$ fragments. In some instances, the anti-PD-L1 antibody is a humanized antibody. In some instances, the anti-PD-L1 antibody is a human antibody. In some instances, the anti-PD-L1 antibody is selected from the group consisting of YW243.55.S70, MPDL3280A (atezolizumab), MDX-1105, and MED14736 (durvalumab), and MSB0010718C (avelumab). Antibody YW243.55.S70 is an anti-PD-L1 described in WO 2010/077634. MDX-1105, also known as BMS-936559, is an anti-PD-L1 antibody described in WO2007/005874. MED14736 (durvalumab) is an anti-PD-L1 monoclonal antibody described in WO2011/066389 and US2013/034559. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559, which are incorporated herein by reference.

Anti-PD-L1 antibodies described in WO 2010/077634 A1 and U.S. Pat. No. 8,217,149 may be used in the methods described herein. In some instances, the anti-PD-L1 antibody comprises a heavy chain variable region sequence of SEQ ID NO: 3 and/or a light chain variable region sequence of SEQ ID NO: 4. In a still further instance, provided is an isolated anti-PD-L1 antibody comprising a heavy chain variable region and/or a light chain variable region sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                              (SEQ ID NO: 3)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS,
``` and (b) the light chain sequence has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In one instance, the anti-PD-L1 antibody comprises a heavy chain variable region comprising an HVR-H1, HVR-H2 and HVR-H3 sequence, wherein:

(SEQ ID NO: 5)
(a) the HVR-H1 sequence is GFTFSX$_1$SWIH;

(SEQ ID NO: 6)
(b) the HVR-H2 sequence is AWIX$_2$PYGGSX$_3$YYADSVKG;

(SEQ ID NO: 7)
(c) the HVR-H3 sequence is RHWPGGFDY;

further wherein: $X_1$ is D or G; $X_2$ is S or L; $X_3$ is T or S. In one specific aspect, $X_1$ is D; $X_2$ is S and $X_3$ is T. In another aspect, the polypeptide further comprises variable region heavy chain framework sequences juxtaposed between the HVRs according to the formula: (FR-H1)-(HVR-H1)-(FR-H2)-(HVR-H2)-(FR-H3)-(HVR-H3)-(FR-H4). In yet another aspect, the framework sequences are derived from human consensus framework sequences. In a further aspect, the framework sequences are VH subgroup III consensus framework. In a still further aspect, at least one of the framework sequences is the following:

(SEQ ID NO: 8)
FR-H1 is EVQLVESGGGLVQPGGSLRLSCAAS (SEQ ID NO: 9)
FR-H2 is WVRQAPGKGLEWV (SEQ ID NO: 10)
FR-H3 is RFTISADTSKNTAYLQMNSLRAEDTAVYYCAR (SEQ ID NO: 11)
FR-H4 is WGQGTLVTVSS.

In a still further aspect, the heavy chain polypeptide is further combined with a variable region light chain comprising an HVR-L1, HVR-L2 and HVR-L3, wherein:

(SEQ ID NO: 12)
(a) the HVR-L1 sequence is RASQX$_4$X$_5$X$_6$TX$_7$X$_8$A;

(SEQ ID NO: 13)
(b) the HVR-L2 sequence is SASX$_9$LX$_{10}$S,;

(SEQ ID NO: 14)
(c) the HVR-L3 sequence is QQX$_{11}$X$_{12}$X$_{13}$X$_{14}$PX$_{15}$T;

wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A.

In a still further aspect, the light chain further comprises variable region light chain framework sequences juxtaposed between the HVRs according to the formula: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the framework sequences are VL kappa I consensus framework. In a still further aspect, at least one of the framework sequence is the following:

(SEQ ID NO: 15)
FR-L1 is DIQMTQSPSSLSASVGDRVTITC (SEQ ID NO: 16)
FR-L2 is WYQQKPGKAPKLLIY (SEQ ID NO: 17)
FR-L3 is GVPSRFSGSGSGTDFTLTISSLQPEDFATYYC (SEQ ID NO: 18)
FR-L4 is FGQGTKVEIKR.

In another instance, provided is an isolated anti-PD-L1 antibody or antigen binding fragment comprising a heavy chain and a light chain variable region sequence, wherein:

(a) the heavy chain comprises an HVR-H1, HVR-H2 and HVR-H3, wherein further:

(SEQ ID NO: 5)
(i) the HVR-H1 sequence is GFTFSX$_1$SWIH;

(SEQ ID NO: 6)
(ii) the HVR-H2 sequence is AWIX$_2$PYGGSX$_3$YYADSVKG (SEQ ID NO: 7)
(iii) the HVR-H3 sequence is RHWPGGFDY, and (b) the light chain comprises an HVR-L1, HVR-L2 and HVR-L3, wherein further:

(SEQ ID NO: 12)
(i) the HVR-L1 sequence is RASQX$_4$X$_5$X$_6$TX$_7$X$_8$A (SEQ ID NO: 13)
(ii) the HVR-L2 sequence is SASX$_9$LX$_{10}$S; and (SEQ ID NO: 14)
(iii) the HVR-L3 sequence is QQX$_{11}$X$_{12}$X$_{13}$X$_{14}$PX$_{15}$T;

wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_1$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10, and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs: 15, 16, 17, and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In yet another instance, provided is an anti-PD-L1 antibody comprising a heavy chain and a light chain variable region sequence, wherein:
  (a) the heavy chain further comprises an HVR-H1, HVR-H2 and an HVR-H3 sequence having at least 85% sequence identity to GFTFSDSWIH (SEQ ID NO: 19), AWISPYGGSTYYADSVKG (SEQ ID NO: 20) and RHWPGGFDY (SEQ ID NO: 21), respectively, or
  (b) the light chain further comprises an HVR-L1, HVR-L2 and an HVR-L3 sequence having at least 85% sequence identity to RASQDVSTAVA (SEQ ID NO: 22), SASFLYS (SEQ ID NO: 23) and QQYLYHPAT (SEQ ID NO: 24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs: 8, 9, 10, and 11. In a still further aspect, the light chain framework sequences are derived from a Kabat kappa I, II, II, or IV subgroup sequence. In a still further aspect, the light chain framework sequences are VL kappa I consensus framework. In a still further aspect, one or more of the light chain framework sequences are set forth as SEQ ID NOs: 15, 16, 17, and 18.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                         (SEQ ID NO: 27)
FR-H1  EVQLVESGGGLVQPGGSLRLSCAASGFTFS (SEQ ID NO: 28)
FR-H2  WVRQAPGKGLEWVA (SEQ ID NO: 10)
FR-H3  RFTISADTSKNTAYLQMNSLRAEDTAVYYCAR (SEQ ID NO: 11)
FR-H4  WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                         (SEQ ID NO: 15)
FR-L1  DIQMTQSPSSLSASVGDRVTITC (SEQ ID NO: 16)
FR-L2  WYQQKPGKAPKLLIY (SEQ ID NO: 17)
FR-L3  GVPSRFSGSGSGTDFTLTISSLQPEDFATYYC (SEQ ID NO: 26)
FR-L4  FGQGTKVEIK.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In yet another instance, provided is an anti-PD-L1 antibody comprising a heavy chain and a light chain variable region sequence, wherein:
  (c) the heavy chain further comprises an HVR-H1, HVR-H2 and an HVR-H3 sequence having at least 85% sequence identity to GFTFSDSWIH (SEQ ID NO: 19), AWISPYGGSTYYADSVKG (SEQ ID NO: 20) and RHWPGGFDY (SEQ ID NO: 21), respectively, and/or
  (d) the light chain further comprises an HVR-L1, HVR-L2 and an HVR-L3 sequence having at least 85% sequence identity to RASQDVSTAVA (SEQ ID NO: 22), SASFLYS (SEQ ID NO: 23) and QQYLYHPAT (SEQ ID NO: 24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs: 8, 9, 10, and WGQGTLVTVSSASTK (SEQ ID NO: 29).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs: 15, 16, 17, and 18. In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In a still further instance, provided is an isolated anti-PD-L1 antibody comprising a heavy chain and a light chain variable region sequence, wherein:
(a) the heavy chain sequence has at least 85% sequence identity to the heavy chain sequence:

(SEQ ID NO: 25)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTK, (b) the light chain sequences has at least 85% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In some instances, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 4. In some instances, provided is an isolated anti-PD-L1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 25. In some instances, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 4 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 25. In some instances, one, two, three, four, or five amino acid residues at the N-terminal of the heavy and/or light chain may be deleted, substituted or modified.

In a still further instance, provided is an isolated anti-PD-L1 antibody comprising a heavy chain and a light chain sequence, wherein:
(a) the heavy chain sequence has at least 85% sequence identity to the heavy chain sequence:

(SEQ ID NO: 30)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG, and/or
(b) the light chain sequences has at least 85% sequence identity to the light chain sequence:

(SEQ ID NO: 31)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some instances, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 31. In some instances, provided is an isolated anti-PD-L1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 30. In some instances, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 31 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 30.

In some instances, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the instances herein, the isolated anti-PD-L1 antibody can bind to a human PD-L1, for example a human PD-L1 as shown in UniProtKB/Swiss-Prot Accession No. Q9NZQ7.1, or a variant thereof.

In a still further instance, provided is an isolated nucleic acid encoding any of the antibodies described herein. In some instances, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragments in a form suitable for expression, under conditions suitable to produce such antibody or fragment, and recovering the antibody or fragment.

It is expressly contemplated that such PD-L1 axis binding antagonist antibodies (e.g., anti-PD-L1 antibodies, anti-PD-1 antibodies, and anti-PD-L2 antibodies), or other antibodies described herein for use in any of the instances enumerated above may have any of the features, singly or in combination, described in Sections 1-7 below.

1. Antibody Affinity

In certain instances, an antibody provided herein (e.g., an anti-PD-L1 antibody or an anti-PD-1 antibody) has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one instance, Kd is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another instance, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one instance, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain instances, an antibody (e.g., an anti-PD-L1 antibody or an anti-PD-1 antibody) provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain instances, an antibody (e.g., an anti-PD-L1 antibody or an anti-PD-1 antibody) provided herein is a chimeric antibody. Certain chimeric antibodies are described, e.g., in U.S. Pat. No. 4,816,567; and Morrison et al. *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl. Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain instances, an antibody (e.g., an anti-PD-L1 antibody or an anti-PD-1 antibody) provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention (e.g., anti-PD-L1 antibodies and anti-PD-1 antibodies) may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, an antibody (e.g., an anti-PD-L1 antibody or an anti-PD-1 antibody) provided herein may be a multispecific antibody, for example, a bispecific antibody. Multispecific antibodies are monoclonal antibodies that have binding specificities for at least two different sites. In certain instances, an antibody provided herein is a multispecific antibody, e.g., a bispecific antibody. In certain instances, one of the binding specificities is for PD-L1 and the other is for any other antigen. In certain instances, bispecific antibodies may bind to two different epitopes of PD-L1. Bispecific antibodies may also be used to localize cytotoxic agents to cells which express PD-L1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (see, e.g., WO 2009/089004A1); cross-linking two or more antibodies or fragments (see, e.g., U.S. Pat. No. 4,676,980, and Brennan et al., *Science* 229: 81 (1985)); using leucine zippers to produce bi-specific antibodies (see, e.g., Kostelny et al., *J. Immunol.* 148(5): 1547-1553 (1992)); using "diabody" technology for making bispecific antibody fragments (see, e.g., Hollinger et al., *Proc. Natl. Acad. Sci. USA* 90:6444-6448 (1993)); using single-chain Fv (sFv) dimers (see, e.g., Gruber et al., *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to PD-L1 as well as another, different antigen.

7. Antibody Variants

In certain instances, amino acid sequence variants of the antibodies of the invention (e.g., anti-PD-L1 antibodies and anti-PD-1 antibodies) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

I. Substitution, Insertion, and Deletion Variants

In certain instances, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved Antibody-Dependent Cell-Mediated Cytotoxicity (ADCC) or Complement Dependant Cytotoxicity (CDC).

TABLE 2

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, lie;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)). In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen-contacting residues in the HVRs. In certain instances of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

II. Glycosylation Variants

In certain instances, antibodies of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention may be made in order to create antibody variants with certain improved properties.

In one instance, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, U.S. Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); U.S. Pat. Appl. No. US 2003/0157108 A1; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

III. Fc Region Variants

In certain instances, one or more amino acid modifications may be introduced into the Fc region of an antibody of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest are described in U.S. Pat. No. 5,500,362 (see, e.g., Hellstrom, I. et al. *Proc. Natl. Acad. Sci. USA* 83:7059-7063 (1986)) and Hellstrom, I et al., *Proc. Natl. Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.))). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al., *J. Immunol. Methods* 202:163 (1996); Cragg et al., *Blood.* 101:1045-1052 (2003); and Cragg et al., *Blood.* 103:2738-2743 (2004)). FcRn binding and in vivo clearance/half life determinations can also be performed using methods known in the art (see, e.g., Petkova et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain instances, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

IV. Cysteine Engineered Antibody Variants

In certain instances, it may be desirable to create cysteine engineered antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

V. Antibody Derivatives

In certain instances, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and nonproteinaceous moiety that may be selectively heated by exposure to radiation are provided. In one instance, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

VI. Immunoconjugates

The invention also provides immunoconjugates comprising an antibody herein (e.g., an anti-PD-L1 antibody or an anti-PD-1 antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one instance, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another instance, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron. Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate) which are commercially available (e.g., from Pierce Biotechnology, Inc., Rockford, Ill., U.S.A).

V. Pharmaceutical Formulations

Therapeutic formulations of the immune checkpoint inhibitors, e.g., PD-L1 axis binding antagonists (e.g., an anti-PD-L1 antibody (e.g., MPDL3280A)) and antagonists directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)) used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 18th Edition, Mack Publishing Co., Pennsylvania, 1990; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

It is to be understood that any of the above articles of manufacture may include an immunoconjugate described herein in place of or in addition to an immune checkpoint inhibitor, for example, a PD-L1 axis binding antagonist.

VI. Diagnostic Kits and Articles of Manufacture

Provided herein are diagnostic and prognostic kits including one or more reagents for identifying an individual having a cancer (e.g., a lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor) who may benefit from a treatment including an immune checkpoint inhibitor, for example, a PD-L1 axis binding antagonist, by determining a blood tumor mutational burden (bTMB) score, or a bTMB score and a maximum somatic allele frequency (MSAF), as described herein, from a sample (e.g., a whole blood sample, a plasma sample, a serum sample, or a combination thereof) from the individual. In some embodiments, the kit further includes one or more reagents for determining a tTMB score from a sample (e.g., a tumor sample) from the individual.

Optionally, the kit may further include instructions to use the kit to select a medicament (e.g., an immune checkpoint inhibitor, for example, a PD-L1 axis binding antagonist (e.g., anti-PD-L1 antibody, e.g., MPDL3280A)), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, for treating a cancer if the bTMB score obtained from the sample from the individual is above a reference bTMB score. In another instance, the instructions are to use the kit to select an anti-cancer therapy other than, or in addition to, an immune checkpoint inhibitor, for example, a PD-L1 axis binding antagonist, if the bTMB score obtained from the sample from the individual is below a reference bTMB score. In some instances, the kit may further include instructions to use the kit to select a medicament for treating a cancer based a combination of a bTMB score and an MSAF determined from the sample from the individual. In some instances, the kit may further include instructions to use the kit to select a medicament for treating a cancer based a combination of a bTMB score determined from the sample from the individual and a tTMB score determined from a tumor sample from the individual.

Provided herein are also articles of manufacture including, packaged together, an immune checkpoint inhibitor, for example, a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, in a pharmaceutically acceptable carrier and a package insert indicating that the immune checkpoint inhibitor is for treating a patient with a cancer as described herein based on the presence of somatic mutations. Treatment methods include any of the treatment methods disclosed herein. The invention also concerns a method for manufacturing an article of manufacture comprising combining in a package a pharmaceutical composition comprising an immune checkpoint inhibitor, for example, a PD-L1 axis binding antagonist (e.g., an anti-PD-L1 antibody), an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, and a package insert indicating that the pharmaceutical composition is for treating a patient with a disease or disorder based on the bTMB score obtained from a sample from the individual. In some embodiments, the package insert indicates that the pharmaceutical composition is for treating a patient with a disease or disorder based on the bTMB score obtained from a sample from the individual and the tTMB score obtained from a tumor sample from the individual.

The article of manufacture may include, for example, a container and a label or package insert on or associated with the container. Suitable containers include, for example, bottles, vials, syringes, and the like. The container may be formed from a variety of materials such as glass or plastic. The container holds or contains a composition comprising the cancer medicament as the active agent and may have a sterile access port (e.g., the container may be an intravenous solution bag or a vial having a stopper pierceable by a hypodermic injection needle).

The article of manufacture may further include a second container comprising a pharmaceutically-acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer based on the presence of the somatic mutation(s) and/or based on the expression of a biomarker (e.g., PD-L1 expression levels, for instance, in tumor cells and/or tumor-infiltrating immune cells) herein. The insert or label may take any form, such as paper or on electronic media such as a magnetically recorded medium (e.g., floppy disk), a CD-ROM, a Universal Serial Bus (USB) flash drive, and the like. The label or insert may also include other information concerning the pharmaceutical compositions and dosage forms in the kit or article of manufacture.

EXAMPLES

The following is an example of the methods of the invention. It is understood that various other embodiments may be practiced, given the general description provided above.

Example 1. Methods

A blood-based assay was used to evaluate the association between clinical response to treatment with atezolizumab (MPDL3280A) and blood tumor mutational burden (bTMB) score in patients with non-small cell lung cancer (NSCLC) enrolled in two clinical trials, a phase II clinical trial, POPLAR (Clinical Trial ID No.: NCT01903993), and a phase III clinical trial, OAK (Clinical Trial ID No.: NCT02008227), in which atezolizumab was administered as a monotherapy.

Study Design

Pre-treatment blood samples from patients with NSCLC who were enrolled in the POPLAR and/or the OAK studies, in which atezolizumab was administered as a monotherapy, were evaluated for bTMB score and/or maximum somatic allele frequency (MSAF).

The POPLAR (Clinical Trial ID No.: NCT01903993) patient population evaluated for bTMB score consisted of 273 patients. Patients were eligible for enrollment in the POPLAR study if they had locally advanced or metastatic (e.g., stage IIIB, stage IV, or recurrent) non-small cell lung cancer (NSCLC); disease progression during or following treatment with a prior platinum-containing regimen for locally advanced, unresectable/inoperable, or metastatic NSCLC, or disease recurrence within 6 months of treatment with a platinum-based adjuvant/neoadjuvant regimen; measurable disease, as defined by RECIST v1.1; and an Eastern Cooperative Oncology Group (ECOG) performance status of 0 or 1. Participants were randomized to receive either atezolizumab at a dose of 1200 mg intravenously every three weeks or docetaxel 75 mg per meter square (mg/m$^2$) intravenously every three weeks. Treatment with atezolizumab could be continued as long as participants were experiencing clinical benefit, i.e., in the absence of unacceptable toxicity or symptomatic deterioration attributed to disease progression.

The OAK (Clinical Trial ID No.: NCT02008227) patient population evaluated for bTMB score consisted of 583 patients. Patients were eligible for enrollment in the OAK study if they had locally advanced or metastatic (e.g., stage IIIB, stage IV, or recurrent) NSCLC; disease progression during or following treatment with a prior platinum-containing regimen for locally advanced, unresectable/inoperable, or metastatic NSCLC, or disease recurrence within 6 months of treatment with a platinum-based adjuvant/neoadjuvant regimen; measurable disease, as defined by RECIST v1.1; and an ECOG performance status of 0 or 1. Participants were randomized to receive either atezolizumab at a dose of 1200 mg intravenously every three weeks or docetaxel 75 mg per square meter (mg/m$^2$) intravenously every three weeks. Treatment with atezolizumab could be continued as long as participants were experiencing clinical benefit, i.e., in the absence of unacceptable toxicity or symptomatic deterioration attributed to disease progression.

Both POPLAR and OAK were performed in full accordance with the guidelines for Good Clinical Practice and the Declaration of Helsinki, and all patients gave written informed consent. Protocol approval was obtained from independent ethics committees for each participating site for both studies.

Analysis of bTMB was performed retrospectively. Progression-free survival (PFS) was defined as the time between date of randomization and date of first documented disease progression as assessed by the investigator using RECIST v.1.1 or death from any cause, whichever occurred first. Overall survival (OS) was defined as the time between the date of randomization until death due to any cause. Treatment arms were compared for OS and PFS individually using a univariate Cox regression model without stratification in the biomarker evaluable-population (BEP) and their subgroups or using a stratified (by randomization stratification factors) Cox model in the ITT population. No multiplicity correction was applied to p-values or confidence intervals (CI). Kaplan-Meier methodology was used to estimate median OS and PFS and construct survival curves.

The patients who made up the BEP for each study were defined as follows:

In the OAK ITT population (N=850), 797 samples were available for analysis. Of these samples, 13 were removed for sample contamination >1%; 42 were removed for median exon coverage <800×; and 100 were removed for low MSAF<1%.

The OAK BEP (N=642) included 59 patients with EGFR mutation or ALK rearrangement, and 583 without known alterations.

In the POPLAR ITT population (N=287), 273 samples were available for analysis. Of these, 6 were removed for sample contamination >1%; 9 were removed for median exon coverage <800×; and 47 were removed for low MSAF<1%.

The POPLAR BEP (N=211) includes 15 patients with EGFR mutation or ALK rearrangement, and 196 without known alterations.

The efficacy outcomes of these two trials are summarized in Tables 8 and 9 in Example 2.

Plasma Isolation and Cell-Free DNA (cfDNA) Extraction

Clinical samples were received as frozen plasma stored at −80° C. Plasma was thawed and a second centrifugation was performed at 16,000×g for 20 min at 4° C., following which the supernatant was collected as plasma to be used for cfDNA extraction. Plasma was treated with proteinase K for 20 min at 60° C. and mixed with 1.25× volume of cfDNA binding solution (Thermo Scientific, Waltham Mass.) and 500 ng/mL of paramagnetic MYONE™ SILANE beads (Thermo Scientific). Beads were washed twice with cfDNA wash solution (Thermo Scientific), washed twice with 80% ethanol, and eluted in cfDNA elution solution (Thermo Scientific). The cfDNA concentration was determined using the D1000 ScreenTape assay on the 4200 TapeStation (Agilent Technologies) by focusing on fragments between 100-700 base pairs. 20-100 ng cfDNA was used for library construction.

Library Construction

Library construction was performed on the BRAVO™ Benchbot (Agilent Technologies) automation system with NEBNEXT® library preparation reagents (New England BioLabs Inc.) containing mixes for end-repair, dA addition, and ligation using the "with-bead" protocol to maximize library yield and complexity. A set of specific designed fragment-level indexed adaptors were ligated randomly onto both ends of each input duplex cfDNA fragment. Ligated sequencing libraries were PCR amplified with a universal PCR primer and an indexed PCR primer with a high-fidelity polymerase (Kapa Biosystems, Wilmington Mass.) for 10 cycles, 1.8× SPRI purified and quantified by PICOGREEN® DNA quantification solution (Invitrogen). Samples yielding 500-2,000 ng of sequencing library proceeded to hybrid capture.

Panel Design, Hybrid Capture and Sequencing

Solution hybridization was performed using a >50-fold molar excess of a pool of individually synthesized 5'biotinylated ssDNA oligonucleotide "baits" (assay baitset version T7) (Integrated DNA Technology). The baitset targeted 1.125 coding megabases (Mb) of the human genome. Bait design and hybridization capture was performed using 500-2,000 ng of sequencing library lyophilized with human Cot-1 DNA, sheared salmon sperm DNA, and adaptor-specific blocking oligonucleotides, resuspended in water, heat denatured at 95° C. for 5 min, incubated at 68° C., with the final addition of the baitset into hybridization buffer. The hybridization reaction was incubated at 68° C. for 12-24 h and library-baitset duplexes were captured on paramagnetic MYONE™ streptavidin beads (Invitrogen). Off-target library was removed by washing once with 1× saline-sodium citrate (SSC) buffer at 25° C. and 4 times with 0.25×SSC at 55° C. PCR master mix (Kapa Biosystems) was added directly to the beads to amplify the captured library. Samples were 1.8× solid phase reversible immobilization (SPRI) purified and quantified by PICOGREEN® (Invitrogen). Libraries were normalized to 1.05 nM, pooled, and loaded onto an Illumina cBot for the template extension reaction directly on the flowcell that was loaded onto an Illumina HISEQ® 4000 with 2×151 bp (Illumina).

Analysis of bTMB Score and Efficacy of Atezolizumab

To identify somatic mutations and calculate a bTMB score, whole blood samples obtained from each patient (collected in EDTA or Streck tubes) were processed through a series of spins to isolate plasma, from which cell free DNA (cfDNA) was extracted for sequencing analysis. Specifically, at least 20 ng purified cfDNA was used for library construction. Next-generation sequencing libraries using fragment barcodes and hybrid capture were constructed to analyze and sequence a pre-determined set of 394 genes that covered approximately 1.125 Mb of the exome. Specifically, purified libraries were hybrid captured using a 394-gene bait set and then further purified, pooled and loaded on an ILLUMINA® HISEQ® 4000 sequencing system. Sequenced libraries were aligned and sorted. In order to accurately call variants at low allele frequencies and minimize artifacts from sequencing, PCR, or DNA damage-related errors, sequenced libraries were processed by a cfDNA computational pipeline that corrected errors via the use of fragment barcodes. Briefly, fragment barcoded error correction was performed by sequencing to sufficiently high depth to obtain multiple observations for most DNA fragments in each sample and using the fragment barcodes to accurately detect and exclude errors introduced during library preparation and sequencing. Error-corrected reads were aligned to the hg19 reference genome and base substitutions were called. Library size was based off a comparative analysis of bTMB scores calculated using whole exome sequence (WES) data from The Cancer Genome Atlas (TCGA) according to the methodology described in Chalmers et al. (*Genome Medicine.* 9(34), 2017). In this analysis, a bTMB score of 10 calculated using sequence data covering 0.5 Mb or 1.0 Mb of the exome was found to deviate by only 20% or 10%, respectively, from a bTMB score of 10 calculated using WES data. This analysis showed that a sequencing library targeting 0.5 Mb of coding genome can accurately assess bTMB compared with sequencing the whole exome.

The bTMB score was measured as the number of somatic, coding, base substitutions. All base substitutions in the coding region of targeted genes, including synonymous alterations, were initially counted before filtering as described below. Non-coding alterations were not counted. Alterations listed as known somatic alterations in the COSMIC database (Forbes et al. (2014) Nucl. Acids Res. 43:D805-11) and truncations in tumor suppressor genes were not counted. Alterations predicted to be germline by the somatic-germline-zygosity (SGZ) algorithm were not counted (Sun et al. Cancer Research 2014; 74(19S):1893-1893). The SGZ method utilizes a statistical model of genome-wide copy number and tumor/normal admixture to characterize the status of the variant as likely somatic or germline. The remaining mutations were further filtered according to their predicted driver status to minimize the bias associated with the genes used for capture. Alterations that were recurrently predicted to be germline in the cohort of clinical specimens assessed were not counted. Known germline alterations listed in the dbSNP database (Sherry et al. (2001) Nucleic Acids Res. 29(1):308-11) were not counted. Germline alterations occurring with two or more counts in the Exome Aggregation Consortium (ExAC) database were not counted (Lek et al. Nature 2016; 536:285-91). Additionally, base substitutions deemed to be known or likely driver mutations in cancer were removed from the bTMB calculation to counter the bias associated with the gene panel.

To estimate the total amount of ctDNA and calculate an MSAF, somatic mutations in the blood samples obtained from each patient were identified as described above. The frequency of the most commonly occurring allele (e.g., a gene variant having a somatic mutation) below 20% for a sample was then identified as the MSAF.

The BEP was defined as patients having a bTMB score at, or above, a reference bTMB score. In some of the following examples, the BEP was defined as patients having a bTMB score at, or above, a reference bTMB score and a pre-determined MSAF, or defined as patients having only a pre-determined MSAF.

Analytic Validation

As part of the analytical validation of the bTMB assay, an agreement analysis was performed between the previously validated FOUNDATIONONE® TMB method and the bTMB method described herein using an independent cohort of non-trial samples (N=69) that were split and analyzed by both assays.

The analytic validation of the blood tumor mutational burden (bTMB) assay focused on establishing both precision and reliability of the bTMB count and status, respectively, as well as MSAF. The bTMB count was determined by identifying all base substitutions present at an allele frequency ≥0.5% across the coding region of 394 genes (=1.1 Mb), and filtering out germline events by comparing against the dbSNP and ExAC databases. Additionally, rare germline events not found in these databases were removed using a somatic-germline zygosity algorithm that uses copy number modelling to assign a germline status probability (see Sun et al. *PLoS Computational Biology* 14(2): e1005965, 2018). The remaining mutations were further filtered according to their predicted driver status to minimize the bias associated with the genes used for capture. The estimation of tumor fraction by the MSAF is defined according to the highest allele fraction for confirmed somatic base substitutions <20%, regardless of their driver status. This threshold was chosen to minimize the chance of rare germline events in highly aneuploid tumors affecting the estimation.

The concordance of the variant allele frequency calls in bTMB versus the previously analytically-validated FOUNDATIONACT® was assessed as follows. Positive percentage agreement (PPA) or sensitivity was measured by dividing the number of variants detected by both the bTMB assay and FOUNDATIONACT® over the number of variants detected by the FOUNDATIONACT® assay. Positive predictive value (PPV) was measured by dividing the number of variants detected by both the bTMB assay and FOUNDATIONACT® by the number of variants detected with the bTMB assay. Both PPA and PPV were limited to the region targeted by both assays, which is the region covered by the FOUNDATIONACT® assay.

The accuracy of bTMB was evaluated against an orthogonally validated method (FOUNDATIONONE® TMB), which was previously shown to correlate well with whole-exome sequencing measurements of TMB. Comparability was established by evaluating both PPA and negative percent agreement (NPA). Additionally, MSAF values were evaluated for accuracy by comparing the observed value against the expected value in a dilution series.

Precision of the bTMB count (score) was established by measuring the average coefficient of variation (CV) of 77 total samples across 23 groups, with bTMB counts spanning a clinically meaningful range observed in patients with non-small cell lung cancer (NSCLC) (0 to 34 mutations). Within each replicate group, samples were evaluated against the majority call and reproducibly was calculated according to the bTMB score of ≥16. Precision for MSAF was calculated similarly from 127 replicate samples across 38 groups, and reliability was determined according to the quality control criterion of ≥1% MSAF in a cfDNA sample to make reliable and accurate bTMB calls.

In order to evaluate the accuracy of the MSAF value, extracted DNA from six different cancer reference cell lines were diluted into DNA from non-tumor cell lines to reflect a range of MSAF values from 0.1% to 20%. The accuracy of MSAF was determined by evaluating the linear regression from observed and expected values across all six cell lines, and the coefficient of determination ($R^2$) was calculated for each respective cell line. The average $R^2$ value was computed from all six measurements (Table 3).

TABLE 3

Accuracy of MSAF Comparing Expected vs. Observed Values Across Six Cell Lines in a Dilution Series

| | |
|---|---|
| AGS | 0.96 |
| HCC-1599 | 0.99 |
| NCI-H146 | 0.98 |
| NCI-H2009 | 1.00 |
| NCI-H727 | 0.96 |
| TUR | 0.96 |

MSAF, maximum somatic allele frequency.
[a] Pearson correlation squared.

Tumor mutational burden from tissue (tTMB) was determined after comprehensive genomic profiling was performed on formalin-fixed, paraffin-embedded (FFPE) tissue samples from the POPLAR and OAK studies using the FoundationOne (F1) assay, as described in Frampton et al. *Nat. Biotechnol.* 31:1023-1031, 2013. Tumor purity was computationally derived from the copy-number model based on coverage across the genome (relative to a control) and single-nucleotide polymorphism (SNP) allele frequencies (Frampton et al. supra). tTMB was defined as the number of somatic, coding, single-nucleotide variants (SNVs) and insertions and deletions (indels) detected at an allele frequency of ≥5% after the removal of known and likely oncogenic driver events and germline SNPs, as previously described (Chalmers et al. *Genome Med.* 9:34-017-0424-2, 2017). Artifact removal was performed by comparison to an artifact database comprised from normal, healthy FFPE tissue and computational filtering for strand bias as previously described (Frampton et al. supra).

The blood-based TMB (bTMB) assay uses the exact same hybridization capture panel as the F1 TMB test, which includes 1.1 Mb of coding region in the genome. This panel is described in detail in Chalmers et al. supra. While Chalmers et al. mention 315 genes, this number refers to the genes used for reporting specific alterations associated with cancer in the F1 test. There are an additional 79 genes that are included in the technology described by Chalmers et al. that are considered exploratory genes of interest which are not included on the F1 report and therefore were not described in the Chalmers reference. However, the bait set (1.1 Mb) utilized in the Chalmers study is the same as the bait set described here. The full 1.1 Mb were used for the calculation of bTMB in this study.

The accuracy of the bTMB score was established by evaluating the agreement of calling TMB≥10 or ≥16 using an orthogonally validated method that is part of the FOUNDATIONONE® (F1) workflow. This method uses a laboratory workflow similar to that described for the bTMB assay, however, the process was optimized for formalin-fixed, paraffin-embedded tissue samples with ≥20% tumor content. Furthermore, bTMB computational analysis differs from the tissue-based TMB (tTMB) calculation in two ways: first, the blood-based assay uses only single-nucleotide variant (SNV) calls to determine bTMB whereas the tTMB assay uses both SNVs and insertions or deletions; second, the bTMB computational pipeline calls SNVs down to much lower allele frequencies (0.5%) compared with tTMB. Therefore, the same next-generation sequencing (NGS) data analyzed through both pipelines will yield somewhat different results depending on the spectrum of genetic variants in a given sample. A total of 69 samples were split after the DNA extraction stage and analyzed according to each separate process. The PPA was calculated by dividing the number of true positives, defined as orthogonally determined TMB values ≥16, by the total sum of true positives and false negatives. NPA was calculated by dividing the number of true negatives, defined as orthogonally determined TMB values <16, by the sum of all true negatives and false positives. PPVs were also calculated by dividing the number of true positives by the sum of all true positives and false positives. A similar analysis was performed for a bTMB cut-point of 10.

Both PPV and precision of the bTMB calculation are affected by the tumor content within a cfDNA sample (MSAF). Therefore, evaluation of the minimum MSAF required to maintain a consistent bTMB biomarker score of ≥10 or ≥16 was assessed using 129 contrived tumor cell line DNA samples with a range of starting bTMB values, serially diluted in normal DNA to yield a range of MSAF values down to 0.1%. For each MSAF replicate group, the bTMB status of ≥16 was compared to the non-diluted sample status, and the resulting cumulative status reproducibility was calculated starting from 20% MSAF down to 0.1% MSAF.

Additionally, the quality control metric of median exon target coverage was evaluated by assessing the precision of both the bTMB score and MSAF value using in silico down sampling of eight clinical specimens. Coverage down-sampling was performed in silico by randomly reducing the total number of consensus reads to reflect median exon coverages from 2000× down to 800×. At each respective coverage, 10 in silico replicates were assessed in order to calculate the CV, and the lowest coverage that yielded an average CV for both the bTMB score and MSAF calculation <30% in the majority samples was chosen.

The minimum cfDNA input mass to achieve at least 800× sequence coverage was determined by evaluating the relationship between input mass and sequence coverage across more than 1,000 clinical samples. The lowest mass that achieved at least 800× coverage at 100% frequency was chosen as the minimum cfDNA input mass.

Statistical methods for calculating the aforementioned assay performance metrics, including Pearson and Spearman correlations, coefficient of variations, PPA, NPA, PPV and NPV, were performed using statistical software provided by Microsoft EXCEL® (2016 M S Office) or JMP software (©SAS Institute, Inc.).

The simulated sensitivity and specificity of a TMB assay are shown according to the size of the panel used for its calculation (FIG. 15). To generate these values, a total of 250 million random samplings were performed for each panel size (from 5 Mb down to 50 Kb) and whole exome TMB (from 100 mut/Mb down to 0.5 mut/Mb). The fraction of samplings that maintained a TMB value of ≥ or <14 mut/Mb, or 16 total mutations from the bTMB assay, was compared with the underlying whole exome-derived TMB value and computed for each respective panel size. The results were compared with the real-world distribution of TMB values derived from patients with NSCLC using the Foundation Medicine database (n=19,320). Sensitivity was calculated as the fraction of true positives divided by the sum of all true positives and false negatives, and the specificity was calculated as the number of true negatives divided by the sum of all true negatives and false positives. The plotted values represent the results derived from this analysis, and the shaded regions represent the size of the panel required to maintain at least 85% sensitivity and specificity.

Immunohistochemical (IHC) Analysis of PD-L1 Expression in Tumor Samples

Formalin-fixed, paraffin-embedded tissue sections were deparaffinized prior to antigen retrieval, blocking and incubation with primary anti-PD-L1 antibody. Following incubation with secondary antibody and enzymatic color development, sections were counterstained and dehydrated in series of alcohols and xylenes before coverslipping.

The following protocol was used for IHC. The Ventana Benchmark XT or Benchmark Ultra system was used to perform PD-L1 IHC staining using the following reagents and materials:

Primary antibody: anti-PD-L1 Rabbit Monoclonal Primary Antibody (SP142)

Specimen Type: Formalin-fixed paraffin embedded (FFPE) section of tumor samples

Epitope Recovery Conditions: Cell Conditioning, standard 1 (CC1, Ventana, cat #950-124)

Primary Antibody Conditions: 1/100, 6.5 µg/ml for 16 minutes at 36° C.

Diluent: Antibody dilution buffer (Tris-buffered saline containing carrier protein and BRIJ™-35)

Negative control: Naive Rabbit IgG at 6.5 µg/ml (Cell Signaling) or diluent alone Detection: Optiview or ultraView Universal DAB Detection kit (Ventana), and amplification kit (if applicable) were used according to manufacturer's instructions (Ventana).

Counterstain: Ventana Hematoxylin II (cat #790-2208)/with Bluing reagent (Cat #760-2037) (4 minutes and 4 minutes, respectively)

The Ventana Benchmark Protocol is described, for example, in International Patent Application Publication No. WO 2016/183326, which is incorporated herein by reference in its entirety.

Tumor samples were scored for PD-L1 positivity in tumor-infiltrating immune cells and in tumor cells according to both of the criteria for diagnostic assessment shown in Table 4 and Table 5, respectively.

TABLE 4

Tumor-infiltrating immune cell (IC) IHC diagnostic criteria

| PD-L1 Diagnostic Assessment | IC Score |
|---|---|
| Absence of any discernible PD-L1 staining OR Presence of discernible PD-L1 staining of any intensity in tumor-infiltrating immune cells covering < 1% of tumor area occupied by tumor cells, associated intratumoral stroma, and contiguous peri-tumoral desmoplastic stroma | IC0 |
| Presence of discernible PD-L1 staining of any intensity in tumor-infiltrating immune cells covering ≥ 1% to < 5% of tumor area occupied by tumor cells, associated intratumoral stroma, and contiguous peri-tumoral desmoplastic stroma | IC1 |
| Presence of discernible PD-L1 staining of any intensity in tumor-infiltrating immune cells covering ≥ 5% to < 10% of tumor area occupied by tumor cells, associated intratumoral stroma, and contiguous peri-tumoral desmoplastic stroma | IC2 |
| Presence of discernible PD-L1 staining of any intensity in tumor-infiltrating immune cells covering ≥ 10% of tumor area occupied by tumor cells, associated intratumoral stroma, and contiguous peri-tumoral desmoplastic stroma | IC3 |

TABLE 5

Tumor cell (TC) IHC diagnostic criteria

| PD-L1 Diagnostic Assessment | TC Score |
|---|---|
| Absence of any discernible PD-L1 staining OR Presence of discernible PD-L1 staining of any intensity in < 1% of tumor cells | TC0 |
| Presence of discernible PD-L1 staining of any intensity in ≥ 1% to < 5% of tumor cells | TC1 |
| Presence of discernible PD-L1 staining of any intensity in ≥ 5% to < 50% of tumor cells | TC2 |
| Presence of discernible PD-L1 staining of any intensity in ≥ 50% of tumor cells | TC3 |

Figure 1A:
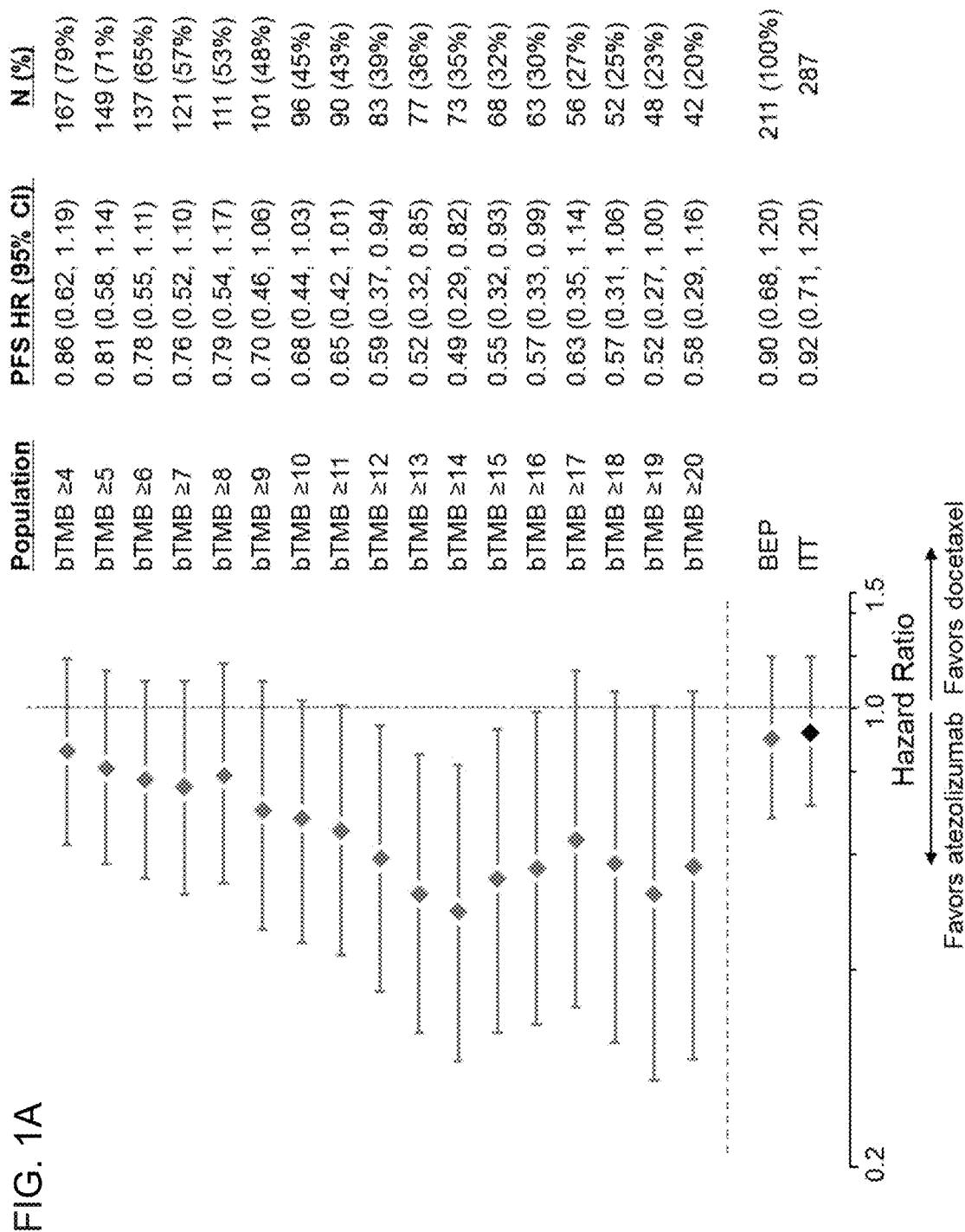
FIG. 1A is a graph showing hazard ratios (HRs) for progression-free survival (PFS) in patients in the POPLAR study (Clinical Trial ID No.: NCT01903993) who are diagnostic-positive (Dx+), based on blood tumor mutational burden (bTMB) scores at or above the indicated reference bTMB scores. ITT, intention to treat; BEP, biomarker-evaluable population. Stratified HRs are shown for the ITT, while unstratified HRs are shown for the BEP and for the subgroups having the indicated reference bTMB scores.
Figure 1B:
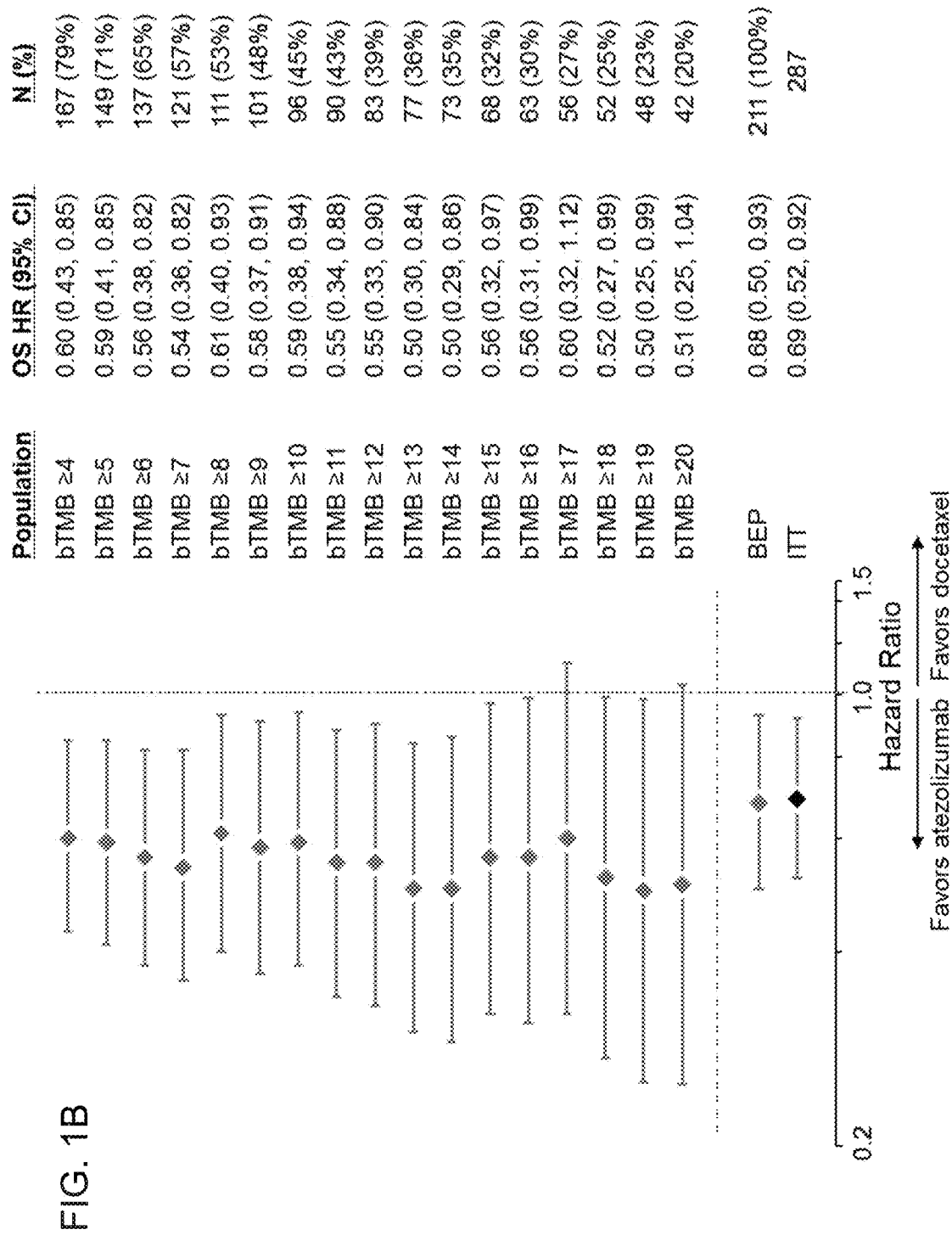
FIG. 1B is a graph showing HRs for overall survival (OS) in patients in the POPLAR study who are Dx+ based on bTMB scores at or above the indicated reference bTMB scores. This figure shows unstratified hazard ratios.
Figure 7A:
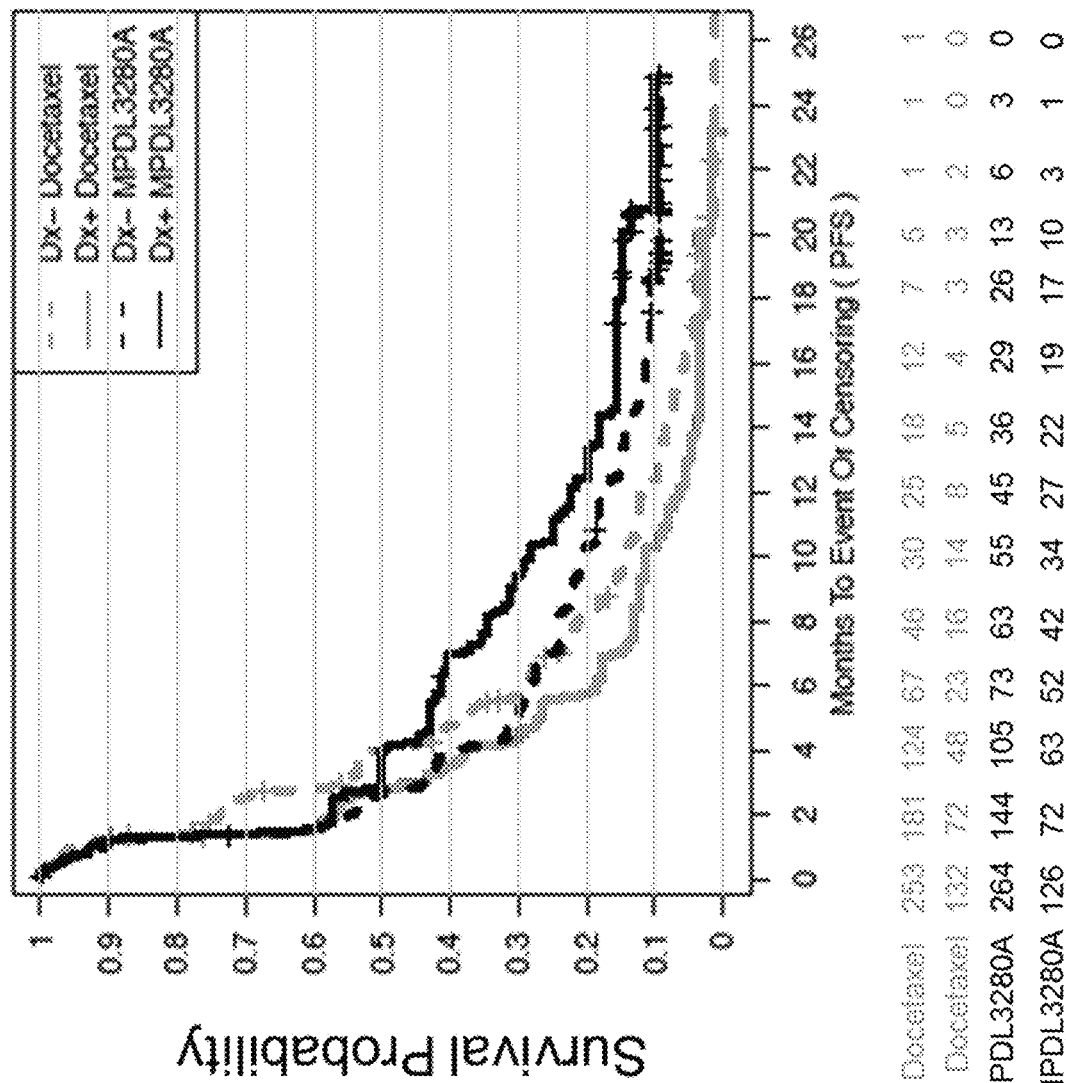
FIG. 7A is a graph showing the Kaplan-Meier Curve of PFS of the combined BEP of patients (nBEP=775 patients; HR=0.62) in the atezolizumab treatment arm (black) and docetaxel control arm (gray) of the POPLAR and OAK studies, each arm stratified according to bTMB score. Patients with a bTMB score that is greater than, or equal to, a reference bTMB score of 14 are indicated by solid lines (Dx+) and patients with a bTMB that is lower than a reference bTMB score of 14 are indicated by dashed lines (Dx−). Also shown is a table listing the number of patients who did not have a PFS event within each subgroup of the BEP at a given time point. The time point for each column corresponds to the times shown along the x-axis of the above graph. Patient samples having an MSAF less than 1% were excluded from analysis. Sequence coverage was greater than, or equal to, 800.
Figure 7B:
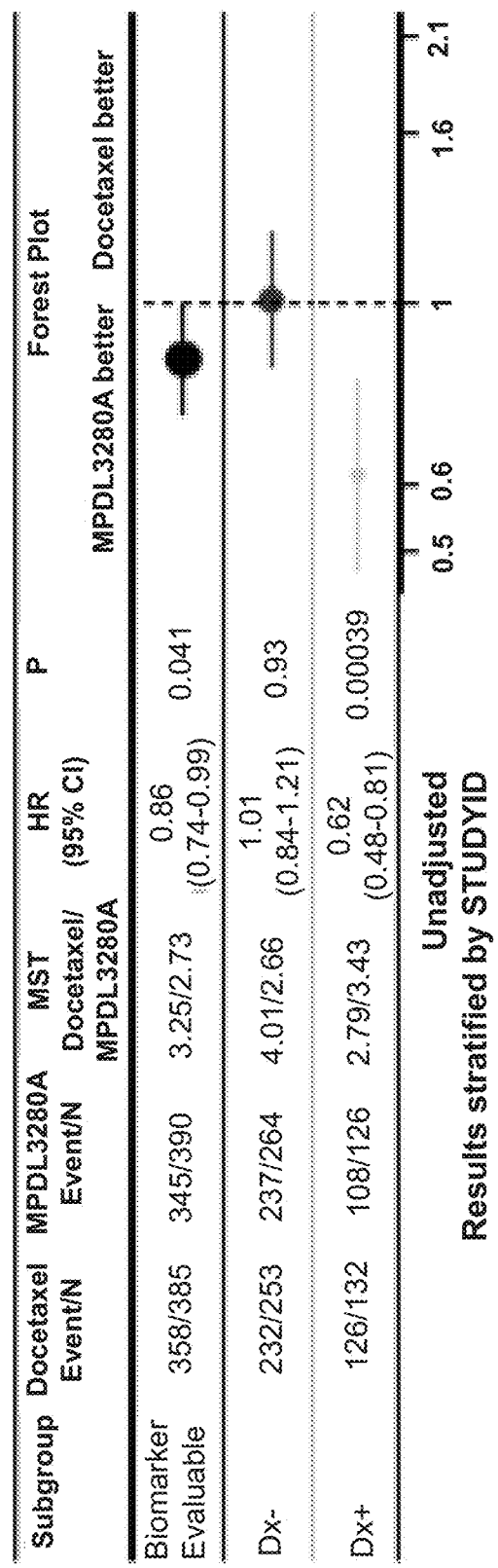
FIG. 7B is a table with forest plots showing HRs for PFS in patients in the POPLAR and OAK studies treated with atezolizumab compared to docetaxel (control). The HRs are listed across subgroups of patients defined by bTMB scores greater than, or equal to, a reference bTMB score ("cut-off value") of 14 (Dx+) and less than 14 (Dx−).

Example 2. Analysis of the Association Between bTMB Score and Clinical Response of Patients Having NSCLC to Treatment with Atezolizumab To evaluate whether a bTMB score can be used as a predictive biomarker of patient response to atezolizumab treatment, bTMB scores were assessed in pre-treatment blood samples obtained from patients in the POPLAR or OAK trials as described in Example 1. The overall survival (OS) and progression-free survival (PFS) from the POPLAR and OAK trials were observed in patients who were diagnostic positive (Dx+) based on bTMB scores at, or above, reference scores between ≥4 to ≥20 and ≥4 to ≥26, respectively (FIGS. 1A, 1B, 2A, and 2B). PFS and OS benefit were observed at all bTMB score cut-offs between ≥10 and ≥20 in POPLAR (e.g., between ≥12 and ≥20) (FIGS. 1A and 1B). Dx+ patients with a bTMB score greater than, or equal to, a reference bTMB score of 18 were found to derive a greater PFS benefit from atezolizumab treatment than diagnostic negative (Dx−) patients in both the POPLAR and OAK studies (FIGS. 3A, 3B, 4A, and 4B). PFS benefit from atezolizumab treatment was also observed in Dx+ patients with a bTMB score greater than, or equal to, a reference bTMB score of 16 or 14 in the OAK study (FIGS. 5A, 5B, 6A, and 6B). bTMB score was found to be associated with better PFS when POPLAR and OAK data was combined (FIGS. 7A and 7B). A summary of the association of bTMB score with efficacy endpoints in the POPLAR and OAK patient populations is presented in Tables 8 and 9 below. These results demonstrate that a bTMB score can be used as a predictive biomarker of patient response to atezolizumab treatment. The results from these studies are discussed in additional detail below.

POPLAR

Of the 287 patients in the ITT population in POPLAR, 273 had baseline (cycle 1 day 1 pre-treatment) plasma samples available for retrospective bTMB analysis. Due to suboptimal sample volume, 211 of 273 samples (the BEP) achieved a minimum of 800× coverage. Clinicopathological and demographic variables were consistent between the ITT population and BEP in the POPLAR study (Table 6). Comparable clinical benefit was observed in the POPLAR ITT population compared with the BEP for PFS (ITT HR, 0.92 vs. BEP HR, 0.90) and OS (ITT HR, 0.69 vs. BEP HR, 0.68) (FIGS. 1A and 1B). The median bTMB score in POPLAR was 8 mutations (lower quartile limit: 4 mutations; upper quartile limit: 17 mutations).

Figure 1C:
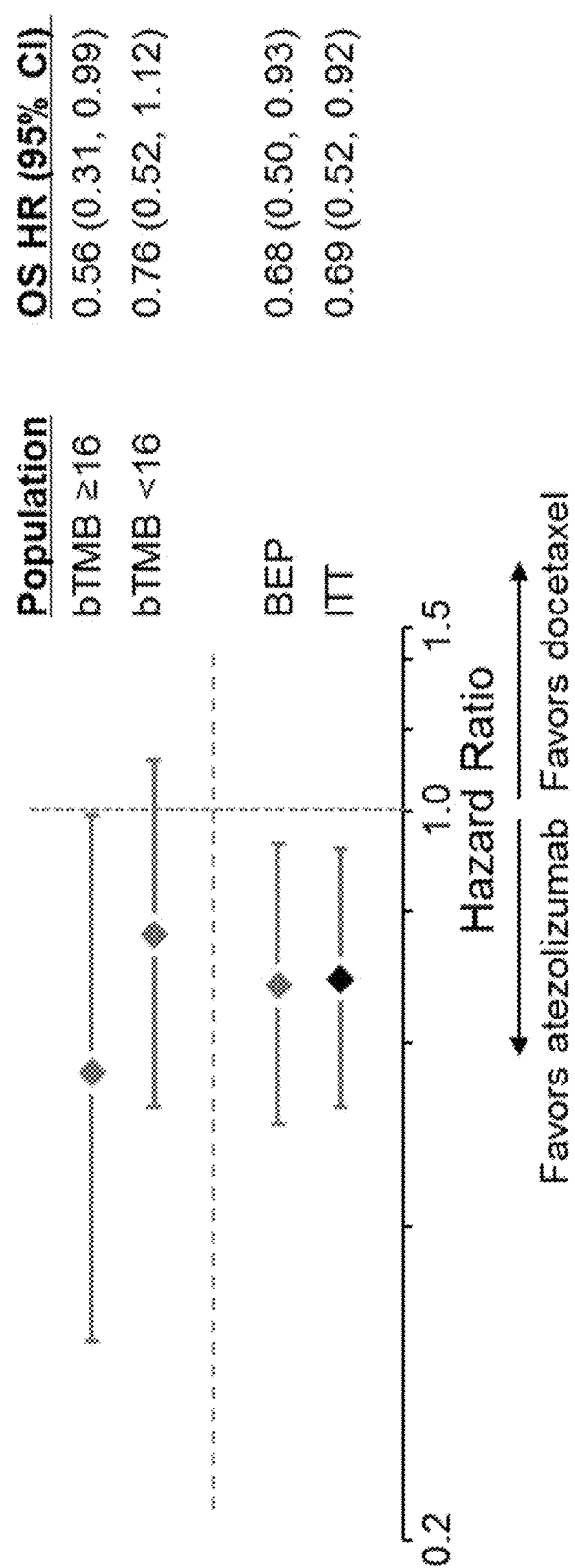
FIG. 1C is a table with forest plots showing OS in the ITT, BEP, bTMB<16, and bTMB≥16 subgroups.
Figure 1D:
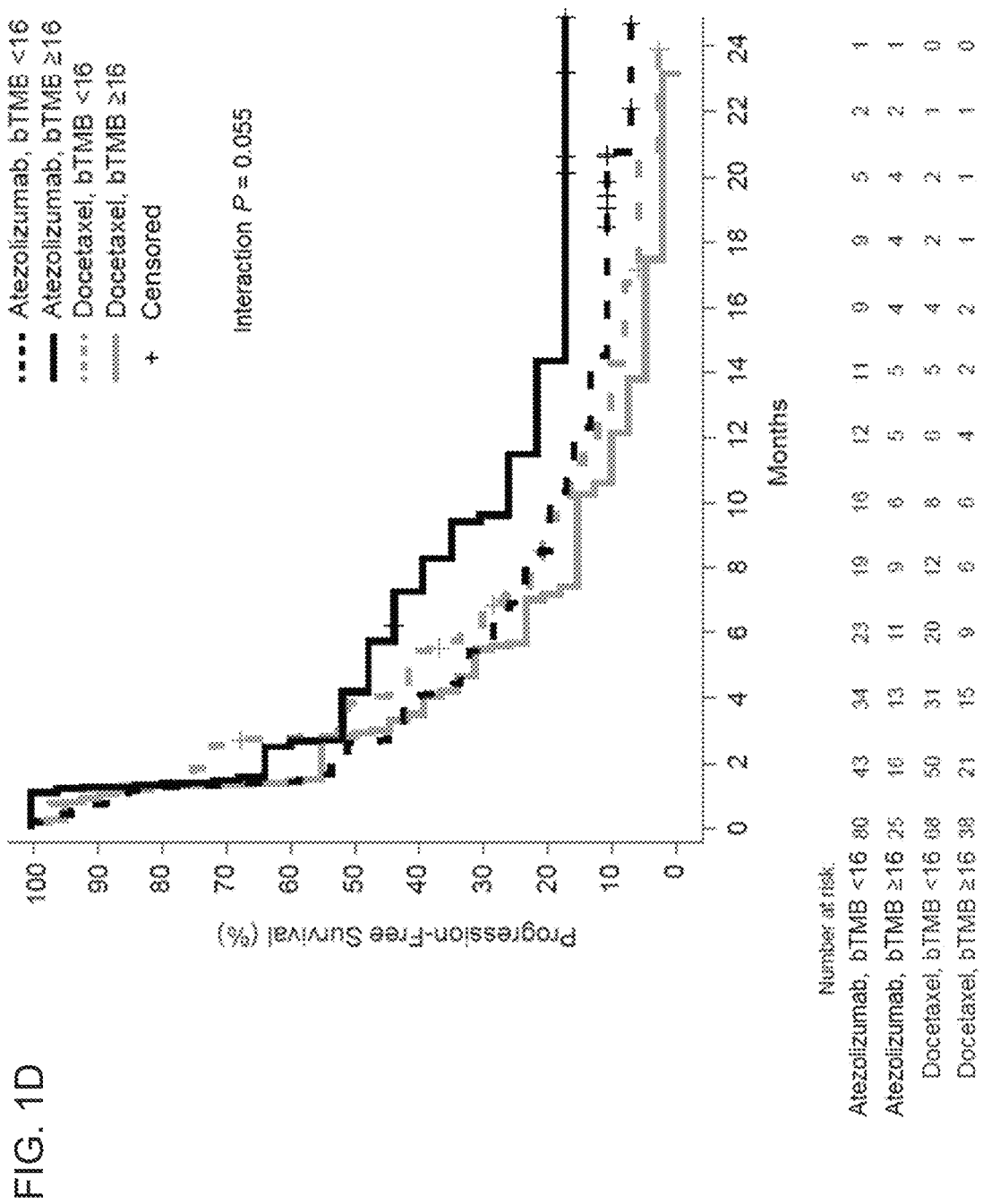
FIG. 1D is a graph showing the Kaplan-Meier Curve of PFS in the bTMB<16 and bTMB≥16 subgroups in the atezolizumab and docetaxel treatment arms.
Figure 1E:
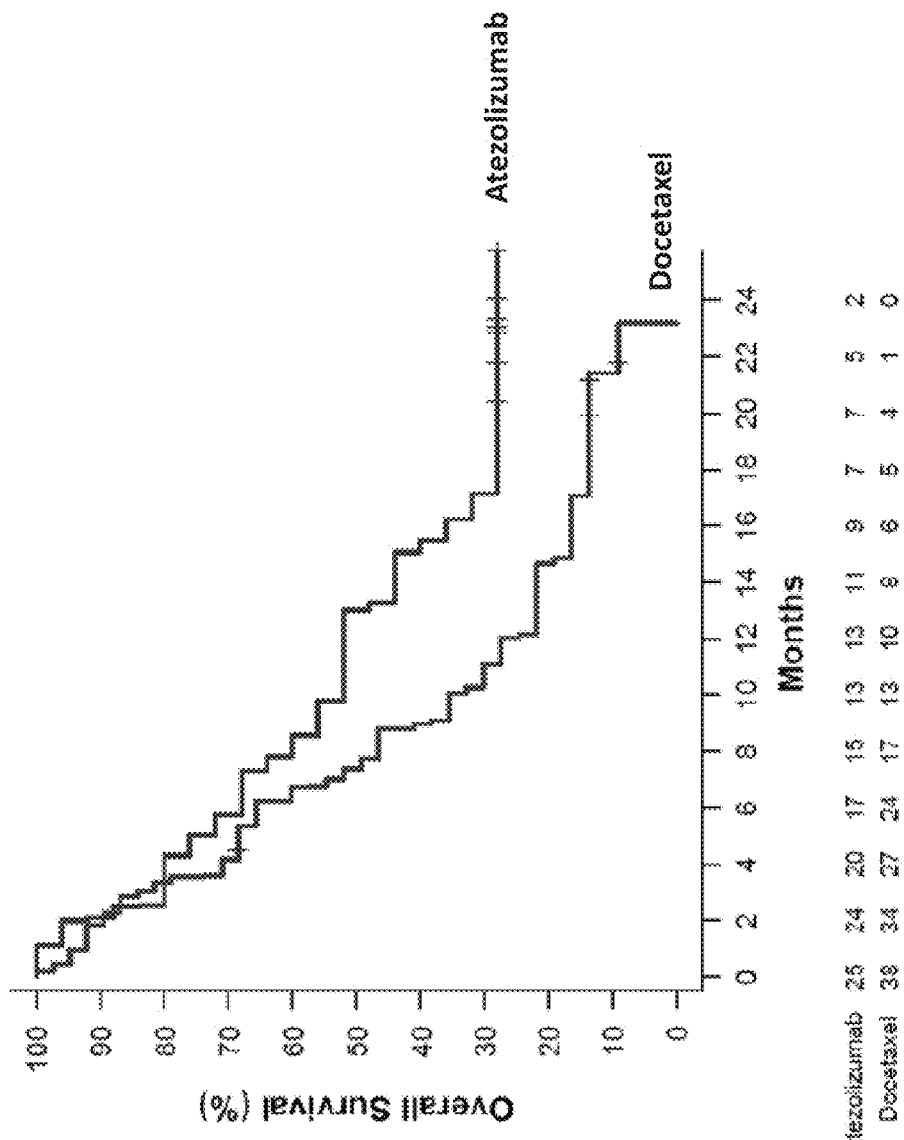
FIGS. 1E and 1F are a series of graphs showing the Kaplan-Meier Curves for OS in the POPLAR study in the bTMB≥16 subgroup (FIG. 1E) and the bTMB<16 subgroup (FIG. 1F) (P interaction=0.34) in the atezolizumab and docetaxel treatment arms. The interaction P value is from an unstratified proportional Cox model including terms of treatment, bTMB subgroup, and treatment by subgroup interaction.
Figure 1F:
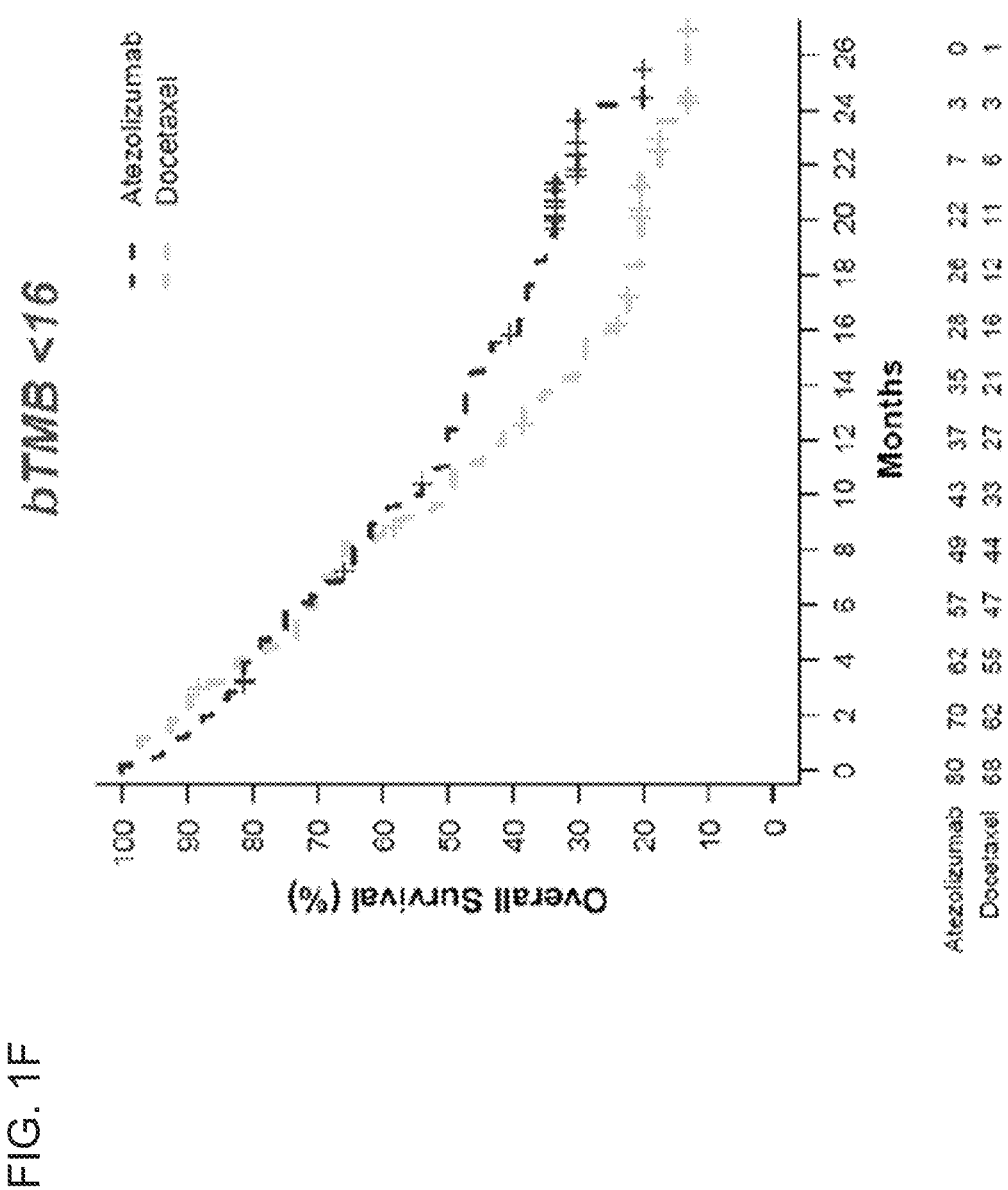

We explored the association between bTMB and clinical outcomes in POPLAR across a range of reference bTMB scores (also referred to as "bTMB cut-points"), with integer values from bTMB≥4 to ≥20 mutations. PFS and OS benefit were observed at bTMB score cut-points ≥10 (FIGS. 1A and 1B). For example, improved PFS and OS benefit was observed for all three bTMB cut-points ≥10, ≥16, and ≥20 relative to the BEP and ITT populations in the POPLAR study (FIGS. 1A and 1B). The upper bound of the 95% CIs for ≥10 and ≥20 were >1 for PFS HR and also for ≥20 for OS HR. At the bTMB cut-point ≥16, PFS HR was 0.57 (95% CI, 0.33 to 0.99) (FIGS. 1A-1C). At bTMB≥16, the median PFS was 4.2 months in the atezolizumab arm and 2.9 months in the docetaxel arm; the respective median OS values were 13.0 months and 7.4 months, respectively. Patients with bTMB≥16 had longer PFS with atezolizumab compared to docetaxel (interaction P=0.055) (FIG. 1D). The prevalence of bTMB≥16 in the BEP of the POPLAR study was 29.9%. Kaplan-Meier estimates of overall survival in the bTMB≥16 subgroup and <16 subgroup are shown in FIGS. 1E and 1F, respectively.

Based on the technical performance of the bTMB assay at the cut-point of ≥16, and the stronger PFS treatment effect compared to ≥10 or ≥20, ≥16 was selected for confirmatory analysis in the OAK study.

OAK

Figure 5A:
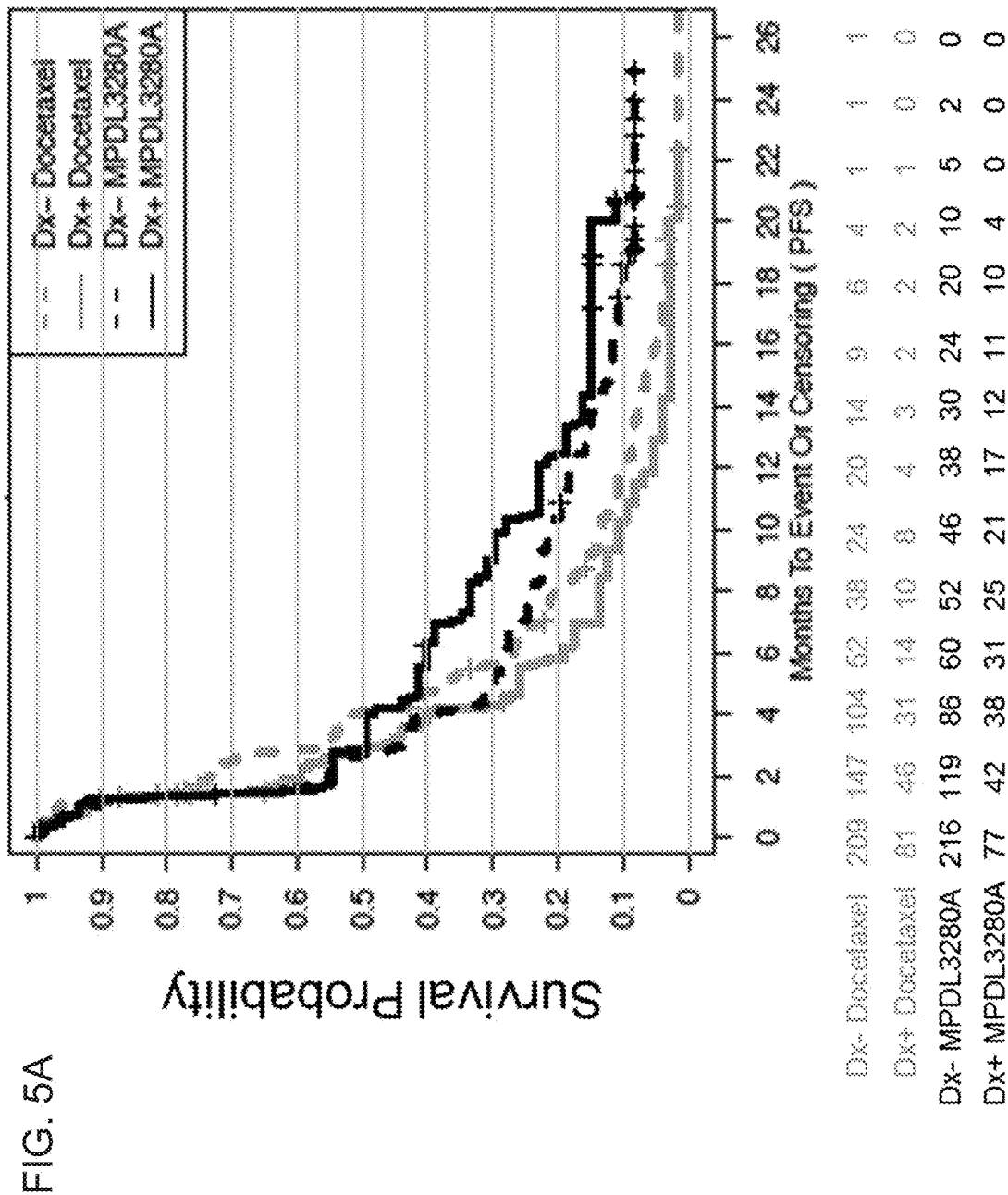
FIG. 5A is a graph showing the Kaplan-Meier Curve of PFS of the BEP of patients (nBEP=583 patients) in the atezolizumab treatment arm (black) and docetaxel control arm (gray) of the OAK study, each arm stratified according to bTMB score. Patients with a bTMB score that is greater than, or equal to, a reference bTMB score of 16 are indicated by solid lines (Dx+) and patients with a bTMB that is lower than a reference bTMB score of 16 are indicated by dashed lines (Dx−). Also shown is a table listing the number of patients who did not have a PFS event within each subgroup of the BEP at a given time point. The time point for each column corresponds to the times shown along the x-axis of the above graph. A bTMB score greater than, or equal to, reference bTMB score of 16 had a prevalence of approximately 23% in the population without mutations in EGFR or ALK (nITT=850, patient samples (all)=803; patient samples (excluding samples contaminated by laboratory error)=777; patient samples without mutations in EGFR or ALK=697; nDx+=158; HR=0.65; interaction p-value of PFS=0.036). Patient samples having an MSAF less than 1% were excluded from analysis. Sequence coverage was greater than, or equal to, 800.
Figure 5B:
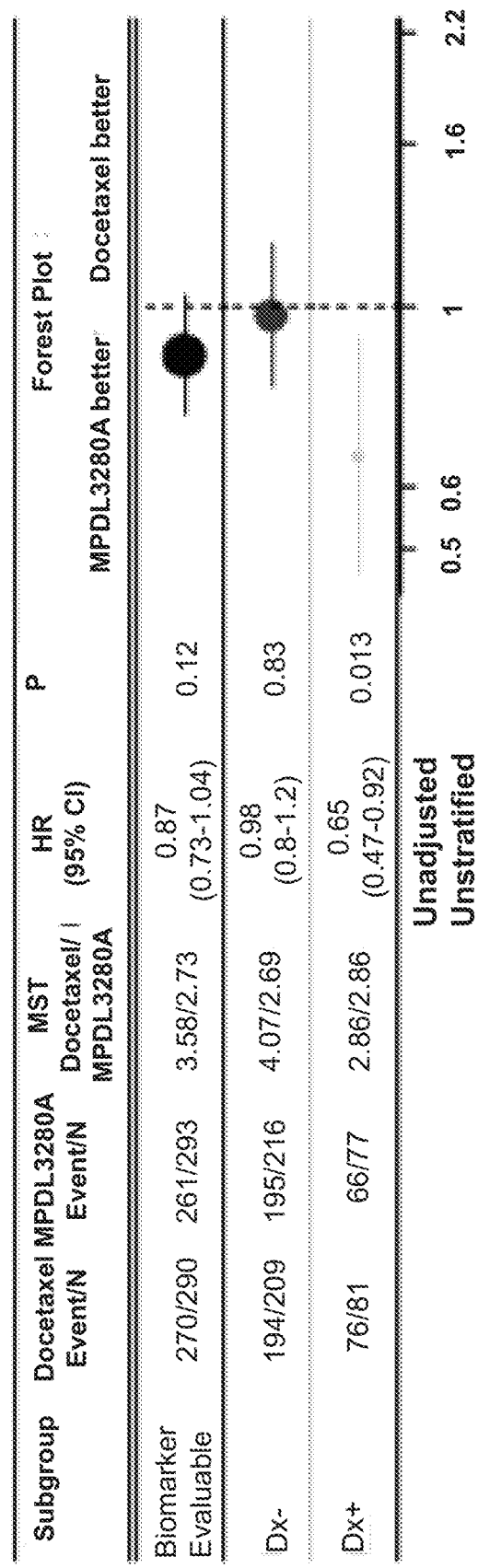
FIG. 5B is a table with forest plots showing HRs for PFS in patients in the OAK study treated with atezolizumab compared to docetaxel (control). The HRs are listed across subgroups of patients defined by bTMB scores greater than, or equal to, a reference bTMB score ("cut-off value") of 16 (Dx+) and less than 16 (Dx−).

Having demonstrated that bTMB was associated with efficacy in POPLAR, bTMB analysis was performed using plasma samples from the pivotal OAK trial. Baseline plasma samples from 797 patients with clinical outcomes were analyzed; 583 (BEP) had sufficient cfDNA to achieve a minimum of 800× with ≥1% tumor content (MSAF). Demographics between the primary-analysis ITT population (N=850) and BEP (N=583) in the OAK study were similar across both treatment arms, except for the exclusion of EGFR and ALK driver mutations from the BEP (as these patients would not be enrolled in future cancer immunotherapy trials). See Table 7. In OAK, outcomes were better in the BEP (PFS: HR, 0.87; OS: HR, 0.64) than in the ITT (PFS: HR, 0.95; OS: HR, 0.73) (FIGS. 5A and 5B).

TABLE 6

Characteristics of the BEP and ITT Population in the POPLAR Study

| | Atezolizumab | | Docetaxel | |
|---|---|---|---|---|
| | BEP (n = 105) | ITT (n = 144) | BEP (n = 106) | ITT (n = 143) |
| Median age (range), years | 61 (42, 82) | 62 (42, 82) | 63 (36, 80) | 62 (36, 84) |
| Male, n (%) | 72 (69%) | 93 (64%) | 58 (55%) | 76 (53%) |
| Race, n (%) | | | | |
| Asian | 18 (17%) | 23 (16%) | 8 (8%) | 13 (9%) |
| White | 78 (74%) | 110 (76%) | 89 (84%) | 116 (81%) |
| Other | 9 (9%) | 11 (8%) | 9 (8%) | 14 (10%) |
| ECOG performance status, n (%) | | | | |
| 0 | 29 (28%) | 48 (33%) | 30 (28%) | 46 (32%) |
| 1 | 76 (72%) | 96 (67%) | 76 (72%) | 97 (68%) |
| Smoking status, n (%) | | | | |
| Current/previous | 78 (84%) | 117 (81%) | 88 (83%) | 114 (80%) |
| Never | 17 (16%) | 27 (19%) | 18 (17%) | 29 (20%) |
| Previous therapy, n (%) | | | | |
| 1 | 67 (64%) | 93 (65%) | 76 (72%) | 96 (67%) |
| 2 | 38 (36%) | 51 (35%) | 30 (28%) | 47 (33%) |
| Tumor histology, n (%) | | | | |
| Non-squamous | 67 (64%) | 95 (66%) | 68 (64%) | 95 (66%) |
| Squamous | 38 (36%) | 49 (34%) | 38 (36%) | 48 (34%) |
| Median sum of the longest diameters (SLD) (range) | 80 (11, 241) | 71 (11, 241) | 78 (11, 269) | 74 (10, 269) |

TABLE 7

| Characteristics of the BEP and ITT Population in the OAK Study | | | | |
|---|---|---|---|---|
| | Atezolizumab | | Docetaxel | |
| | BEP (n = 293) | ITT (n = 425) | BEP (n = 290) | ITT (n = 425) |
| Median age (range), years | 63 (41, 82) | 63 (33, 82) | 64 (34, 85) | 64 (34, 85) |
| Male, n (%) | 193 (66%) | 261 (61%) | 183 (63%) | 259 (61%) |
| Race, n (%) | | | | |
| Asian | 55 (19%) | 85 (20%) | 54 (19%) | 95 (22%) |
| White | 212 (72%) | 302 (71%) | 213 (73%) | 296 (70%) |
| Other | 26 (9%) | 38 (9%) | 23 (8%) | 34 (8%) |
| ECOG performance status, n (%) | | | | |
| 0 | 101 (34%) | 155 (36%) | 99 (34%) | 160 (38%) |
| 1 | 192 (66%) | 270 (64%) | 191 (66%) | 265 (62%) |
| Smoking status, n (%) | | | | |
| Current/previous | 251 (86%) | 341 (80%) | 260 (90%) | 353 (83%) |
| Never | 42 (14%) | 84 (20%) | 30 (10%) | 72 (17%) |
| Previous therapy, n (%) | | | | |
| 1 | 225 (77%) | 320 (75%) | 219 (76%) | 320 (75%) |
| 2 | 68 (23%) | 105 (25%) | 71 (24%) | 105 (25%) |
| Tumor histology, n (%) | | | | |
| Non-squamous | 206 (70%) | 313 (74%) | 201 (69%) | 315 (74%) |
| Squamous | 87 (30%) | 112 (26%) | 89 (31%) | 110 (26%) |

Figure 5D:
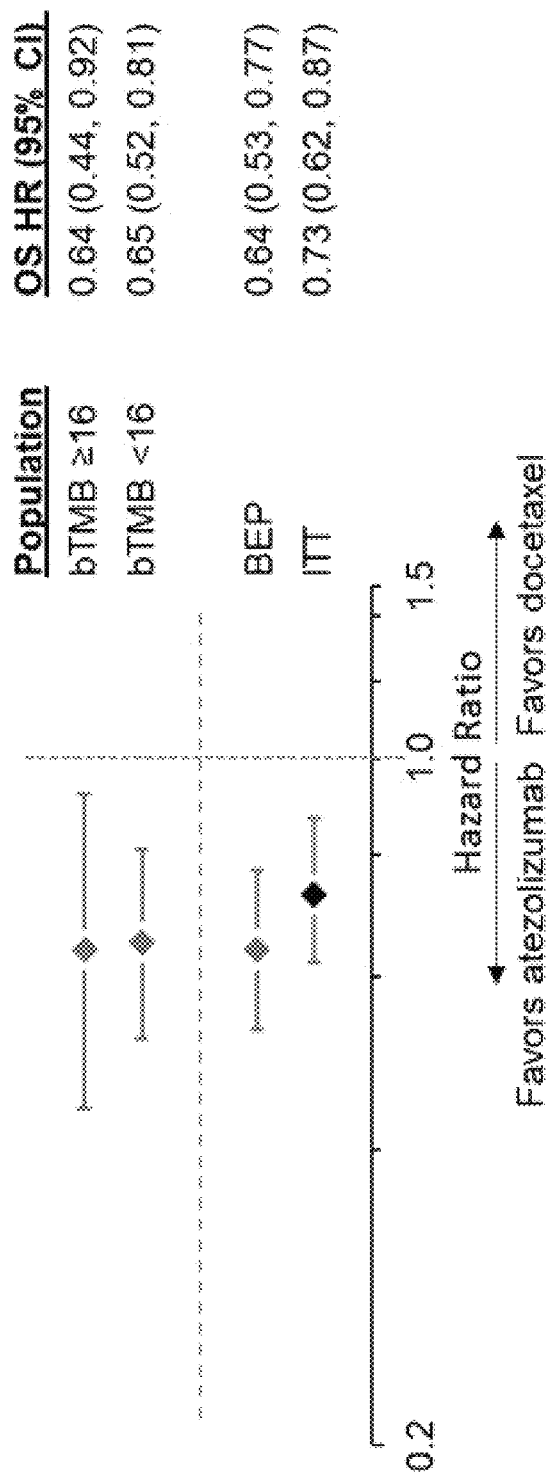
FIG. 5D is a table with forest plots showing unstratified HRs for OS in patients in the OAK study treated with atezolizumab compared to docetaxel (control) in the ITT, BEP, bTMB≥16, and bTMB<16 subgroups.
Figure 6A:
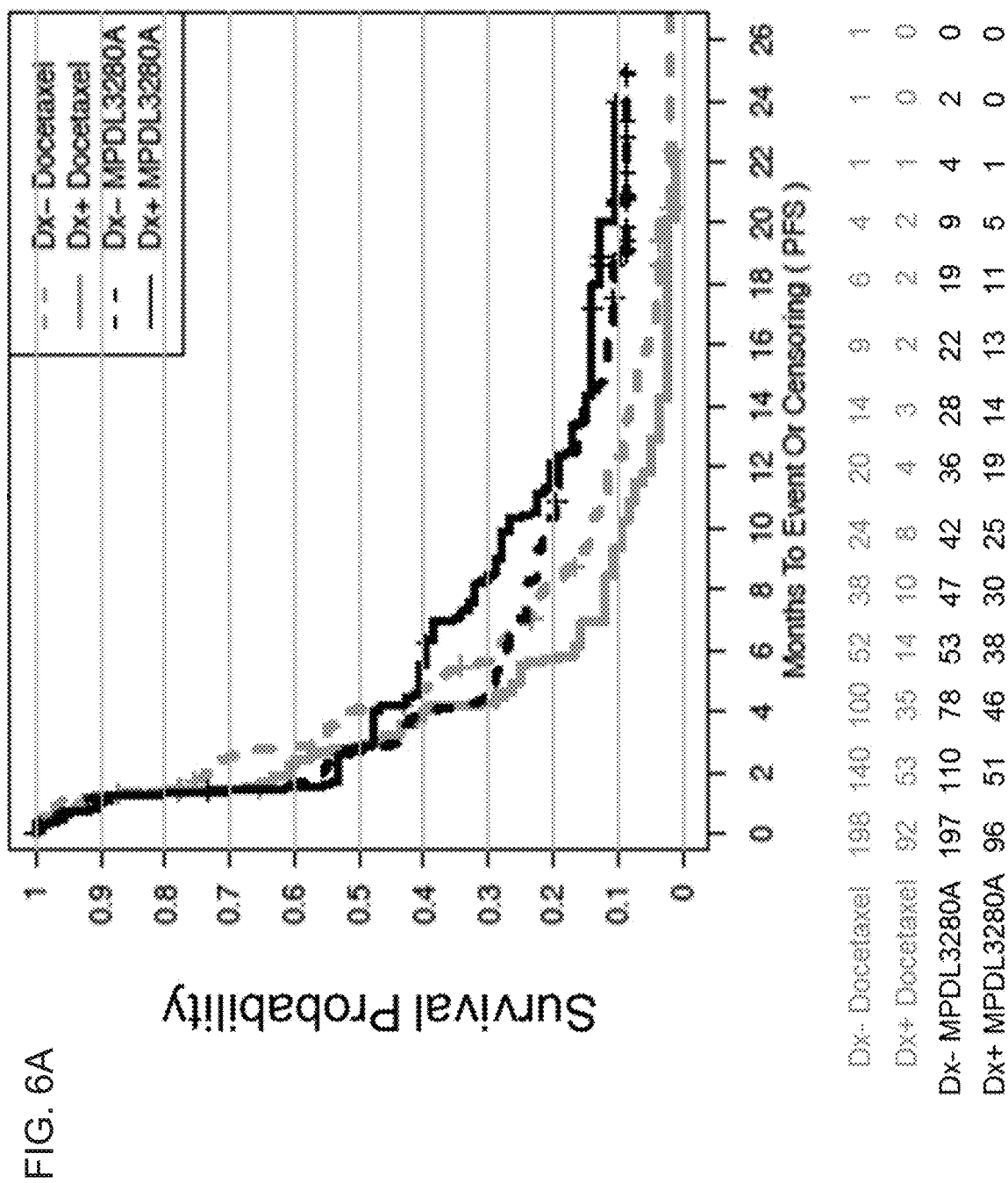
FIG. 6A is a graph showing the Kaplan-Meier Curve of PFS of the BEP of patients (nBEP=583 patients) in the atezolizumab treatment arm (black) and docetaxel control arm (gray) of the OAK study, each arm stratified according to bTMB score. Patients with a bTMB score that is greater than, or equal to, a reference bTMB score of 14 are indicated by solid lines (Dx+) and patients with a bTMB that is lower than a reference bTMB score of 14 are indicated by dashed lines (Dx−). Also shown is a table listing the number of patients who did not have a PFS event within each subgroup of the BEP at a given time point. The time point for each column corresponds to the times shown along the x-axis of the above graph. A bTMB score greater than, or equal to, a reference bTMB score of 14 had a prevalence of approximately 27% in the population without mutations in EGFR or ALK (nITT=850, patient samples (all)=803; patient samples (excluding samples contaminated by laboratory error)=777; patient samples without mutations in EGFR or ALK=697; nDx+=188; HR=0.68; interaction p-value of PFS=0.047). Patient samples having an MSAF less than 1% were excluded from analysis. Sequence coverage was greater than, or equal to, 800.
Figure 6B:
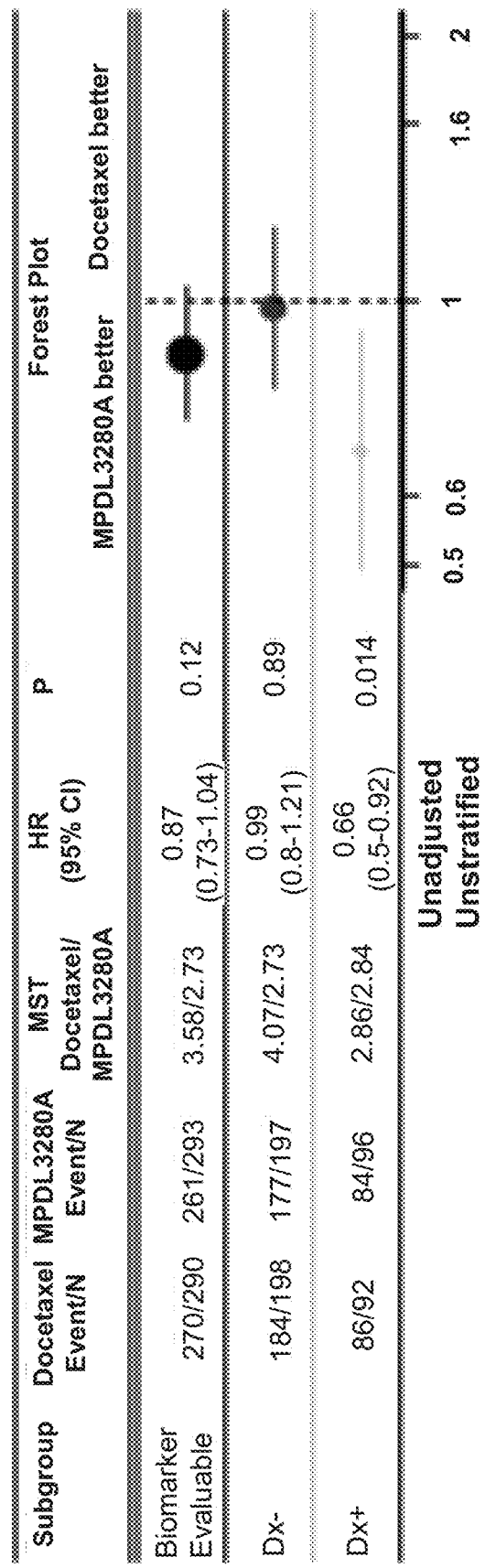
FIG. 6B is a table with forest plots showing HRs for PFS in patients in the OAK study treated with atezolizumab compared to docetaxel (control). The HRs are listed across subgroups of patients defined by bTMB scores greater than, or equal to, a reference bTMB score ("cut-off value") of 14 (Dx+) and less than 14 (Dx−).

OAK patients with bTMB≥16 had a significant PFS benefit (HR, 0.65; 95% CI, 0.47, to 0.92; P=0.013) with atezolizumab vs docetaxel (FIG. 5A). While the association for the biomarker with PFS was independently validated, the bTMB high subgroup did not demonstrate a further improvement in OS compared to BEP (HR, 0.64 [95% CI: 0.44, 0.92]; P=0.017) (FIGS. 5C and 5D). The OS benefit observed in the BEP was preserved in the biomarker positive subgroup. Median OS was 13.5 months for patients with bTMB≥16 in the atezolizumab treatment arm compared with 6.8 months in the docetaxel arm. The interaction between a bTMB score of ≥16 was significant for PFS (interaction p-value: 0.036). The prevalence of bTMB≥16 in the OAK BEP was 27%. The inability to validate the improved OS benefit observed in POPLAR is considered likely to be due to the superior OS HR of 0.64 in the OAK BEP. These results suggest that a bTMB score of ≥16 reproducibly identifies patients who benefit from atezolizumab, for example, a PFS benefit from atezolizumab treatment.

Using multivariate adaptive regression splines (MARS; Friedman et al. *Stat. Methods Med. Res.* 4:197-217, 1995), we modeled the relationship between PFS HRs and cut-point values. This data-driven approach in OAK suggests an "elbow" region between 12 and 18 (FIG. 2C), which is consistent with the cut-point value of 16 carried forward from the analysis of the POPLAR data.

Figure 2A:
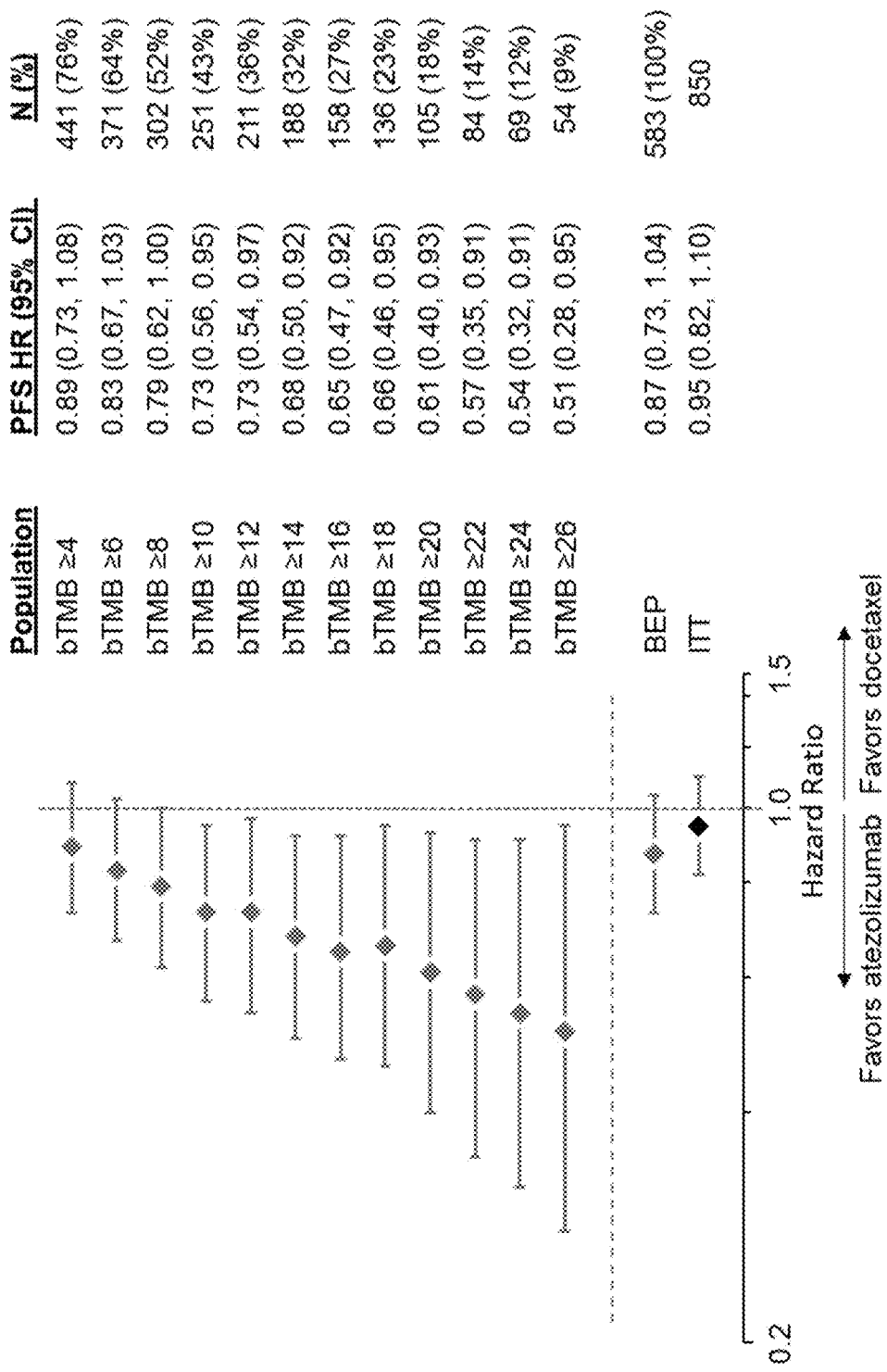
FIG. 2A is a graph showing HRs for PFS in patients in the OAK study (Clinical Trial ID No.: NCT02008227) who are diagnostic-positive (Dx+), based on blood tumor mutational burden (bTMB) scores at or above the indicated reference bTMB scores.
Figure 2B:
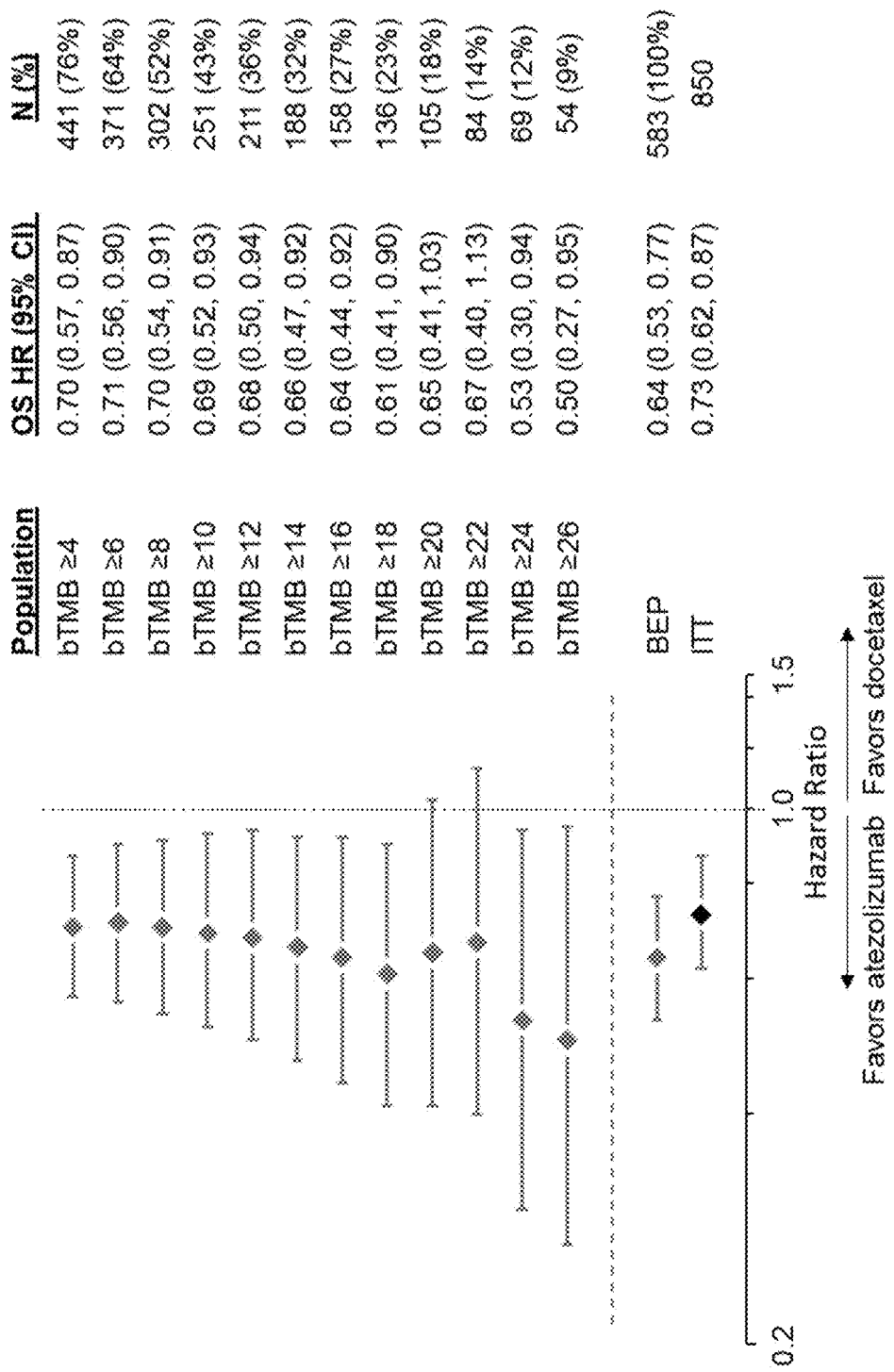
FIG. 2B is a graph showing HRs for OS in patients in the OAK study who are diagnostic-positive (Dx+), based on blood tumor mutational burden (bTMB) scores at or above the indicated reference bTMB scores.
Figure 2C:
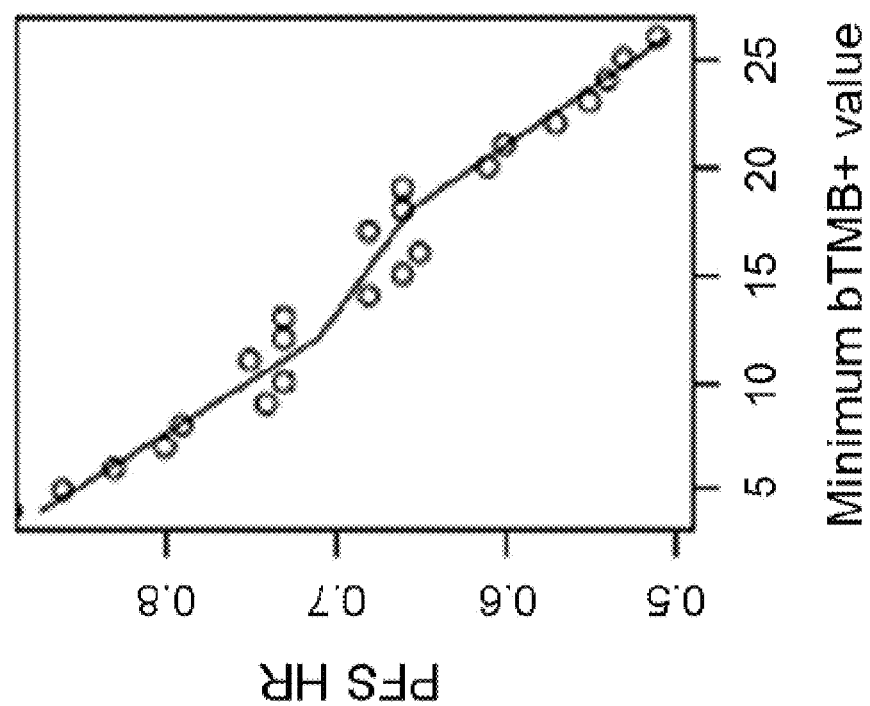
FIG. 2C is a graph showing multivariate adaptive regression splines (MARS) analysis of the relationship between PFS HRs and bTMB score values (≥4: n=441; ≥5: n=403; ≥6: n=371; ≥7: n=340; ≥8: n=302; ≥9: n=272; ≥10: n=251; ≥11: n=235; ≥12: n=211; ≥13: n=200; ≥14: n=188; ≥15: n=166; ≥16: n=158; ≥17: n=147; ≥18: n=136; ≥19: n=121; ≥20: n=105; ≥21: n=97; ≥22: n=84; ≥23: n=76; ≥24: n=69; ≥25: n=62; ≥26: n=54 patients).
Figure 3A:
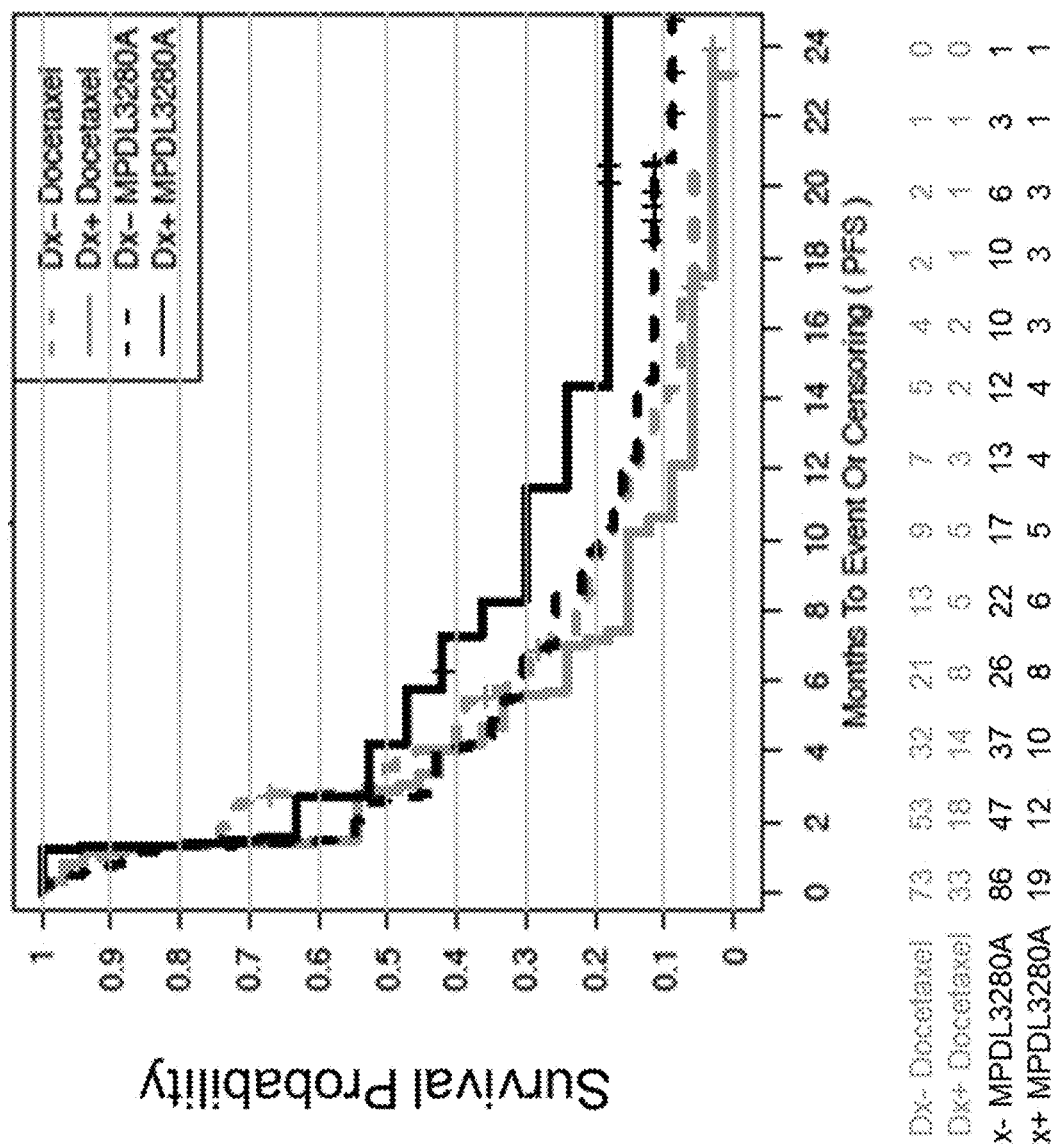
FIG. 3A is a graph showing the Kaplan-Meier Curve of PFS of the BEP of patients (nBEP=211 patients) in the atezolizumab (MPDL3280A) treatment arm (black) and docetaxel control arm (gray) of the POPLAR study, each arm stratified according to bTMB score. Patients with a bTMB score that is greater than, or equal to, a reference bTMB score of 18 are indicated by solid lines (Dx+) and patients with a bTMB that is lower than a reference bTMB score of 18 are indicated by dashed lines (Dx−). Also shown is a table listing the number of patients who did not have a PFS event within each subgroup of the BEP at a given time point. The time point for each column corresponds to the times shown along the x-axis of the above graph. A bTMB score greater than, or equal to, a reference bTMB score of 18 had a prevalence of approximately 20% in this population (nITT=287, patient samples (all)=273; patient samples (excluding samples contaminated by laboratory error)=265; nDx+=52; HR=0.57; interaction p-value of PFS=0.11). Patient samples that were positive for mutations in EGFR or ALK were not excluded from analysis. Patient samples having a maximum somatic allele frequency (MSAF) less than 1% were excluded from analysis. Sequence coverage was greater than, or equal to, 800.
Figure 3B:
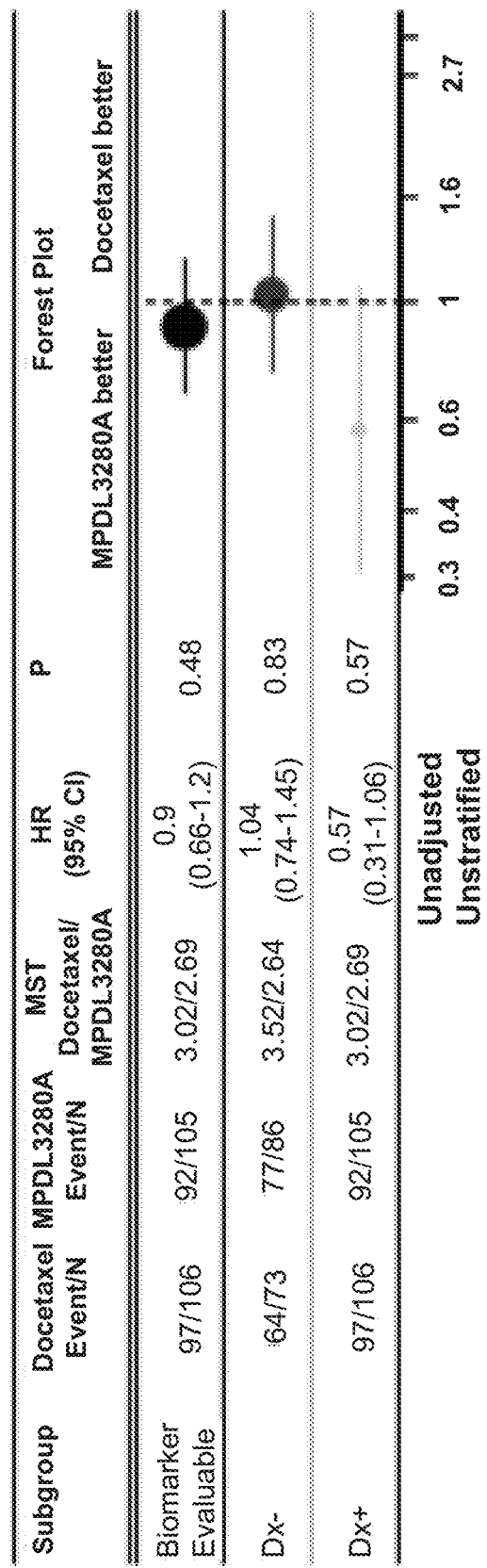
FIG. 3B is a table with forest plots showing HRs for PFS in patients in the POPLAR study treated with atezolizumab compared to docetaxel (control). The HRs are listed across subgroups of patients defined by bTMB scores greater than, or equal to, a reference bTMB score ("cut-off value") of 18 (Dx+) and less than a cut-off value of 18 (Dx−).
Figure 4A:
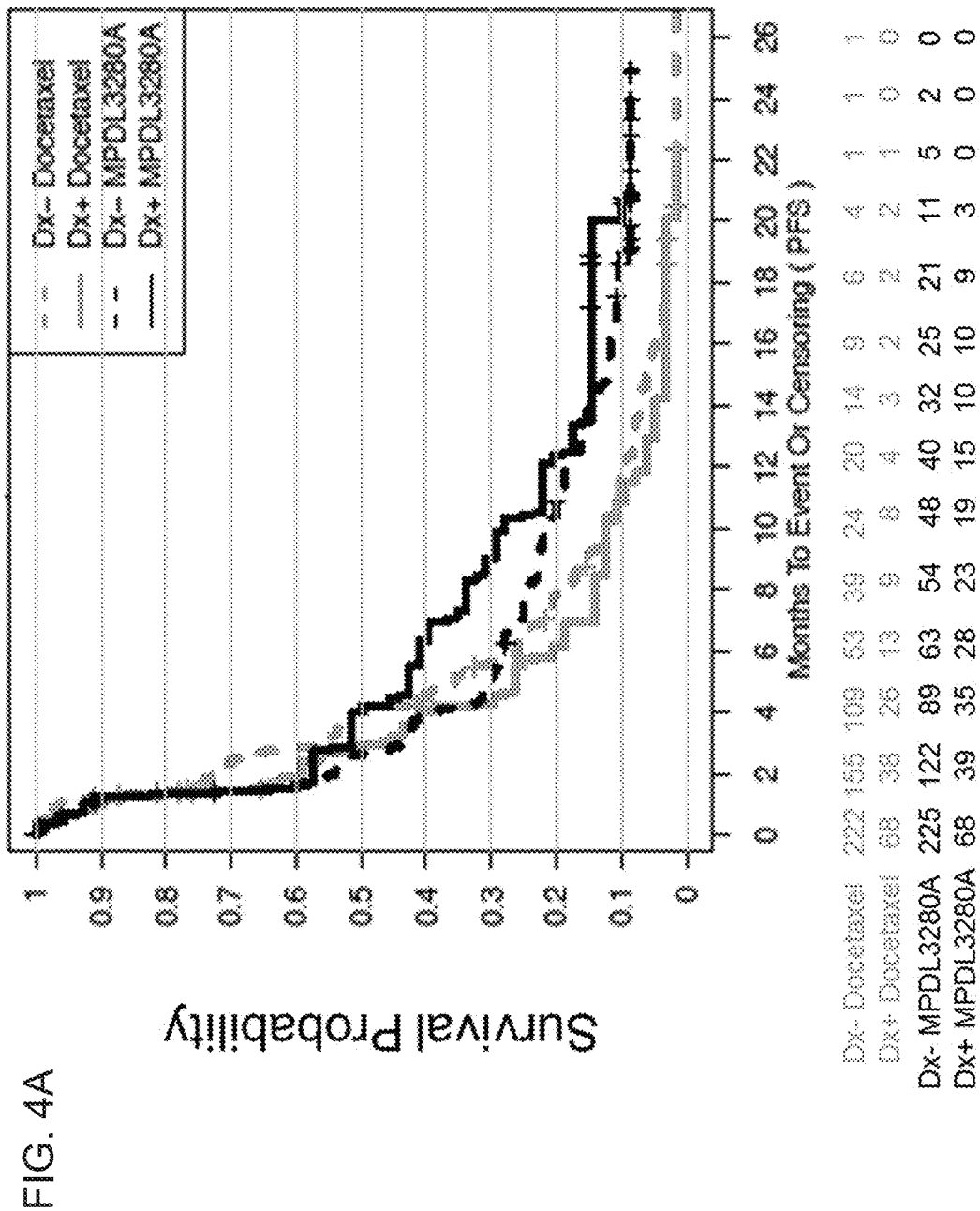
FIG. 4A is a graph showing the Kaplan-Meier Curve of PFS of the BEP of patients (nBEP=583 patients) in the atezolizumab treatment arm (black) and docetaxel control arm (gray) of the OAK study, each arm stratified according to bTMB score. Patients with a bTMB score that is greater than, or equal to, a reference bTMB score of 18 are indicated by solid lines (Dx+) and patients with a bTMB that is lower than a reference bTMB score of 18 are indicated by dashed lines (Dx−). Also shown is a table listing the number of patients who did not have a PFS event within each subgroup of the BEP at a given time point. The time point for each column corresponds to the times shown along the x-axis of the above graph. A bTMB score greater than, or equal to, reference bTMB score of 18 had a prevalence of approximately 20% in the population without mutations in EGFR or ALK (nITT=850, patient samples (all)=803; patient samples (excluding samples contaminated by laboratory error)=777; patient samples without mutations in EGFR or ALK=697; nDx+=132; HR=0.66; interaction p-value of PFS=0.068). Patient samples having an MSAF less than 1% were excluded from analysis. Sequence coverage was greater than, or equal to, 800.
Figure 4B:
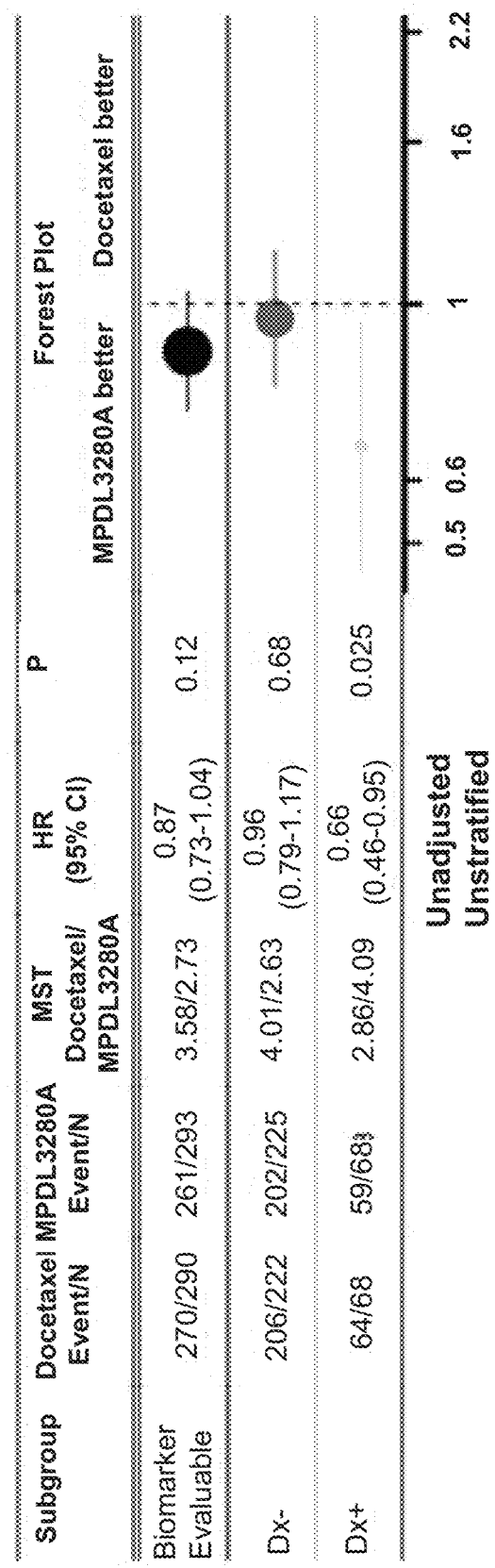
FIG. 4B is a table with forest plots showing HRs for PFS in patients in the OAK Trial treated with atezolizumab compared to docetaxel (control). The HRs are listed across subgroups of patients defined by bTMB scores greater than, or equal to, a reference bTMB score ("cut-off value") of 18 (Dx+) and less than 18 (Dx−).
Figure 8:
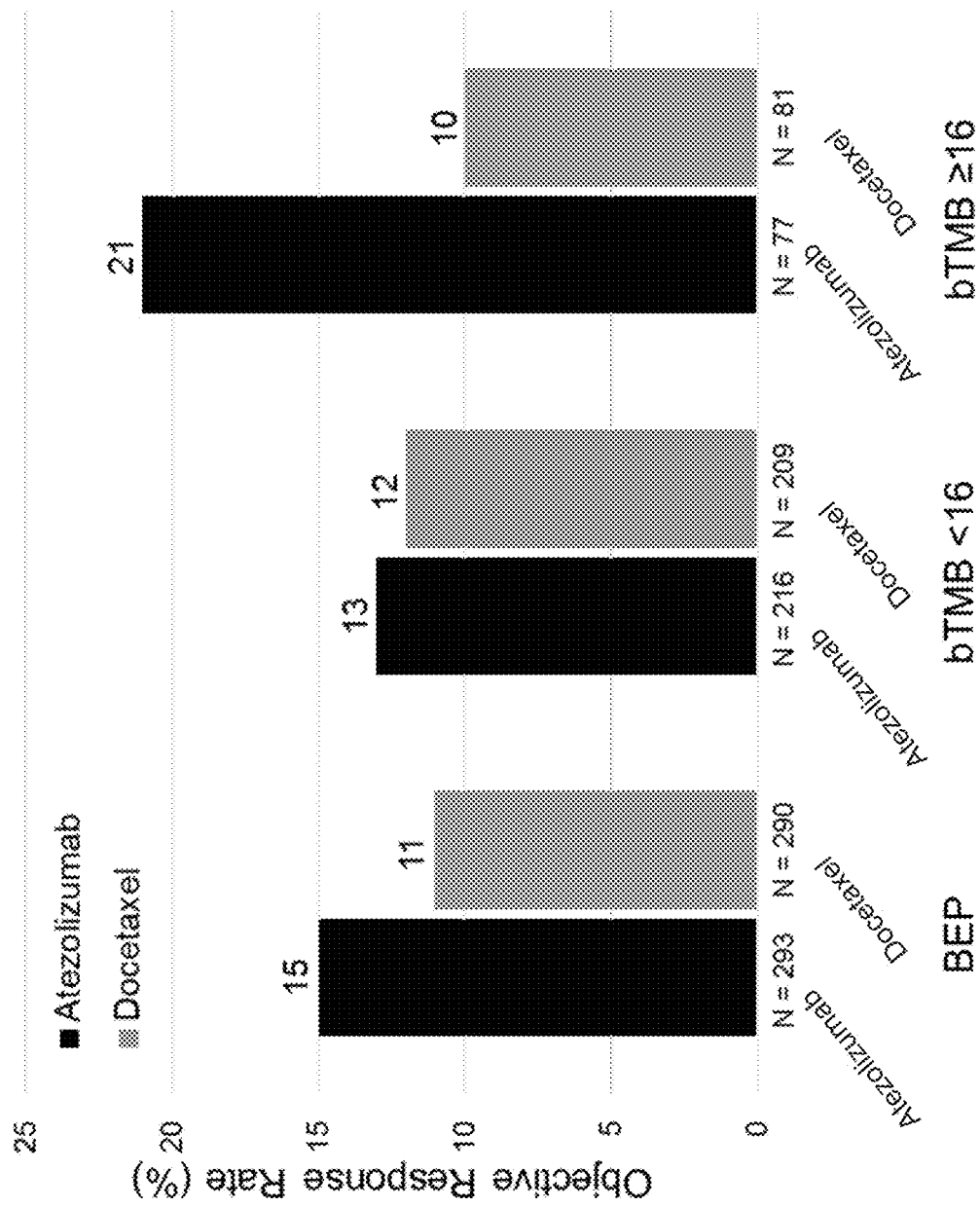
FIG. 8 is a graph showing the best confirmed objective response rate (ORR) in the BEP and bTMB subgroups in OAK. ORRs were plotted for the BEP, bTMB<16, and bTMB≥16 subgroups in the atezolizumab and docetaxel treatment arms.

Additional exploratory analyses were conducted at various cut-points of bTMB. Similar to what was observed in POPLAR, the association of bTMB with PFS benefit was observed at bTMB cut-points as low as 10 mutations (FIG. 2A). Overall, there was a clear monotonic relationship between increasing bTMB score and PFS outcomes (FIG. 2A). A similar, although less compelling monotonic trend was observed for OS (FIG. 2B). Notably, associations with OS were only observed at the highest bTMB cut-points (bTMB≥24 and ≥26) (FIG. 2B). Given the low prevalence of this subgroup, we were unable to assess the reproducibility of this observation in the POPLAR study. The best overall response rate trended towards benefit with atezolizumab (21%) versus docetaxel (10%) in bTMB≥16 patients (FIG. 8).

Summary

Together, these data show that a bTMB score can serve as a predictive biomarker that is predictive of therapeutic efficacy of a treatment including a PD-L1 binding antagonist (e.g., an anti-PD-L1 antibody, e.g., atezolizumab). Consequently, evaluation of the bTMB score can be used, for example, to identify patients having a cancer (e.g., NSCLC) who derive a PFS benefit, an OS benefit, or both a PFS and OS benefit from treatment including a PD-L1 binding antagonist (e.g., an anti-PD-L1 antibody, e.g., atezolizumab). The use of a blood sample (e.g., plasma) instead of tissue as a DNA source makes the bTMB assay a particularly attractive alternative for patients who are not amenable to biopsy or whose tumor tissue is unavailable, for example, for patients with metastatic NSCLC. The identification of bTMB as a biomarker predictive of therapeutic efficacy (e.g., in terms of PFS) can be an important component in identifying patients for immune checkpoint inhibitors (e.g., PD-L1 axis binding antagonists such as anti-PD-L1 antibodies (e.g., atezolizumab), for example, in the front-line setting. These data also show that bTMB identifies a population of patients not identified by PD-L1 IHC who derive a PFS benefit from atezolizumab and retained the OS benefit in the second-line setting. A similar application to the front-line setting may be appropriate, for example, in the 30% of patients with NSCLC who lack tissue for molecular testing.

TABLE 8

Efficacy endpoints in the POPLAR patient population

| | POPLAR (Clinical Trial ID No.: NCT01903993) | |
|---|---|---|
| | ITT (n = 287) | BEP (n = 211) |
| OS HR (95% CI) | 0.73 | 0.68 |
| | (0.53, 0.99) | (0.50, 0.93) |
| PFS HR (95% CI) | 0.94 | 0.9 |
| | (0.72, 1.23) | (0.68, 1.20) |
| bTMB score subgroup | ≥10 | ≥16 ≥20 |
| No. of patients | 96 | 63 42 |
| OS HR | 0.59 | 0.56 0.51 |
| PFS HR | 0.68 | 0.57 0.58 |

BEP, biomarker-evaluable population;
bTMB, tumor mutational burden in blood;
ITT, intention to treat.

TABLE 9

Efficacy endpoints in the OAK patient population

| | OAK (Clinical Trial ID No.: NCT02008227) | |
|---|---|---|
| | ITT (n = 850) | BEP (n = 583) |
| OS HR (95% CI) | 0.73 | 0.64 |
| | (0.62, 0.87) | (0.53, 0.77) |
| PFS HR (95% CI) | 0.95 | 0.87 |
| | (0.82, 1.10) | (0.73, 1.04) |
| bTMB score subgroup | ≥10 | ≥16 ≥20 |
| No. of patients | 251 | 158 105 |
| OS HR | 0.69 | 0.64 0.65 |
| PFS HR | 0.73 | 0.65 0.61 |

Example 3: bTMB is Independent of PD-L1 IHC and Histology

The clinical characteristics of the bTMB subgroups in OAK are shown in Tables 10 and 11. Within the OAK BEP, positive bTMB status (≥16) was associated with smoking (P=1.3e−10), consistent with heavy mutagen exposure, SLD of target lesions at baseline (P=4.8e−08), number of metastatic sites (P=0.0055), and PD-L1 expression (TC1/2/3 or IC1/2/3 (P=0.0062) (Table 10). Baseline characteristics were balanced between treatment arms above the bTMB≥16 cut-point (Table 11). Mean bTMB value in patients with non-squamous histologies was 11.22 (95% CI: 10.09, 12.36) and 12.4 (95% CI: 11, 13.8) in those with squamous histology (FIG. 10).

TABLE 10

Characteristics of the bTMB ≥16 Subgroup in the OAK Study

| | Atezolizumab (N = 77) | Docetaxel (N = 81) | P value |
|---|---|---|---|
| Median age (range), years | 62 (44, 78) | 63 (41, 79) | 0.3 |
| Race, n (%) | | | 0.52 |
| Asian | 10 (13%) | 12 (15%) | |
| Other | 10 (13%) | 6 (7%) | |
| White | 57 (74%) | 63 (78%) | |
| Male, n (%) | 55 (71%) | 60 (74%) | 0.72 |
| Tumor histology, n (%) | | | 1 |

TABLE 10-continued

Characteristics of the bTMB ≥16 Subgroup in the OAK Study

| | | | |
|---|---|---|---|
| Non-squamous | 50 (65%) | 53 (65%) | |
| Squamous | 27 (35%) | 28 (35%) | |
| ECOG performance status, n (%) | | | 0.61 |
| 0 | 23 (30%) | 28 (35%) | |
| 1 | 54 (70%) | 53 (65%) | |
| Prior therapies, n (%) | | | 0.15 |
| 1 | 53 (69%) | 64 (79%) | |
| 2 | 24 (31%) | 17 (21%) | |
| IC, n (%) | N = 77 | N = 79 | 0.15 |
| 0 | 38 (49%) | 31 (39%) | |
| 1 | 28 (36%) | 31 (39%) | |
| 2 | 8 (10%) | 12 (15%) | |
| 3 | 3 (4%) | 5 (6%) | |
| TC, n (%) | N = 77 | N = 79 | 0.69 |
| 0 | 42 (55%) | 51 (65%) | |
| 1 | 9 (12%) | 2 (3%) | |
| 2 | 18 (23%) | 15 (19%) | |
| 3 | 8 (10%) | 11 (14%) | |
| Smoking status, n (%) | | | 0.78 |
| Current | 20 (26%) | 20 (25%) | |
| Previous | 56 (73%) | 61 (75%) | |
| Never | 1 (1%) | 0 (0%) | |
| Baseline SLD, median (range) | 82 (22, 309) | 93 (12, 227) | 0.21 |
| Number of metastatic sites, mean (range) | 3 (1, 7) | 3 (1, 7) | 0.6 |
| KRAS mutation status, n (%) | N = 21 | N = 26 | 1 |
| Negative | 17 (81%) | 22 (85%) | |
| Positive | 4 (19%) | 4 (15%) | |
| PD-L1 IHC[a], n (%) | | | |
| TC3IC3 | N = 76 | N = 80 | 0.84 |
| TC0/1/2 and IC0/1/2 | 62 (82%) | 64 (80%) | |
| TC3 or IC3 | 14 (18%) | 16 (20%) | |
| TC2IC2 | N = 75 | N = 79 | 1 |
| TC0/1 and IC0/1 | 46 (61%) | 48 (61%) | |
| TC2/3 or IC2/3 | 29 (39%) | 31 (39%) | |
| TC1IC1 | N = 77 | N = 79 | 0.87 |
| TC0 and IC0 | 27 (35%) | 26 (33%) | |
| TC1/2/3 or IC1/2/3 | 50 (65%) | 53 (67%) | |

TC0 and IC0, <1% of TC and IC expressing PD-L1;
TC1/2/3 or IC1/2/3, ≥1% of TC or IC expressing PD-L1;
TC2/3 or IC2/3, ≥5% of TC or IC expressing PD-L1;
TC3 or IC3, ≥50% of TC or ≥10% of IC expressing PD-L1.

[a]"TC3 or IC3" were from TC3IC3 binary pathologist reading, "TC2/3 or IC2/3" and "TC2/3" were from TC2IC2 pathologist reading; "TC1/2/3 or IC1/2/3", "TC0 and IC0" and "TC123" were from TC1IC1 pathologist reading.

TABLE 11

Characteristics of the bTMB <16 and bTMB ≥16 Subgroups across Treatment Arms in the OAK Study

| | bTMB <16 N = 425 | bTMB ≥16 N = 158 | P value |
|---|---|---|---|
| Median age (range), years | 65 (34, 85) | 63 (41, 79) | 0.0071 |
| Race, n (%) | | | |
| Asian | 87 (20%) | 22 (14%) | |
| Other | 33 (8%) | 16 (10%) | |
| White | 305 (72%) | 120 (76%) | |
| Male, n (%) | 261 (61%) | 115 (73%) | 0.011 |
| Tumor histology, n (%) | | | 0.16 |
| Non-squamous | 304 (72%) | 103 (65%) | |
| Squamous | 121 (28%) | 55 (35%) | |
| ECOG performance status, n (%) | | | 0.56 |
| 0 | 149 (35%) | 51 (32%) | |
| 1 | 276 (65%) | 107 (68%) | |
| Prior therapies, n (%) | | | 0.51 |
| 1 | 327 (77%) | 117 (74%) | |
| 2 | 98 (23%) | 41 (26%) | |
| IC n (%) | n = 422 | n = 156 | 0.059 |
| 0 | 219 (52%) | 69 (44%) | |
| 1 | 150 (36%) | 59 (38%) | |
| 2 | 37 (9%) | 20 (13%) | |
| 3 | 16 (4%) | 8 (5%) | |
| TC (n (%) | n = 422 | n = 156 | 0.058 |
| 0 | 293 (69%) | 93 (60%) | |
| 1 | 18 (4%) | 11 (7%) | |
| 2 | 70 (17%) | 33 (21%) | |
| 3 | 41 (10%) | 19 (12%) | |
| Smoking status, n (%) | n = 425 | n = 158 | 1.3e−10 |
| Current | 54 (13%) | 40 (25%) | |
| Previous | 300 (71%) | 117 (74%) | |
| Never | 71 (17%) | 1 (1%) | |
| Baseline SLD, median (range)[b] | 63.9 (10, 316) | 86.5 (12, 309) | 4.8e−08 |
| KRAS mutation status, n (%) | n = 128 | n = 47 | 0.17 |
| Negative | 92 (72%) | 39 (83%) | |
| Positive | 36 (28%) | 8 (17%) | |
| Number of metastatic sites, mean (range) | 2.9 (0, 8) | 3.2 (1, 7) | 0.0055 |
| PD-L1 IHC[a], n (%) | | | |
| TC3IC3 | n = 423 | n = 156 | 0.62 |
| TC0/1/2 and IC0/1/2 | 350 (83%) | 126 (81%) | |
| TC3 or IC3 | 73 (17%) | 30 (19%) | |
| TC2IC2 | n = 421 | n = 154 | 0.24 |
| TC0/1 and IC0/1 | 281 (67%) | 94 (61%) | |
| TC2/3 or 1C2/3 | 140 (33%) | 60 (39%) | |
| TC1IC1 | n = 422 | n = 156 | 0.0062 |
| TC0 and IC0 | 197 (47%) | 53 (34%) | |
| TC1/2/3 or IC1/2/3 | 225 (53%) | 103 (66%) | |

TC0 and IC0, <1% of TC and IC expressing PD-L1;
TC1/2/3 or IC1/2/3, ≥1% of TC or IC expressing PD-L1;
TC2/3 or IC2/3, ≥5% of TC or IC expressing PD-L1;
TC3 or IC3, 50% of TC or ≥10% of IC expressing PD-L1.

[a]"TC3 or IC3" were from TC3IC3 binary pathologist reading, "TC2/3 or IC2/3" and "TC2/3" were from TC2IC2 pathologist reading; "TC1/2/3 or IC1/2/3", "TC0 and IC0" and "TC123" were from TC1IC1 pathologist reading.
[b]For comparison, median baseline SLD for ≥16 based on tTMB assay was 78.4 (15, 281.6) and 71.7 (`0.1, 237.8) for <16.

Previously we showed that OAK ITT had significant OS benefit, which improved in PD-L1-positive patients (TC1/2/3 or IC1/2/3 by VENTANA SP142 PD-L1 IHC assay), although an enhanced PFS benefit was observed only at the highest cut-off of PD-L1 IHC (TC3 or IC3, ≥50% staining of tumor cells [TC] or ≥10% staining of tumor-infiltrating immune cells [IC]), representing a prevalence of ~16%). We evaluated whether bTMB and PD-L1 IHC identify similar patient populations. Comparing PD-L1 expression and bTMB in OAK, we found no significant association (FIG. 9A); the median bTMB score did not differ between the mutually exclusive IHC subgroups (FIGS. 9A and 9E) and the maximum values were likewise similar across all subgroups (FIG. 9E). These data indicate that bTMB is independent of PD-L1 expression (by IHC).

To determine if the clinical benefit observed in the bTMB≥16 population might be explained by an over-representation of the PD-L1 TC3/IC3 positive population, we examined the extent of overlap between the positive patient populations in OAK, as defined by bTMB≥16, and several PD-L1 expression subgroups. We found similar proportions of overlap between bTMB and PD-L1 IHC subgroups; the median and maximum bTMB values were also similar (FIG. 9E, Table 10). A total of 229 patients were positive for either bTMB or the highest levels of PD-L1 IHC (TC3 or IC3), whereas only 30 patients (19.2% of bTMB≥16 patients; 29.1% of TC3 or IC3 patients) were found to be positive by both assays (Fisher exact test, P=0.62) (FIG. 9B). The extent of overlap at other IHC cut-points was also examined (FIGS. 9C and 9D; Tables 10 and 11).

Although no statistically significant correlation was observed between high PD-L1 expression and bTMB, we further evaluated the independence of their contribution toward PFS benefit using two different approaches: first we fitted a Cox model for PFS benefit from treatment adjusted for PD-L1 status (TC3 or IC3, or not), bTMB status (≥16 or not), PD-L1 by treatment interaction, and bTMB status by treatment interaction. The interaction HRs were 0.73 (95% CI: 0.46, 1.13; P=0.160) for PD-L1 and 0.66 (95% CI: 0.45, 0.97; P=0.035) for bTMB. The significant treatment interaction suggests bTMB status would impact PFS HR while controlling for PD-L1 status and its interaction with treatment.

Second, we examined the PFS benefit in overlapping and non-overlapping subsets between the two biomarkers. Patients who were positive for both biomarkers appeared to derive the most clinical benefit from atezolizumab (PFS: HR, 0.38 [95% CI, 0.17 to 0.85]; OS: HR, 0.23 [95% CI, 0.09 to 0.58]), whereas patients with only TC3 or IC3 or only bTMB≥16 (negative for the other marker) had PFS HRs of 0.71 (95% CI: 0.43, 1.16) or 0.70 (95% CI: 0.48, 1.03), respectively (Table 12), compared with an HR of 0.87 (95% CI: 0.73, 1.04) in the BEP in OAK. Notably, TC0 and IC0 patients with bTMB≥16 showed a trend toward a PFS benefit (HR, 0.68 [95% CI, 0.37 to 1.25]) (Table 12).

TABLE 12

Progression-Free Survival in Biomarker Subgroups in OAK

|  | n | PFS HR[a] (95% CI) |  |  |
|---|---|---|---|---|
| ITT | 850 | 0.95 (0.82, 1.10) |  |  |
| BEP | 583 | 0.87 (0.73, 1.04) |  |  |

|  | IHC+ (bTMB evaluable) | | IHC+ and bTMB <16 | |
|---|---|---|---|---|
| PD-L1 IHC Subgroup[b] | n | PFS HR[a] (95% CI) | n | PFS HR[a] (95% CI) |
| TC3 or IC3 | 103 | 0.62 (0.41, 0.93) | 73 | 0.71 (0.43, 1.16) |
| TC2/3 or IC2/3 | 200 | 0.71 (0.52, 0.95) | 140 | 0.73 (0.51, 1.05) |
| TC1/2/3 or IC1/2/3 | 328 | 0.83 (0.66, 1.05) | 225 | 0.94 (0.71, 1.24) |
| TC0 and IC0 | 250 | 0.95 (0.73, 1.24) | 197 | 1.03 (0.77, 1.39) |
| TC2/3 | 150 | 0.65 (0.46, 0.92) | 106 | 0.70 (0.46, 1.05) |
| TC1/2/3 | 192 | 0.65 (0.48, 0.89) | 129 | 0.72 (0.50, 1.04) |

|  | IHC+ and bTMB ≥16 | | IHC−[c] and bTMB ≥16 | |
|---|---|---|---|---|
| PD-L1 IHC Subgroup[b] | n | PFS HR[a] (95% CI) | n | PFS HR[a] (95% CI) |
| TC3 or IC3 | 30 | 0.38 (0.17, 0.85) | 126 | 0.70 (0.48, 1.03) |
| TC2/3 or IC2/3 | 60 | 0.65 (0.38, 1.11) | 94 | 0.65 (0.42, 1.02) |
| TC1/2/3 or IC1/2/3 | 103 | 0.65 (0.43, 0.98) | 53 | 0.68 (0.37, 1.25) |
| TC0 and IC0 | 53 | 0.68 (0.37, 1.25) | 103 | N/A |
| TC2/3 | 44 | 0.55 (0.29, 1.04) | 110 | 0.69 (0.46, 1.04) |
| TC1/2/3 | 63 | 0.55 (0.32, 0.96) | 93 | 0.78 (0.50, 1.22) |

TC0 and IC0, <1% of TC and IC expressing PD-L1;
TC1/2/3 or 1C1/2/3, ≥1% of TC or IC expressing PD-L1;
TC2/3 or 1C2/3, ≥5% of TC or IC expressing PD-L1;
TC3 or IC3, ≥50% of TC or ≥10% of IC expressing PD-L1.
n represents the number of patients in each subgroup.
N/A, not applicable.
[a]Stratified HR in ITT; unstratified HR in BEP and biomarker subgroups.
[b]"TC3 or IC3" were from TC3IC3 binary IHC cut, "TC2/3 or IC2/3" and "TC2/3" were from TC2IC2; "TC1/2/3 or IC1/2/3," "TC0 and IC0" and "TC123" were from TC1IC1.
[c]IHC—indicates patients complementary to the PD-L1 IHC subgroup listed.

Within the OAK BEP, positive bTMB status was associated with smoking (P=1.3e−10), consistent with heavy mutagen exposure, with the sum of longest distances (SLD) (P=4.8e−08), and with the number of metastatic sites (P=0.0055). See also Table 13. This finding was consistent with a higher overall disease burden, which may result in increased ctDNA shedding into the bloodstream. The likelihood of detecting ctDNA is dependent on overall tumor burden. Consistent with this, among OAK patients whose samples passed sequence coverage and contamination QC, those with MSAF<1% had a lower mean baseline SLD compared to those with MSAF>1% (62.3 mm vs. 80.4 mm, respectively). No other baseline characteristics were associated with bTMB, and no apparent prognostic effect was observed at the reference bTMB score of ≥16. There appeared to be no difference in the mean distribution of bTMB values between non-squamous and squamous histologies (FIG. 10). Table 14 shows a summary of OS and PFS HRs in the OAK BEP with valid bTMB and PD-L1 IHC results.

TABLE 13

Significant differences in baseline
characteristics in bTMB subgroups in OAK

|  | bTMB <16<br>N = 425 | bTMB 16<br>N = 158 | P-value |
|---|---|---|---|
| Smoking status, n (%) |  |  | 1.3e-10 |
| Current | 54 (13%) | 40 (25%) |  |
| Previous | 300 (71%) | 117 (74%) |  |
| Never | 71 (17%) | 1 (1%) |  |
| SLD, median (range) | 63.9 (10, 316) | 86.5 (12, 309) | 4.8e-8 |
| Metastatic sites, mean (range) | 2.9 (0, 8) | 3.2 (1, 7) | 0.0055 |

TABLE 14

OS and PFS HRs in OAK BEP with
valid bTMB and PD-L1 IHC results

|  | n | PFS HR<br>(95% CI) | OS HR<br>(95% CI) |
|---|---|---|---|
| bTMB ≥16 | 156 | 0.64 (0.46, 0.91) | 0.64 (0.44-0.93) |
| TC3 or IC3 | 103 | 0.62 (0.41-0.93) | 0.44 (0.27-0.71) |
| bTMB ≥16 and<br>TC3 or IC3 | 30 | 0.38 (0.17, 0.85) | 0.23 (0.09, 0.58) |

Example 4: bTMB Analytic Validation bTMB assay validation studies were performed to compare the TMB score using the bTMB algorithm versus the FOUNDATIONONE® TMB algorithm on the same set of sequencing data from ctDNA samples.

As part of the development of the bTMB assay, we compared results from a tissue-based analysis of TMB obtained from the subset of POPLAR (N=74) and OAK (N=244) with sufficient tissue for analysis with corresponding bTMB results obtained from pre-treatment plasma from the same patients. Overall, a positive correlation between tTMB and bTMB scores was observed (Spearman's correlation=0.59; 95% CI, 0.49 to 0.67) (FIG. 11E). In another experiment, a positive correlation between tTMB and bTMB scores was observed (Spearman's correlation=0.64; 95% CI, 0.56 to 0.71) (FIG. 11F). While there was a positive correlation, several factors may account for why the correlation between tTMB and bTMB was not higher, including tumor heterogeneity (single biopsy versus net ctDNA output from potentially multiple lesions, e.g., metastatic tumors), differences in computational pipelines (tTMB calls single-nucleotide variants (SNVs) at ≥5% allele frequency (AF) and includes both insertions and deletions (indels) whereas bTMB only calls SNVs but at ≥0.5% AF), or differences in sample characteristics (e.g., FFPE tissue-derived DNA versus ctDNA), collection times (e.g., archival tumor tissue versus pre-treatment plasma), sample type (e.g., biopsy versus resection), stage at diagnosis, tissue purity, ctDNA MSAF, and cell-free DNA input, which could result in differences in TMB.

The tTMB computational algorithm counts both indels and SNVs, whereas the bTMB computational algorithm counts only SNVs. Therefore, we compared the correlation between the two measures using only SNVs. Interestingly, this did not change the pairwise correlation (Spearman rank correlation=0.65; 95% CI: 0.57, 0.71; FIG. 11G), perhaps because indels accounted for only 4% of the somatic variants in this study.

To distinguish what factors might account for the variation between the bTMB and tTMB computational pipelines, an agreement analysis was performed using an independent cohort of non-trial ctDNA samples (N=69) each of which was split and analyzed using the either the F1 tTMB or the bTMB computational pipelines (FIGS. 11A, 11B, and 11H). In this analysis, the Spearman correlation was 0.93 (95% CI, 0.59 to 0.96). The Spearman's rank correlation coefficient was markedly higher in this comparison of ctDNA from the non-trial samples versus the comparison of tissue-derived DNA and plasma-derived ctDNA obtained from the trial patients. These data, along with the extensive analytic validation experiments described herein, suggest that assay performance accounts for only a small fraction of the observed variance between TMB calculated from blood-derived ctDNA or tissue-derived DNA.

To further validate that the variant calls made by the bTMB assay were reliable, we sought to orthogonally validate individual variant calls made by the bTMB assay. For this analysis, we used a combination of clinical samples and cell lines, and compared variant calls in overlapping regions detected by the bTMB assay and those found by FoundationACT (FACT), a previously validated assay that uses high-depth sequencing to detect low-abundance variants in cfDNA from plasma (He et al. *Blood* 127:3004-3014, 2016). Positive percentage agreement (PPA) was calculated by comparing the fraction of somatic variants detected by FACT that were also detected by the bTMB assay. The PPA was 93.4%. We measured positive predictive value (PPV) by limiting the variants detected in bTMB to those in the overlapping genomic regions interrogated by FACT, and calculated the fraction that was shared between the two tests. The PPV was 93.5% (FIG. 11I). For both PPA and PPV, discordant variant calls were the result of low AFs (<1%) or nearby homopolymers (FIGS. 11I and 11J). To further evaluate consistency between the assays, we compared the variant allele frequencies (VAFs) for each matching variant. The VAFs detected by each assay were highly concordant ($R^2=1.00$, FIG. 11J, upper panel), however, concordance was lower below 1% VAF (R2=0.68, FIG. 11J, lower panel). These data show that both assays detect the same variants.

NSCLC has been shown to harbor significant intra-tumoral heterogeneity (see, e.g., Abbosh et al. *Nature* 545: 446-451, 2017 and Jamal-Hanjani et al. *N. Engl. J. Med.* 376:2109-2121, 2017), and thus, the set of variants found in any single, localized biopsy may differ significantly from the aggregate set of variants found in the DNA fragments released into the blood by the tumor cells present in the patient. To determine if such heterogeneity might account for differences in TMB values between the blood and tissue samples described herein, we evaluated the fraction of individual variants that were present in both blood and tissue specimens. In patients with high TMB (>30 mutations) in both blood and tissue, on average one-third of the variants were unique to the blood sample and one-fourth of the total variants were unique to the tissue sample, with the remaining variants identified in both (FIG. 11K). Patients with >30 mutations in tissue had a range of concordance between bTMB and tTMB. Seven of 22 had very few mutations detected in blood and therefore very little overlap with tissue. By contrast, approximately 68% of samples shared the majority of TMB variants between tissue and blood. This shows that the presence of different variants can account for a large portion of the difference between tissue and blood TMB.

To determine if factors associated with the samples themselves contributed to the variation observed in the pairwise comparison of tTMB and bTMB in POPLAR and OAK, we evaluated a series of sample characteristics including sample type (biopsy versus resection), stage at diagnosis, fraction of cfDNA that is ctDNA as measured by the maximum somatic allele frequency (MSAF) detected in a sample, sample collection time (blood versus tissue), baseline tumor burden as determined by RECIST v1.1, and tumor purity, as well as other factors. A summary of the raw metadata appears in Table 15.

TABLE 15

| | Overall (N = 259) | bTMB+ tTMB+ (N = 56) | bTMB+ tTMB− (N = 16) | bTMB− tTMB+ (N = 32) | bTMB− tTMB− (N = 155) | bTMB− tTMB− (concordant) (N = 109) | bTMB− tTMB− (discordant) (N = 46) |
|---|---|---|---|---|---|---|---|
| Blood vs. Tissue Metadata in POPLAR and OAK Studies | | | | | | | |
| Median bTMB score | 8 | 22.5 | 22 | 11 | 6 | 7 | 4 |
| Median tTMB score | 11 | 24 | 12.5 | 19.5 | 8 | 7 | 11 |
| Median fraction indels, blood | 0 | 0 | 0 | 0 | 0 | 0 | 0 |
| Median fraction indels, tissue | 0.18 | 0.09 | 0.20 | 0.13 | 0.23 | 0.25 | 0.15 |
| Median Jaccard | 0.33 | 0.60 | 0.29 | 0.26 | 0.25 | 0.35 | 0.07 |
| Median MSAF | 6.3% | 13.3% | 16.8% | 4.6% | 5.2% | 5.7% | 3.6% |
| Median sensitivity, blood | 58.3% | 78.3% | 80.9% | 30.8% | 46.2% | 60.0% | 10.0% |
| Median sensitivity, tissue | 50.0% | 70.6% | 32.4% | 63.6% | 40.0% | 50.0% | 20.0% |
| Median days between tissue and blood collection | −239.0 | −207.0 | −199.5 | −267.0 | −225.0 | −246.0 | −235.0 |
| SLD | 77.5 | 88.5 | 96.5 | 83.0 | 67.5 | 72.0 | 76.8 |
| Median percent tumor nuclei | 30.0 | 30.0 | 32.5 | 35.0 | 30.0 | 30.0 | 30.0 |
| Median purity assessment | 40.8 | 41.8 | 45.3 | 40.4 | 40.0 | 40.0 | 42.1 |

For each case, we determined the Jaccard index between tissue and blood variants, defined as the number of shared SNVs divided by the union of all tissue and blood SNVs, as a measure of concordance. We then interrogated how the variables of interest affected the Jaccard index in each blood-versus-tissue concordance group: MSAF, baseline sum of longest distances (SLD), and time between sample collections differed between concordance groups based on summary statistics (Table 15). We found that the most important factors affecting concordance between tissue and blood were low MSAF and longer time between sample collections (interval in days) ($P<2 \times 10_{-16}$ in both cases) (FIGS. 11L and 11M). Interestingly, we noted a negative relationship between sample collection day and Jaccard index in older ($\geq \sim 3$ months) tissue samples (Spearman rank correlation and bootstrap 95% CI: −0.3 [95% CI: −0.42, −0.16]) that was absent in freshly collected (<100 days) tissues (0.06 [95% CI: −0.18, 0.3]) (FIG. 11L). FIG. 11N shows a Venn diagram of the SNVs observed by the tTMB and bTMB assays.

As part of the bTMB analytic validation, the accuracy of bTMB was evaluated against an orthogonally validated method (FOUNDATIONONE® TMB), which was previously shown to correlate well with whole-exome sequencing-based measurements of TMB. Comparability was established by evaluating both PPA and negative percent agreement (NPA) for a range of putative cut-points (bTMB≥10 to ≥20). The PPA for different cut-points ranged from 85.7% (bTMB≥15) to 100% (bTMB≥10) (FIGS. 11C and 11H). NPAs ranged from 81.8% (bTMB≥19) to 100% (bTMB≥10, ≥16). These results show that, with respect to the data from the POPLAR study, assay performance was especially favorable at three cut-points, bTMB≥10, ≥16, and ≥20.

Table 16 shows a summary of the averaged performance of the bTMB assay for the two distinct cut-points of ≥10 and ≥16. PPA and NPA, as well as PPV, were determined by evaluating the TMB scores derived from the same sample when processed using the bTMB assay described above against the previously validated FOUNDATIONONE® TMB assay. Precision was evaluated as the reliability of the bTMB result against the distinct cut-points of ≥10 and ≥16. CV represents the repeatability of the bTMB score from replicate samples. Limit of detection (LoD) was defined for the purposes of this Example as minimum tumor content (in terms of MSAF) required to maintain reliability exceeding 80%. It is to be understood that the LoD is expected to be higher when the sequenced genomic region is smaller, while sequencing of a larger part of the genome is expected to yield lower LoDs.

TABLE 16

Performance of the bTMB assay

| Metric | Result |
|---|---|
| PPA | 95.2% (CI: 88.6%-98.2%) |
| NPA | 100.0% (CI: 87.4%-100.0%) |
| PPV | 100.0% (CI: 92.7%-100.0%) |
| Precision | 95.5% |
| CV | 16.7% |
| LoD | 1% MSAF in 20 ng cfDNA |

The average precision of bTMB≥16 was 97.8% (6.3% CV). The precision of the MSAF≥1% quality control metric was 99.3% (12.1% CV). Spearman's correlation derived from a linear regression analysis of the observed versus expected MSAF values across 6 cell line dilution series was 0.98. In a dilution series of 129 samples, 91% maintained the correct bTMB biomarker status of ≥16 with as little as 1% tumor content, as estimated by MSAF. Precision values for bTMB and MSAF values were consistently maintained when the median exon coverage exceeded 800× (FIG. 16 and Table 17). In an analysis of 1,076 clinical samples, 100.0% achieved this target depth with at least 20 ng input of cfDNA (FIGS. 11A-11D). FIG. 13 shows a precision analysis evaluated according to reproducibility of the assay for the two distinct bTMB cut-points of ≥10 and ≥16, as well as the quality control metric of 1% circulating tumor DNA (ctDNA), as estimated by the MSAF. Previous studies have shown that tumor burden is an important determinant of the likelihood of detecting cfDNA or ctDNA in plasma samples. Due to the suboptimal volume of plasma (mean, 4.2 ml) collected for each patient in the OAK and POPLAR studies, we tested whether the total mass of extracted cfDNA (median, 29.3 ng) had an impact on the bTMB measurement for all samples that passed quality control. There was a small but statistically significant positive Spearman correlation between total extracted cfDNA and bTMB score (Spearman r=0.15, [95% CI: 0.07, 0.23], FIG. 17). There was a positive correlation between bTMB and MSAF ($r^2$=0.2223) and none between bTMB and SLD ($r^2$=0.05373), suggesting that MSAF variation accounts for a small portion of bTMB variation and SLD accounts for a minimal portion of bTMB variation (FIGS. 18A and 18B).

TABLE 17

Coefficient of variance of bTMB across 6 samples with bTMB scores ranging from 14-42 and MSAF values ranging from 1.1%-2.0%

| Sample | bTMB score | MSAF | 800X CV | 1000X CV | 1200X CV | 1400X CV | 1600X CV | 1800X CV | 2000X CV |
|---|---|---|---|---|---|---|---|---|---|
| 15-049_DNAx0068 | 14 | 1.1% | 0.248 | 0.184 | 0.106 | 0.173 | 0.096 | 0.112 | |
| 15-049_DNAx0155 | 15 | 1.6% | 0.211 | 0.163 | 0.119 | 0.087 | 0.08 | 0.044 | |
| 15-049_DNAx0163 | 16 | 1.5% | 0.222 | 0.165 | | | | | |
| 15-049_DNAx0076 | 16 | 2.0% | 0.192 | 0.077 | 0.088 | 0.08 | 0.043 | 0.047 | 0.062 |
| 15-049_DNAx0044 | 19 | 1.8% | 0.162 | 0.083 | 0.113 | 0.056 | 0.035 | | |
| 16-035_DNAx_0120 | 20 | 1.5% | 0.194 | 0.175 | 0.131 | 0.063 | 0.058 | | |
| 16-035_DNAx_0128 | 23 | 1.9% | 0.134 | 0.137 | 0.066 | 0.024 | | | |
| GO29436_DNAx_0026 | 42 | 1.3% | 0.183 | 0.139 | 0.087 | 0.075 | 0.056 | | |
| average bTMB CV | | | 0.193 | 0.140 | 0.101 | 0.080 | 0.061 | 0.068 | 0.062 |

While the biology underlying the variability in absolute mass of ctDNA in a given patient's blood is unknown, it is not unexpected that there was an association between overall tumor burden and increasing bTMB. Both the POPLAR and OAK studies had a mandatory tissue requirement, which may have had an impact on factors that influence the detection of ctDNA (such as tumor burden). We found that 20 ng of input cfDNA, with ≥1% derived from ctDNA, as estimated by MSAF, allowed for accurate and reproducible calling of bTMB scores (FIG. 12). FIG. 14 shows reproducibility of the bTMB assay according to the cut-points of ≥10 and ≥16 as a function of tumor content in the sample, as estimated by MSAF. Samples with less input material or lower ctDNA content, estimated by the MSAF, tended to underestimate tumor mutational burden; however, there were no false positive samples (FIGS. 11A-11D). This result is consistent with the performance of other blood-based assays and suggests that a high bTMB score may be predictive of outcome regardless of whether the quality control criteria were met.

Table 18 shows the clinical characteristics of patients who were evaluable for both bTMB and tTMB. Overall, these patients had similar characteristics compared to the BEP and ITT populations.

TABLE 18

Characteristics of patients who were evaluable for both bTMB and tTMB

| | Double BEP$^a$ N = 229 | ITT Population N = 850 |
|---|---|---|
| Median age (range), years | 64 | 64 |
| Race, n (%) | | |
| Asian | 49 (21%) | 180 (21%) |
| Other | 21 (9%) | 72 (8%) |
| White | 159 (69%) | 598 (70%) |
| Male, n (%) | 152 (66%) | 520 (61%) |
| Tumor histology, n (%) | | |
| Non-squamous | 152 (66%) | 628 (76%) |
| Squamous | 77 (33%) | 222 (23%) |
| ECOG performance status, n (%) | | |
| 0 | 71 (31%) | 315 (37%) |
| 1 | 158 (69%) | 535 (63%) |
| Prior therapies, n (%) | | |
| 1 | 174 (76%) | 640 (75%) |
| 2 | 55 (24%) | 210 (25%) |
| IC, n (%) | n = 229 | n = 842 |
| 0 | 97 (42%) | 429 (51%) |
| 1 | 97 (42%) | 300 (36%) |
| 2 | 28 (12%) | 79 (9.4%) |
| 3 | 7 (3%) | 34 (4%) |
| TC, n (%) | n = 229 | n = 842 |
| 0 | 154 (67%) | 590 (70%) |
| 1 | 17 (7%) | 40 (5%) |
| 2 | 38 (16%) | 133 (16%) |
| 3 | 20 (9%) | 79 (9%) |
| Smoking status, n (%) | | |
| Current | 29 (13%) | 126 (16%) |
| Previous | 163 (71%) | 568 (67%) |
| Never | 37 (16%) | 156 (18%) |
| Baseline SLD, median (range) | 76 (10, 309) | 63 (10, 316) |
| Number of metastatic sites, mean (range) | 3 (0, 8) | 3 (1, 8) |
| KRAS mutation status, n (%) | n = 72 | n = 262 |
| Negative | 60 (83%) | 203 (75%) |
| Positive | 12 (17%) | 59 (23%) |

TABLE 18-continued

Characteristics of patients who were evaluable for both bTMB and tTMB

| EGFR mutation status, n (%) | n = 189 | n = 713 |
|---|---|---|
| Negative | 171 (91%) | 628 (88%) |
| Positive | 18 (10%) | 85 (12%) |
| PD-L1 IHC[b], n (%) | | |
| TC3IC3 | n = 229 | n = 850 |
| TC0/1/2 and IC0/1/2 | 193 (84%) | 704 (83%) |
| TC3 or IC3 | 36 (16%) | 137 (16%) |
| TC2IC2 | n = 229 | n = 50 |
| TC0/1 and IC0/1 | 147 (64%) | 574 (67%) |
| TC2/3 or IC2/3 | 82 (36%) | 265 (31%) |
| TC1IC1 | n = 229 | n = 850 |
| TC0 and IC0 | 84 (37%) | 379 (45%) |
| TC1/2/3 or IC1/2/3 | 145 (63%) | 463 (54%) |

[b]TMB, blood-based tumor mutational burden;
ECOG, Eastern Cooperative Oncology Group;
IC, tumor-infiltrating immune cell;
IHC, immunohistochemistry;
ITT, intention-to-treat;
PD-L1, programmed death-ligand 1;
SLD, sum of the longest diameters;
TC, tumor cell;
TC0 and IC0, <1% of TC and IC expressing PD-L1;
TC1/2/3 or IC1/2/3, ≥1% of TC or IC expressing PD-L1;
TC2/3 or IC213, ≥5% of TC or IC expressing PD-L1; TC3 or IC3, 50% of TC or ≥10% of IC expressing PD-L1.
[a]Double BEP included patients from the OAK ITT population (N = 850) who had baseline samples that were evaluable for both blood and tissue based TMB analyses.
[b]"TC3 or IC3" were from TC3IC3 binary pathologist reading, "TC2/3 or IC2/3" and "TC2/3" were from TC2IC2 pathologist reading; "TC1/2/3 or IC1/2/3", "TC0 and IC0" and "TC123" were from TC1IC1 pathologist reading.

Example 5. Blood First-Line Ready Screening Trial (B-F1RST) and Blood First Assay Screening Trial (BFAST) in Patients Having First-Line (1L) Advanced or Metastatic NSCLC Study Design To further evaluate and prospectively validate blood-based diagnostic assays that measure bTMB score and somatic mutations (e.g., the presence and/or absence of a somatic mutation, e.g., an oncogenic somatic mutation, such as an ALK or RET alteration), and to determine the efficacy and safety of 1 L atezolizumab or alectinib treatment in NSCLC patients, two clinical trials are being conducted.

The B-F1 RST (Clinical Trial ID No.: NCT02848651) patient population being evaluated for bTMB score consists of approximately 150 patients at 20 to 25 study sites (N=153). Patients are eligible for enrollment in the B-F1 RST study if they have treatment-naïve, locally advanced or metastatic (e.g., stage IIIB-IVB) NSCLC; measurable disease, as defined by RECIST v1.1; and an ECOG performance status of 0 or 1. Exclusion criteria include sensitizing EGFR mutations or ALK rearrangements; active brain metastases requiring treatment; leptomeningeal disease; other malignancies within 5 years of enrollment; HBV, HCV, or HIV infection; or history of autoimmune disorder. Participants are divided into cohorts based on bTMB score and receive atezolizumab at a dose of 1200 mg intravenously every three weeks. All patients undergo tumor assessment at baseline and every 6 weeks for the first 12 months following cycle 1, day 1, and then every 9 weeks therafter. Treatment with atezolizumab can be continued as long as participants were experiencing clinical benefit, i.e., in the absence of unacceptable toxicity or symptomatic deterioration attributed to disease progression. Tumor assessments continue until disease progression per RECIST v1.1 or loss of clinical benefit (investigator assessed), consent withdrawal, study discontinuation, study completion, or death. Mandatory blood samples are taken at baseline, during therapy, and at progression to evaluate changes in exploratory biomarkers. The interim analysis was prespecified to occur at 6 months after 50% of the patients have been enrolled, with a pre-specified bTMB score of ≥16. The co-primary endpoints are the clinical efficacy of atezolizumab (as evaluated by investigator-assessed ORR per RECIST v1.1) and the relationship between bTMB and PFS benefit (as evaluated by investigator-assessed PFS per RECIST v1.1). The secondary objectives are safety and assessment of efficacy by investigator-assessed duration of response (DOR) and OS.

The BFAST (Clinical Trial ID No.: NCT03178552) patient population is being evaluated for bTMB score and/or somatic mutation status (e.g., the presence and/or absence of a somatic mutation, e.g., an oncogenic somatic mutation, such as a mutation in ALK or RET). Patients are eligible for enrollment in the BFAST study if they have histologically or cytologically confirmed, locally advanced or metastatic (e.g., stage IIIB-IVB) NSCLC that is not amenable to treatment with combined modality chemoradiation; measurable disease, as defined by RECIST v1.1; an ECOG performance status of 0-2; adequate organ function; a life expectancy greater than or equal to 12 weeks; and for female participants of childbearing potential and male participants, willingness to use acceptable methods of contraception; and provision of blood samples. Exclusion criteria include active, untreated brain metastases; history of other malignancies within 5 years prior to screening; or significant cardiovascular disease. Participants are divided into cohorts based on bTMB score and/or somatic mutation status (e.g., an ALK or RET mutation status, e.g., ALK or RET negative) and receive atezolizumab at a dose of 1200 mg intravenously every three weeks, alectinib, an anaplastic lymphoma kinase (ALK) inhibitor, at a dose of 600 mg or an escalating dose between 900 mg and 1200 mg by mouth twice a day. Cohort 1 randomizes patients with qualifying ALK fusions for treatment with alectinib that do not also have ALK 11171 N, ALK 11171S, or ALK G1202R base substitutions; cohort 2 randomizes patients with qualifying RET fusions for treatment with alectinib; and cohort 3 randomizes patients with qualifying bTMB scores for treatment with atezolizumab that do not contain any previously identified qualifying ALK or RET fusions, or EGFR L858R or exon 19 non-frameshift deletions and that have had no prior treatment with CD137 agonists or immune checkpoint inhibitors such as anti-PD-1 or anti-PD-L1 therapeutic antibodies. Treatment with atezolizumab or alectinib can be continued as long as participants were experiencing clinical benefit, i.e., in the absence of unacceptable toxicity or symptomatic deterioration attributed to disease progression. Additional cohorts can be added in the future to address other somatic mutations (e.g., somatic mutations other than an ALK or RET mutation). Patients undergo tumor assessment at baseline and every 6 weeks for 48 weeks, following cycle 1, day 1, then every 9 weeks thereafter. Mandatory blood samples are collected at baseline, during therapy (i.e., at each tumor assessment), and at disease progression to evaluate exploratory prognostic and/or predictive biomarkers.

The desired efficacy endpoints of these two trials are summarized in Table 19 below.

TABLE 19

B-F1RST and BFAST Study Details

| Study | Treatment | Planned Enrollment (N) | Primary Endpoints | Key Secondary Endpoints |
|---|---|---|---|---|
| B-F1RST Phase II | Atezolizumab (MPDL3280A) 1200 mg IV q3w | 150 | ORR per RECIST v1.1 (INV-assessed) for the efficacy objective Relationship between PFS per RECIST v1.1 and various bTMB score quantiles for the biomarker objective | PFS and DOR per RECIST v1.1 (INV-assessed) OS Evaluation of various biomarkers and correlations with clinical outcomes |
| BFAST—Phase II/III | | | | |
| Cohort A ALK+ | Alectinib 600 mg PO b.i.d. | 78 | ORR per RECIST v1.1 (INV-assessed) | DOR, CBR and PFS per RECIST v1.1 (INV-assessed) ORR, DOR, CBR and PFS per RECIST v1.1 (IRF-assessed) OS |
| Cohort B RET+ | Alectinib 900, 1200, or 750 mg PO b.i.d. mg dose escalation | 52-62 | ORR per RECIST v1.1 (INV-assessed) | DOR, CBR and PFS per RECIST v1.1 (INV-assessed) ORR, DOR, CBR and PFS per RECIST v1.1 (IRF-assessed) OS |
| Cohort C bTMB score+ | atezolizumab (MPDL3280A) 1200 mg IV q3w or platinum-based chemotherapy[a] | 440 (R, 1:1) | PFS per RECIST v1.1 (INV-assessed) | OS PFS, ORR and DOR per RECIST v1.1 (IRF-assessed) ORR and DOR per RECIST v1.1 (INV-assessed) 6- and 12-month PFS rates |

[a]Cisplatin or carboplatin + pemetrexed (500 mg/m$^2$) for non-squamous histology (pemetrexed are administered on day 1 of each 21 day cycle, followed by carboplatin or cisplatin approximately 30 min later), and cisplatin or carboplatin + gemcitabine for squamous histology (gemcitabine 1250 mg/m$^2$ (in combination with cisplatin) or 1000 mg/m$^2$ (in combination with carboplatin) are administered by IV infusion over 30 min on days 1 and 8 of each 21 day cycle, followed by cisplatin or carboplatin at approximately 30 min after completion of gemcitabine infusion on Day 1 only). Administered per standard of care.
INV, investigator;
IRF, independent review facility;
R, randomized;
bTMB, blood Tumor Mutational Burden;
PO, by mouth;
b.i.d., two times a day.

Results from B-F1RST Interim Analysis Population

Of 78 treated patients in the interim analysis population (IAP) from the B-F1 RST study, 58 had adequate blood samples with sufficient detection of circulating tumor DNA (MSAF≥1%) and comprised the biomarker-evaluable population (BEP). One patient of the IAP was never treated and therefore not safety- or efficacy-evaluable. A bTMB score of 16 (prevalence, 19% [11/58]) was prespecified to evaluate clinical efficacy in the BEP (bTMB high, ≥16; bTMB low, <16). Statistical tests were 2-sided at a 0.1 level and 90% confidence interval. See FIG. 19.

Baseline characteristics were similar in the IAP and BEP (FIG. 20). With a minimum follow-up of 6 months, median PFS was 9.5 versus 2.8 months for bTMB high vs low; HR, 0.51 (90% CI, 0.24, 1.08; P=0.1315) (FIG. 24 and Table 20). PFS HRs improved as bTMB scores increased (Table 21 and FIG. 25). In the BEP, the ORR was 12.1% (7/58) and disease control rate was 25.9% (15/58) (Table 22 and FIG. 21). In the bTMB high versus low groups, the ORR was 36.4% (4/11) versus 6.4% (3/47); odds ratio, 8.38 (90% CI, 2.02, 34.79; P=0.02) (Table 22 and FIG. 21). FIG. 22 shows the maximum SLD reduction from baseline by bTMB subgroup in the interim analysis population. These data indicate that most bTMB high patients had clinical benefit as measured by reduced SLD. FIGS. 23A and 23B show the change in tumor burden over time by bTMB subgroup. These data show that the bTMB high subgroup had improved response in terms of higher numbers of PRs and fewer PDs, and the benefit was durable. Treatment-related serious AEs and treatment-related grade 3/4 AEs occurred in 14.1% and 16.7% of patients, respectively; 15.4% experienced AEs leading to discontinuation (Table 23). Table 24 shows AEs of special interest according to the Medical Dictionary for Regulatory Activities (MedDRA). FIG. 27 shows AEs observed in ≥10% of the safety-evaluable interim analysis population.

TABLE 20

Progression-Free Survival in bTMB ≥16 versus <16 Subgroups

| | bTMB high (n = 11) | bTMB low (n = 47) |
|---|---|---|
| Median PFS | 9.5 mo | 2.8 mo |
| 90% CI[a] | 1.3, 9.5 | 1.7, 4.3 |
| HR | 0.51 | |
| 90% CI[a] | 0.24, 1.08 | |
| p value | 0.1315 | |

[a]Per protocol, efficacy differences between bTMB high vs low subgroups are tested at a significance level of 0.1, and 90% CIs are provided.

TABLE 21

PFS (months) by bTMB Cut-off Scores (BEP, n = 58)

| bTMB Score | bTMB High Median (n) | bTMB Low Median (n) | HR | 90% CI |
|---|---|---|---|---|
| 12 | 3.0 (22) | 3.2 (36) | 0.95 | 0.55, 1.63 |
| 14 | 3.4 (14) | 3.2 (44) | 0.73 | 0.39, 1.39 |
| 16 | 9.5 (11) | 2.8 (47) | 0.49 | 0.23, 1.04 |
| 20 | 9.5 (8) | 2.7 (50) | 0.23 | 0.08, 0.62 |

TABLE 22

ORR per RECIST v.1.1

| | IAP (n = 78) | BEP (n = 58) | bTMB low (n = 47) | bTMB high (n = 11) |
|---|---|---|---|---|
| ORR | 15.4% | 12.1% | 6.4% | 36.4% |
| PR | 15.4% | 12.1% | 6.4% | 36.4% |
| SD | 33.3% | 34.5% | 36.2% | 27.3% |
| PD | 37.2% | 37.9% | 38.3% | 36.4% |

TABLE 23

Safety Summary for Interim Analysis Population (IAP)

| Patients in IAP (n = 78) | n (%) |
|---|---|
| AEs, any cause | 78 (100.0%) |
| Treatment-related AEs | 59 (75.6%) |
| SAEs, any cause | 35 (44.9%) |
| Treatment-related SAEs | 12 (15.4%) |
| Grade 3-4 AEs, any cause | 40 (51.3%) |
| Treatment-related Grade 3-4 AEs | 15 (19.2%) |
| Grade 5 AEs, any cause[a,b] | 3 (3.8%) |
| AEs leading to treatment discontinuation | 12 (15.4%) |

[a] Grade 5 events reported as 'death' (n = 1), cardiac arrest (n = 1) and pulmonary embolism (n = 1).
[b] No treatment-related Grade 5 AEs were reported.

TABLE 24

AEs of Special Interest

| AEs of Special Interest, n (%) MedDRA PT | Overall (n = 78) | Grade 3-4[c] (n = 78) |
|---|---|---|
| Pneumonitis | 6 (7.7%) | 4 (5.1%) |
| Skin and subcutaneous | 12 (15.4%) | 0 |
| AST elevation | 5 (6.4%) | 0 |
| ALT elevation | 5 (6.4%) | 0 |
| Hypothyroidism | 5 (6.4%) | 0 |
| Hyperthyroidism | 2 (2.6%) | 0 |
| Adrenal insufficiency | 1 (1.3%) | 1 (1.3%) |
| Colitis | 2 (2.6%) | 1 (1.3%) |
| Keratitis | 1 (1.3%) | 0 |

ALT, alanine aminotransferase;
AST, aspartate aminotransferase;
PT, preferred term;
SAE, serious adverse event.
[c] All Grade 3 events except for colitis (Grade 4).

CONCLUSIONS

B-F1 RST is the first prospective clinical trial evaluating bTMB as a predictive treatment marker for atezolizumab in 1L NSCLC. The interim data indicate that a bTMB score of ≥16 may be predictive for PFS benefit in patients treated with atezolizumab monotherapy (median PFS for bTMB high versus low subgroups, 9.5 versus 2.8 months; HR=0.51, 90% CI: 0.24, 1.08; p=0.1315). ORR of 36.4 and 6.4% were observed in the bTMB high and low subgroups, respectively, indicating that bTMB high patients have a higher ORR. Atezolizumab was well tolerated and no new safety signals were observed. These data support the bTMB selection of patients in the ongoing Phase III BFAST trial. B-F1 RST is ongoing and has completed enrollment at 153 patients. The data described in Examples 1-5 indicate that high bTMB may serve as a cancer-agnostic biomarker that can be used to identify patients who are likely to respond to PD-L1 axis binding antagonists such as the anti-PD-L1 antibody, atezolizumab.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating an individual having locally advanced NSCLC or metastatic NSCLC, the method comprising administering to the individual an effective amount of atezolizumab, wherein a bTMB score that is at or above a reference bTMB score has been determined from a blood sample obtained from the individual prior to administration of atezolizumab to the individual, thereby identifying the individual as one who may benefit from a treatment comprising atezolizumab, wherein the reference bTMB score is 16,
    wherein the blood sample comprises an aggregate set of DNA fragments released into the blood by tumor cells present in the individual,
    wherein the bTMB score is represented as the number of somatic mutations counted over a defined number of sequenced bases of between about 100 kb to about 10 Mb, and
    wherein the benefit from a treatment comprising atezolizumab is an increase in PFS and/or an increase in OS.

2. The method of claim 1, wherein the blood sample comprises DNA fragments from two or more heterogeneous tumor sites in the individual.

3. The method of claim 2, wherein the two or more heterogeneous tumor sites comprise at least one metastatic tumor site.

4. The method of claim 1, wherein the benefit from a treatment comprising atezolizumab is an increase in OS.

5. The method of claim 1, wherein the number of somatic mutations is (i) the number of single nucleotide variants (SNVs) counted or (ii) a sum of the number of SNVs and the number of indel mutations counted.

6. The method of claim 1, further comprising determining a maximum somatic allele frequency (MSAF) from a blood sample from the individual, wherein the MSAF from the sample is greater than, or equal to, 1%.

7. The method of claim 1, wherein prior to the administering a blood sample from the individual has been determined to have an MSAF greater than, or equal to, 1%.

8. The method of claim 1, further comprising determining an MSAF from a blood sample from the individual, wherein the MSAF from the sample is less than 1%.

9. The method of claim 1, wherein prior to the administering a blood sample from the individual has been determined to have an MSAF less than 1%.

10. The method of claim 1,
(i) wherein a tumor sample obtained from the individual has been determined to have a detectable expression level of PD-L1 in less than 1% of the tumor cells in the tumor sample; or
(ii) wherein a tumor sample obtained from the individual has been determined to have a detectable expression level of PD-L1 in 1% or more of the tumor cells in the tumor sample; or
(iii) wherein a tumor sample obtained from the individual has been determined to have a detectable expression level of PD-L1 in tumor-infiltrating immune cells that comprise 1% or more of the tumor sample.

11. The method of claim 1, wherein the treatment comprising atezolizumab is a monotherapy.

12. The method of claim 1, further comprising administering to the individual an effective amount of an additional therapeutic agent.

13. The method of claim 12, wherein the additional therapeutic agent is an anti-neoplastic agent, a chemotherapeutic agent, a growth inhibitory agent, an anti-angiogenic agent, a radiation therapy, or a cytotoxic agent.

14. The method of claim 1, wherein the somatic mutations are substitutions, and wherein the substitutions are in coding regions.

15. The method of claim 1, wherein the sample is a plasma sample or a serum sample obtained from the blood sample.

16. The method of claim 1, wherein the defined number of sequenced bases is about 1.1 Mb or about 0.8 Mb.

* * * * *

SEQUENCE LISTING

```
<160> NUMBER OF SEQ ID NOS: 31

<210> SEQ ID NO 1
<211> LENGTH: 440
<212> TYPE: PRT
<213> ORGANISM: Artificial Sequence
<220> FEATURE:
<223> OTHER INFORMATION: Synthetic construct

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30
```

```
Gly Met His Trp Val Arg Gln Ala Pro Gly Lys Gly Leu Glu Trp Val
         35                  40                  45
Ala Val Ile Trp Tyr Asp Gly Ser Lys Arg Tyr Ala Asp Ser Val
 50                  55                  60
Lys Gly Arg Phe Thr Ile Ser Arg Asp Asn Ser Lys Asn Thr Leu Phe
 65                  70                  75                  80
Leu Gln Met Asn Ser Leu Arg Ala Glu Asp Thr Ala Val Tyr Tyr Cys
                 85                  90                  95
Ala Thr Asn Asp Asp Tyr Trp Gly Gln Gly Thr Leu Val Thr Val Ser
                100                 105                 110
Ser Ala Ser Thr Lys Gly Pro Ser Val Phe Pro Leu Ala Pro Cys Ser
        115                 120                 125
Arg Ser Thr Ser Glu Ser Thr Ala Ala Leu Gly Cys Leu Val Lys Asp
130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Lys
            180                 185                 190
Thr Tyr Thr Cys Asn Val Asp His Lys Pro Ser Asn Thr Lys Val Asp
195                 200                 205
Lys Arg Val Glu Ser Lys Tyr Gly Pro Pro Cys Pro Pro Cys Pro Ala
    210                 215                 220
Pro Glu Phe Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser Gln Glu Asp Pro Glu Val Gln Phe Asn Trp Tyr Val
            260                 265                 270
Asp Gly Val Glu Val His Asn Ala Lys Thr Lys Pro Arg Glu Glu Gln
        275                 280                 285
Phe Asn Ser Thr Tyr Arg Val Val Ser Val Leu Thr Val Leu His Gln
290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
                325                 330                 335
Arg Glu Pro Gln Val Tyr Thr Leu Pro Pro Ser Gln Glu Glu Met Thr
            340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
            420                 425                 430
Ser Leu Ser Leu Ser Leu Gly Lys
        435                 440
```

-continued

```
<210> SEQ ID NO 2
<211> LENGTH: 214
<212> TYPE: PRT
<213> ORGANISM: Artificial Sequence
<220> FEATURE:
<223> OTHER INFORMATION: Synthetic construct

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 118
<212> TYPE: PRT
<213> ORGANISM: Artificial Sequence
<220> FEATURE:
<223> OTHER INFORMATION: Synthetic construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Arg His Trp Pro Gly Gly Phe Asp Tyr Trp Gly Gln Gly Thr
            100                 105                 110

Leu Val Thr Val Ser Ser
            115

<210> SEQ ID NO 4
<211> LENGTH: 108
<212> TYPE: PRT
<213> ORGANISM: Artificial Sequence
<220> FEATURE:
<223> OTHER INFORMATION: Synthetic construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 5
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Asp or Gly

<400> SEQUENCE: 5

Gly Phe Thr Phe Ser Xaa Ser Trp Ile His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Ser or Leu
<220> FEATURE:
<221> NAME/KEY: MISC_FEATURE
<222> LOCATION: (10)..(10)
<223> OTHER INFORMATION: Xaa is Thr or Ser

<400> SEQUENCE: 6

Ala Trp Ile Xaa Pro Tyr Gly Gly Ser Xaa Tyr Tyr Ala Asp Ser Val
1               5                   10                  15

Lys Gly

<210> SEQ ID NO 7
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Arg His Trp Pro Gly Gly Phe Asp Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 13
<212> TYPE: PRT
<213> ORGANISM: Artificial Sequence
<220> FEATURE:
<223> OTHER INFORMATION: Synthetic construct

<400> SEQUENCE: 9

Trp Val Arg Gln Ala Pro Gly Lys Gly Leu Glu Trp Val
1               5                   10

<210> SEQ ID NO 10
<211> LENGTH: 32
<212> TYPE: PRT
<213> ORGANISM: Artificial Sequence
<220> FEATURE:
<223> OTHER INFORMATION: Synthetic construct

<400> SEQUENCE: 10

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Trp Gly Gln Gly Thr Leu Val Thr Val Ser Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
```

```
<223> OTHER INFORMATION: Xaa is Asp or Val
<220> FEATURE:
<221> NAME/KEY: MISC_FEATURE
<222> LOCATION: (6)..(6)
<223> OTHER INFORMATION: Xaa is Val or Ile
<220> FEATURE:
<221> NAME/KEY: MISC_FEATURE
<222> LOCATION: (7)..(7)
<223> OTHER INFORMATION: Xaa is Ser or Asn
<220> FEATURE:
<221> NAME/KEY: MISC_FEATURE
<222> LOCATION: (9)..(9)
<223> OTHER INFORMATION: Xaa is Ala or Phe
<220> FEATURE:
<221> NAME/KEY: MISC_FEATURE
<222> LOCATION: (10)..(10)
<223> OTHER INFORMATION: Xaa is Val or Leu

<400> SEQUENCE: 12

Arg Ala Ser Gln Xaa Xaa Xaa Thr Xaa Xaa Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Phe or Thr
<220> FEATURE:
<221> NAME/KEY: MISC_FEATURE
<222> LOCATION: (6)..(6)
<223> OTHER INFORMATION: Xaa is Tyr or Ala

<400> SEQUENCE: 13

Ser Ala Ser Xaa Leu Xaa Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Tyr, Gly, Phe, or Ser
<220> FEATURE:
<221> NAME/KEY: MISC_FEATURE
<222> LOCATION: (4)..(4)
<223> OTHER INFORMATION: Xaa is Leu, Tyr, Phe, or Trp
<220> FEATURE:
<221> NAME/KEY: MISC_FEATURE
<222> LOCATION: (5)..(5)
<223> OTHER INFORMATION: Xaa is Tyr, Asn, Ala, Thr, Gly, Phe, or Ile
<220> FEATURE:
<221> NAME/KEY: MISC_FEATURE
<222> LOCATION: (6)..(6)
<223> OTHER INFORMATION: Xaa is His, Val, Pro, Thr, or Ile
<220> FEATURE:
<221> NAME/KEY: MISC_FEATURE
<222> LOCATION: (8)..(8)
<223> OTHER INFORMATION: Xa is Ala, Trp, Arg, Pro, or Thr

<400> SEQUENCE: 14

Gln Gln Xaa Xaa Xaa Xaa Pro Xaa Thr
1               5

<210> SEQ ID NO 15
```

```
<211> LENGTH: 23
<212> TYPE: PRT
<213> ORGANISM: Artificial Sequence
<220> FEATURE:
<223> OTHER INFORMATION: Synthetic construct

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys
             20

<210> SEQ ID NO 16
<211> LENGTH: 15
<212> TYPE: PRT
<213> ORGANISM: Artificial Sequence
<220> FEATURE:
<223> OTHER INFORMATION: Synthetic construct

<400> SEQUENCE: 16

Trp Tyr Gln Gln Lys Pro Gly Lys Ala Pro Lys Leu Leu Ile Tyr
 1               5                  10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic construct

<400> SEQUENCE: 17

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
             20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Synthetic construct

<400> SEQUENCE: 18

Phe Gly Gln Gly Thr Lys Val Glu Ile Lys Arg
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Gly Phe Thr Phe Ser Asp Ser Trp Ile His
 1               5                  10

<210> SEQ ID NO 20
<211> LENGTH: 18
<212> TYPE: PRT
<213> ORGANISM: Artificial Sequence
<220> FEATURE:
<223> OTHER INFORMATION: Synthetic construct

<400> SEQUENCE: 20
```

-continued

```
Ala Trp Ile Ser Pro Tyr Gly Gly Ser Thr Tyr Tyr Ala Asp Ser Val
1               5                   10                  15

Lys Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic construct

<400> SEQUENCE: 21

Arg His Trp Pro Gly Gly Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic construct

<400> SEQUENCE: 22

Arg Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic construct

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic construct

<400> SEQUENCE: 24

Gln Gln Tyr Leu Tyr His Pro Ala Thr
1               5

<210> SEQ ID NO 25
<211> LENGTH: 122
<212> TYPE: PRT
<213> ORGANISM: Artificial Sequence
<220> FEATURE:
<223> OTHER INFORMATION: Synthetic construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
            115                 120
```

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

```
Phe Gly Gln Gly Thr Lys Val Glu Ile Lys
 1               5                  10
```

<210> SEQ ID NO 27
<211> LENGTH: 30
<212> TYPE: PRT
<213> ORGANISM: Artificial Sequence
<220> FEATURE:
<223> OTHER INFORMATION: Synthetic construct

<400> SEQUENCE: 27

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser
            20                  25                  30
```

<210> SEQ ID NO 28
<211> LENGTH: 14
<212> TYPE: PRT
<213> ORGANISM: Artificial Sequence
<220> FEATURE:
<223> OTHER INFORMATION: Synthetic construct

<400> SEQUENCE: 28

```
Trp Val Arg Gln Ala Pro Gly Lys Gly Leu Glu Trp Val Ala
 1               5                  10
```

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

```
Trp Gly Gln Gly Thr Leu Val Thr Val Ser Ser Ala Ser Thr Lys
 1               5                  10                  15
```

<210> SEQ ID NO 30
<211> LENGTH: 447
<212> TYPE: PRT
<213> ORGANISM: Artificial Sequence
<220> FEATURE:
<223> OTHER INFORMATION: Synthetic construct

<400> SEQUENCE: 30

```
Glu Val Gln Leu Val Glu Ser Gly Gly Gly Leu Val Gln Pro Gly Gly
 1               5                  10                  15
```

-continued

```
Ser Leu Arg Leu Ser Cys Ala Ala Ser Gly Phe Thr Phe Ser Asp Ser
         20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
50                   55                  60

Lys Gly Arg Phe Thr Ile Ser Ala Asp Thr Ser Lys Asn Thr Ala Tyr
65                   70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
         195                 200                 205

Asn Thr Lys Val Asp Lys Lys Val Glu Pro Lys Ser Cys Asp Lys Thr
     210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Ala Ser Thr Tyr Arg Val Val
     290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Arg Glu Glu Met Thr Lys Asn Gln Val Ser Leu Thr Cys
         355                 360                 365

Leu Val Lys Gly Phe Tyr Pro Ser Asp Ile Ala Val Glu Trp Glu Ser
     370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
             420                 425                 430
```

```
Leu His Asn His Tyr Thr Gln Lys Ser Leu Ser Leu Ser Pro Gly
        435                 440                 445

<210> SEQ ID NO 31
<211> LENGTH: 214
<212> TYPE: PRT
<213> ORGANISM: Artificial Sequence
<220> FEATURE:
<223> OTHER INFORMATION: Synthetic construct

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```